United States Patent
Macdonald et al.

(10) Patent No.: US 11,259,510 B2
(45) Date of Patent: Mar. 1, 2022

(54) HUMANIZED T CELL MEDIATED IMMUNE RESPONSES IN NON-HUMAN ANIMALS

(71) Applicant: Regeneron Pharmaceuticals, Inc., Tarrytown, NY (US)

(72) Inventors: Lynn Macdonald, Harrison, NY (US); Andrew J. Murphy, Croton-on-Hudson, NY (US); Cagan Gurer, Chappaqua, NY (US); Christos Kyratsous, Irvington, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 243 days.

(21) Appl. No.: 15/564,723

(22) PCT Filed: Apr. 6, 2016

(86) PCT No.: PCT/US2016/026260
§ 371 (c)(1),
(2) Date: Oct. 5, 2017

(87) PCT Pub. No.: WO2016/164492
PCT Pub. Date: Oct. 13, 2016

(65) Prior Publication Data
US 2018/0139940 A1 May 24, 2018

Related U.S. Application Data

(60) Provisional application No. 62/186,935, filed on Jun. 30, 2015, provisional application No. 62/158,804, filed on May 8, 2015, provisional application No. 62/143,687, filed on Apr. 6, 2015.

(51) Int. Cl.
*A01K 67/027* (2006.01)
*C07K 16/28* (2006.01)
*C07K 16/00* (2006.01)

(52) U.S. Cl.
CPC ...... *A01K 67/0278* (2013.01); *C07K 16/2803* (2013.01); *A01K 2207/15* (2013.01); *A01K 2217/072* (2013.01); *A01K 2217/15* (2013.01); *A01K 2267/01* (2013.01); *C07K 16/00* (2013.01)

(58) Field of Classification Search
CPC ............ A01K 67/0278; A01K 2207/15; A01K 2217/072; A01K 2217/15; A01K 2267/01; C07K 16/2803; C07K 16/00; C07K 14/7051; C07K 14/70517; C07K 14/70539; C07K 2319/03; C07K 2319/00
See application file for complete search history.

(56) References Cited

U.S. PATENT DOCUMENTS

| 5,175,384 A | 12/1992 | Krimpenfort et al. |
| 5,413,923 A | 5/1995 | Kucherlapati et al. |
| 5,416,260 A | 5/1995 | Koller et al. |
| 5,574,205 A | 11/1996 | Kucherlapati et al. |
| 5,644,065 A | 7/1997 | Benoist et al. |
| 5,859,312 A | 1/1999 | Littman et al. |
| 5,942,435 A * | 8/1999 | Wheeler ............ A01K 67/0271 435/325 |
| 5,958,678 A | 9/1999 | Maddon et al. |
| 5,965,787 A | 10/1999 | Luthra et al. |
| 6,002,066 A | 12/1999 | Leung et al. |
| 6,139,835 A | 10/2000 | Kucherlapati et al. |
| 6,150,584 A | 11/2000 | Kucherlapati et al. |
| 6,270,772 B1 | 8/2001 | Burrows et al. |
| 6,372,955 B1 | 4/2002 | Karlsson et al. |

(Continued)

FOREIGN PATENT DOCUMENTS

| CA | 2471392 A1 | 8/2003 |
| EP | 0437576 B1 | 7/2002 |

(Continued)

OTHER PUBLICATIONS

Lavial et al. "Molecular control of pluripotency and germ line competency in chicken embryonic stem cells." Cell Res 18, S106 (2008) (Year: 2008).*
Kawamata et al. "Generation of genetically modified rats from embryonic stem cells."PNAS Aug. 10, 2010 107 (32) 14223-14228 (Year: 2010).*
Hall et al. "Porcine embryonic stem cells: a possible source for cell replacement therapy."Stem Cell Rev. Dec. 2008;4(4):275-82. (Year: 2008).*

(Continued)

*Primary Examiner* — Titilayo Moloye
(74) *Attorney, Agent, or Firm* — FisherBroyles, LLP; Rita S. Wu; Margarita Zippin

(57) ABSTRACT

Disclosed herein are non-human animals (e.g., rodents, e.g., mice or rats) genetically engineered to express a humanized T cell co-receptor (e.g., humanized CD4 and/or CD8 (e.g., CD8α and/or CD8β)), a human or humanized T cell receptor (TCR) comprising a variable domain encoded by at least one human TCR variable region gene segment and/or a human or humanized major histocompatibility complex that binds the humanized T cell co-receptor (e.g., human or humanized MHC II (e.g., MHC II α and/or MHC II β chains) and/or MHC I (e.g., MHC I α) respectively, and optionally human or humanized β 2 microglobulin). Also provided are embryos, tissues, and cells expressing the same. Methods for making a genetically engineered animal that expresses at least one humanized T cell co-receptor (e.g., humanized CD4 and/or CD8), at least one humanized MHC that associates with the humanized T cell co-receptor (e.g., humanized MHC II and/or MHC I, respectively) and/or the humanized TCR are also provided. Methods for using the genetically engineered animals that mount a substantially humanized T cell immune response for developing human therapeutics are also provided.

31 Claims, 28 Drawing Sheets
Specification includes a Sequence Listing.

(56) References Cited

U.S. PATENT DOCUMENTS

| | | |
|---|---|---|
| 6,514,752 B1 | 2/2003 | Kucherlapati et al. |
| 6,586,251 B2 | 7/2003 | Economides et al. |
| 6,596,541 B2 | 7/2003 | Murphy et al. |
| 6,815,171 B2 | 11/2004 | Burrows et al. |
| 7,105,348 B2 | 9/2006 | Murphy et al. |
| 7,265,218 B2 | 9/2007 | Burrows et al. |
| 7,294,754 B2 | 11/2007 | Poueymirou et al. |
| 7,339,089 B2 | 3/2008 | Gotch |
| 7,462,486 B2 | 12/2008 | Vandernbark |
| 7,569,664 B2 | 8/2009 | Jakobsen et al. |
| 7,663,017 B2 | 2/2010 | Lone et al. |
| 7,745,690 B2 | 6/2010 | Kanazawa et al. |
| 7,763,718 B2 | 7/2010 | Jakobsen et al. |
| 8,178,653 B2 | 5/2012 | Tureci et al. |
| 8,847,005 B2 | 9/2014 | Macdonald et al. |
| 9,043,996 B2 | 6/2015 | Macdonald et al. |
| 9,113,616 B2 | 8/2015 | Macdonald et al. |
| 9,585,373 B2 | 3/2017 | Macdonald et al. |
| 9,591,835 B2 | 3/2017 | Macdonald et al. |
| 9,615,550 B2 | 4/2017 | Macdonald et al. |
| 9,848,587 B2 | 12/2017 | Macdonald et al. |
| 2002/0164721 A1 | 11/2002 | Firat et al. |
| 2003/0093818 A1 | 5/2003 | Belmont et al. |
| 2003/0124524 A1 | 7/2003 | Kornman et al. |
| 2004/0137537 A1 | 7/2004 | Montero-Julian et al. |
| 2005/0050580 A1 | 3/2005 | Gotch et al. |
| 2005/0066375 A1 | 3/2005 | Thiam et al. |
| 2005/0114910 A1 | 5/2005 | Lone et al. |
| 2006/0107339 A1 | 5/2006 | Gotch et al. |
| 2007/0209083 A1 | 9/2007 | Thiam et al. |
| 2008/0153131 A1* | 6/2008 | Jakobsen ............ C07K 14/7051 435/69.1 |
| 2008/0181899 A1 | 7/2008 | Papadopoulos et al. |
| 2008/0219947 A1 | 9/2008 | Linette et al. |
| 2009/0304657 A1 | 12/2009 | Morgan et al. |
| 2009/0328240 A1 | 12/2009 | Sing et al. |
| 2010/0011450 A1 | 1/2010 | Garcia et al. |
| 2010/0011452 A1 | 1/2010 | Tomizuka et al. |
| 2010/0111993 A1 | 5/2010 | Tureci et al. |
| 2010/0138938 A1 | 6/2010 | Garcia et al. |
| 2010/0175141 A1 | 7/2010 | Collins et al. |
| 2011/0067121 A1 | 3/2011 | Lone et al. |
| 2011/0158957 A1 | 6/2011 | Bonini et al. |
| 2011/0243995 A1 | 10/2011 | Voss et al. |
| 2013/0109053 A1* | 5/2013 | Macdonald ........ A01K 67/0278 435/69.1 |
| 2013/0111617 A1 | 5/2013 | Macdonald et al. |
| 2013/0117873 A1 | 5/2013 | Wang et al. |
| 2013/0185819 A1 | 7/2013 | Macdonald et al. |
| 2014/0134662 A1 | 5/2014 | Flavell et al. |
| 2014/0245466 A1 | 8/2014 | Macdonald et al. |
| 2014/0245467 A1 | 8/2014 | Macdonald et al. |
| 2015/0040253 A1 | 2/2015 | Macdonald et al. |
| 2015/0245598 A1 | 9/2015 | Macdonald et al. |
| 2015/0342163 A1 | 12/2015 | Voronina et al. |
| 2016/0021856 A1 | 1/2016 | Macdonald et al. |
| 2017/0142944 A1 | 5/2017 | Macdonald et al. |
| 2017/0164590 A1 | 6/2017 | Macdonald et al. |
| 2017/0273286 A1 | 9/2017 | Macdonald et al. |
| 2018/0288986 A1 | 10/2018 | Macdonald et al. |

FOREIGN PATENT DOCUMENTS

| | | |
|---|---|---|
| EP | 1878342 A1 | 1/2008 |
| EP | 1878798 A1 | 1/2008 |
| EP | 0950707 B1 | 2/2009 |
| EP | 1017721 B1 | 2/2009 |
| EP | 1409646 B1 | 6/2012 |
| WO | 199101140 A1 | 2/1991 |
| WO | 199211753 A1 | 7/1992 |
| WO | 199305817 A1 | 4/1993 |
| WO | 199503331 A1 | 2/1995 |
| WO | 1997032603 A1 | 9/1997 |
| WO | 1998024893 A2 | 6/1998 |
| WO | 2001027291 A1 | 4/2001 |
| WO | 2002059263 A2 | 8/2002 |
| WO | 2002066630 A1 | 8/2002 |
| WO | 2003006639 A1 | 1/2003 |
| WO | 2004042004 A2 | 5/2004 |
| WO | 2005004592 A2 | 1/2005 |
| WO | 2007131092 A2 | 11/2007 |
| WO | 2008010099 A2 | 1/2008 |
| WO | 2008010100 A2 | 1/2008 |
| WO | 2009114400 A1 | 9/2009 |
| WO | 2012071592 A2 | 5/2010 |
| WO | 2010107400 A1 | 9/2010 |
| WO | 2011004192 A1 | 1/2011 |
| WO | 2011039508 A2 | 4/2011 |
| WO | 2011044186 A1 | 4/2011 |
| WO | 2012007951 A1 | 1/2012 |
| WO | 2012039779 A1 | 3/2012 |
| WO | 2013063340 A1 | 5/2013 |
| WO | 2013063346 A1 | 5/2013 |
| WO | 2013063361 A2 | 5/2013 |
| WO | 2014130667 A1 | 8/2014 |
| WO | 2014130671 A1 | 8/2014 |
| WO | 2014164638 A1 | 10/2014 |
| WO | 2014164640 A1 | 10/2014 |

OTHER PUBLICATIONS

Murphy and Silha. "Unexpected and unexplained phenotypes in transgenic models."Growth Horm IGF Res. Oct. 2000;10(5):233-5. (Year: 2000).*

Brouwers, B. et al., Unexpected Phenotypes in Mouse Models Carrying the Human Growth Hormone Minigene to Enhance Transgene Expression, Journal of Steroids & Hormonal Science, 6(2): 2 pages (2015). (Year: 2015).*

Choi et al. "Expression of the metabotropic glutamate receptor 5 (mGluR5) induces melanoma in transgenic mice." PNAS Sep. 13, 2011 108 (37) 15219-15224 (Year: 2011).*

Yantha et al. "Unexpected acceleration of type 1 diabetes by transgenic expression of B7-H1 in NOD mouse peri-islet glia." Diabetes. Oct. 2010;59(10):2588-96. (Year: 2010).*

Linder et al. "Genetic Variables That Influence Phenotype." ILAR Journal, vol. 47, Issue 2, 2006, pp. 132-140 (Year: 2006).*

Zhu et al. "Humanising the mouse genome piece by piece."Nature Communications vol. 10, Article No. 1845 (2019) (Year: 2019).*

Sittig et al. "Genetic Background Limits Generalizability of Genotype-Phenotype Relationships."Neuron. Sep. 21, 2016;91(6):1253-1259. (Year: 2016).*

Abarrategui and Krangel (2006) "Regulation of T cell receptor alpha gene recombination by transcription," Nat. Immunol., 7:1109-1115 and Corrigendum.

Aggen et al. (2011) "Identification and engineering of human variable regions that allow expression of stable single-chain T cell receptors," Protein Eng., Design & Selection, 24:361-372.

Allen et al. (1986) "B2-Microglobulin is not required for Cell surface expression of the murine class I histocompatibility antigen H-2Db or of a truncated H-2Db," PNAS, 83:7447-7451.

Altmann et al. (1995) "The T Cell Response to HLA-DR Transgenic Mice to Human Myelin Basic Protein and other Antigens in the Presence and Absence of Human CD4," J. Exp. Med., 181:867-875.

Alvarez et al. (1995) "V(D)J Recomination and Allelic Exclusion of a TCR B-Chain Minilocus Occurs in the Absence of a Functional Promoter," J. Immunol., 155:1191-1202.

Arnold and Hammerling (1991) "MHC Class-1 Transgenic Mice," Annu. Rev. Immunol., 9:297-322.

Auerbach et al. (2000) "Establishment and Chimera Analysis of 129/SvEV- and C57BL/6-Derived Mouse Embryonic Stem Cell Lines," BioTechniques, 29:1024-1032.

Baer, et al. (1986) "Organization of the T-Cell receptor alpha-chain gene and rearrangement in human T-Cell leukemias," Mol. Biol. Med., 3:265-277.

Baker et al. (1996) "Adaptation of TCR Expression Vectors for the Construction of Mouse-Human Chimeric MBP-Specific TCR Transgenes," J. Neurosci. Research, 45:487-491.

(56) References Cited

OTHER PUBLICATIONS

Barber and Lechler (1991) "Interactions between the amino-terminal domains of MCH class II molecules have a profound effect on serologic and T cell recognition: an analysis using recombinant HLA-DR/H-2E molecules," J. Immunol., 147:2346-2353.
Barnden, et al. (1988) "Defective TCR expression in transgenic mice constructed using eDNA-based alpha- and beta-chain genes under the control of heterologous regulatory elements," Immunol. Cell Biol., 76:34-40.
Barthold (2004) "Genetically altered mice: phenotypes, no phenotypes, and Faux phenotypes," Genetica, 122:75-88.
Basha et al.(2008) "MHC Class I Endosomal and Lysosomal Trafficking Coincides with Exogenous Antigen Loading in Dendritic cells," PLoS ONE, 3:e3247, 11 pages.
Bassing et al. (2000) Recombination signal sequences restrict chromosomal V(D)J recombination beyond the 12/23 rule, Nature, 405:583-586.
Benmohamed et al. (2000)"Induction of CTL Response by a Minimal Epitope Vaccine in HLA-A*0201/DR1 Transgenic Mice: Dependence on HLA Class II Restricted TH Response," Hum. Immunol., 61:764-779.
Bernabeu et al. (1984) "B2-Microglobulin from serum associates with MHC class I antigens on the surface of cultured cells," Nature, 308:642-645.
Betser-Cohen et al. (2010) "The Association of MHC Class I Proteins with the 2B4 Receptor Inhibits Self-Killing of Human NK cells," J. Immunol., 184:2761-2768.
Bialer et al. (2010) "Selected Murine Residues Endow Human TCR with Enhanced Tumor Recognition," J. Immunol., 184:6232-6241.
Bonnet, et al. (2009) "Molecular Genetics at the T-Cell Receptor β Locus: Insights into the Regulation of V(D)J Recombination," V(D)J Recombination, 650:116-132.
Botten et al. (2007) "HLA-A2-Restricted Protection against Lethal Lymphocytic Choriomeningitis," J. Virol. 81:2307-17.
Bouffard et al. (1997) "A Physical Map of Human Chromosome 7: An Integrated YAC Contig Map with Average STS Spacing of 79 kb," Genome Research, 7:673-692.
Boulter and Jakobsen (2005) "Stable, soluble, high-affinity, engineered T cell receptors: novel antibody-like proteins for specific targeting of peptide antigens," Clin. Exp. Immunol., 142:454-460.
Brehm et al. (2010) "Humanized Mouse Models to Study Human Diseases," Curr. Opin. Endocrinol. Diabetes Obes., 17:120-125.
Brevini et al. (2010) "Embryonic Stem Cells in Domestic Animals; No shortcuts to pig embryonic stem cells," Theriogenology, 74:544-550.
Brusko et al. (2010) "Human Antigen-Specific Regulatory T cells Generated by T cell receptor Gene Transfer," PLoS ONE, 5:e11726, 12 pages.
Buta et al. (2013) "Reconsidering pluripotency tests: Do we still need teratoma assays?," Stem Cell Res., 11:552-562.
Call and Wucherpfennig (2005) "The T cell receptor: Critical Role of the Membrane Environment in Receptor Assembly and Function," Annu. Rev. Immunol., 23:101-125.
Campbell (1997) "Totipotency or Multipotentiality of Cultured cells: Applications and Progress," Theriogenology, 47:(1), 63-72.
Capone, et al. (1995) "T Cell Development in TCR-alphabeta Transgenic Mice Analysis using V(D)J Recombination Substrates," J. Immunol., 5165-5172.
Carrasco et al. (2003) "A role for the cytoplasmic tail of the pre-T cell receptor (TCR) alpha chain in promoting constitutive internalization and degradation of the pre-TCR," J. Biol. Chem., 278:14507-13.
Carstea et al. (2009) "Germline competence of mouse ES and iPS Cell lines: Chimera technologies and genetic background," World Journals of Stem Cells, 1(1):22-29.
Chamberlain et al. (1988)"Tissue-specific and Cell surface expression of human major histocompatibility complex class I heavy (HLA-B7) and light (B2-microglobulin) chain genes in transgenic mice," PNAS, 86:7690-7694.
Chhabra (2011) "TCR-Engineered, Customized, Antitumor T cells for Cancer Immunotherapy: Advantages and Limitations," The Scientific World J., 11:121-129.
Chung et al. (1994) "Functional three-domain single-chain T-Cell receptors," PNAS, 91:12654-12658.
Clark et al. (1987) "Peptide and nucleotide sequences of rat CD4 (W3/25) antigen: evidence for derivation from a structure with four immunoglobulin-related domains," PNAS, 84(6):1649-1653.
Cohen, et al. (2006) "Enhanced Antitumor Activity of Murine-Human Hybrid T-Cell Receptor (TCR) in Human Lymphocytes is Associated with Improved Pairing and TCR/CD3 Stability," Cancer Res., 66:8878-8886.
Connolly et al. (1988) "The Lyt-2 Molecule Recognizes Residues in the Class I alpha3 Domain in Allogeneic Cytotoxic T Cell Responses," J. Exp. Med., 168:325-341.
Cooper et al. (2007) "An Impaired Breeding Phenotype in Mice with a Genetic Deletion of Beta-2 Microglobulin and Diminished MHC Class I Expression: Role in Reproductive Fitness," Biol. Reprod., 77:274-279.
Corbeil et al. (1996) "HIV-induced Apoptosis Requires the CD4 Receptor Cytoplasmic Tail and Is Accelerated by Interaction of CD4 with p56lck," J. Exp. Med.,183:39-48.
Cosson and Bonifacino (1992) "Role of Transmembrane Domain Interactions in the Assembly of Class II MHC Molecules," Science, 258:659-662.
Crusio et al. (2004) "Flanking Gene and Genetic Background Problems in Genetically Manipulated Mice," Biol. Psychiatry, 56:381-385.
Daniel-Meshulam et al. (2012) "How (specific) would you like your T-cells today? Generating T-Cell therapeutic function through TCR-gene transfer," Front. Immunol., 3:186, 13 pages.
Danner et al. (2011) "Expression of HLA Class II Molecules in Humanized NOD.Rag1KO.IL2RgKO Mice is Critical for Development and Function of Human T and B cells," PLoS ONE, 6:e19826, 12 pages.
Database entry for NCB I Reference Sequence: NG 001333.2 (Sep. 19, 2006) "Homo sapiens T cell receptor beta locus (TRB) on chromosome 7".
De Bakker et al. (2006) "A high-resolution HLA and SNP haplotype map for disease association studies in the extended human MHC," Nature Genet. Online Supplement, 33 pages.
De Bakker et al. (2006) "A high-resolution HLA and SNP haplotype map for disease association studies in the extended human MHC," Nature Genet., 38:1166-1172.
De Gassart et al. (2008) "MHC class II stabilization at the surface of human dendritic cells is the result of maturation-dependent MARCH I down-regulation," PNAS, 105:3491-3496.
Dennis (2002) "Welfare issues of genetically modified animals," ILAR Journal, 43(2):100-109.
Dietrich et al. (2003) "Prevalent Role of TCR alpha-chain in the Selection of the Preimmune Repertoire Specific for a Human Tumor-Associated Self-Antigen," J. Immunol., 170:5103-5109.
Doetschman (2009) "Influence of Genetic Background on Genetically Engineered Mouse Penotypes," Methods Mol. Biol., 530:423-433.
Dolan et al. (2004) "Invariant Chain and the MHC Class II Cytoplasmic Domains Regulate Localization of MHC Class II Molecules to Lipid Rafts in Tumor Cell-Based Vaccines," J. Immunol., 172:907-914.
Duke (1989) "Self Recognition by T Cell," J. Exp. Med. 170:59-71.
El Fakhry et al. (2004) "Delineation of the HLA-DR Region and the Residues Involved in the Association with the Cytoskeleton," J. Biol. Chem., 279:18472-18480.
Ellmeier et al. (1998) "Multiple developmental stage-specific enhancers regulate CDS expression in developing thymocytes and in thymus-independent T cells," Immunity, 9(4):485-496.
Epel et al. (2002) "A functional recombinant single-chain T cell receptor fragment capable of selectively targeting antigen-presenting cells," Cancer Immunol. Immunother., 51:565-573.
Ferrier et al. (1990) "Separate elements control DJ and VDJ rearrangement in a transgenic recombination substrate," EMBO J., 9:117-125.

(56) References Cited

OTHER PUBLICATIONS

Festing et al. (1999) "Revised nomenclature for strain 129 mice," Mamm. Genome, 10:836.
Firat et al. (2002) "Comparative analysis of the CO8+ T Cell repertoires of H-2 class I wild-ype/HLA-2.1 and H-2 class I knockout/HLA-A2.1 transgenic mice," Internal. Immunol., 14:925-934.
Fleischer et al. (1996) Reactivity of Mouse T-Cell Hybridomas Expressing Human Vβ Gene Segments with Staphylococcal and Streptococcal Superantigens, Infection and Immunity, 64(3):997-994.
Fooksman et al. (2009) "Cutting Edge: Phospholidylinositol 4, 5-Bisphosphate Concentration at the APC Side of the Immunological Synapse Is Required for Effector T Cell Function," J. Immunol., 182:5179-5182.
Friese et al. (2006) "Humanized mouse models for organ-specific autoimmune diseases," Curr. Opin. Immunol., 18:704-709.
Friese et al., (2008) "Opposing effects of HLA class I molecules in tuning autoreactive CDS+ T cells in multiple scelerosis," Nature Med., 14(11): 1227-1235.
Fugger et al. (1994) "Expression of HLA-DR4 and human CD4 transgenes in mice determines the variable region beta-chain T-Cell repertoire and mediates an HLA-DR-restricted immune response," PNAS, 91:6151-6155.
Fukui et al. (1993) "T-cell repertoire in a stain of transgenic C57BL/6 mice with the HLA-DRA gene on the X-chromosome," Immunogenetics, 37(3):204-211.
Fukui et al. (1997) "Differential requirement of MHC class II molecules expressed on hematopoietic cells for positive selection of CD4+ thymocytes in TCR α β and TCR β transgenic mice," Internal. Immunol., 9(9):1385-1391.
Gao et al. (1997) "Crystal structure of the complex between human CD88alpha-alpha and HLA-A2," Nature, 387:630-634.
Gao et al. (2000) "Molecular interactions of coreceptor CD8 and MHC class 1: the molecular basis for functional coordination with the T-Cell receptor," Immunol. Today, 21 (12):630-636.
Ge and Stanley (2008) "The O-fucose glycan in the ligand-binding domain of Notch 1 regulates embryogenesis and T Cell development," PNAS, 105:1539-1544.
Germain et al., (2002) "T-Cell Development and The CD4-CDS Lineage Decision, Nature Reviews, Immunol.," 2:309-322.
Glusman et al. (2001) "Comparative Genomics of the Human and Mouse T Cell Receptor Loci," Immunity, 15:337-349.
Godfrey et al. (1993) "Control Points in early T-Cell development," Immunol. Today, 14:547-553.
Goldman et al. (2004) "Transgenic animals in medicine: Integration and expression of foreign genes, theoretical and applied aspects," Med. Sci. Monit., 10(11): RA274-285.
Gomez et al. (2010) "Derivation of cat embryonic stem-like cells from in vitro-produced blastocysts on homologous and heterologous feeder cells," Theriogenology, 74:498-515.
Gonnet et al. (1992) Exhaustive Matching of the Entire Protein Sequence Database, Science 256:1443-1445.
Gruda et al. (2007) "Intracellular Cysteine Residues in the Tail of MHC Class I Proteins Are Crucial for Extracellular Recognition by Leukocyte Ig-Like Receptor 1," J. Immunol., 179:3655-3661.
Günther and Walter (2001) "The major histocompatibility complex of the rat (*Rattus norvegicus*)," Immunogenetics, 53:520-542.
Gur et al. (1997) "Structural Analysis of Class I MHC Molecules: The Cytoplasmic Domain Is Not Required for Cytoskeletal Association, Aggregation and Internalization," Mol. Immunol., 34:125-132.
Güssow et al. (1987) "The Human B2-Microglobulin Gene. Primary Structure and Definition of the Transcriptional Unit," J. Immunol., 139:3132-3138.
Haks et al. (1999) "Cell-fate decisions in early T cell development: regulation by cytokine receptors and the pre-TCR," Immunol., 11:23-37.
Hanna et al. (1994) "Specific expression of the human CD4 gene in mature CD4 + CD8- and immature CD4+ and CD8+ T cells and in macrophages of transgenic mice," Mol. Cellular Biol., 14(2):1084-1094.
Harton et al. (2016) "Immunological Functions of the Membrane Proximal Region of MHC Class II Molecules," F1000Research, 5:1-12, doi: 10.12688/f1000research.7610.1.
Holdsworth et al. (2009) "The HLA dictionary 2008: a summary of HLA-A, -B, -C -DRB1/3/4/5, and -DQB1 alleles and their association with serologically defined HLA-A, -B, -C, -DR, and -DO antigens," Tissue Antigens, 73:95-170.
Holst, et al. (2006) "Generation of T-Cell receptor retrogenic mice," Nat. Protoc., 1:406-417.
Hong et al. (2012) "Derivation and Characterization of Embryonic Stem Cells Lines Derived from Transgenic Fischer 344 and Dark Agouti Rats," Stem Cells and Development, 21(9):1571-1586.
Hostert et al. (1997) "A CD8 genomic fragment that directs subset-specific expression of CD8 in transgenic mice," J. Immunol., 158(9):4270-4281.
Hou et al. (2016) "Derivation of Porcine Embryonic Stem-Like Cells from In Vitro-Produced Blastocyst-Stage Embryos," Scientific Research, 6:1-13.
Houdebine, et al (2002) "The methods to generate transgenic animals and to control transgene expression," J. of Biotech., 98:145-160.
Houdebine, et al (2007) "Methods in Molecular," Biology, 360:163-202.
Huang et al. (1997) "Analysis of the contact sites on the CD4 Molecule with Class II MHC Molecule," J. Immunol., 158:215-225.
Intarapat and Stern (2013) "Chick stem cells: Current progress and future prospects," Stem Cell Res., 11:1378-1392.
International MHC and Autoimmunity Genetics Network (IMAGEN) (2009) "Mapping of multiple 40 susceptibility variants within the MHC region for 7 immune-mediated diseases," PNAS, 1 06: 18680-18685.
Irie et al. (1998) "The cytoplasmic domain of CD8 beta regulates Lck kinase activation and CD8 T cell development," J. Immunol., 161(1):183-191.
Irwin et al. (1989) "Species-restricted interactions between COB an the alpha3 domain of class I influence the magnitude of the xenogeneic response," J. Exp. Med., 170:1091-1101.
Ishimoto et al. (1997) "In vitro and in vivo evidence for high frequency of I-Ab-reactive CD4+ t cells in HLA-DQ or HLA-DRA transgenic mice lacking endogenous MHC class I and/or class II expression," J. Immunol., 159(8):3717-3722.
Itano et al. (1996) "The Cytoplasmic Domain of CD4 Promotes the Development of CD4 Lineage T Cells," J. Exp. Med., 183(3):731-741.
Ito et al. (1996) "HLA-DR4-IE Chimeric Class II Transgenic, Murine Class 11-Deficient Mice Are Susceptible to Experimental Allergic Encephalomyelitis," J. Exp. Med., 183:2635-2644.
Janeway's Immunobiology, Chapter 7, 7th Ed., Murphy et al. eds., Garland Science, 2008.
Jakobovits (1994) "Humanizing the mouse genome," Cur. Biol., 4(8):761-763.
Jakubke et at. (1986) "Aminokisloty, peptidy, belki:" translated from German, Moscow, Mir, 1986, 456 pages (p. 356-363) English Translation Only.
Jean et al. (2013) "Pluripotent genes in avian stem cells," Develop. Growth Differ., 55:41-51.
Johansson et al. (2005) "Natural killer Cell education in mice with single or multiple major histocompatibility complex class I molecules," J. Exp. Med., 201:1145-1155.
Johnson et al. (1987) "A human homolog of the mouse CD8 molecule, Lyt-3" genomic sequence and expression, Immunogenetics, 26(3):174-177.
Johnson et al. (2009) "Gene therapy with human and mouse T-Cell receptors mediates cancer regression and targets normal tissues expressing cognate antigen," Blood, 114:535-546.
Josson et al. (2011) "B2 microglobulin induces epithelial to mesenchymal transition and confers cancer lethality and bone metastasis in human cancer cells," Cancer Res., 71:1-11.

(56) References Cited

OTHER PUBLICATIONS

Kalinke et al. (1990) "Strong Xenogeneic HLA Response in Transgenic Mice after Introducing an Alpha3 Domain into HLA B27," Nature, 348:642-644.
Kaplan et al. (2005) "A new murine tumor model for studying HLA-A2-restricted anti-tumor immunity," Cancer Letters, 224:153-166.
Khor et al. (2002) "Allelic exclusion at the TCRβ locus," Curr. Opin. Immunol., 14:230-234.
Kievits et al. (1987) "HLA-restricted recognition of viral antigens in HLA transgenic mice," Nature 329:447-449.
Killeen et al. (1993) "Regulated expression of human CD4 rescues helper T cell development in mice lacking expression of endogenous CD4," EMBO J., 12(4): 1547-1553.
Kioussis et al. (2002) "Chromatin and CD4, CD8A and CD8B gene expression during thymic differentiation," Nature Rev. Immunol., 2(12):909-919.
Kirwan et al. (2005) "Killer Cell Ig-Like Receptor-Dependent Signaling by Ig-Like Transcript 2 (ILT2/CD85j/LILRB1/ LIR-1)," J. Immunol., 175:5006-5015.
Koller and Orr (1985) "Cloning and complete sequence of an HLA-A2 gene: Analysis of two HLA-A Alleles at the nucleotide Level" J. Immunol. 134(4):2727-2733.
Koller et al. (1990) "Normal Development of Mice Deficient in B2M, MHC Class I Proteins, and CD8+ T cells," Science, 248:1227-1230.
Koop et al., (1994) "The human T-cell receptor TCRAC/TCRDC (C alpha/C delta) region: organization, sequence, and evolution of 97.6 kb of DNA," Genomics 19(3):478-493.
Kouskoff et al. (1995) "Cassette vectors directing expression of T cell receptor genes in transgenic mice," J. Immunol. Methods, 180:273-280.
Krangel et al. (1998) "Development regulation of V(D)J recombination at the TCR α/δ locus," Immunol. Rev., 165:131-147.
Kruisbeek et al., (2000) "Branching out to gain control: how the pre-TCR is linked to multiple functions," Rev. Immunol. Today, 21 (12):637-644.
Kuhns et al. (2006) "Deconstructing the Form and Function of the TCR/CD3 Complex," Immunity, 24:133-139.
Kumanovics et al. (2003) "Genomic Organization of the Mammalian MHC," Annu. Rev. Immunol., 21:629-657.
Laface et al. (1995) "Human CD8 Transgene Regulation of HLA Recognition by Murine T cells," J. Exp. Med., 182:1315-1325.
Lalor et al. (1992) "Molecular cloning, reconstruction and expression of the gene encoding the alpha-chain of the bovine CD8-definition of three peptide regions conserved across species," Immunology, 76:95-102.
Landau et al. (1988) "The envelope glycoprotein of the human immunodeficiency virus binds to the immunoQiobulin-like domain of CD4," Nature, 334(6178): 159-162.
Laub et al. (2000) "A multiple transgenic mouse model with a partially humanized activation pathway for helper T cell responses," J. Immunol. Methods, 246(1-2):37-50.
Lauzurica et al. (1994) "Temporal and Lineage-specific control of T cell receptor alpha/delta gene rearrangement by T Cell, receptor alpha and delta enhancers," J. Exp. Med., 179:1913-1921.
Lauzurica P. and Krangel M.S. (1994) "Enhancer-dependent and -independent Steps in the Rearrangement of a Human T Cell Receptor Delta Transgene," J. Exp. Med., 179:43-55.
Law et al. (1994) "Human CD4 Restores Normal T Cell Development and Function in Mice Deficient in Murine CD4," J. Exp. Med., 179(4): 1233-1242.
Leahy (1995) "A structural view of CD4 and CD8," FASEB J., 9:17-25.
Leduc et al. (2000) "T Cell Development in TCRβ Enhancer-Deleted Mice: Implications for αβ T Cell Lineage Commitment and Differentiation," J. Immunol., 165:1364-1373.
Lee et al. (1982) "Sequence of an HLA-DR alpha-chain eDNA clone and intron-exon organization of the corresponding gene," Nature, 299:750-752.
Li et al. (2009) "Mamu-A*01/Kb transgenic and MHC Class I knockout mice as a tool for HIV vaccine development," Virology, 387:16-28.
Li et al. (2010) "Transgenic mice with a diverse human T Cell antigen receptor repertoire," Nature Med., 16(9):1029-1034, doi:10.1038/nm.2197.
Li et al. (2010) "Transgenic mice with a diverse human T Cell antigen receptor repertoire," Nature Med., 16, supplementary materials, 22 pages.
Li et al. (2013) "Generation of transgenic mice with megabase-sized human yeast artificial chromosomes by yeast spheroplast-embryonic stem cell fusion," Nat. Protoc., 8(8):1567-1582, doi:10.1038/nprot.2013.093.
Lie and Petropoulos (1998) "Advances in quantitative PCR technology: 5' nuclease assays," Curr. Opin. Biotech., 9:43-48.
Linnemann et al. (2011) "T-Cell Receptor Gene Therapy: Critical Parameters for Clinical Success," J. Invest. Dermalol., 131:1806-1816.
Linnenbach et al. (1980) "DNA-transformed murine teratocarcinoma cells: regulation of expression of simian virus 40 tumor antigen in stem versus differentiated cells," PNAS, 77(8):4875-4879.
Littman (1987) "The Structure of the CD4 and CD8 Genes," Annual Review of Immunology, 5:561-584.
Lizee et al. (2003) "Control of dendritic cell cross-presentation by the major histocompatibility complex class I cytoplasmic domain," Nature Immunol., 4:1065-1073.
Love and Hayes (2010) "ITAM-Mediated Signaling by the T-Cell Antigen Receptor," Cold Spring Harb. Perspecl. Biol., 2:e002485.
Lynch et al. (2009) "Novel MHC Class I Structures on Exosomes," J. Immunol., 183:1884-1891.
Mackay (1999) "Dual personality of memory T cells," Nature, 401:659-660.
Maddon et al. (1987) "Structure and expression of the human and mouse T4 genes," PNAS, 84(24):9155-9159.
Madsen et al. (1999) "A humanized model for multiple sclerosis using HLA-DR2 and a human T-cell receptor," Nature Genet., 23:343-347.
Maksimenko et al. (2013) "Use of Transgenic Animals in Biotechnology: Prospects and Problems," ACTNA Naturae, 5(1):33-46.
Mantovani et al. (2002) Dominant TCR-alpha Requirements for a Self Antigen Recognition in Humans, J. Immunol., 169:6253-6260.
Manz et al. (2009) "Renaissance for mouse models of human hematopoiesis and immunobiology," Nature Immunology, 10(10):1039-1042.
Marsh et al. (2010) "Nomenclature for factors of the HLA system," 2010, Tissue Antigens, 75:291-455.
Marten et al. (2003) "Transgenic mouse methods and protocols," Methods in Molecular Biology, 209:51-58.
Matloubian et al. (1994) "CD4+ T cells are required to sustain CD8+ cytotoxic T-cell responses during chronic viral infection," J. Virol., 68(12):8056-8063.
McMurry et al. (1997) "Enhancer Control of Local Accessibility to V(D)J Recombinase," Molecular and Cellular Biology, 17(8):5443-5461.
Mendez et al. (1997) "Functional transplant of megabase human immunoglobulin loci recapitulates human antibody response in mice," Nature Genet., 15(2):146-156.
Moir et al. (1996) "Postbinding events mediated by human immunodeficiency virus type 1 are sensitive to modifications in the D4-transmembrane linker region of CD4," J. Virology, 70(11):8019-8028.
Moldovan et al. (2002) "CD4 Dimers Constitute the Functional Component Required forT Cell Activation," J. Immunol., 169:6261-6268.
Mombaerts P. et al. (1991) "Creation of a large genomic deletion at the T-cell antigen receptor β-subunit locus in mouse embryonic stem cells by gene targeting," PNAS, 88:3084-3087.
Mombaerts et al. (1992) "Mutations in T-cell antigen receptor genes a and B block thymocyte development at different stages," Nature, 360:225-231.
Mombaerts et al. (1993) "Spontaneous Development of Inflammatory Bowel Disease in T Cell Receptor Mutant Mice," Cell, 75:275-282.

(56) References Cited

OTHER PUBLICATIONS

Morgan et al. (2006) "Cancer Regression in Patients After Transfer of Genetically Engineered Lymphocytes," Science, 314:126-129.
Munoz et al. (2008) "Technical note; Conventional pluripotency markers are unspecific for bovine embryonic-derived cell-lines," Theriogenology, 69:1159-1164.
Murphy et al. (2008) "Janeway's Immunobiology" 7th ed., Garland Science, pp. 125-13B and 196-213.
Musser G. (Encyclopedia Britannica, May 31, 2016) Rodent, Mammal, http://www.britannica.com/animal/rodent.
Nakayama et al. (1989) "Structure and expression of the gene encoding CD8α chain (Leu-2/T8)," Immunogenetics, 30:393-397.
Nakayama et al. (1992) "Recent Duplication of the Two Human CD8 β-chain genes," J. Immunol., 148:1919-1927.
NCBI Accession No. NG_001332.2 (2012) "Homo sapiens T cell receptor alpha delta locus (TCRA/TCRD) on chromosome 14," NCBI, 2 pages.
Nickerson et al. (1990) "Expression of HLA-B27 in Transgenic Mice Is Dependent on the Mouse H-20 Genes," J. Exp. Med., 172:1255-1261.
Noordzij et al. (2000) "N-terminal truncated human RAG1 proteins can direct T-cell receptor but not immunogiobulin gene rearrangements," Blood, 96(1):203-209.
Norment et al. (1988) "A second subunit of CD8 is expressed in human T cells," EMBO J., 7(11):3433-3439.
Norment et al. (1989) "Alternatively Spliced mRNA Encodes a Secreted Form of Human CD8α, Characterization of the Human CD8α gene," J. Immunol., 142:3312-3319.
Ostrand-Rosenberg et al. (1991) "Abrogation of Tumorigenicity by MHC Class II Antigen Expression Requires the Cytoplasmic Domain of the Class II Molecule," J. Immunol., 147:2419-2422.
Pajot et al. (2004) "A mouse model of human adaptive immune functions: HLA-A2.1/HLA-DR1-trasngenic H-2 class 1-/class 11-knockout mice," Eur. J. Immunol., 34:3060-3069.
Paris and Stout (2010) "Embryonic Stem Cells in Domestic Animals; Equine embryos and ebryonic stem cells: Defining reliable markers of pluripotency," Theriogenology, 74:516-524.
Pasare et al. (2001) "T cells in mice expressing a transgenic human TCRβ chain get positively selected but cannot be activated in the periphery by signaling through TCR," Intl. Immunol., 13(1):53-62.
Pascolo, et al. (1997) "HLA-A2.1-restricted Education and Cytolytic Activity of CD8+ T Lymphocytes from from β2 Microglobulin (β2m) HLA-A2.1 Monochain Transgenic H-2Db β2m Double Knockout Mice," J. Exp. Med., 185:2043-2051.
Pascolo, et al. (2005) "HLA class I transgenic mice: development, utilisation and improvement," Expert Opinion Biol. Ther., 5(7):919-938.
Perarnau et al. (1988) "Human B2-microglobulin specifically enhances cell-surface expression of HLA class I molecules in transfected murine cells," J. Immunol., 141:1383-1389.
Pettersen et al. (1998) "The TCR-Binding Region of the HLA Class 1 α2 Domain Signals Rapid Fast Independent Cell, Death: A Direct Pathway for T Cell-Mediated Killing of Target cells," J. Immunol., 160:4343-4352.
Pittet et al. (2003) "Alpha3 Domain Mutants of Peptide/MHC Class I Multimers Allow the Selective Isolation of High Avidity Tumor-Reactive CD8 T cells," J. Immunol., 171:1844-1849.
Potter et al. (1989) "Substitution at residue 227 of H-2 class I molecules abrogates recognition by CD8-dependent, but not CD8-independent, cytotoxic T lymphocytes," Nature, 337:73-75.
Poueymirou et al. (2007) "F0 generation mice fully derived from gene-targetedembryonic stem cells allowing immediate phenotypic analyses," Nature Biotech., 25:91-99.
Quinn et al. (1997) "Virus-Specific, CD8+ Major Histocompatibility Complex Class 1-Restricted Cytotoxic T Lymphocytes in Lymphocytic Choriomeningitis Virus-Infected B2-Microglobulin-Deficient Mice," J. Virol., 71:8392-8396.
Rack et al. (1997) "A Chromosome 14q11/TCRα/δ Specific Yeast Artificial Chromosome Improves the Detection Rate and Characterization of Chromosome Abnormalities in T-Lymphoproliferative Disorders," Blood, 90(3):1233-1240.
Raffegerst et al. (2009) "Diverse Hematological Malignancies Including Hodgkin-Like Lymphomas Develop in Chimeric MHC Class II Transgenic Mice," PLoS ONE, 4:e8539, 12 pages.
Ravetech and Lanier (2000) "Immune Inhibitory Receptors," Science, 290:84-89.
Reipert et al. (2009) "Opportunities and limitations of mouse models humanized for HLA class II antigens," Thrombosis and Haemostasis, 7(Suppl. l):92-97.
Ren et al. (2006) "Construction of bioactive chimeric MHC class I tetramer by expression and purification of human-murine chimeric MHC heavy chain and β2M as a fusion protein in *Escherichia coli*," Protein Expression and Purification, 50:171-78.
Restifo et al. (2012) "Adoptive immunotherapy for cancer: harnessing the T cell response," Nature Reviews, 12:269-281.
Richman et al. (2009) "Structural features of T cell receptor variable regions that enhance domain stability and enable expression as single-chain ValphaVbela fragments," Mol. Immunol., 43:902-916.
Rodriguez-Cruz et al. (2011) "Natural Splice Variant of MHC Class I Cytoplasmic Tail Enhances Dendritic Cell-Induced CD8+ T-Cell, Responses and Boosts Anti-Tumor Immunity," PLoS ONE, 6:e22939, 10 pages.
Rohrlich et al. (2003) "HLA-B*0702 transgenic, H-2$K^b D^b$ doubleknockout mice: phenotypical and functional characterization in response to influenza virus," International Immunology, 15(6):765-772.
Rosano et al. (2005) "The three-dimensional structure of B2 microglobulin: Results from X-ray crystallography," Biochim. Biophys. Acta, 1753:85-91.
Rosenberg et al. (2011) "Durable Complete Responses in Heavily Pretreated Patients with Metastatic Melanoma Using T-Cell Transfer," Immunotherapy, 17:4550-4557.
Rothe et al. (1993) Functional expression of a human TCRβ gene in transgenic mice, Intl. Immunol., 5(1):11-17.
Rowen et al., (1996) "The Complete 685-Kilobase DNA Sequence of the Human β T Cell Receptor Locus," Science, 272:1755-1762.
Rubio et al. (2004) "Cross-linking of MHC class I molecules on human NK cells inhibits NK cell function, segregates MHC I from the NK cell synapse, and induces intracellular phosphotyrosines," J. Leukoc. Biol., 76:116-124.
Sallusto et al. (1999) "Two subsets of memory T lymphocytes with distinct homing potentials and effector functions," Nature, 401:708-712.
Salter et al. (1989) "Polymorphism in the alpha3 domain of HLA-A molecules affects binding to CD8," Nature, 338:345-347.
Salter et al. (1990) "A binding site for the T-cell co-receptor CD8 on the alpha 3 domain of HLA-A2," Nature, 345:41-46.
Samberg et al. (1989) "The α3 domain of major histocompatibility complex class I molecules plays a critical role in cytotoxic T lymphocyte stimulation," Eur. J. Immunol., 19(12):2349-2354.
Sanders et al. (1991) "Mutations in CD8 that Affect Interactions with HLA Class I and Monoclonal Anti-CD8 Antibodies," J. Exp. Med., 174:371-379.
Santagata et al. (2000) "The genetic and biochemical basis of Omenn syndrome," Immunological Reviews, 178:64-74.
Satyanarayana et al. (1988) "Genomic organization of the human T-cell antigen-receptor alpha/delta locus," PNAS, 85:8166-8170.
Scheer et al. (2013) "Generation and utility of genetically humanized mouse models." Drug Discovery Today, 18(23/24):1200-1211.
Schwarz et al. (1996) "RAG mutations in human B cell negative SCID," Science, 274(5284):97-99.
Sebzda et al. (1999) "Selection of the T Cell Repertoire," Annu. Rev. Immunol., 17:829-874.
Shani et al. (2009) "Incomplete T-cell receptor β peptides target the mitochondrion and induce apoptosis," Blood, 113:3530-3541.
Shankarkumar (2004) "The Human Leukocyte Antigen (HLA) System," Int. J. Hum. Genet., 4:91-103.
Sherman et al. (1992) "Selecting T Cell Receptors with High Affinity for Self-MHC by Decreasing the Contribution of CD8," Science, 258:815-818.

(56) References Cited

OTHER PUBLICATIONS

Shin et al. (2006) "Surface expression of MHC class II in dendritic cells is controlled by regulated ubiquitination," Nature, 444:115-118.
Shinkai et al. (1992) "RAG-2-deficient mice lack mature lymphocytes owing to inability to initiate V(D)J rearrangement," Cell 68(5):855-67.
Shinohara et al. (2007) "Active integration: new strategies for transgenesis," Transgenic Res., 16:333-339.
Shiroishi et al. (2003) "Human inhibitory receptors Ig-like transcript 2 (ILT2) and ILT4 compete with CD8 for MHC class I binding and bind preferentially to HLA-G," PNAS, 100:8856-8861.
Shirwan et al. (1995) "Structure and Repertoire Usage of Rat TCR α-Chain Genes in T Cells Infiltrating Heart Allografts[1]," J. Immunol., 154:1964-1972.
Shultz et al. (2007) "Humanized mice in translational biomedical research," Nature Rev., 7:118-130.
Sigmund (2000) "Viewpoint: Are Studies in Genetically Altered Mice Out of Control?," Arterioscler. Thromb. Vasc. Biol., p. 1425-1429.
Sim et al. (1984) "Primary structure of human T-cell receptor alpha-chain," Nature, 312:771-775.
Sims et al (2004) "Genetic Susceptibility to Ankylosing Spondylitis," Cur. Mol. Med., 4(1):13-20.
Singer et al. (2008) "Lineage fate and intense debate: myths, models and mechanisms of CD4/CD8 lineage choice," Nature Rev. Immunol., 8(10):788-801.
Siu et al. (1994) "A transcriptional silencer controls the developmental expression of the CD4 gene," EMBO J., 13(15):3570-3579.
Sleckman et al. (2000) "Mechanisms that direct ordered assembly of T cell receptor β locus V, D, and J gene segments," PNAS, 97(14):7975-7980.
Smiley et al. (1995) "Transgenic mice expressing MHC class II molecules with truncated A-beta cytoplasmic domains reveal signaling-independent defects in antigen presentation," Internal. Immunol., 7:665-677.
Smiley et al. (1996) "Truncation of the class II beta-chain cytoplasmic domain influences the level of class II/invariant chain-derived peptide complexes," PNAS, 93:241-244.
Sommermeyer et al. (2010) "Minimal Amino Acids Exchange in Human TCR Constant Regions Fosters Improved Function of TCR Gene-Modified T cells," J. Immunol., 184:6223-6231.
Street et al. (2002) "Limitations of HLA-transgenic mice in presentation of HLA-restricted cytotoxic T-cell epitopes from endogenously processed human papillomavirus type 16 E7 protein," Immunology, 106:526-536.
Takaki et al. (2006) "HLA-A*0201-Restricted T cells from Humanized NOD Mice Recognize Autoantigens of Potential Clinical Relevance to Type I Diabetes," J. Immunol., 176:3257-3265.
Tanabe et al. (1989) "Analysis of xenoantigenicity of HLA Class I molecules by a complete series of human-mouse hybrid genes," Transplantation, 48:1, 135-140.
Taneja and David (1998) "HLA Transgenic Mice as Humanized Mouse Models of Disease and Immunity," J. Clin. Invest., 101:921-926.
Taneja and David (2009) "Spontaneous autoimmune myocarditis and cardiomyopathy in HLA-DQ8.NODAbo transgenic mice," Journal of Autoimmunity 33:260-269.
Taylor et al. (1993) "Human immunoglobulin transgenes undergo rearrangement, somatic mutation and class switching in mice that lack endogenous IgM," Int. Immunol., 6(4):579-591.
Theobald et al. (1995) "Targeting p53 as a general tumor antigen," PNAS, 92:11993-11997.
Thomas et al. (2010) "Molecular immunology lessons from therapeutic T-cell receptor gene transfer," Immunol., 129:170-177.
Tishon et al. (2000) "Transgenic Mice Expressing Human HLA and CD8 Molecules Generate HLA-Restricted Measles Virus Cytotoxic T Lymphocytes of the Same Specificity as Humans with Natural Measles Infection," Virology, 275:286-293.
Tong et al. (2010) "Production of p53 gene knockout rats by homologous recombination in embryonic stem cells," Nature Letters, 467:211-215.
Toyonaga et al. (1985) "Organization and sequences of the diversity, joining, and constant region genes of the human T-cell receptor beta chain," PNAS. 82(24):8624-8628.
Uematsu et al. (1988) "In transgenic mice the introduced functional T cell receptor Beta Gene Prevents Expression of Endogenous Beta Genes," Cell, 52:831-841.
Ureta-Vidal et al. (1999) "Phenotypical and Functional Characterization of the CD8 + T Cell Repertoire of HLA- A2.1 Transgenic, H-2Kb°Db° Double Knockout Mice," J. Immunol., 163:2555-2560.
Valenzuela et al. (2003) "High-throughput engineering of the mouse genome coupled with high-resolution expression analysis", Nature Biotech., 21:652-659.
Van Meerwijk et al. (1990) "T-cell specific rearrangement of T-cell receptor Beta transgenes in mice," EMBO J., 9:1057-1062.
Vignali et al. (1992) "Species-specific Binding of CD4 to the Beta2 Domain of Major Histocompatibility Complex Class II Molecules," J. Exp. Med., 175:925-932.
Vignali et al. (1996) "The Two Membrane Proximal Domains of CD4 Interact with the T Cell Receptor," J. Exp. Med., 183:2097-2107.
Villa et al. (1998) "Partial V(D)J recombination activity leads to Omenn syndrome," Cell 93(5):855-896.
Villa et al. (1999) "Omenn syndrome: a disorder of Rag1 and Rag2 genes," J. Clin. Immunol., 19(2):87-97.
Viney et al. (1992) "Generation of Monoclonal Antibodies Against a Human T Cell Receptor β chain Expressed in Transgenic Mice," Hybridoma, 11(6):701-714.
Vitiello et al. (1991) "Analysis of the HLA-restricted Influenza-specific Cytotoxic T Lymphocyte Response in 6 Transgenic Mice Carrying a Chimeric Human-Mouse Class I Major Histocompatibility Complex," J. Exp. Med., 173:1007-1015.
Vollmer et al. (2000) "Antigen contacts by Ni-reactive TCR: typical αβ chain cooperation versus a chain-dominated specificity," IntL. Immunol.,12(12):1723-1731.
Vugmeyster et al. (1998) "Major histocompatibility complex (MHC) class I KbDb -/- deficient mice possess functional CD8 + T cells and natural killer cells," PNAS, 95:12492-12497.
Wagner et al. (1994) "Antibodies generated from human immunoglobulin miniloci in transgenic mice," Nucleic Acids Res., 22(8):1389-1393.
Wagner et al. (1994) "Ligation of MHC Class I and Class II Molecules Can Lead to Heterologous Desensitization of Signal Transduction Pathways That Regulate Homotypic Adhesion in Human Lymphocytes," J. Immunol., 152:5275-5287.
Wagner et al. (1994) "The diversity of antigen-specific monoclonal antibodies from transgenic mice bearing human immunogiobulin gene miniloci," Eur. J. Immunol., 24(11):2672-2681.
Wall (1996) "Transgenic Livestock: Progress and Prospects for the Future," Theriogenology, 45:57-68.
Wang and Reinherz (2001) "Structural basis of T cell recognition of peptides bound to MHC molecules," Mol. Immunol., 38:1039-1049.
Wei et al. (1996) "Repertoire and Organization of Human T-Cell Receptor α Region Variable Genes," Short Communication, Genomics, 38:442-445.
Wen et al. (1998) "Induction of Insulitis by Glutamic Acid Decarboxylase Peptide-specific and HLA-DQ8-restricted CD4+ T Cells from Human DQ Transgenic Mice," J. Clin. Invest., 102(5):947-957.
Willcox et al. (2003) "Crystal structure of HLA-A2 bound to LIR-1, a host and viral major histocompatibility complex receptor," Nature Immunol., 4:913-919.
Willemsen et al. (2003) "Genetic Engineering of T Cell Specificity for Immunotherapy of Cancer," Human Immunol., 64:56-68.
Williams and Barclay et al. (1988) "The Immunoglobulin Superfamily-Domains for Cell Surface Recognition," Ann. Rev. Immunol., 6:381-405.
Wong and Wen (2004) "What can the HLA transgenic mouse tell us about autoimmune diabetes?," Diabetologia, 47:1476-1487.
Woodle et al. (1997) "Anti-Human Class I MHC Antibodies Induce Apoptosis by a Pathway That Is Distinct from the Fas Antigen-Meidaled Pathway," J. Immunol., 158:2156-2164.

(56) References Cited

OTHER PUBLICATIONS

Woods et al. (1994) "Human Major Histocompatibility Complex Class 11-Restricted T Cell, Responses in Transgenic Mice," J. Exp. Med., 180:173-181.
Wooldridge et al. (2010) "MHC Class I Molecules with Superenhanced CD8 Binding Properties Bypass the Requirement for Cognate TCR Recognition and Nonspecifically Activate CTLs," J. Immunol., 184:3357-3366.
Wu et al. (1997) "Dimeric association and segmental variability in the structure of human CD4," Nature, 387:527.
Wucherpfennig et al. (2010) "Structural Biology of the T-Cell Receptor: Insights into Receptor Assembly, Ligand Recognition, and Initiation of Signaling," Cold Spring Harb. Perspect. Biol., 2:a005140, 14 pages.
Xue et al. (2005) "Exploiting T cell receptor genes for cancer immunotherapy," Clin. Exp. Immunol., 139:167-172.
Yamamoto et al. (1994) "Functional Interaction between Human Histocompatibility Leukocyte Antigen (HLA) Class 27 II and Mouse CD4 Molecule in Antigen Recognition by T cells in HLA-DR and DQ Transgenic Mice," J. Exp. Med., 180:165-171.
Yancopoulos et al. (1986) "Introduced T cell receptor variable region gene segments recombine in pre-B cells: evidence that B and T cells use a common recombinase," Cell, 44:251-259.
Yashiro-Ohtani et al. (2010) "Notch regulation of early thymocyte development," Seminars in Immunol., 22:261-269.
Yoshikai et al. (1985) "Organization and sequences of the variable, joining and constant region genes of the human T-cell receptor alpha-chain," Nature, 316(6031):837-840.
Zamoyska (1998) "CD4 and CD8: modulators of T cell receptor recognition of antigen and of immune responses?," Curr. Opin. Immunol., 10:82-87.
Zhou et al., (2009) "Developing tTA transgenic rats for inducible and reversible gene expression," International Journal of Biological Sciences, 5:171-181.
Zijlstra et al. (1990) "B2-Microglobulin deficient mice lack CD4-8+ cytolytic T Cells," Nature, 344:742-746.
Zumla et al. (1992) "Co-expression of human T cell receptor chains with mouse CD3 on the cell surface of a mouse T cell hybridoma," J. Immunol. Methods., 149(l):69-76.
Zumla et al. (1992) "Use of a murine T-cell hybridoma expressing human T-cell receptor alpha-and betagene products as a tool for the production of human T-cell receptor-specific monoclonal antibodies," Human Immunol., 35(3):141-148.
International Search Report and Written Opinion for PCT/US2014/023076, dated Jul. 18, 2014.
International Search Report and Written Opinion for PCT/US2012/062042, dated Feb. 18, 2013
International Search Report and Written Opinion for PCT/US2012/062065, dated May 8, 2014.
International Search Report and Written Opinion for PCT/US2012/062029, dated Feb. 28, 2013.
International Search Report and Written Opinion for PCT/US2014/023068, dated Jul. 24, 2014.
International Search Report and Written Opinion for PCT/US2014/017395, dated Jun. 2, 2014.
International Search Report and Written Opinion for PCT/US2014/017387, dated Jun. 2, 2014.
International Search Report and Written Opinion for PCT/US2016/026260, dated Aug. 11, 2016.
Extended European Search Report with respect to Europe Application No. 17184955.7, dated Nov. 24, 2017.
Non-Final Office Action with Respect to U.S. Appl. No. 14/185,316, dated Dec. 17, 2015.
Non-Final Office Action with Respect to U.S. Appl. No. 14/185,301 dated Jun. 16, 2016.
Final Office Action with Respect to U.S. Appl. No. 14/185,301 dated Jan. 8, 2016.
English Translation of Office Action with Respect to Japan Application No. 2014-539027 dated Sep. 6, 2016.
Statement of Relatedness under MPEP 2001.06 with Respect to U.S. Appl. No. 15/564,723 dated Jun. 22, 2018.
Beta-2 microglobulin https://en.wikipedia.org/w/index.php?title=Beta-2_microglobulin&oldid=452509865.
Harari et al., "Bridging the Species Divide: Transgenic Mice Humanized for Type-I Interferon Response," PLOS One, Jan. 2014, 9(1):e84259, 12 pages.
Kawamura et al. (2008) "Different Development of Myelin Basic Protein Agonist-and-Antagonist-Specific Human TCR Transgenic T Cells in the Thymus and Periphery," J. Immunol., 181(8):5462-5472.
Li et al. (2016) "The Implication and Significance of Beta 2 Microglobulin: A Conservative Multifunctional Regulator," Chinese Medical Journal, 129(4):448-455.
Massimo et al. (2008) "Primer: Immunity and Autoimmunity," Diabetes, 57(11):2872-2882.
Murphy, K., Travers, P., Walport, M., & Janeway, C. (2008) Janeway's Immunobiology. New York: Garland Science, 2008, at pp. 156-157.
Shankar Pradhan and Majumdar, (2016) "An Efficient Method for Generation of Transgenic Rats Avoiding Embryo Manipulation," Molecular Therapy—Nucleic Acids, 5, e293:1-11 doi:10.1038/mtna.2016.9.
Shields et al. (1998) "Functional comparison of bovine, murine, and human $\beta_2$-microglobulin: interactions with murine MHC I molecules," Molecular Immunology, 35:919-928.
Extended European Search Report with respect to Europe Application No. 18176096.8, dated Oct. 1, 2018.
Statement of Relatedness under MPEP 2001.06 with Respect to U.S. Appl. No. 15/564,723 dated Jun. 5, 2019.
Boyd and Wood (2009) "Variation in MHC expression between undifferentiated mouse ES cells and ES cell derived insulin-producing cell clusters," Transplantation, 87(9):13001304.
Cheuk et al. "Human MHC Class I Transgenic Mice Deficient for H2 Class I Expression Facilitate Identification and Characterization of New HLA Class I-Restricted Viral T Cell Epitopes," Journal of Immunology, 2002, 169:5571-5580.
Epstein et al. "Expression and function of HLA-A2.1 in transgenic mice," Eur. J. Immunol., 1989, 19:1575-1583.
Lavial and Pain (2010) "Chicken embryonic stem cells as a non-mammalian embryonic stem cell model," Develop. Growth Differ., 52:101-114.
Magliocca et al. (2006) "Undifferentiated Murine Embryonic Stem Cells Cannot Induce Portal Tolerance but May Possess Immune Privilege Secondary to Reduced Major Histocompatibility Complex Antigen Expression," Stem Cells and Development, 15(5):707-717.
Miao (2012) "Recent Advances and Applications of Transgenic Animal Technology," Polymerase Chain Reaction, Dr. Patricia Hernandez-Rodriguez (Ed.), ISBN: 978-953-51-0612-8, InTech, pp. 255-282, Available from: http://www.intechopen.com/books/polymerase-chain-reaction/recent-advances-and-applications-of-transgenic-animal-technology.
Newberg et al. "Importance of MHC class I alpha2 and alpha3 domains in the recognition of self and non-self MHC molecules," Journal of Immunology, 1996, 156:2473-2480.
Parnes, et al. (1982) "Structure of Wild-Type and Mutant Mouse β2-Microglobulin Genes," Cell, 29:661-669.
Petitte et al. (2004) "Avian pluripotent stem cells," Mechanisms of Development, 121:1159-1168.
Vignali and Vignali (1999) "Profound Enhancement of T Cell Activation Mediated by the Interaction Between the TCR and the D3 Domain of CD41," J. Immunol., 162:1431-1439.
Statement of Relatedness under MPEP 2001.06 with Respect to U.S. Appl. No. 15/564,723 dated Oct. 8, 2019.
Cameron, E. (1997) "Recent Advances in Transgenic Technology," Molecular Biotechnology, 7:253-265.
Giraldo and Montoliu (2001) "Size matters: use of YACs, BACs and PACs in transgenic animals," Transgenic Research, 10:83-103.
Houdebine, (1994) "Production of pharmaceutical proteins from transgenic animals," J. Biotechnology, 34:269-287.
Kappel et al. (1992) "Regulating gene expression in transgenic animals," Current Opinion in Biotechnology, 3:548-553.

(56) References Cited

OTHER PUBLICATIONS

Scardino et al. (2003) "In vivo study of the GC90/IRIV vaccine for immune response and autoimmunity into a novel humanised transgenic mouse," British Journal of Cancer, 89:199-205.
Tran et al. (2006) "Additional human β2-microglobulin curbs HLA-B27 misfolding and promotes arthritis and spondylitis without colitis in male HLA-B27-transgenic rats," Arthritis & Rheumatism, 54:1317-1327.
Statement of Relatedness under MPEP 2001.06 with Respect to U.S. Appl. No. 15/564,723 dated Apr. 3, 2020.
Statement of Relatedness under MPEP 2001.06 with Respect to U.S. Appl. No. 15/564,723 dated Nov. 6, 2020.
Declaration from Dr. Andrew Murphy regarding Mar. 1, 2007 meeting (81 pages), which includes the following Exhibits: Exhibit A: Agenda for meeting between "Regeneron and a Whole Bunch of Interested Academics" re "The Humanized TCR Mouse Project"; "Investigators (in alphabetical order)"; and "List of Relevant Papers" (4 pages) Exhibit B: "'Veloci-T': Humanization of mouse TCR and MHC" (19 slides) Exhibit C: "VelociGene and VelociMouse Background" (13 slides) Exhibit D: "VelocImmune Introduction" (16 slides) Exhibit E: "VelocImmune Phenotyping" (19 slides).
Cao et al., (2009) "Isolation and Culture of Primary Bovine Embryonic Stem Cell Colonies by a Novel Method," Journal of Experimental Zoology, 311A:368-376.
Glick and Pasternak Dzh. Moleculyarnaya biotehnologiya. Printsipy i primeneniye. Moscow: Mir, 2002 (with English translation).
Houdebine (2009) Methods to Generate Transgenic Animals, Genetic Engineering in Livestock, New Applications and Interdisciplinary Perspectives, Engelhard M, et al., 2009, XVI, 1 46 p. 8 illus., pp. 31-47, see p. 36.
Statement of Relatedness under MPEP 2001.06 with Respect to U.S. Appl. No. 15/564,723 dated Jul. 9, 2021.

\* cited by examiner

FIG. 1
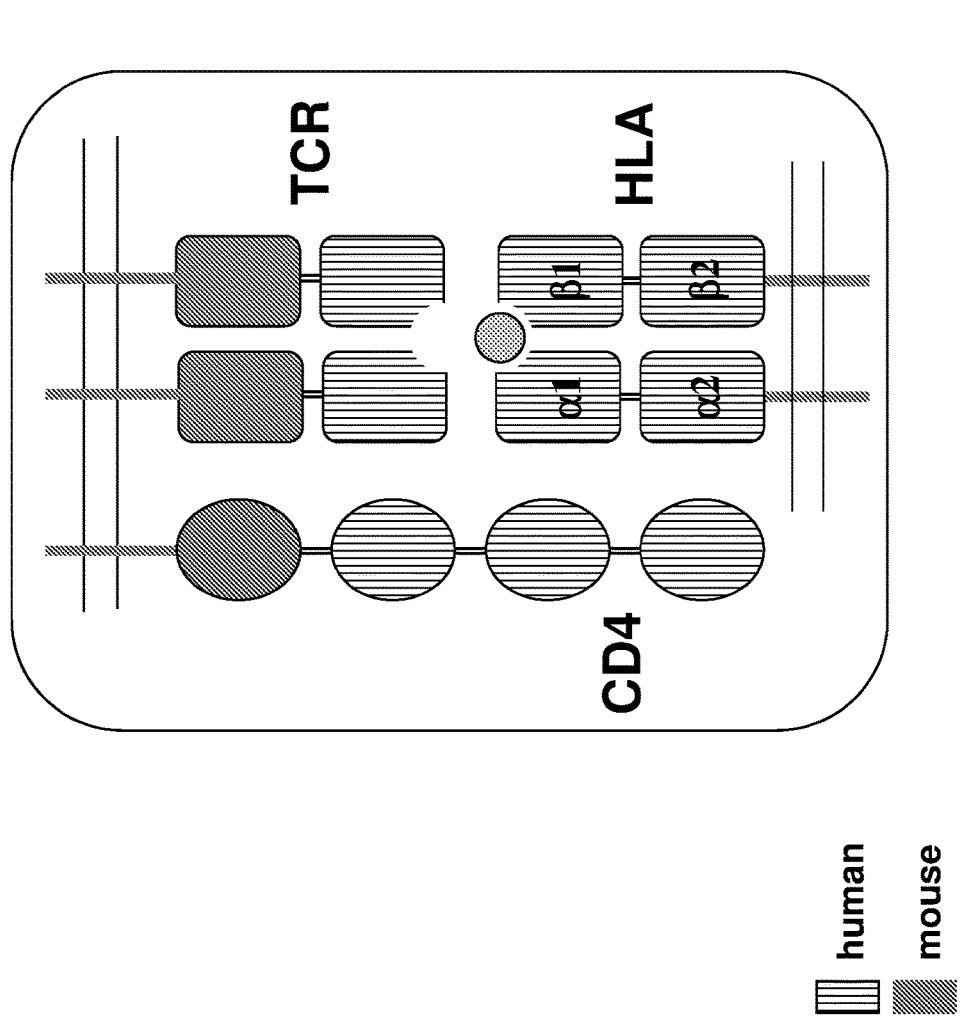
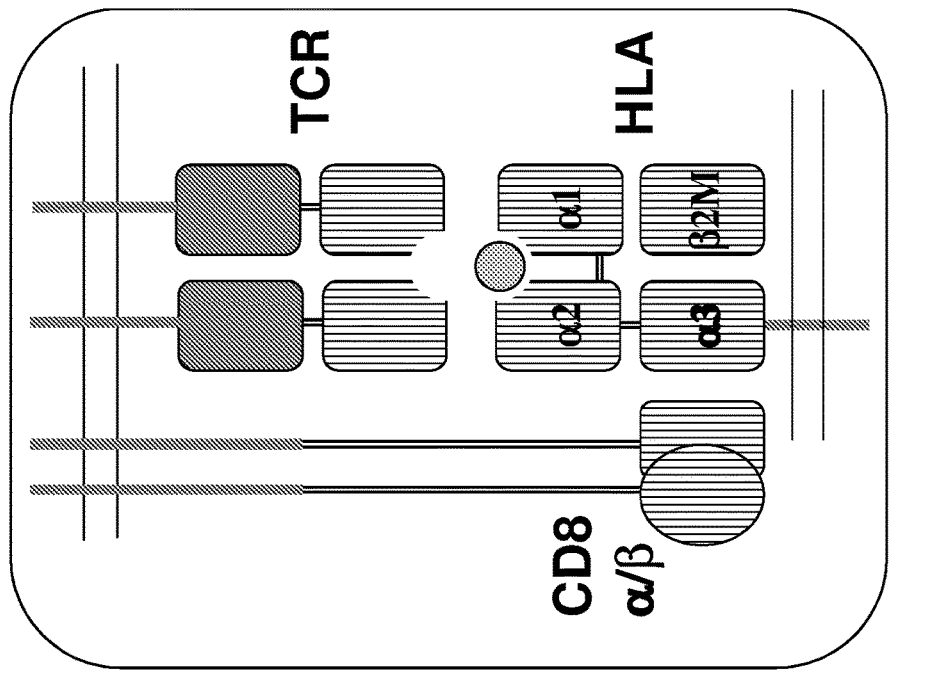

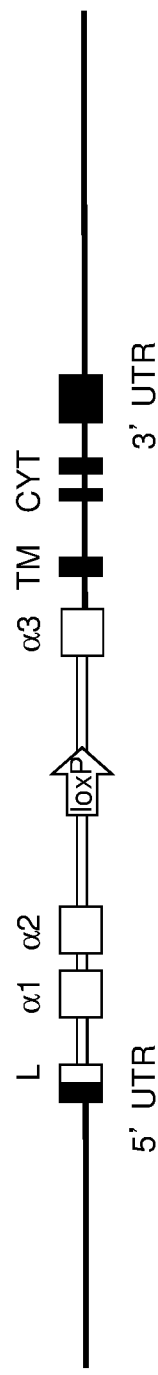
FIG. 2A Chimeric HLA-A2/H-2K locus
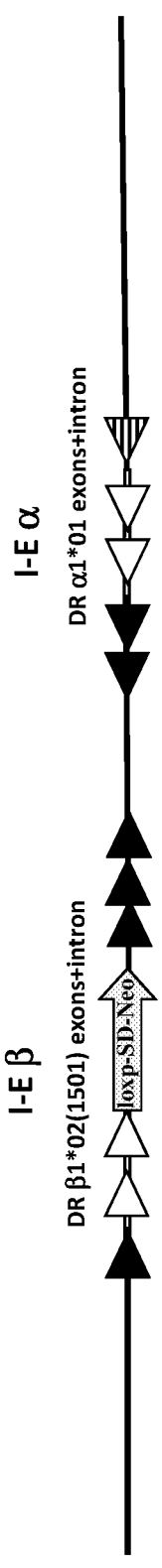
FIG. 2B Chimeric HLA-DR2/H-2E Locus
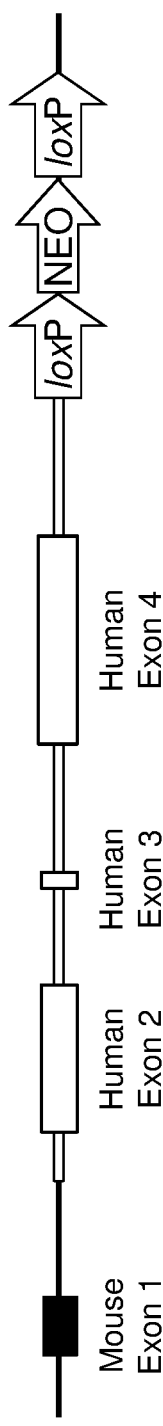
FIG. 2C Humanized β2m Locus Chimeric CD4 gene

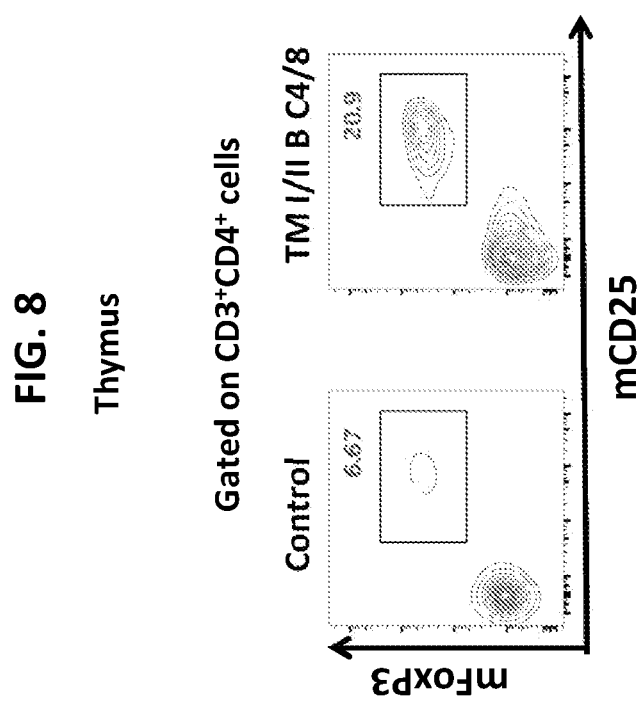
FIG. 8 Thymus

Spleen

Spleen

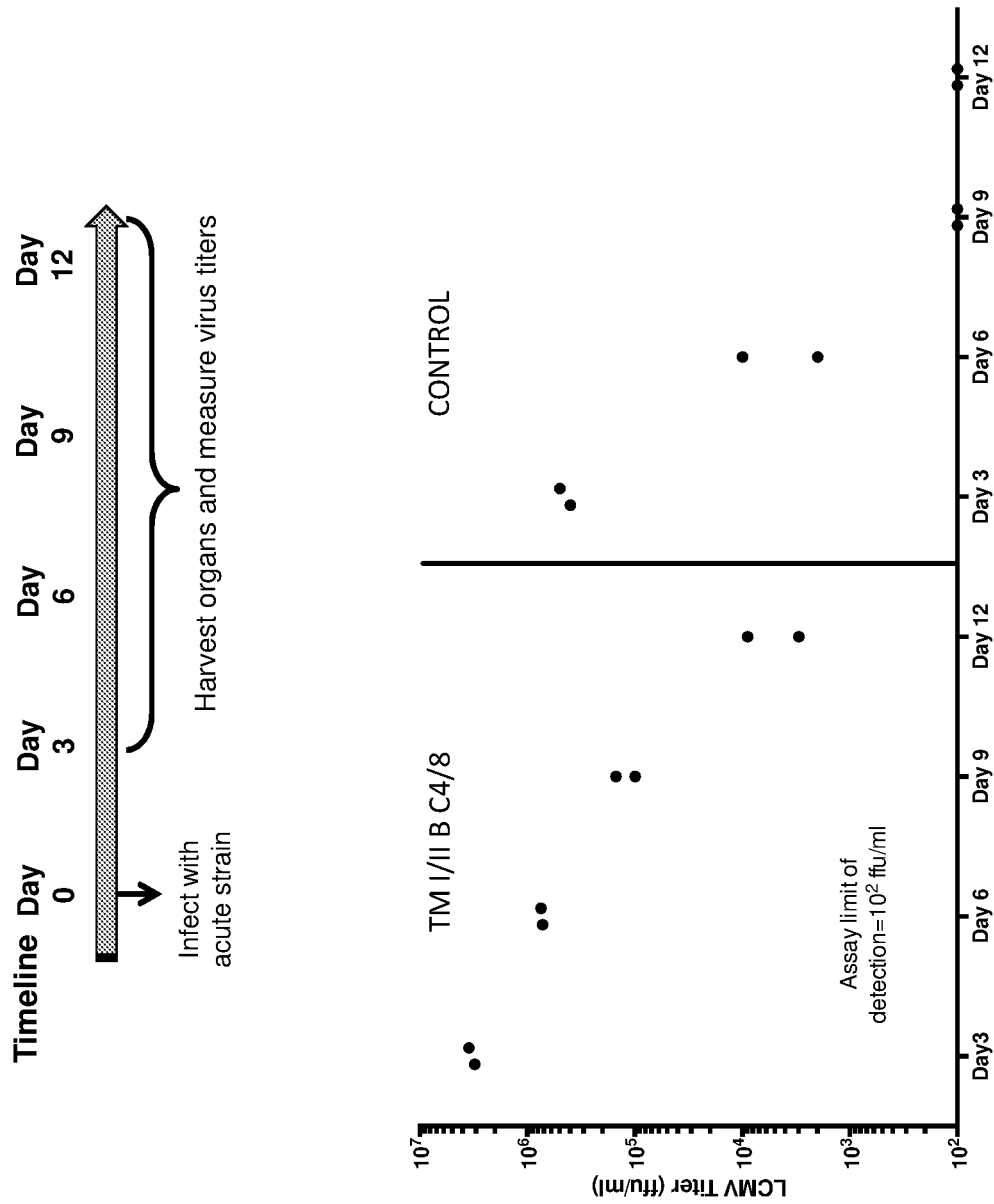

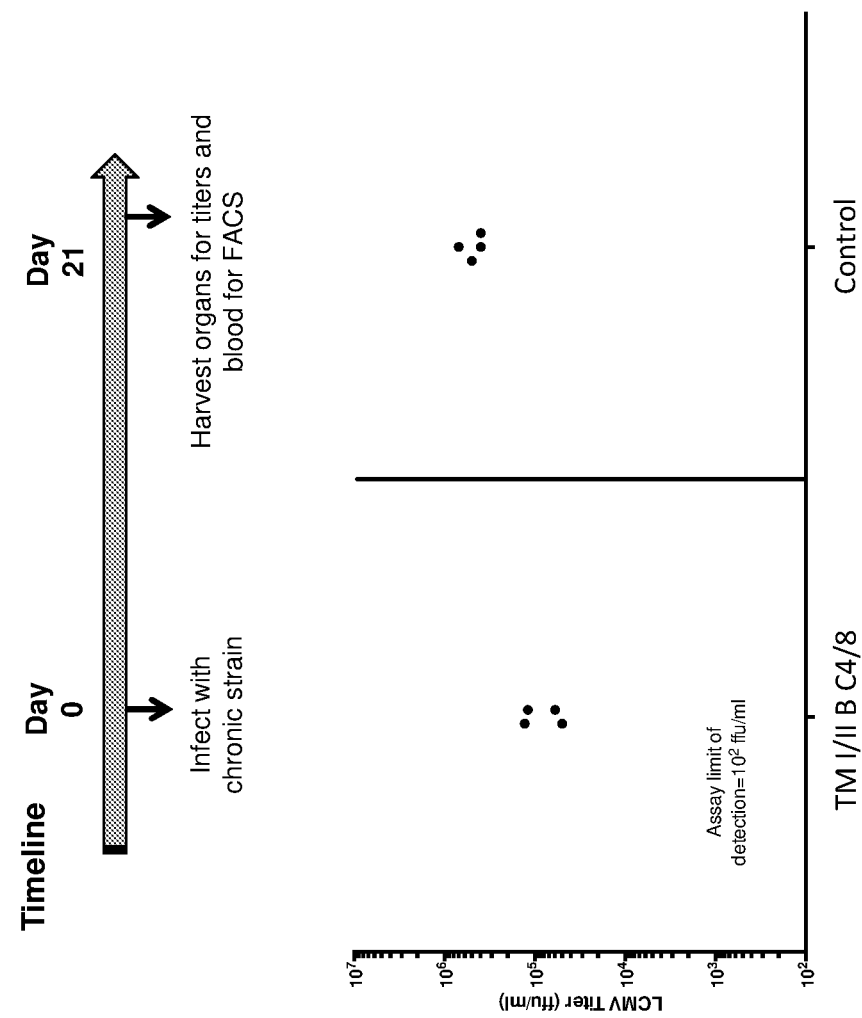

FIG. 14

Timeline

Day 0 → Infect with acute strain

Day 17 → Super-infect with chronic strain

Day 31 → Harvest organs and measure virus titers

Control

TM I/II B C4/8

Assay limit of detection = $10^2$ ffu/ml

LCMV Titer (ffu/ml)

Mock (n = 2) | Armstrong (n = 4) | Mock (n = 2) | Armstrong (n = 5)

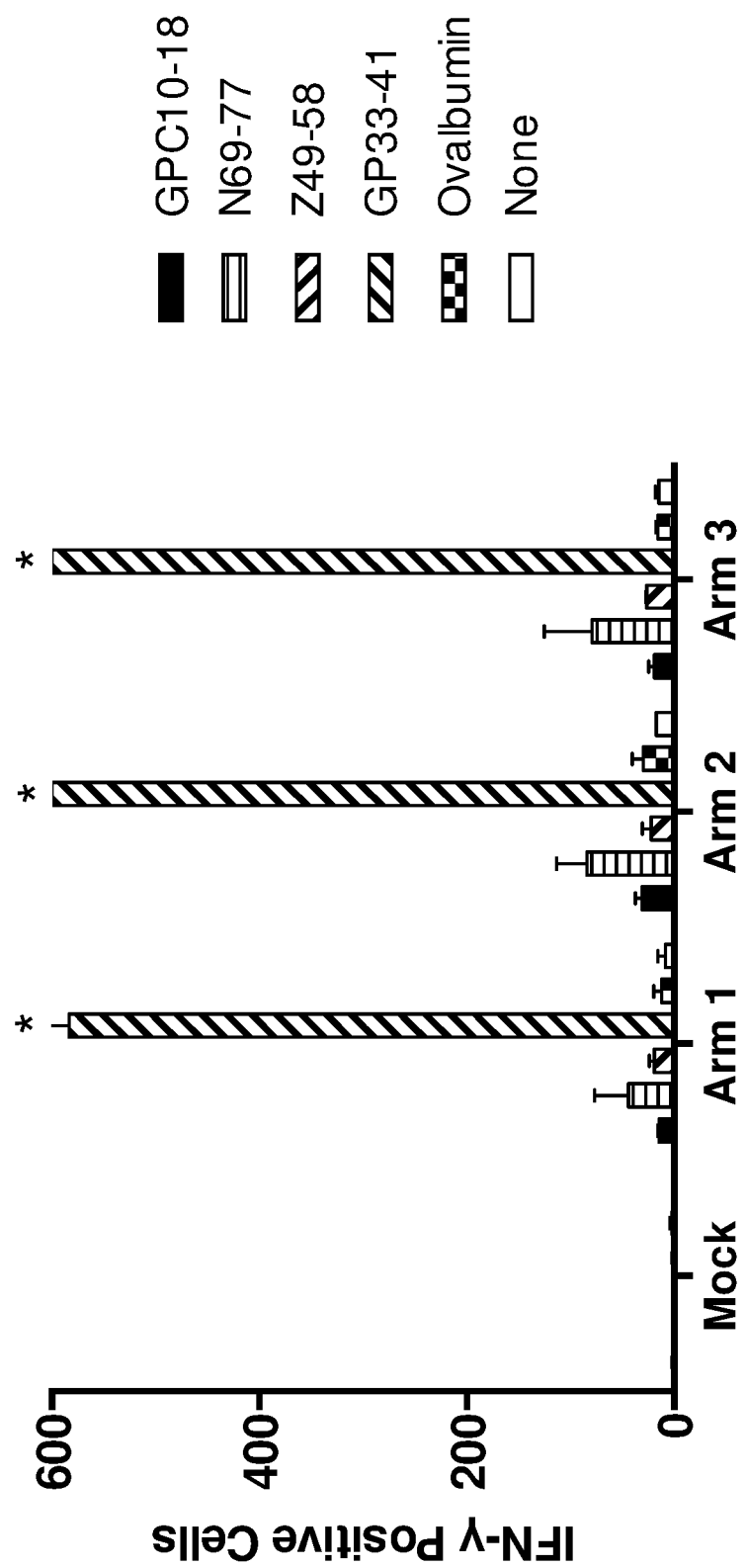

SEQUENCE LISTING

<160> NUMBER OF SEQ ID NOS: 91

<210> SEQ ID NO 1
<211> LENGTH: 19
<212> TYPE: DNA
<213> ORGANISM: Artificial Sequence
<220> FEATURE:
<223> OTHER INFORMATION: synthetic

<400> SEQUENCE: 1
cagaacgcca ggctgtaac                                           19

<210> SEQ ID NO 2
<211> LENGTH: 20
<212> TYPE: DNA
<213> ORGANISM: Artificial Sequence
<220> FEATURE:
<223> OTHER INFORMATION: synthetic

```
<400> SEQUENCE: 2
ggagagcagg gtcagtcaac                                               20

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
caccgccact cacagctcct taca                                          24

<210> SEQ ID NO 4
<211> LENGTH: 22
<212> TYPE: DNA
<213> ORGANISM: Artificial Sequence
<220> FEATURE:
<223> OTHER INFORMATION: synthetic

<400> SEQUENCE: 4
gtgggcacca tcttcatcat tc                                            22

<210> SEQ ID NO 5
<211> LENGTH: 22
<212> TYPE: DNA
<213> ORGANISM: Artificial Sequence
<220> FEATURE:
<223> OTHER INFORMATION: synthetic

<400> SEQUENCE: 5
cttcctttcc agggtgtgac tc                                            22

<210> SEQ ID NO 6
<211> LENGTH: 23
<212> TYPE: DNA
<213> ORGANISM: Artificial Sequence
<220> FEATURE:
<223> OTHER INFORMATION: synthetic

<400> SEQUENCE: 6
aggcctgcga tcaggtggca cct                                           23

<210> SEQ ID NO 7
<211> LENGTH: 19
<212> TYPE: DNA
<213> ORGANISM: Artificial Sequence
<220> FEATURE:
<223> OTHER INFORMATION: synthetic

<400> SEQUENCE: 7
ggtggagagg ctattcggc                                                19

<210> SEQ ID NO 8
<211> LENGTH: 17
<212> TYPE: DNA
<213> ORGANISM: Artificial Sequence
<220> FEATURE:
<223> OTHER INFORMATION: synthetic

<400> SEQUENCE: 8
gaacacggcg gcatcag                                                  17

<210> SEQ ID NO 9
<211> LENGTH: 23
```

```
<212> TYPE: DNA
<213> ORGANISM: Artificial Sequence
<220> FEATURE:
<223> OTHER INFORMATION: synthetic

<400> SEQUENCE: 9
tgggcacaac agacaatcgg ctg                                             23

<210> SEQ ID NO 10
<211> LENGTH: 140
<212> TYPE: DNA
<213> ORGANISM: Artificial Sequence
<220> FEATURE:
<223> OTHER INFORMATION: synthetic

<400> SEQUENCE: 10
tttgtaaaca aagtctaccc agagacagat gacagacttc agctccaatg ctgattggtt     60
cctcacttgg gaccaaccct accggtataa cttcgtataa ggtatcctat acgaagttat    120
atgcatggcc tccgcgccgg                                                140

<210> SEQ ID NO 11
<211> LENGTH: 140
<212> TYPE: DNA
<213> ORGANISM: Artificial Sequence
<220> FEATURE:
<223> OTHER INFORMATION: synthetic

<400> SEQUENCE: 11
cgacctgcag ccggcgcgcc ataacttcgt ataaggtatc ctatacgaag ttatctcgag     60
cacaggcatt tgggtgggca gggatggacg gtgactggga caatcgggat ggaagagcat    120
agaatgggag ttagggaaga                                                140

<210> SEQ ID NO 12
<211> LENGTH: 17
<212> TYPE: DNA
<213> ORGANISM: Artificial Sequence
<220> FEATURE:
<223> OTHER INFORMATION: synthetic

<400> SEQUENCE: 12
cgaggagccc cggtaca                                                    17

<210> SEQ ID NO 13
<211> LENGTH: 20
<212> TYPE: DNA
<213> ORGANISM: Artificial Sequence
<220> FEATURE:
<223> OTHER INFORMATION: synthetic

<400> SEQUENCE: 13
aagcgcacga actccttgtt                                                 20

<210> SEQ ID NO 14
<211> LENGTH: 17
<212> TYPE: DNA
<213> ORGANISM: Artificial Sequence
<220> FEATURE:
<223> OTHER INFORMATION: synthetic

<400> SEQUENCE: 14
ctctgtcggc tatgtgg                                                    17

<210> SEQ ID NO 15
```

```
<211> LENGTH: 22
<212> TYPE: DNA
<213> ORGANISM: Artificial Sequence
<220> FEATURE:
<223> OTHER INFORMATION: synthetic

<400> SEQUENCE: 15
ggactcccag aatctcctga ga                                                  22

<210> SEQ ID NO 16
<211> LENGTH: 25
<212> TYPE: DNA
<213> ORGANISM: Artificial Sequence
<220> FEATURE:
<223> OTHER INFORMATION: synthetic

<400> SEQUENCE: 16
gagtcatgaa ccatcactgt gaaga                                               25

<210> SEQ ID NO 17
<211> LENGTH: 16
<212> TYPE: DNA
<213> ORGANISM: Artificial Sequence
<220> FEATURE:
<223> OTHER INFORMATION: synthetic

<400> SEQUENCE: 17
tggtgggttg ctggaa                                                         16

<210> SEQ ID NO 18
<211> LENGTH: 90
<212> TYPE: DNA
<213> ORGANISM: Artificial Sequence
<220> FEATURE:
<223> OTHER INFORMATION: synthetic

<400> SEQUENCE: 18
ctgtttcttc cctaactccc attctatgct cttccatccc gaccgcggcc caatctctct         60
ccactacttc ctgcctacat gtatgtaggt                                          90

<210> SEQ ID NO 19
<211> LENGTH: 80
<212> TYPE: DNA
<213> ORGANISM: Artificial Sequence
<220> FEATURE:
<223> OTHER INFORMATION: synthetic

<400> SEQUENCE: 19
caaggtttcc tcctatgatg cttgtgtgaa actcggggcc ggccagcatt taacagtaca         60
gggatgggag cacagctcac                                                     80

<210> SEQ ID NO 20
<211> LENGTH: 80
<212> TYPE: DNA
<213> ORGANISM: Artificial Sequence
<220> FEATURE:
<223> OTHER INFORMATION: synthetic

<400> SEQUENCE: 20
gaaagcagtc ttcccagcct tcacactcag aggtacaaat ccccattttc atattagcga         60
ttttaattta ttctagcctc                                                     80

<210> SEQ ID NO 21
<211> LENGTH: 80
```

```
<212> TYPE: DNA
<213> ORGANISM: Artificial Sequence
<220> FEATURE:
<223> OTHER INFORMATION: synthetic

<400> SEQUENCE: 21
tcttccctaa ctcccattct atgctcttcc atcccgaccg cggcccaatc tctctccact    60
acttcctgcc tacatgtatg                                                80

<210> SEQ ID NO 22
<211> LENGTH: 100
<212> TYPE: DNA
<213> ORGANISM: Artificial Sequence
<220> FEATURE:
<223> OTHER INFORMATION: synthetic

<400> SEQUENCE: 22
gagttcctcc atcacttcac tgggtagcac agctgtaact gtccagcctg tcctgggctg    60
caggtggtgg gcgttgcggg tggggccggt taaggttcca                         100

<210> SEQ ID NO 23
<211> LENGTH: 100
<212> TYPE: DNA
<213> ORGANISM: Artificial Sequence
<220> FEATURE:
<223> OTHER INFORMATION: synthetic

<400> SEQUENCE: 23
tcccacatcc tattttaatt tgctccatgt tctcatctcc atcagcacag ctcgagataa    60
cttcgtataa tgtatgctat acgaagttat atgcatggcc                         100

<210> SEQ ID NO 24
<211> LENGTH: 100
<212> TYPE: DNA
<213> ORGANISM: Artificial Sequence
<220> FEATURE:
<223> OTHER INFORMATION: synthetic

<400> SEQUENCE: 24
atacgaagtt atgctagtaa ctataacggt cctaaggtag cgagtggctt acaggtaggt    60
gcgtgaagct tctacaagca cagttgcccc ctgggaagca                         100

<210> SEQ ID NO 25
<211> LENGTH: 17
<212> TYPE: DNA
<213> ORGANISM: Artificial Sequence
<220> FEATURE:
<223> OTHER INFORMATION: synthetic

<400> SEQUENCE: 25
tgcggccgat cttagcc                                                   17

<210> SEQ ID NO 26
<211> LENGTH: 18
<212> TYPE: DNA
<213> ORGANISM: Artificial Sequence
<220> FEATURE:
<223> OTHER INFORMATION: synthetic

<400> SEQUENCE: 26
ttgaccgatt ccttgcgg                                                  18

<210> SEQ ID NO 27
```

```
<211> LENGTH: 21
<212> TYPE: DNA
<213> ORGANISM: Artificial Sequence
<220> FEATURE:
<223> OTHER INFORMATION: synthetic

<400> SEQUENCE: 27
acgagcgggt tcggcccatt c                                                   21

<210> SEQ ID NO 28
<211> LENGTH: 18
<212> TYPE: DNA
<213> ORGANISM: Artificial Sequence
<220> FEATURE:
<223> OTHER INFORMATION: synthetic

<400> SEQUENCE: 28
ccccacagca cgtttcct                                                       18

<210> SEQ ID NO 29
<211> LENGTH: 23
<212> TYPE: DNA
<213> ORGANISM: Artificial Sequence
<220> FEATURE:
<223> OTHER INFORMATION: synthetic

<400> SEQUENCE: 29
cgtcccattg aagaaatgac act                                                 23

<210> SEQ ID NO 30
<211> LENGTH: 15
<212> TYPE: DNA
<213> ORGANISM: Artificial Sequence
<220> FEATURE:
<223> OTHER INFORMATION: synthetic

<400> SEQUENCE: 30
tggcagccta agagg                                                          15

<210> SEQ ID NO 31
<211> LENGTH: 18
<212> TYPE: DNA
<213> ORGANISM: Artificial Sequence
<220> FEATURE:
<223> OTHER INFORMATION: synthetic

<400> SEQUENCE: 31
ccccacagca cgtttcct                                                       18

<210> SEQ ID NO 32
<211> LENGTH: 17
<212> TYPE: DNA
<213> ORGANISM: Artificial Sequence
<220> FEATURE:
<223> OTHER INFORMATION: synthetic

<400> SEQUENCE: 32
acccgctccg tcccatt                                                        17

<210> SEQ ID NO 33
<211> LENGTH: 18
<212> TYPE: DNA
<213> ORGANISM: Artificial Sequence
<220> FEATURE:
<223> OTHER INFORMATION: synthetic

<400> SEQUENCE: 33
```

-continued agcctaagag ggagtgtc                                                        18

<210> SEQ ID NO 34
<211> LENGTH: 20
<212> TYPE: DNA
<213> ORGANISM: Artificial Sequence
<220> FEATURE:
<223> OTHER INFORMATION: synthetic

<400> SEQUENCE: 34
agaccctggt gatgctggaa                                                      20

<210> SEQ ID NO 35
<211> LENGTH: 18
<212> TYPE: DNA
<213> ORGANISM: Artificial Sequence
<220> FEATURE:
<223> OTHER INFORMATION: synthetic

<400> SEQUENCE: 35
cgcttgggtg ctccactt                                                        18

<210> SEQ ID NO 36
<211> LENGTH: 18
<212> TYPE: DNA
<213> ORGANISM: Artificial Sequence
<220> FEATURE:
<223> OTHER INFORMATION: synthetic

<400> SEQUENCE: 36
tcgaagtgga gaggttta                                                        18

<210> SEQ ID NO 37
<211> LENGTH: 21
<212> TYPE: DNA
<213> ORGANISM: Artificial Sequence
<220> FEATURE:
<223> OTHER INFORMATION: synthetic

<400> SEQUENCE: 37
tggaatggag tgagcagctt t                                                    21

<210> SEQ ID NO 38
<211> LENGTH: 20
<212> TYPE: DNA
<213> ORGANISM: Artificial Sequence
<220> FEATURE:
<223> OTHER INFORMATION: synthetic

<400> SEQUENCE: 38
gcacggtccc cttcttagtg                                                      20

<210> SEQ ID NO 39
<211> LENGTH: 18
<212> TYPE: DNA
<213> ORGANISM: Artificial Sequence
<220> FEATURE:
<223> OTHER INFORMATION: synthetic

<400> SEQUENCE: 39
tgacttccta aatttctc                                                        18

<210> SEQ ID NO 40
<211> LENGTH: 21
<212> TYPE: DNA

```
<213> ORGANISM: Artificial Sequence
<220> FEATURE:
<223> OTHER INFORMATION: synthetic

<400> SEQUENCE: 40
ctggcggctt gaagaatttg g                                              21

<210> SEQ ID NO 41
<211> LENGTH: 24
<212> TYPE: DNA
<213> ORGANISM: Artificial Sequence
<220> FEATURE:
<223> OTHER INFORMATION: synthetic

<400> SEQUENCE: 41
catgatttcc aggttggctt tgtc                                           24

<210> SEQ ID NO 42
<211> LENGTH: 26
<212> TYPE: DNA
<213> ORGANISM: Artificial Sequence
<220> FEATURE:
<223> OTHER INFORMATION: synthetic

<400> SEQUENCE: 42
cgatttgcca gctttgaggc tcaagg                                         26

<210> SEQ ID NO 43
<211> LENGTH: 21
<212> TYPE: DNA
<213> ORGANISM: Artificial Sequence
<220> FEATURE:
<223> OTHER INFORMATION: synthetic

<400> SEQUENCE: 43
cctcacttgg gaccaaccct a                                              21

<210> SEQ ID NO 44
<211> LENGTH: 20
<212> TYPE: DNA
<213> ORGANISM: Artificial Sequence
<220> FEATURE:
<223> OTHER INFORMATION: synthetic

<400> SEQUENCE: 44
ttgtcccagt caccgtccat                                                20

<210> SEQ ID NO 45
<211> LENGTH: 24
<212> TYPE: DNA
<213> ORGANISM: Artificial Sequence
<220> FEATURE:
<223> OTHER INFORMATION: synthetic

<400> SEQUENCE: 45
tgcatctcga gcacaggcat ttgg                                           24

<210> SEQ ID NO 46
<211> LENGTH: 100
<212> TYPE: DNA
<213> ORGANISM: Artificial Sequence
<220> FEATURE:
<223> OTHER INFORMATION: synthetic

<400> SEQUENCE: 46
atggagtagt cagaacacac tcttcagaag ggactcctga tttcaaaggg ggtaccgggc    60
```
cccccctcga ggtcgacata acttcgtata gcatacatta                         100

<210> SEQ ID NO 47
<211> LENGTH: 108
<212> TYPE: DNA
<213> ORGANISM: Artificial Sequence
<220> FEATURE:
<223> OTHER INFORMATION: synthetic

<400> SEQUENCE: 47
ggccatgcat ataacttcgt atagcataca ttatacgaag ttataccggt gcgatcgcgc    60
gcttccctct tctaaccact aattcaaaaa ggattgtaag taatgttt                108

<210> SEQ ID NO 48
<211> LENGTH: 145
<212> TYPE: DNA
<213> ORGANISM: Artificial Sequence
<220> FEATURE:
<223> OTHER INFORMATION: synthetic

<400> SEQUENCE: 48
agacagaccc ctaaacacct ccaaattaaa agcggcaaag agataaggtt ggagctccac    60
cgcggtggcg gccgccaccg cggtggagct cgaggtttcc ggtacttaac aacagagcac   120
agatttagtg gtgagggact ctctc                                         145

<210> SEQ ID NO 49
<211> LENGTH: 100
<212> TYPE: DNA
<213> ORGANISM: Artificial Sequence
<220> FEATURE:
<223> OTHER INFORMATION: synthetic

<400> SEQUENCE: 49
atggagtagt cagaacacac tcttcagaag ggactcctga tttcaaaggg ggtaccgggc    60
cccccctcga ggtcgacata acttcgtata gcatacatta                         100

<210> SEQ ID NO 50
<211> LENGTH: 109
<212> TYPE: DNA
<213> ORGANISM: Artificial Sequence
<220> FEATURE:
<223> OTHER INFORMATION: synthetic

<400> SEQUENCE: 50
ggccatgcat ataacttcgt atagcataca ttatacgaag ttataccggt gcgatcgctc    60
aagcatgcaa gggtaacata tgttatgaga ttatattttc tttatctca               109

<210> SEQ ID NO 51
<211> LENGTH: 100
<212> TYPE: DNA
<213> ORGANISM: Artificial Sequence
<220> FEATURE:
<223> OTHER INFORMATION: synthetic

<400> SEQUENCE: 51
atggagtagt cagaacacac tcttcagaag ggactcctga tttcaaaggg gggtaccggg    60 cccccccctcg agaagttcct attccgaagt tcctattctc                        100

<210> SEQ ID NO 52
<211> LENGTH: 108
<212> TYPE: DNA

<210> SEQ ID NO 52
<211> LENGTH: 108
<212> TYPE: DNA
<213> ORGANISM: Artificial Sequence
<220> FEATURE:
<223> OTHER INFORMATION: synthetic

<400> SEQUENCE: 52

```
gttcctattc cgaagttcct attctctaga aagtatagga acttcctagg gcgatcgctc      60
ctctccaggc tcgaattagt attacagttg aggcacgttg tcctcccg                  108
```

<210> SEQ ID NO 53
<211> LENGTH: 100
<212> TYPE: DNA
<213> ORGANISM: Artificial Sequence
<220> FEATURE:
<223> OTHER INFORMATION: synthetic

<400> SEQUENCE: 53

```
atggagtagt cagaacacac tcttcagaag ggactcctga tttcaaaggg ggtaccgggc      60 ccccccctcga ggtcgacata acttcgtata gcatacatta                         100
```

<210> SEQ ID NO 54
<211> LENGTH: 108
<212> TYPE: DNA
<213> ORGANISM: Artificial Sequence
<220> FEATURE:
<223> OTHER INFORMATION: synthetic

<400> SEQUENCE: 54

```
ggccatgcat ataacttcgt atagcataca ttatacgaag ttataccggt gcgatcgccg      60
cctccatttc cttcatagga aacatgaagt gaatggggct gtgtgtgt                 108
```

<210> SEQ ID NO 55
<211> LENGTH: 100
<212> TYPE: DNA
<213> ORGANISM: Artificial Sequence
<220> FEATURE:
<223> OTHER INFORMATION: synthetic

<400> SEQUENCE: 55

```
atggagtagt cagaacacac tcttcagaag ggactcctga tttcaaaggg ggtaccgggc      60 ccccccctcga ggtcgacata acttcgtata gcatacatta                         100
```

<210> SEQ ID NO 56
<211> LENGTH: 108
<212> TYPE: DNA
<213> ORGANISM: Artificial Sequence
<220> FEATURE:
<223> OTHER INFORMATION: synthetic

<400> SEQUENCE: 56

```
ggccatgcat ataacttcgt atagcataca ttatacgaag ttataccggt gcgatcgctg      60
ggagcacgtt ccattattat aacaactttc tgaacacaag agggcagt                 108
```

<210> SEQ ID NO 57
<211> LENGTH: 100
<212> TYPE: DNA
<213> ORGANISM: Artificial Sequence
<220> FEATURE:
<223> OTHER INFORMATION: synthetic

<400> SEQUENCE: 57

```
atggagtagt cagaacacac tcttcagaag ggactcctga tttcaaaggg ggtaccgggc      60 ccccccctcga ggtcgacata acttcgtata gcatacatta                         100
```

<210> SEQ ID NO 58
<211> LENGTH: 108
<212> TYPE: DNA
<213> ORGANISM: Artificial Sequence
<220> FEATURE:
<223> OTHER INFORMATION: synthetic

<400> SEQUENCE: 58
ggccatgcat ataacttcgt atagcataca ttatacgaag ttataccggt gcgatcgctt      60
taaggtgagg aggcaggcaa taccccctct ccaccgcatt ctcaatcc                 108

<210> SEQ ID NO 59
<211> LENGTH: 100
<212> TYPE: DNA
<213> ORGANISM: Artificial Sequence
<220> FEATURE:
<223> OTHER INFORMATION: synthetic

<400> SEQUENCE: 59 ggggggggtgg ggtggaggag gagggtacag catctcctct ccttcctctc tggtaccgaa     60
gttcctattc cgaagttcct attctctaga aagtatagga                          100

<210> SEQ ID NO 60
<211> LENGTH: 108
<212> TYPE: DNA
<213> ORGANISM: Artificial Sequence
<220> FEATURE:
<223> OTHER INFORMATION: synthetic

<400> SEQUENCE: 60
gaagttccta ttctctagaa agtataggaa cttcctaggg tttcaccggt gcgatcgcgt      60
gaatatacta aaaccactt aattatatat ttgaaagggt ggatgtta                  108

<210> SEQ ID NO 61
<211> LENGTH: 108
<212> TYPE: DNA
<213> ORGANISM: Artificial Sequence
<220> FEATURE:
<223> OTHER INFORMATION: synthetic

<400> SEQUENCE: 61
ctctctccta cccagctcct ctcacacgag cctgaaggcc ctgccaaggt ggcgcgcctt      60
tcaaattgtt gttgagttca aagtgggcaa cagaaaaggg ggtgtgag                 108

<210> SEQ ID NO 62
<211> LENGTH: 130
<212> TYPE: DNA
<213> ORGANISM: Artificial Sequence
<220> FEATURE:
<223> OTHER INFORMATION: synthetic

<400> SEQUENCE: 62
aataaatagt aaatttctgt agaatcataa tgaggtctag accccggggc tcgataacta      60
taacggtcct aaggtagcga aatggcgcgt aatcaagccc agctcttcat gctgcatttt    120
tatcttcttt                                                           130

<210> SEQ ID NO 63
<211> LENGTH: 100
<212> TYPE: DNA
<213> ORGANISM: Artificial Sequence
<220> FEATURE:

```
<223> OTHER INFORMATION: synthetic

<400> SEQUENCE: 63
ttgactcggg ggtgcctggg tttgactgca atgatcagtt gctgggaagg accggtataa    60
cttcgtataa tgtatgctat acgaagttat atgcatggcc                          100

<210> SEQ ID NO 64
<211> LENGTH: 100
<212> TYPE: DNA
<213> ORGANISM: Artificial Sequence
<220> FEATURE:
<223> OTHER INFORMATION: synthetic

<400> SEQUENCE: 64
ccggcgcgcc ataacttcgt ataatgtatg ctatacgaag ttatgtcgac ataaggtaag    60
acagagtcgt cccttcccat ctggaaccct ctacctttct                          100

<210> SEQ ID NO 65
<211> LENGTH: 107
<212> TYPE: DNA
<213> ORGANISM: Artificial Sequence
<220> FEATURE:
<223> OTHER INFORMATION: synthetic

<400> SEQUENCE: 65
gttgatgaat cataaaagaa gagatattca agaaaaggat ggccacactg cggccgcaga    60
ggtattcaag gaaaatgcag actcttcacg taagagggat gaggggc                  107

<210> SEQ ID NO 66
<211> LENGTH: 100
<212> TYPE: DNA
<213> ORGANISM: Artificial Sequence
<220> FEATURE:
<223> OTHER INFORMATION: synthetic

<400> SEQUENCE: 66
tccccggagt cggagggtgg accggagctg gaggagctgc cgcggtggcg gccgatgcca    60
tttcattacc tctttctccg cacccgacat agataaagct                          100

<210> SEQ ID NO 67
<211> LENGTH: 100
<212> TYPE: DNA
<213> ORGANISM: Artificial Sequence
<220> FEATURE:
<223> OTHER INFORMATION: synthetic

<400> SEQUENCE: 67 ggggggggtgg ggtggaggag gagggtacag catctcctct ccttcctctc tggtaccgaa   60
gttcctattc cgaagttcct attctctaga aagtatagga                          100

<210> SEQ ID NO 68
<211> LENGTH: 108
<212> TYPE: DNA
<213> ORGANISM: Artificial Sequence
<220> FEATURE:
<223> OTHER INFORMATION: synthetic

<400> SEQUENCE: 68
gaagttccta ttctctagaa agtataggaa cttcctaggg tttcaccggt gcgatcgcga    60
agcaattaac tgccccctggt ccagttgcct cctctgataa tgcattgt                108
```

```
<210> SEQ ID NO 69
<211> LENGTH: 100
<212> TYPE: DNA
<213> ORGANISM: Artificial Sequence
<220> FEATURE:
<223> OTHER INFORMATION: synthetic

<400> SEQUENCE: 69
gggggggtgg ggtggaggag gagggtacag catctcctct ccttcctctc tggtaccgaa    60
gttcctattc cgaagttcct attctctaga aagtatagga                         100

<210> SEQ ID NO 70
<211> LENGTH: 108
<212> TYPE: DNA
<213> ORGANISM: Artificial Sequence
<220> FEATURE:
<223> OTHER INFORMATION: synthetic

<400> SEQUENCE: 70
gaagttccta ttctctagaa agtataggaa cttcctaggg tttcaccggt gcgatcgcgt    60
tatctagtag acttaattaa ggatcgatcc ggcgcgccaa tagtcatg               108

<210> SEQ ID NO 71
<211> LENGTH: 100
<212> TYPE: DNA
<213> ORGANISM: Artificial Sequence
<220> FEATURE:
<223> OTHER INFORMATION: synthetic

<400> SEQUENCE: 71
gttttccaga cttcaacttg actatcagcc agaaattcag tggcaaaccc ccacccagtc    60
cctaagtgaa ggcccctggg gagtatggtt agggctcagg                         100

<210> SEQ ID NO 72
<211> LENGTH: 100
<212> TYPE: DNA
<213> ORGANISM: Artificial Sequence
<220> FEATURE:
<223> OTHER INFORMATION: synthetic

<400> SEQUENCE: 72
cacccaccaa agaaagtgcc caggagaagg gcaaggagag agcagagcat agttcaagat    60
ggtctttgtc taggcttgtc tactctgcac ttgtacttcc                         100

<210> SEQ ID NO 73
<211> LENGTH: 202
<212> TYPE: DNA
<213> ORGANISM: Artificial Sequence
<220> FEATURE:
<223> OTHER INFORMATION: synthetic

<400> SEQUENCE: 73
aggggaaacc cgcaaaggat gggacatagg gagacagctg ttaacatctg aaacatgacc    60
ttcttttctg tgcagcacaa ctcctagctg tcactcaagg gaagaaagtg gtgctgggca   120
aaaaggggga tacagtggaa ctgacctgta cagcttccca gaagaagagc atacaattcc   180
actggaaaaa ctccaaccag at                                            202

<210> SEQ ID NO 74
<211> LENGTH: 240
<212> TYPE: DNA
<213> ORGANISM: Artificial Sequence
<220> FEATURE:
```

<223> OTHER INFORMATION: synthetic

<400> SEQUENCE: 74

```
ctggtcacct ggatgaagtg agggagggcc ctctgggttt ggggctggtt ttgaactgag    60
acatccatga gccagcctgg ggctggcttc actgaagatc atctatgtcg ggtgcggaga   120
aagaggtaat gaaatggcac atgctatgta caaactctat tgctgagcag cacccagtcc   180
tgagctggct ctgaattgag ggtgaaattc acacattctc ccccaacatc tataatctgg   240
```

<210> SEQ ID NO 75
<211> LENGTH: 151
<212> TYPE: DNA
<213> ORGANISM: Artificial Sequence
<220> FEATURE:
<223> OTHER INFORMATION: synthetic

<400> SEQUENCE: 75

```
tatggagtga aagcctttgg tgtctgagat ctggtcttag ttaaactctg ggatcggcgc    60
gccgaattcc tgcagcccgg gctcgagata acttcgtata atgtatgcta tacgaagtta   120
tatgcatccg ggtaggggag cgcttttcc c                                    151
```

<210> SEQ ID NO 76
<211> LENGTH: 151
<212> TYPE: DNA
<213> ORGANISM: Artificial Sequence
<220> FEATURE:
<223> OTHER INFORMATION: synthetic

<400> SEQUENCE: 76

```
agtattgttt tgccaagttc taattccatc agacctcgac ctgcagccct agataacttc    60
gtataatgta tgctatacga agttatccta ggccagaggg cttgggttga cagaaactca   120
gtggcattct tatccagagt ttctctacac c                                    151
```

<210> SEQ ID NO 77
<211> LENGTH: 18263
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2957)..(2957)
<223> OTHER INFORMATION: n = A,T,C or G
<220> FEATURE:
<221> NAME/KEY: misc_feature
<222> LOCATION: (3193)..(3193)
<223> OTHER INFORMATION: n = A,T,C or G

<400> SEQUENCE: 77

```
aagaaagtgg tgctgggcaa aaaggggat  acagtggaac tgacctgtac agcttcccag    60
aagaagagca tacaattcca ctggaaaaac tccaaccaga taaagattct gggaaatcag   120
ggctccttct taactaaagg tagggttgcc tggctcccca tccagggagg aaaacacact   180
atggagtgaa agcctttggt gtctgagatc tggtcttagt taaactctgg gatcggcgcg   240
ccgaattcct gcagcccggg ctcgagataa cttcgtataa tgtatgctat acgaagttat   300
atgcatccgg gtaggggagg cgcttttccc aaggcagtct ggagcatgcg ctttagcagc   360
cccgctgggc acttggcgct acacaagtgg cctctggcct cgcacacatt ccacatccac   420
cggtaggcgc aaccggctcc gttctttgg tggccccttc gcgccacctt ctactcctcc   480
cctagtcagg aagttccccc ccgccccgca gctcgcgtcg tgcaggacgt gacaaatgga   540
```

```
agtagcacgt ctcactagtc tcgtgcagat ggacagcacc gctgagcaat ggaagcgggt    600
aggcctttgg ggcagcggcc aatagcagct ttgctccttc gctttctggg ctcagaggct    660
gggaaggggt gggtccgggg gcgggctcag gggcgggctc aggggcgggg cgggcgcccg    720
aaggtcctcc ggaggcccgg cattctgcac gcttcaaaag cgcacgtctg ccgcgctgtt    780
ctcctcttcc tcatctccgg gcctttcgac ctgcagccaa ttgttgacaa ttaatcatcg    840
gcatagtata tcggcatagt ataatacgac aaggtgagga actaaaccat gggatcggcc    900
attgaacaag atggattgca cgcaggttct ccggccgctt gggtggagag gctattcggc    960
tatgactggg cacaacagac aatcggctgc tctgatgccg ccgtgttccg gctgtcagcg   1020
caggggcgcc cggttctttt tgtcaagacc gacctgtccg gtgccctgaa tgaactgcag   1080
gacgaggcag cgcggctatc gtggctggcc acgacgggcg ttccttgcgc agctgtgctc   1140
gacgttgtca ctgaagcggg aagggactgg ctgctattgg gcgaagtgcc ggggcaggat   1200
ctcctgtcat ctcaccttgc tcctgccgag aaagtatcca tcatggctga tgcaatgcgg   1260
cggctgcata cgcttgatcc ggctacctgc ccattcgacc accaagcgaa acatcgcatc   1320
gagcgagcac gtactcggat ggaagccggt cttgtcgatc aggatgatct ggacgaagag   1380
catcaggggc tcgcgccagc cgaactgttc gccaggctca aggcgcgcat gcccgacggc   1440
gatgatctcg tcgtgaccca tggcgatgcc tgcttgccga atatcatggt ggaaaatggc   1500
cgcttttctg gattcatcga ctgtggccgg ctgggtgtgg cggaccgcta tcaggacata   1560
gcgttggcta cccgtgatat tgctgaagag cttggcggcg aatgggctga ccgcttcctc   1620
gtgctttacg gtatcgccgc tcccgattcg cagcgcatcg ccttctatcg ccttcttgac   1680
gagttcttct gagggggatcc gctgtaagtc tgcagaaatt gatgatctat aaacaataa   1740
agatgtccac taaaatggaa gttttcctg tcatactttg ttaagaaggg tgagaacaga   1800
gtacctacat tttgaatgga aggattggag ctacgggggt gggggtgggg tgggattaga   1860
taaatgcctg ctctttactg aaggctcttt actattgctt tatgataatg tttcatagtt   1920
ggatatcata atttaaacaa gcaaaaccaa attaagggcc agctcattcc tcccactcat   1980
gatctataga tctatagatc tctcgtggga tcattgtttt tctcttgatt cccactttgt   2040
ggttctaagt actgtggttt ccaaatgtgt cagtttcata gcctgaagaa cgagatcagc   2100
agcctctgtt ccacatacac ttcattctca gtattgtttt gccaagttct aattccatca   2160
gacctcgacc tgcagcccta gataacttcg tataatgtat gctatacgaa gttatcctag   2220
gccagagggc ttgggttgac agaaactcag tggcattctt atccagagtt tctctacacc   2280
aactgctggt ggcccaggga aaggtggtat gtgaatttca atattttaat atttaatatt   2340
catgaactta ttttagtgag ttttagaaca atcactatca cttaaaaccc gtgatttctt   2400
gagtattgtt gctacagacc tatgtagata atactttgca cagtgactca tatgtataat   2460
cctagcactg tgggaggctg aggcggagg attgcttgag tccaggagtt caagaccagc   2520
ctgaacaaca tagtgagact ctgtctctat gaaaaaaaat atatatatat ttttttggga   2580
gacaaggtct agttctatca cccaggctcc agtgcagtgg tgtgatctcg gctcactgca   2640
atctccacct cccaggctca agtcatcatc ccacctcagc ctcccaagta gctgggacta   2700
caggcatgca ccaccatgcc aggctaattt ttgtattttt tatagagaca gggtttcacc   2760
atgttggcca ggctggtctc gaactcatga gctcaagtga tccactcacc ttggcctctc   2820
agagtgctgg aattacaggt gtgtgtcact atgcctagcc aaaaaaaatt tttttaatta   2880
```

| | | | | | |
|---|---|---|---|---|---|
| aaaaaaaaaa | ggccggctgt | agtggctcac | acctgtaatc | cagaactttg ggagtttgag | 2940 |
| gtgggcagat | caccggnggt | caggagttca | agaccagtct | ggccaacatg gtgaaacccg | 3000 |
| gtctctacta | aaaatacaaa | aattagccag | gtgtggggt | gcagtcctgt acttccagct | 3060 |
| actcaggagg | ctgaggcagg | agactcgctt | gaacctggga | ggcaaaggct gcagtgagct | 3120 |
| gagattgcac | cactgcactc | cagcctgggt | gacagagcaa | gacttcatct caaaaaaaaa | 3180 |
| aaaaaagctg | canatttatt | attattatta | ttagtttatt | tatttatttt tttgagacag | 3240 |
| agtctcgttc | tgtcgcccag | gctggagtgc | ggtggcgtga | tcttggctca ttgcaacctc | 3300 |
| cacctcccgg | gttcaagtga | ttctcctgcc | tcagcctccc | gagtagctgg gactacaggc | 3360 |
| gtatgccacc | atgcctggct | aattttttgt | acttttagta | gagacagagt ttcacggtgt | 3420 |
| tagccaggct | ggtcttgatc | tcctgacctc | gtgatttacc | ctccttggcc tcccaaagtg | 3480 |
| ctgggattac | aggcgtgagt | cactgtgccc | ggcccagaat | catttttttc acttttttt | 3540 |
| tttttgaggc | aaactctcga | tctgttgccc | aggctggagt | gcagtgggca tgatcttggc | 3600 |
| tcactgcaag | ctctgcctcc | caggttcaag | caattctcct | gcctcagcct cctgagtagc | 3660 |
| tgggactaca | ggcgtgtgcc | accatgcccg | gctaatttgc | gtattttag tagagaccgg | 3720 |
| ttttcatcat | attggccagg | ctggtcttga | actcctgacc | tcaagtgatt ctcccacctt | 3780 |
| agcctcccaa | agtgctggga | ttacaggcat | gagctactgc | acttggcctt ttctcctggt | 3840 |
| tttaaaacta | ttatatgctc | attacaaaat | atttggtcaa | tgaagaaaag aatatggaag | 3900 |
| aaaatcaaat | gcatgcatac | ttctatcact | cagagatatc | ctctgctaac attttgattg | 3960 |
| atttttcttcc | aatcttttt | tttttttttc | ttttgagac | agggtctcac tctgctgccc | 4020 |
| aggctggagt | acagtggcat | gaccacaaca | catcacagcc | tcaagtgatc ttcccacttc | 4080 |
| agccttccca | gtagctggga | ctacaggtgc | acgccaccat | gttcacctaa tttttactt | 4140 |
| tttgtagaga | tgagacttca | ccatgttgct | caggctggtc | ttgaattcct aggctcaagt | 4200 |
| gatcttcccg | ctttggcctc | ccaaagtgct | gggattatag | gtatgagcca ctgcatgtgg | 4260 |
| cctatttct | tccactgttg | ttcggcgtgg | agaatattat | atacataatt acgtaaatga | 4320 |
| tatcatactg | tatataccttt | ttttcctact | ccttccttaa | gttatatcat aatgagacta | 4380 |
| ccaattatta | gacttttttt | ctttttttg | agacggagtc | tcggtctgtc acctaggctg | 4440 |
| gagtgcaatg | gcgcgatctc | agctcgctgc | aacctctgcc | tcccaggttc aagcaattct | 4500 |
| gcctcagcct | cccgagtagc | tgggactaca | gacacgtgcc | accatgccca gctaactttt | 4560 |
| ttattttttt | attagagaca | gggttccacc | atgctagcag | gatggtctca atctctcgac | 4620 |
| ttcgtgatca | gcccggcttg | gcctcccaaa | gtgctgggag | tacaggtgtg agccaccgca | 4680 |
| ctcggcctag | actaactatt | taaagtaatc | tggcaatgtt | taacgaatac aaaactctaa | 4740 |
| aacccttgga | cctaataata | gctatttgg | aaagtctact | tgacagaaat aaaattgtga | 4800 |
| atattctttt | ttgttgtttt | tttgagacag | agtctcattt | ggacgcctag ctggagtgc | 4860 |
| agtggcatga | tctcggctaa | ctgcaacctc | cacctcctgg | gttcaagtga ttctcctgcc | 4920 |
| tcagcctcct | gagcagctgg | gattacaggt | gtgcaccacc | atgtctggct aattttttgca | 4980 |
| tttttagtag | atgggttttc | accatgttga | ccagggtggt | ctggaacttc taccctcaag | 5040 |
| tgatctaccc | accttggcct | cccaaagtgc | tgggattaca | ggtgtgagcc accacgcctg | 5100 |
| accagtgaac | acttaataat | atctatggaa | aggtgttatt | ataagaattg cttgtgggc | 5160 |
| cgggcgtggt | ggctcacgcc | tgtaatccca | gcactttggg | aggctgtggc aggcggatca | 5220 |
| cgaggtcagg | agatcaagat | catcctggct | aacacggtga | aaccccgtct ctactaaaaa | 5280 |

```
taccaaaaaa ttagccaggc gtggtggcgg gcacttgtaa tcccagctat ccaggaggct    5340
gaggcaggag aattgcgtga acccaggagg cggaggtcgc agtgagctga gaccgtgcca    5400
ttgcactcca gcctgagtga cagagtgaga ctccatcaca aaaataaat aaataaataa     5460 ataaaatata aataagtaaa taaaggtcag gagtggtggc tcacgcctgt aatcccagca    5520
ctttgggagg ccgaggtgga cagatcatga ggtcatgaga tcaagaccat cctggctaac    5580
acagtgaaac cctgcctcta ctaaaaatac aaaaagtcat ccaggtgtgg tggcacacac    5640
ctatagtccc agctacttgg gaggctgagg caggagaatc acttgaaccc aggaggcaga    5700
ggttgcagtg agctgagatc gcgccactac actccagcct aggcgacaga gcaagactct    5760
gtctcaaaat aaataaataa ataaatatat aaataaataa ataaataaaa taaaaagcac    5820
acacacacac acacacacac acacacaatg caaaagaccc accctactac aactaacatt    5880
atatttaatg gtgaaaaact gaattctttc tccctaagtg caggaataag acaaagatgt    5940
ctgctcttac tactcttatt caacataata ctgcaatccc ttgccagtgc aataaggcaa    6000
gaaaaatgaa ataaaaggaa aactgatcag aaagaaagaa ataaaactgt tcctatttgt    6060
ggatgacatg attacataga aaatctcaaa gaatctgtaa gaaacttctt agaattaata    6120
aatgaattca tcaaggttgc agaatataag ataaacataa aaaatctatt gtatttctat    6180
atattagcaa ggaacatgtg tacacagaaa ttaaaactac aataccattt ataattgctc    6240
aaaaaggcca ggcatggtgg ctcacacctg taattcctgc actttgggag gccaaggtgg    6300
gaagattgct taagcccagg agttcaagac cagcccgggc aacatagtga gaccttgtct    6360
ctacaaaaag taaaaaatta gctgagcatg gccgggtgca gtggctcact cctgtaaccc    6420
caacactttg ggaggctgag gcgggcggat catgaggtca ggagatcgag accatcctgg    6480
ctaacacggt gaaaccctgt ctctactaaa aacacaaaaa attagctgga tgtggtggca    6540
ggcgcctgta gacccagcta ctcgggaagc tgaggcagga gaatggcgtg aacctgggag    6600
gcggagcttg cagtgagctg agattgtgcc actgcactcc agcctgggtg acacagtgag    6660
actacgtctc aaaaaaaaaa aaaaaaaaat tagctgagca ttatggtgta tgcctgtagt    6720
cccagctact ggggaggctg aggtgggagg attgcttgag ccctaggagg gcaaggctgc    6780
agtgagccat gatcacacca ctgctttcca gcctcggtag agagcaaga ccctatctca     6840 aaaaaaaaaa aaaaaaaaaa agaaaagaaa agaaagaaa agaaaagaa agagagaaag      6900 aaatacttag gtgtaaatct aaaaaacatg cgtagggcca ggtgcagtgg ctcatgcctg    6960
taatcccagc acttttgggaa gttgaggctg gcggatcact tgaagtcggg agtttgagac    7020
cagcctggcc aacatggtga aaccccgtct ctactaaaaa tgcaaaaatt aggcaggtgt    7080
tgtggcgcat gcctgatccc agctactttg gaggctgagg caggagaatt gcttcaaccc    7140
gggaggcaga ggttgcagtg agccaagact gttccactgc actccagcct gggcaacaga    7200
gtaagagtct gtctcccgaa aaaaaaaaa agaaaaaaga aagcattgaa ttgtatgcta     7260
aaaactacac gatgctgatt aaagaagtca agaagatct aaatatatgg agagacatgc     7320
tgtactcatg gattgatgga ttggaagact caacataaga cagatatcaa ttttccccaa    7380
attaatatac aagtttaatc caattcctat aaaaatacca gcaagatttt ttgtagatat    7440
aaacaagttg gccaggtgta gtggcttaca cctgtaatcc tagcactttg ggaggctgag    7500
gtgggaagat cgcttgagcc caggtgttca cgactgcagt gagctatgat tgtgtcactg    7560
cattccagct ggcactccag cctaagtgac aaagggagac cctgtctcaa aaacaaaaac    7620
```

```
aaaaccaaaa taattttgct ctgcaaaatc cctattaaga agaagaaaag aggctgggca      7680
cagtggctca ccgctgtaat cccagcacgt tgggaggctg aggcaggctg atcacttcag      7740
cccagaagtt tgagatcagc ctgggcaaca tgaggaaacc ccgtctctac aaaaaaaaa      7800 aaaaggtaca tacacacaca cacacacaca cacacacata cacaagtata tacacatata      7860
tatacacata caggtgaata gatgtatata catctattta ttgtgaatat acatctatac      7920
acacacgtgt gtgtacacat atatttaaaa tttatttta ttatttatt tatttttgag       7980 acagagtctt gctctgtcac ccaggctggg tgcacctgta ttcccaacga cacaggaggc      8040
tgaggtggga gaatcactga gccagggagg cagaggttgc agtgagccaa gatgttgcct      8100
ggttgcctgg gcaacagagc gagaccctat atcaaaaaag aagaataata agaaaagaca      8160
gtttacagaa tataagaaaa tatattcaca atccacatac ttagcaaagg actggtatct      8220
agaatatgat aaacaactct caaaactcaa aaccaaaaaa atgaacaatt caattagaaa      8280
acaggccgaa aaggacatac agttggcaaa taagcacatg aaaagttgtt caacatcatt      8340
aatcattagg gatatgtaca ttaaaaccac aataggctat cactaaacct atcagaatgg      8400
ctaaatacaa aattggaaca ccaccaaatg ctgatgagga tgtggagaaa ctgggtcatt      8460
cttccaatat tggtgggagg ctaaaatggc aaagccactc tggaaaacag tttgatagtt      8520
tcttataaaa caaaacatgc ggccgggcgc ggtagctcac gcctgtaatc ccagcacttt      8580
gggaggccga ggcgggtgga tcacgaggtc aggagatcga gaccatcctg gctaacacgg      8640
tgaaaccctg tctctactaa aaatacaaaa aattagccgg gcgtggtggc gggcgcctgt      8700
agtcccagct actcgggagg ctgaggcagg agaatggtgt gaacccggga ggcggagctt      8760
gcagtgagcc gagatcgcgc cattgcactc caacctggga gacggaggga gactccgtct      8820
caaaaaaaca aaaacaaaca aacaaaaaac atgcaacaat ccagcaatat tgcacccccta      8880 ggcatttatc ctagagcaat gaagacttat gcccacacaa aaagctgcac acaaatgttc      8940
atagcagctt tattcatggt agccaacaat tagaaacaat ctagatgtcc ttcaactggt      9000
gaatgattac atccatacca cgaaatactt ttcagcaata aaaaggatga atcatagtac      9060
acaccacaac ctggatgaat ctccagggaa ttatgctgag tgaaaaaaag ccaatctcaa      9120
aaggtaatat actgtattaa tccatttata taacattctt aaaataacta attatagaaa      9180
tggagaacag atgagtgatt gccagggggtt aaggggctca gggatgggga ggggaagggg      9240
tatggctaca aaaagcaaca accttatggc gccggaaatg ttctgtattc tgattgtgtc      9300
aatgtgagca tactggttga gatatagtgc tacagttttg caagttatta ccatcagagt      9360
aaactggata gagggcacat aggatttctc tgtattactt cttacaactg caagtgaatc      9420
tacaattatc tcaaaataat aagtttagtt taatgctagg cgtggtggct cacatctgta      9480
atctcagctc tttgggaggc tgagacgggt ggatggcttg agtccaggag ttcgagacca      9540
gcctggccaa catggcaaaa ccggtctcta ctaaaaatac aaaaattagc tgggcgtggt      9600
ggcaagtgcc tgtagtccca gctactcggg aggctgaggc aggagaattg cttgaacccg      9660
ggaggtggag gttgcagtga gccgagatca cgccactaca ctgtagcttg ggcgacagag      9720
tgaggctctt tctcaaaaaa aaaaaaaaaa aaaaaaagc aggcaggcag gccaggaaa       9780 gcgtataatt tttgtagttc aaatgactaa cctaaaaagt gaagattggc caggcgcagt      9840
ggctcacgcc tgtaatccca gcactttggg aggccaaggc gggtggatca cgaggtcagg      9900
agattgagcc actctggcta acacagtgaa acccgtctc tactaaaata caaaaaatta     9960
gctgggcgtg gtggcacccg cctgtagttg cagctacttg ggaggctgag gcaggagaat     10020
```

```
cacttgaacc caggaggcga agttgcagcg agccgagatc acactactgc actccagcct   10080
gggtgacaaa gtgagattct gtctcaaaaa aaaaaaaaaa aaaaaaaaaa aaaaaaagtg   10140
aagtttacct ttttttttaa attttctttc ttttccttcc ctactttgtg agataatttt   10200 cttctttta aaaagccaag agcttacttc tgtaagtaaa gattatctta agacaactta   10260
gaaatgtata ttattagtat tttctatttc attgtaagtt atttgtaaat attggttttg   10320
gtgctaacct agaattccat caaattaatt gtcccctaat atatggccat tatcattttg   10380
tctaacattg tatcctatta acaatgctgt aagtattatt tttgtagcta aattatggtt   10440
tgcattttaa aattattgtt ttaaggataa agttccagaa atgaaattaa ggatatgaac   10500
tttttgagca catcttgtca gcactgagta gtattattta aaacttttgg gggggcaat    10560 tttataattg aaaatatat cattgttta atttgcattt ctttcactgc ctatgagatt    10620
aaaacaatgc actactttcc aaaaattctt aagtctttg tgttgatgct tttgttctgt    10680
ttctatggat ctcatcttcc ttcagaacag ctcccctttcc caacttcctg atttctaaca   10740
ataacagtat caccctcctt gttctcccaa tttctgaaac acagagtcat gttttttct    10800 ctgcttcaat ccctggtttc ctatcgtcat caattatgac cttccttgc tttgaaagtg    10860 ttttgggccg ggcatgatgt ctgccaccta ttgtaatcct agcactttgg gaggctgagg    10920
cggctggatg acttgacctg aggatttcga gaccagcctg ggcaacaggg cgaaacctcg    10980
tctctacaaa aaatacaaaa gttagtcggg agtggtggca catgcttgta gtcccagtta    11040
cttggggggc tgaggtggca ggatctcttg agcccacgag gtagatgttg cagtgagccg    11100
tgattgcgcc actgcacccc agcctaggtg acagagtgag accctgtctc aaaaaaaaaa   11160
aaatgttcta gtttcttcct cttctttgtt cccatgggaa tgccaccatc accagccaag    11220
gctcacatac ctcccacctg gattacagtg agcttccagg taatttggtc tgctactagt    11280
ctcgcctact tggatttccc ttcccccctgc tgcagcattg ccttccaaag ccatgctttg   11340
cacatgccac atcctagccc attagactaa gcctagaagc ctctgcagga cgttcaccct    11400
ctcagcgcca ctgctcagtt tcccagtgga aacctctgca cccaggaggt ttccccacag    11460
cttgcctgtg ctgcctctct ggagcttttc tcccttcctg taatgtcctt gctgctcccc    11520
gtctctagtc cattgcctat acctcttttt tttttttttt ttgagatgga gtctctctct    11580
ctcatccagg ctggagtgca gtggcgcgat ctcggctcac tgcaaccttt gtctcctggg    11640
ttcaagggat tctcctgcct cagcctcccg agtaactggg attacaggcg tgcaccacca    11700
ttcctggcta atttttgtat ttttagtaaa gactgggttt caccatgttg gccaggctgg    11760
tcttgaactc ctgccctcag gtgatccacc tgcctcggcc tcccagagtg ctgggattac    11820
aggcgtgagc caccgcacct gccacaggcc catacctctt ttaagtcttc attcaatacc    11880
agttgtccca tgaatttgtc ccagactcac tcatatgctt agacctttca tattatcttg    11940
ccatagcttt ttcaaagtat gggacagcat ggacaagcag gccatggttt tcttttgaag   12000
agaagcaagg aggcagagtt atttaggag gagggttata catttcattt tgaaccaatt    12060
gcgtttgggg tgatggcagg atattaacat aaacttattt cttggaccat tggaaatgtg    12120
tgcctagaac tgaggagaga ggtcagggct ggcagtaaca acttggccac aatctgcaga    12180
gctgactggg gatgaggtgg aatttagaat gtctgtagaa acggggaaga gaaccaaaga    12240
cagagtctgg gacaacacct aaatgtgat gtcagagcaa gagttcaaga cgaagaaaaa     12300
cgaatcatac ttagaaatgg aggggaggaa caaaagaggc ggagcaaagt ggggcagaac    12360
```

```
cagagtaggc cacgctttta agaagtttgg taaaggaact gtgaaaggaa tgtagttgaa    12420
tttcagggta agctggggaa ttaaagcagt gtgtagatcc agggcaaaca gcaagtaggg    12480
caggaaccac tgaaggaaca aataaagggg gaggttgggt ccaggttgtc ttgagtaggg    12540
aagttttttt aaaaagtgtg aaactgaagg tgtggggtgg attgggtgcc tgccgtgctc    12600
tgaggaagct tggggcaact gtgtgctgag gctgtgaggt tgtctggaag gggctcctgg    12660
acagtaagag ctgagcagtg gggaagagga ctgtgtggtc tggaagagga gagaaaggag    12720
agtgagtgac tgaactggta tccaggctcc cacaccaagg cagaaagagg gagaggacct    12780
gggcatctca gggaggcaga ggcagtacca agcagggtga gaggctttag tcttagccac    12840
ctttgcccca ttcctccaaa tatacattct aagtaaaaac aaaacaaaac agaactgttt    12900
gctatgtaaa tttagcttct aaagcccgtg tctacagaga ttttggagct tccactgcac    12960
ccagaaaatg cacagctaaa gagaaaactt cccttggtga tggttattag attttacaag    13020
aagaggccaa aggagacaca tacttatgcc agaagaactt tccagagata gcattgcata    13080
gcgaaatagc ctgaattatt tttatttttt aaaacatttt ttcttttctt ttttctttc    13140 tttttctttt tttttttttt tttttgagac agagtctcac tctgtcaccc aggctggagt    13200
gcagtggcgt gatcttggct cactgcaatc tccacctccc gggttcaagc cattctcctc    13260
cctcagcctc ccaagtagct gggattacag gcatgcgtca ctatgctctg gctaattttt    13320
tttttctttt ttttttggt attttagta gagatggggt ttcaccatgt tggccaggct    13380
ggtcttgaac tcctgacctc aagtgatcca ccgccttggc ctcccaaagt gctgggattt    13440
caggcgtgag ccaccgcacc cggccaaaaa tttcttttct ttaagatgag gcctcactct    13500
gttgcccagg ctggagtgca gtgttacaat catagctcac tgtaactttg aactcctggg    13560
ctcaagtgat cctcctgctt cagcctctca agtagctggg attacaggca tgtgccacca    13620
cacccagcta atttttttta aaataatttt tttagagac gagggtctcg attggctgcc    13680
taggttggtc ccagactcct gacgggctgc attttaatcc tagctccacc acttacggga    13740
gtcaaaattc aaaagataga aaagggcata taggctgggt gcagtggctc acacctgcaa    13800
tcccagcaat ttgggaggct gaggtgggcg ggttgcttga ggtcaggagt tcgagatcag    13860
cctgggcaac atggcaaaac ttgtatctac taaaaataca aaaattagcc agatgtggtg    13920
gtgtacacct gtaatcccag ctactccgaa ggctgaggca agagaatccc ttgaactcag    13980
gaggcagagg ttacaatgag cagagatcga acactcgact ccataaaaac aaacaaacaa    14040
aaaaagaaag caggctgggt gtggtggctc acgcctgtaa ccccagcact cgggaggcc    14100 aaggcgagcg gatcacctga ggttgggcat tcgagaccag cctgaccaac aaggagaaac    14160
cctgtctcta ctgaaaatac aaaattagcc gggcttggtt gcgcatgcct gtaatctcag    14220
ctactcggga ggcagaggca agataattgc ttgaacccgg gaggcggagg ttgcggtgag    14280
ccaagatcat gccattgcac tccaacctgg caacaatag cgaaactcca tctcaaaaaa    14340
aaaaaagcaa agggcatata gtgaaaagct tcttcctac acatgagtat tcacttcctc    14400
ttcctagagg caaccaaggt tatttttgtg tgtgtgtgtg tgtgtgtgtg tgtgtgtgtg    14460
tgttttggga cagtctcact ctctcaccaa ggctggaatg cagtggtgcg atctcactgc    14520
aaactctgcc tcccagtctc aagcgatctt gtgcctcagc ctcccagttt ttttttcttt    14580 taaatgggt ctcattctgt cgcccagggt ggagtgcagt ggcatgatca tagctcactg    14640
cagcctcgac ctcctgggtc aggttatcct cccacctcag cctccggcat agctgggct    14700 actggcatgc accaccacac tcagttaatt ttttttcttt tttgagacag agtctcactc    14760
```

```
tgtcacctag actggagtgc agtggtgcca tctcatttgt ttcactgcaa cctttgactt    14820
ctgggctcaa gtgattctcc cacctcagcc tcccaaggcg gctaattaaa aaaaatttt     14880 tttttttttt tttagagat ggggtttcgc catgttgccc aggctgatct cgaactcctg     14940
ggcacaaaca atctttccac ctcgatcttt caaagagctg ggatgagaga tttccaccat    15000
gcctggcctc attttctttt ttaattttt tttagacatt atagctcttt ttaatggcct     15060
cattttctta tgtttaattc gagaattatt cttttcatat acaaagaata tattttctcc    15120
acctttaaaa acaaatagta gactgtttaa catctcgctt tattcagtta gtgatgtttc    15180
ttagatacgg gtccaaatta gtacacaaag cacttcctca ttcctctctt acggctgcat    15240
agcagtccac tgaatgggtg agctatgatc tatttaacct attctttatt gatggacatt    15300
tggttttgta tatacatttg taattctgta tagattacaa atcaccatcc aaagaaattg    15360
tactggttta ttctcctaca atgtgtgaga gttgggtaat tacttaatct caatatgtga    15420
gagtttaggc agttacctaa tctctctgag tctcagtttc tctatctgca aaataaacaa    15480
aacagtgttg acagtatcta tttctcggaa ttattgtgga gattactgag atgatgcctg    15540
taaagtattt ggcatgtagg agttggtgct ctccaaataa ggatatgatt ttatttgtat    15600
ttgtgagcta ctgtcccagc caggtaaatg gatatgatga gacctccttg ccagaccggg    15660
tttctctgat tagaacgagg agcagatgtt gcaggaaatt agcaactgat atcagaagag    15720
ccgtgggcat tctcttgcca gaggtgccct gtctccaggg cgcctcagtc cccccccata    15780
tgtcttctgc tcccaggtcc atccaagctg aatgatcgcg ctgactcaag aagaagcctt    15840
tgggaccaag gaaactttcc cctgatcatc aagaatctta agatagaaga ctcagatact    15900
tacatctgtg aagtggagga ccagaaggag gaggtgcaat tgctagtgtt cggatgtgag    15960
tggggcaggt ggggatgagg atacctcctg cctggttccc ttccccacta ctcccacccc    16020
tgcaccaaat ccagcctgag ctggtgatac cgcagcagcc caagaggac caggctgtca    16080 aactggcctc caaatgtctt aaaacccttc ttgatcaggt gagggatgct ggtgggcgga    16140
ggagggaaga ggccttggga aaaggaaaga aagggaagg aggcaaggga aggagggaga    16200
gagactgggg aagagaggat gaggggagag gaggaaagaa gagagagagg aggggagagg    16260
gaaaccctat cttggctggg ggtgcgcagc tgggtgctgg gaggaaggag atgttgggac    16320
ggcgataatg gagagatgtt gttggtttcc tgttgtctgc ccttctcctt ggggatggta    16380
tgtgtgtgac acagctggcc tttccctcca cagtgactgc caactctgac acccacctgc    16440
ttcaggggca gagcctgacc ctgaccttgg agagcccccc tggtagtagc ccctcagtgc    16500
aatgtaggag tccaaggggt aaaaacatac aggggggaa gaccctctcc gtgtctcagc    16560
tggagctcca ggatagtggc acctggacat gcactgtctt gcagaaccag aagaaggtgg    16620
agttcaaaat agacatcgtg gtgctaggta agggaagccc ctcttcgcgc agtctcctcc    16680
ctgccccagg ggctgacagc ccctcccct gctctgactg ccctgtttct ggttctggtg    16740
ctgggaggtc aggagtggag aagactaggt cccctagagc tgaggcctgt cttgaaggac    16800 tcactgggc cctcatcctc aggggctga ttggcagcca ccctcagtg tggtggacat      16860 ggagaaagga aaggctgggg aaggtaagga tgctagaggc ccgagtctcc tttggaggcc    16920
ccaaaggagg aatgtcaggg agcttacttt cttgttgcc tcagctccac acccctacca    16980
agttggcaaa tccacttact cagggacact aacaccagta agccaaccct gatgatgttc    17040
tatgttgtac ctctggacct ctaagccagg ccactgtggg gagaccaagg tcctacccca    17100
```

```
gatcctgtcc cctgggtgct tatgtgactt aaggtagaca taaggtagtg tgccagttta    17160
gtgcatgtac gctgattgaa atcctggttc tgccacaacc atgtgacctt gggtgagtta    17220
ctaaacctct ctgcaccttg gtttcagcct ctgtgaaatg gggatgatgt taactgccat    17280
agtgactacc tcgtattaag ttgaggactg atatacgtaa ggcactgaaa atggtgcctg    17340
gcacagagta agccctagtt aagtgttcgc tgttattttg tgaagggtga tgaatacgcc    17400
tctaaggagt ggaggccaaa tggcttctgt ggtccaggaa tcctaaggac agcaaggatc    17460
ccctgtggct gggctgctct gtgatggctt ccggggaggag ggaggtggcc tgctgtagga    17520
aaatgctggg tggaagaagg gagagaaggc tggagaggta ggaaggaact gaagtatctg    17580
aagtgacaag gtgggtgtct ggactcgtcg ggtcccttc catctccctg ctgcctccac    17640
atgccaaccc cactcgtgca ccctcatctt cctatctcct cacccagggt ctctcccttc    17700
ccacctccag ctttccagaa ggcctccagc atagtctata agaaagaggg ggaacaggtg    17760
gagttctcct tcccactcgc ctttacagtt gaaaagctga cgggcagtgg cgagctgtgg    17820
tggcaggcgg agagggcttc ctcctccaag tcttggatca cctttgacct gaagaacaag    17880
gaagtgtctg taaaacgggt tacccaggac cctaagctcc agatgggcaa gaagctcccg    17940
ctccacctca ccctgcccca ggccttgcct cagtatgctg gctctggaaa cctcaccctg    18000
gcccttgaag cgaaaacagg aaagttgcat caggaagtga acctggtggt gatgagaggt    18060
gaggggccag gccaggagg ggtgggcagg ggaaggagtt ggaggggcct ggcccagggc    18120
tccctctgag gcaagccagg ccccaagagg ggatgcctag gccctggtca cctggatgaa    18180
gtgagggagg gccctctggg tttggggctg gttttgaact gagacatcca tgagccagcc    18240
tggggctggc ttcactgaag atc                                           18263
```

<210> SEQ ID NO 78
<211> LENGTH: 458
<212> TYPE: PRT
<213> ORGANISM: Artificial Sequence
<220> FEATURE:
<223> OTHER INFORMATION: synthetic

<400> SEQUENCE: 78

```
Met Cys Arg Ala Ile Ser Leu Arg Arg Leu Leu Leu Leu Leu Leu Gln
1               5                   10                  15

Leu Ser Gln Leu Leu Ala Val Thr Gln Gly Lys Lys Val Val Leu Gly
            20                  25                  30

Lys Lys Gly Asp Thr Val Glu Leu Thr Cys Thr Ala Ser Gln Lys Lys
        35                  40                  45

Ser Ile Gln Phe His Trp Lys Asn Ser Asn Gln Ile Lys Ile Leu Gly
    50                  55                  60

Asn Gln Gly Ser Phe Leu Thr Lys Gly Pro Ser Lys Leu Asn Asp Arg
65                  70                  75                  80

Ala Asp Ser Arg Arg Ser Leu Trp Asp Gln Gly Asn Phe Pro Leu Ile
                85                  90                  95

Ile Lys Asn Leu Lys Ile Glu Asp Ser Asp Thr Tyr Ile Cys Glu Val
            100                 105                 110

Glu Asp Gln Lys Glu Glu Val Gln Leu Leu Val Phe Gly Leu Thr Ala
        115                 120                 125

Asn Ser Asp Thr His Leu Leu Gln Gly Gln Ser Leu Thr Leu Thr Leu
    130                 135                 140

Glu Ser Pro Pro Gly Ser Ser Pro Ser Val Gln Cys Arg Ser Pro Arg
145                 150                 155                 160
```

Gly Lys Asn Ile Gln Gly Gly Lys Thr Leu Ser Val Gln Leu Glu
                165                 170                 175

Leu Gln Asp Ser Gly Thr Trp Thr Cys Thr Val Leu Gln Asn Gln Lys
            180                 185                 190

Lys Val Glu Phe Lys Ile Asp Ile Val Val Leu Ala Phe Gln Lys Ala
        195                 200                 205

Ser Ser Ile Val Tyr Lys Lys Glu Gly Glu Gln Val Glu Phe Ser Phe
    210                 215                 220

Pro Leu Ala Phe Thr Val Glu Lys Leu Thr Gly Ser Gly Glu Leu Trp
225                 230                 235                 240

Trp Gln Ala Glu Arg Ala Ser Ser Lys Ser Trp Ile Thr Phe Asp
                245                 250                 255

Leu Lys Asn Lys Glu Val Ser Val Lys Arg Val Thr Gln Asp Pro Lys
            260                 265                 270

Leu Gln Met Gly Lys Lys Leu Pro Leu His Leu Thr Leu Pro Gln Ala
        275                 280                 285

Leu Pro Gln Tyr Ala Gly Ser Gly Asn Leu Thr Leu Ala Leu Glu Ala
    290                 295                 300

Lys Thr Gly Lys Leu His Gln Glu Val Asn Leu Val Val Met Arg Val
305                 310                 315                 320

Ala Gln Leu Asn Asn Thr Leu Thr Cys Glu Val Met Gly Pro Thr Ser
                325                 330                 335

Pro Lys Met Arg Leu Thr Leu Lys Gln Glu Asn Gln Glu Ala Arg Val
            340                 345                 350

Ser Glu Glu Gln Lys Val Val Gln Val Val Ala Pro Glu Thr Gly Leu
        355                 360                 365

Trp Gln Cys Leu Leu Ser Glu Gly Asp Lys Val Lys Met Asp Ser Arg
    370                 375                 380

Ile Gln Val Leu Ser Arg Gly Val Asn Gln Thr Val Phe Leu Ala Cys
385                 390                 395                 400

Val Leu Gly Gly Ser Phe Gly Phe Leu Gly Phe Leu Gly Leu Cys Ile
                405                 410                 415

Leu Cys Cys Val Arg Cys Arg His Gln Gln Arg Gln Ala Ala Arg Met
            420                 425                 430

Ser Gln Ile Lys Arg Leu Leu Ser Glu Lys Lys Thr Cys Gln Cys Pro
        435                 440                 445

His Arg Met Gln Lys Ser His Asn Leu Ile
450                 455

<210> SEQ ID NO 79
<211> LENGTH: 293
<212> TYPE: PRT
<213> ORGANISM: Artificial Sequence
<220> FEATURE:
<223> OTHER INFORMATION: synthetic

<400> SEQUENCE: 79

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
        50                  55                  60

```
Gly Asn Phe Pro Leu Ile Ile Lys Asn Leu Lys Ile Glu Asp Ser Asp
 65                  70                  75                  80

Thr Tyr Ile Cys Glu Val Asp Gln Lys Glu Val Gln Leu Leu
             85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
            115                 120                 125

Gln Cys Arg Ser Pro Arg Gly Lys Asn Ile Gln Gly Gly Lys Thr Leu
            130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala Phe Gln Lys Ala Ser Ser Ile Val Tyr Lys Lys Glu Gly Glu
            180                 185                 190

Gln Val Glu Phe Ser Phe Pro Leu Ala Phe Thr Val Glu Lys Leu Thr
            195                 200                 205

Gly Ser Gly Glu Leu Trp Trp Gln Ala Glu Arg Ala Ser Ser Ser Lys
210                 215                 220

Ser Trp Ile Thr Phe Asp Leu Lys Asn Lys Glu Val Ser Val Lys Arg
225                 230                 235                 240

Val Thr Gln Asp Pro Lys Leu Gln Met Gly Lys Lys Leu Pro Leu His
                245                 250                 255

Leu Thr Leu Pro Gln Ala Leu Pro Gln Tyr Ala Gly Ser Gly Asn Leu
            260                 265                 270

Thr Leu Ala Leu Glu Ala Lys Thr Gly Lys Leu His Gln Glu Val Asn
            275                 280                 285

Leu Val Val Met Arg
    290

<210> SEQ ID NO 80
<211> LENGTH: 142
<212> TYPE: DNA
<213> ORGANISM: Artificial Sequence
<220> FEATURE:
<223> OTHER INFORMATION: synthetic

<400> SEQUENCE: 80
tgtttgcctg tgacatgaac tcattgtgac acaaaccact gtgctagggg ggatccacta      60
gtaacggccg ccagtgtgct ggaattcgcc ctcgcaaggg ccaggcatat aagtacacaa     120
taaacaaatg gcagctctct cc                                              142

<210> SEQ ID NO 81
<211> LENGTH: 99
<212> TYPE: DNA
<213> ORGANISM: Artificial Sequence
<220> FEATURE:
<223> OTHER INFORMATION: synthetic

<400> SEQUENCE: 81
cccctccttc cttccccagg cactttccaa gtgtcaactc tagagcctat cgcggccgca      60
ccggtataac ttcgtataat gtatgctata cgaagttat                             99

<210> SEQ ID NO 82
<211> LENGTH: 90
```

```
<212> TYPE: DNA
<213> ORGANISM: Artificial Sequence
<220> FEATURE:
<223> OTHER INFORMATION: synthetic

<400> SEQUENCE: 82
ataacttcgt ataatgtatg ctatacgaag ttatgtcgac gtagcctatt tctctagatc    60
caaaatgatg acaacaaaag gtaccttgtg                                    90

<210> SEQ ID NO 83
<211> LENGTH: 210
<212> TYPE: PRT
<213> ORGANISM: Artificial Sequence
<220> FEATURE:
<223> OTHER INFORMATION: synthetic

<400> SEQUENCE: 83

Met Gln Pro Trp Leu Trp Leu Val Phe Ser Met Lys Leu Ala Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Gly Leu Thr Cys Ser Leu Thr Thr Leu Ser Leu Leu
                165                 170                 175

Val Val Cys Ile Leu Leu Leu Ala Phe Leu Gly Val Ala Val Tyr
            180                 185                 190

Phe Tyr Cys Val Arg Arg Arg Ala Arg Ile His Phe Met Lys Gln Phe
        195                 200                 205

His Lys
    210

<210> SEQ ID NO 84
<211> LENGTH: 151
<212> TYPE: PRT
<213> ORGANISM: Artificial Sequence
<220> FEATURE:
<223> OTHER INFORMATION: synthetic

<400> SEQUENCE: 84

Val Leu His Gly Asn Ser Val Leu Gln Gln Thr Pro Ala Tyr Ile Lys
1               5                   10                  15

Val Gln Thr Asn Lys Met Val Met Leu Ser Cys Glu Ala Lys Ile Ser
            20                  25                  30
```

```
Leu Ser Asn Met Arg Ile Tyr Trp Leu Arg Gln Arg Gln Ala Pro Ser
             35                  40                  45

Ser Asp Ser His His Glu Phe Leu Ala Leu Trp Asp Ser Ala Lys Gly
 50                  55                  60

Thr Ile His Gly Glu Glu Val Glu Gln Glu Lys Ile Ala Val Phe Arg
 65                  70                  75                  80

Asp Ala Ser Arg Phe Ile Leu Asn Leu Thr Ser Val Lys Pro Glu Asp
                 85                  90                  95

Ser Gly Ile Tyr Phe Cys Met Ile Val Gly Ser Pro Glu Leu Thr Phe
                100                 105                 110

Gly Lys Gly Thr Gln Leu Ser Val Val Asp Phe Leu Pro Thr Thr Ala
            115                 120                 125

Gln Pro Thr Lys Lys Ser Thr Leu Lys Lys Arg Val Cys Arg Leu Pro
130                 135                 140

Arg Pro Glu Thr Gln Lys Gly
145                 150

<210> SEQ ID NO 85
<211> LENGTH: 100
<212> TYPE: DNA
<213> ORGANISM: Artificial Sequence
<220> FEATURE:
<223> OTHER INFORMATION: synthetic

<400> SEQUENCE: 85
tgaacctgct gctgctgggt gagtcgatta tcctggggag tggagaagct aggccgagcc    60
agttccgggt gtcgccgctg atcggacct ggaacctggg                          100

<210> SEQ ID NO 86
<211> LENGTH: 90
<212> TYPE: DNA
<213> ORGANISM: Artificial Sequence
<220> FEATURE:
<223> OTHER INFORMATION: synthetic

<400> SEQUENCE: 86
atgccaggga cagccctgat actgtaggta gagtcaaggg ctgtccaagt accggtataa    60
cttcgtataa ggtatcctat acgaagttat                                    90

<210> SEQ ID NO 87
<211> LENGTH: 89
<212> TYPE: DNA
<213> ORGANISM: Artificial Sequence
<220> FEATURE:
<223> OTHER INFORMATION: synthetic

<400> SEQUENCE: 87
ataacttcgt ataaggtatc ctatacgaag ttatctcgac ctgatcttgg agggagacct    60
ggaccgggag acgtgctggg ggcagggtt                                     89

<210> SEQ ID NO 88
<211> LENGTH: 243
<212> TYPE: PRT
<213> ORGANISM: Artificial Sequence
<220> FEATURE:
<223> OTHER INFORMATION: synthetic

<400> SEQUENCE: 88

Met Ala Ser Pro Leu Thr Arg Phe Leu Ser Leu Asn Leu Leu Leu Leu
 1               5                  10                  15
```

```
Gly Glu Ser Ile Ile Leu Gly Ser Gly Glu Ala Arg Pro Ser Gln Phe
            20                  25                  30

Arg Val Ser Pro Leu Asp Arg Thr Trp Asn Leu Gly Glu Thr Val Glu
        35                  40                  45

Leu Lys Cys Gln Val Leu Leu Ser Asn Pro Thr Ser Gly Cys Ser Trp
 50                  55                  60

Leu Phe Gln Pro Arg Gly Ala Ala Ser Pro Thr Phe Leu Leu Tyr
 65                  70                  75                  80

Leu Ser Gln Asn Lys Pro Lys Ala Ala Glu Gly Leu Asp Thr Gln Arg
                85                  90                  95

Phe Ser Gly Lys Arg Leu Gly Asp Thr Phe Val Leu Thr Leu Ser Asp
            100                 105                 110

Phe Arg Arg Glu Asn Glu Gly Tyr Tyr Phe Cys Ser Ala Leu Ser Asn
            115                 120                 125

Ser Ile Met Tyr Phe Ser His Phe Val Pro Val Phe Leu Pro Ala Lys
130                 135                 140

Pro Thr Thr Thr Pro Ala Pro Arg Pro Thr Pro Ala Pro Thr Ile
145                 150                 155                 160

Ala Ser Gln Pro Leu Ser Leu Arg Pro Glu Ala Cys Arg Pro Ala Ala
                165                 170                 175

Gly Gly Ala Val Lys Gly Thr Gly Leu Asp Phe Ala Cys Asp Ile Tyr
            180                 185                 190

Ile Trp Ala Pro Leu Ala Gly Ile Cys Val Ala Leu Leu Leu Ser Leu
            195                 200                 205

Ile Ile Thr Leu Ile Cys Tyr His Arg Ser Arg Lys Arg Val Cys Lys
            210                 215                 220

Cys Pro Arg Pro Leu Val Arg Gln Glu Gly Lys Pro Arg Pro Ser Glu
225                 230                 235                 240

Lys Ile Val

<210> SEQ ID NO 89
<211> LENGTH: 152
<212> TYPE: PRT
<213> ORGANISM: Artificial Sequence
<220> FEATURE:
<223> OTHER INFORMATION: synthetic

<400> SEQUENCE: 89

Arg Pro Ser Gln Phe Arg Val Ser Pro Leu Asp Arg Thr Trp Asn Leu
1               5                   10                  15

Gly Glu Thr Val Glu Leu Lys Cys Gln Val Leu Leu Ser Asn Pro Thr
            20                  25                  30

Ser Gly Cys Ser Trp Leu Phe Gln Pro Arg Gly Ala Ala Ala Ser Pro
            35                  40                  45

Thr Phe Leu Leu Tyr Leu Ser Gln Asn Lys Pro Lys Ala Ala Glu Gly
 50                  55                  60

Leu Asp Thr Gln Arg Phe Ser Gly Lys Arg Leu Gly Asp Thr Phe Val
 65                  70                  75                  80

Leu Thr Leu Ser Asp Phe Arg Arg Glu Asn Glu Gly Tyr Tyr Phe Cys
                85                  90                  95

Ser Ala Leu Ser Asn Ser Ile Met Tyr Phe Ser His Phe Val Pro Val
            100                 105                 110

Phe Leu Pro Ala Lys Pro Thr Thr Thr Pro Ala Pro Arg Pro Pro Thr
            115                 120                 125

Pro Ala Pro Thr Ile Ala Ser Gln Pro Leu Ser Leu Arg Pro Glu Ala
```

```
                130               135              140
Cys Arg Pro Ala Ala Gly Gly Ala
145                 150

<210> SEQ ID NO 90
<211> LENGTH: 149
<212> TYPE: DNA
<213> ORGANISM: Artificial Sequence
<220> FEATURE:
<223> OTHER INFORMATION: Sequence of the chimeric human/mouse MHC I
      locus at the 5' junction of mouse/human sequences

<400> SEQUENCE: 90
agtgtcgccg cggacgctgg atataaagtc cacgcagccc gcagaactca gaagtcgcga        60
atcgccgaca ggtgcgatgg ccgtcatggc gccccgaacc ctcgtcctgc tactctcggg       120
ggctctggcc ctgacccaga cctgggcgg                                         149

<210> SEQ ID NO 91
<211> LENGTH: 159
<212> TYPE: DNA
<213> ORGANISM: Artificial Sequence
<220> FEATURE:
<223> OTHER INFORMATION: Sequence of the chimeric human/mouse MHC I
      locus at the 3' junction of human/mouse sequences

<400> SEQUENCE: 91
ggtggtgcct tctggacagg agcagagata cacctgccat gtgcagcatg agggtttgcc        60
caagcccctc accctgagat ggggtaagga gagtgtgggt gcagagctgg ggtcagggaa       120
agctggagct ttctgcagac cctgagctgc tcagggctg                              159
```

HUMANIZED T CELL MEDIATED IMMUNE RESPONSES IN NON-HUMAN ANIMALS

CROSS-REFERENCE TO RELATED APPLICATIONS

This application is a U.S. National Phase Application filed under 35 U.S.C. § 371 of PCT Application No. PCT/US2016/026260 (filed Apr. 6, 2016), which claims priority to U.S. Provisional Application Ser. Nos. 62/143,687 (filed Apr. 6, 2015), 62/158,804 (filed May 8, 2015), and 62/186,935 (filed Jun. 30, 2015), each applications of which are hereby incorporated by reference in their entireties.

SEQUENCE LISTING

The official copy of the sequence listing is submitted electronically via EFS-Web as an ASCII formatted sequence listing with a file named 2016-04-06-10145WO01-SEQ-LIST_ST25.txt, created on Apr. 6, 2016, and having a size of 56.7 kilobytes, and is filed concurrently with the specification. The sequence listing contained in this ASCII formatted document is part of the specification and is herein incorporated by reference in its entirety.

TECHNICAL FIELD

The present invention relates to a non-human animals (e.g., rodents, e.g., mice or rats) capable of mounting substantially human(ized) T cell mediated immune responses and expressing (i) one or more human(ized) T cell co-receptor(s) (e.g., CD4 and/or CD8 (e.g., CD8α, and/or CD8β)), (ii) one or more human(ized) major histocompatibility complex(es) that associates with the one or more human(ized) T cell co-receptor(s) (e.g., MHC II (e.g., MHC α and/or MHC II β) and/or MHC I (e.g., MHC I α and/or β2 microglobulin)) and/or (iii) a human(ized) T cell receptor (TCR) (e.g., TCRα and/or TCRβ); embryos, tissues, cells and/or nucleic acids isolated from the non-human animals; methods of making the non-human animals; and methods of using the non-human animals for the development of human therapeutics.

BACKGROUND OF THE INVENTION

In the adaptive immune response, foreign antigens are recognized by receptor molecules on B lymphocytes (e.g., immunoglobulins) and T lymphocytes (e.g., T cell receptor also referred to as TCR). These foreign antigens are presented on the surface of cells as peptide fragments by specialized proteins, generically referred to as major histocompatibility complex (MHC) molecules, and specifically referred to as human leukocyte antigen (HLA) in humans. During a T cell-mediated response, antigens presented by MHC molecules are recognized by a T cell receptor. However, more than T cell receptor recognition of MHC-antigen complex is required for an effective immune response. The binding of a T cell co-receptor molecule (e.g., CD4 or CD8) to an invariant portion of MHC is also required.

T cells come in several varieties, including helper T cells and cytotoxic T cells. Helper T cells express co-receptor CD4 and recognize antigens bound to MHC II molecules. CD4+ T cells activate other effector cells in the immune system, e.g., MHC II expressing B cells to produce antibody, MHC II expressing macrophages to destroy pathogens, etc. The binding of CD4 and T cell receptor to the same MHC II-presented foreign antigen makes a T cell significantly more sensitive to that antigen.

In contrast, cytotoxic T cells (CTLs) express co-receptor CD8 and recognize foreign antigens bound to MHC I molecules. CTLs are specialized to kill any cell that bears an MHC I-bound peptide recognized by its own membrane-bound TCR. When a cell displays peptides derived from cellular proteins not normally present (e.g., of viral, tumor, or other non-self origin), such peptides are recognized by CTLs, which become activated and kill the cell displaying the peptide. Similar to CD4, engagement of CD8 makes CTLs more sensitive to MHC I-presented antigen.

Not all antigens will provoke T cell activation due to tolerance mechanisms. However, in some diseases (e.g., cancer, autoimmune diseases) peptides derived from self-proteins become the target of the cellular component of the immune system, which results in destruction of cells presenting such peptides. There has been significant advancement in recognizing antigens that are clinically significant (e.g., antigens associated with various types of cancer) and/or TCR sequences that bind the clinically significant antigens. However, in order to improve identification and selection of clinically significant peptides that will provoke a suitable response in a human T cell and/or of TCR capable of binding the clinically significant antigens (e.g., for adoptive immunotherapy of cancer, T cell vaccination for autoimmunity, etc.), there remains a need for in vivo and in vitro systems that mimic aspects of human immune system. Thus, there is a need for biological systems (e.g., genetically modified non-human animals and cells) that can display components of a human immune system, particularly components of the T cell immune response.

SUMMARY OF THE INVENTION

As disclosed herein, the thymus of genetically modified non-human animals comprising a substantially humanized T cell immune system has similar absolute numbers of thymocytes and CD3+ T cells as control animals. Additionally, these cells show comparable development into single positive T cells to control animals and are capable of generating a robust human cellular response against antigen, e.g., a viral antigen. The human cellular response of the non-human animals generally comprises activated non-human T cells expressing human or humanized T cell receptor (TCR) variable domains that recognize antigen presented in the peptide binding cleft formed by human leukocyte antigen (HLA) extracellular domains, which may be expressed on the surface of non-human antigen presenting cells. In some embodiments, the substantially humanized T cell immune system comprises (A) a non-human T cell that expresses
  (i) a T cell co-receptor polypeptide comprising a part or all of the extracellular portion of a human T cell co-receptor, e.g., a T cell co-receptor polypeptide comprising one or more human T cell co-receptor extracellular domains such that the T cell co-receptor polypeptide is capable of associating with and/or associates with
    (a) one or more extracellular domains of a human or humanized HLA molecule (e.g., a first human HLA extracellular domain that is a binding site for the T cell co-receptor polypeptide and/or a second human HLA extracellular domain that forms a peptide binding cleft, e.g., with a third human HLA extracellular domain), (b) an extracellular domain of a human or humanized TCR variable domain (e.g., a human or humanized TCRα variable domain and/or a human or humanized TCRβ variable domain that is respectively encoded by at least one human TCRα and/or TCRβ variable region gene segment), and/or (c) an extracellular domain of a human TCR constant domain, and (ii) a T cell receptor (TCR) comprising at least a human TCR variable domain; and optionally (B) a non-human antigen presenting cell that presents antigen in the context of human HLA, e.g., a non-human antigen presenting cell that expresses on its cell surface at least one MHC molecule that comprises a peptide binding cleft formed by two human HLA extracellular domains, and is capable of activating and/or activates the non-human T cell.

In one aspect, the non-human T cell and the non-human antigen presenting cell are found in or isolated from the same non-human animal.

Accordingly, provided herein are non-human animals (e.g., rodents, e.g., mice or rats) genetically engineered to express (A) a human or humanized T cell co-receptor (e.g., human or humanized CD4 and/or human or humanized CD8 (e.g., human or humanized CD8α and/or human or humanized CD8β)), (B) a human or humanized major histocompatibility complex that associates with the human or humanized T cell co-receptor (e.g., human or humanized MHC II (e.g., human or humanized MHC II α and/or human or humanized MHC IIβ) that binds the human or humanized CD4 and/or human or humanized MHC I (e.g., human or humanized MHC Iα, and optionally human or humanized β2 microglobulin) that binds the human or humanized CD8), and/or (C) a human or humanized T cell receptor (TCR);

as well as embryos, tissues, and cells expressing the same, and nucleic acids encoding the same. Also provided are methods of making and using the disclosed non-human animals.

In one aspect, provided is a genetically modified non-human animal, comprising (A) a humanized CD4 co-receptor and/or a humanized CD8 co-receptor comprising a humanized CD8α polypeptide and a humanized CD8β polypeptide (e.g., the non-human animal comprises, e.g., in its germline genome, first nucleotide sequence encoding a chimeric human/non-human CD4 polypeptide, and/or a second nucleotide sequence encoding a chimeric human/non-human CD8α polypeptide and a third nucleotide sequence encoding a chimeric human/non-human CD8β polypeptide), wherein each humanized T cell co-receptor polypeptide comprises at least transmembrane and cytoplasmic domains of a non-human T cell co-receptor, e.g., wherein the humanized CD4 co-receptor comprises at least transmembrane and cytoplasmic domains of a non-human CD4 co-receptor and/or the humanized CD8 co-receptor comprises at least transmembrane and cytoplasmic domains of non-human CD8α and non-human CD8β polypeptides, wherein each chimeric T cell co-receptor polypeptide comprises part or all of an extracellular portion of a human T cell co-receptor, e.g., one or more extracellular domains of a human T cell co-receptor, e.g., at least an extracellular domain of a human T cell co-receptor that associates with an HLA molecule, e.g., wherein the humanized CD4 co-receptor comprises the extracellular portion (or parts thereof, e.g., extracellular domain(s)) of human CD4 that is responsible for interacting with MHC II, T cell receptor variable domains, T cell receptor constant domains, or a combination thereof, and/or e.g., wherein the humanized CD8 co-receptor comprises the extracellular portions (or parts thereof, e.g., extracellular domains) of human CD8α and human CD8β that is responsible for interacting with MHC I, T cell receptor variable domains, T cell receptor constant domains, or a combination thereof;

(B) a human(ized) TCR (e.g., the non-human animal comprises, e.g., in its germline genome, an unrearranged T cell receptor (TCR) α variable gene locus comprising at least one human Vα segment and at least one human Jα segment, operably linked to a non-human TCRα constant gene sequence and/or an unrearranged TCRβ variable gene locus comprising at least one human Vβ segment, at least one human Dβ segment, and at least one human Jβ segment, operably linked to a non-human TCRβ constant gene sequence); and optionally, (C) a human(ized) MHC II complex that associates with the humanized CD4 co-receptor and/or a human(ized) MHC I complex that associates with the humanized CD8 co-receptor (e.g., the non-human animal comprises, e.g., in its germline genome, first nucleic acid sequence encoding a chimeric human/non-human MHC IIα polypeptide and a second nucleic acid sequence encoding a chimeric human/non-human MHC IIβ polypeptide, and/or a third nucleic acid sequence encoding a chimeric human/non-human MHC I polypeptide), wherein each chimeric MHC polypeptide comprises at least an extracellular portion (or part thereof) of a human MHC polypeptide (e.g., HLA polypeptide) that, either alone (e.g., MHC I) or when complexed with another chimeric MHC polypeptide (e.g., MHC II α and MHC II β) is respectively capable of associating with the human(ized) CD8 co-receptor or human(ized)CD4 co-receptor and presenting peptide in the context of HLA, e.g., wherein a humanized MHC II complex comprises (i) a chimeric human/non-human MHC II α polypeptide comprising α1 and β2 domains of a human HLA class II α polypeptide and the transmembrane and cytoplasmic domains of a non-human HLA class II α polypeptide and (ii) a chimeric human/non-human MHC II β polypeptide comprises β1 and β2 domains of a human HLA class II β polypeptide the transmembrane and cytoplasmic domains of a non-human HLA class II β polypeptide and/or wherein a humanized MHC I complex comprises α1, α2, and α3 domains of a human MHC I polypeptide, and optionally a human(ized) β2 microglobulin.

In some embodiments, the non-human animal comprises (A) a humanized CD4 co-receptor and a humanized CD8 co-receptor comprising a humanized CD8α polypeptide and a humanized CD8β polypeptide (e.g., the non-human animal comprises, e.g., in its germline genome, first nucleotide sequence encoding a chimeric human/non-human CD4 polypeptide, a second nucleotide sequence encoding a chimeric human/non-human CD8α polypeptide and a third nucleotide sequence encoding a chimeric human/non-human CD8β polypeptide), wherein each humanized T cell co-receptor polypeptide comprises at least transmembrane and cytoplasmic domains of a non-human T cell co-receptor, e.g., wherein the humanized CD4 co-receptor comprises at least transmembrane and cytoplasmic domains of a non-human CD4 co-receptor and the humanized CD8 co-receptor comprises at least transmembrane and cytoplasmic domains of non-human CD8α and non-human CD8β polypeptides, wherein each chimeric T cell co-receptor polypeptide comprises part or all of an extracellular portion of a human T cell co-receptor, e.g., one or more extracellular domains of a human T cell co-receptor, e.g., at least an extracellular domain of a human T cell co-receptor that associates with an HLA molecule, e.g., wherein the humanized CD4 co-receptor comprises the extracellular portion (or parts thereof, e.g., extracellular domain(s)) of human CD4 that is responsible for interacting with MHC II, T cell receptor variable domains, T cell receptor constant domains, or a combination thereof, and/or e.g., wherein the humanized CD8 co-receptor comprises the extracellular portions (or parts thereof, e.g., extracellular domains) of human CD8α and human CD8β that is responsible for interacting with MHC I, T cell receptor variable domains, T cell receptor constant domains, or a combination thereof;

(B) a humanized TCR (e.g., the non-human animal comprises, e.g., in its germline genome, an unrearranged T cell receptor (TCR) α variable gene locus comprising at least one human Vα segment and at least one human Jα segment, operably linked to a non-human TCRα constant gene sequence and/or an unrearranged TCRβ variable gene locus comprising at least one human Vβ segment, at least one human Dβ segment, and at least one human Jβ segment, operably linked to a non-human TCRβ constant gene sequence); and (C) a humanized MHC II complex that associates with the humanized CD4 co-receptor and a humanized MHC I complex that associates with the humanized CD8 co-receptor (e.g., the non-human animal comprises, e.g., in its germline genome, first nucleic acid sequence encoding a chimeric human/non-human MHC IIα polypeptide, a second nucleic acid sequence encoding a chimeric human/non-human MHC IIβ polypeptide and a third nucleic acid sequence encoding a chimeric human/non-human MHC I polypeptide), wherein each chimeric MHC polypeptide comprises at least an extracellular portion (or part thereof) of a human MHC polypeptide (e.g., HLA polypeptide) that, either alone (e.g., MHC I) or when complexed with another chimeric MHC polypeptide (e.g., MHC II α and MHC II β) is respectively capable of associating with the humanized CD8 co-receptor or humanized CD4 co-receptor and presenting peptide in the context of HLA, e.g., wherein a humanized MHC II complex comprises (i) a chimeric human/non-human MHC II α polypeptide comprising α1 and β2 domains of a human HLA class II α polypeptide and the transmembrane and cytoplasmic domains of a non-human HLA class II α polypeptide and (ii) a chimeric human/non-human MHC II β polypeptide comprises β1 and β2 domains of a human HLA class II β polypeptide the transmembrane and cytoplasmic domains of a non-human HLA class II β polypeptide and (iii) a humanized MHC I complex comprises α1, α2, and α3 domains of a human MHC I polypeptide, and optionally a human(ized) β2 microglobulin (e.g., the non-human animal further comprises a β2 microglobulin locus encoding a polypeptide comprising a human β2 microglobulin amino acid sequence, or a portion thereof).

In some embodiments, the first nucleotide sequence encoding a chimeric T cell CD4 co-receptor polypeptide is present at an endogenous CD4 T cell co-receptor locus, and/or the second nucleotide sequence encoding a chimeric T cell CD8α co-receptor polypeptide is present at an endogenous CD8α T cell co-receptor locus and the third nucleotide sequence encoding a chimeric T cell CD8β co-receptor polypeptide is present at an endogenous CD8β T cell co-receptor locus. Additional embodiments include a chimeric human/non-human CD4 polypeptide encoded by the gene set forth in FIG. 5A (e.g., wherein the human portion of the resulting chimeric human/non-human CD4 T cell co-receptor polypeptide comprises at least human Ig1, human Ig2 and human Ig3 domains, otherwise respectively referred to as D1, D2 and D3 domains) and/or a chimeric CD8 co-receptor encoded by the genes set forth in FIG. 5B (e.g., wherein the human portion of the chimeric CD8 co-receptor comprises all or substantially all of the extracellular portion of a human CD8 polypeptide (e.g., CD8α and/or CD8β), including human immunoglobulin V (IgV)-like α and β domains. In some embodiments, the human portion of the chimeric CD4 T cell co-receptor polypeptide comprises one or more extracellular domains of a human CD4 polypeptide (e.g., D1, D2, D3, D4, or any combination thereof) and the non-human portion of the chimeric CD4 T cell co-receptor polypeptide comprises the transmembrane and cytoplasmic domains of a non-human CD4 T cell co-receptor, the human portion of the chimeric CD8α polypeptide comprises an extracellular domain (e.g., an IgV-like domain) of a human CD8α polypeptide and the non-human portion of the chimeric CD8α polypeptide comprises the transmembrane and cytoplasmic domains of a non-human CD8α polypeptide, and/or the human portion of the CD8β polypeptide comprises an extracellular domain (e.g., an IgV-like domain) of the human CD8β polypeptide and the non-human portion of the chimeric CD8β T cell co-receptor polypeptide comprises the transmembrane and cytoplasmic domains of a non-human CD8β polypeptide.

In some embodiments, the first nucleic acid sequence encoding the human(ized) MHC II α is present at an endogenous non-human MHC II α locus and the second nucleic acid sequence encoding the human(ized) MHC II β is present at an endogenous non-human MHC II β locus, and/or the third nucleic acid sequence encoding the human (ized) MHC I is present at an endogenous non-human MHC I locus. In one aspect, the human(ized) MHC IIα polypeptide comprises the extracellular portion (or part thereof) of a human MHD IIα polypeptide (e.g., an HLA class IIα polypeptide), the human(ized) MHC IIβ polypeptide comprises the extracellular portion (or part thereof) of a human MHC IIβ polypeptide (e.g., an HLA class Iβ polypeptide) and/or the human(ized) MHC I polypeptide comprises the extracellular portion (or part thereof) of a human MHC I polypeptide (e.g., an HLA class I polypeptide). In some embodiments, the humanized MHC II α polypeptide comprises human MHC II α 1 and α2 domains, the humanized MHC II β polypeptide comprises human MHC II β1 and β2 domains and/or the humanized MHC I polypeptide comprises human MHC I α1, α2, and α3 domains. In some embodiments, the first nucleic acid sequence encoding the chimeric human/non-human MHC II α polypeptide is expressed under regulatory control of endogenous non-human MHC II α promoter and regulatory elements, the second nucleic acid sequence encoding the chimeric human/non-human MHC II β polypeptide is expressed under regulatory control of endogenous non-human MHC II β promoter and regulatory elements, and/or the third nucleic acid sequence encoding the chimeric human/non-human MHC I polypeptide is expressed under regulatory control of an endogenous non-human MHC I promoter and regulatory elements. In additional embodiments, a non-human portion of the chimeric human/non-human MHC II α polypeptide comprises transmembrane and cytoplasmic domains of an endogenous non-human MHC II α polypeptide, a non-human portion of the chimeric human/non-human MHC II β polypeptide comprises transmembrane and cytoplasmic domains of an endogenous non-human MHC II β polypeptide and/or a non-human portion of the chimeric human/non-human MHC I polypeptide comprises transmembrane and cytoplasmic domains of an endogenous non-human MHC I polypeptide. Embodiments include non-human animals wherein the human portion of the proteins of chimeric human/non-human MHC II complex is derived from corresponding human HLA class II proteins selected from the group consisting of HLA-DR, HLA-DQ, and HLA-DP and/or wherein the human portion of the third chimeric human/non-human MHC I polypeptide is derived from human HLA-A, human HLA-B, or human HLA-C. As non-limiting examples, in some embodiments, the chimeric MHC II α polypeptide comprises the extracellular portion, or a part thereof, of a HLA-DRα protein, a HLA-DQ α protein, or a HLA-DP α protein, the chimeric MHC II β polypeptide comprises the extracellular portion, or a part thereof, of a HLA-DRβ protein, a HLA-DQ β protein, or a HLA-DP β protein, and/or the chimeric MHC I polypeptide comprises the extracellular portion, or a part thereof, of a human HLA-A protein, a human HLA-B protein, or a human HLA-C protein. Non-human animals are also provided, wherein the human portion of the chimeric human/non-human MHC II proteins derived from corresponding human HLA-DR proteins, e.g., the human portion of the human/non-human MHC II α polypeptide comprises α1 and β2 domains of the α chain of HLA-DR2 and the human portion of the human/non-human MHC II β polypeptide comprises β1 and β2 domains of the β chain of HLA-DR2 and/or wherein the human portion of the MHC I polypeptide is derived from a human HLA-A polypeptide, e.g., the human portion of the human/non-human MHC I polypeptide comprises the α1, α2, and α3 domains of a human HLA-A2 polypeptide, e.g., the α1, α2, and α3 domains of a human HLA-A2.1 polypeptide. Non-human animals wherein the non-human portions of the MHC II complex are derived from a murine H-2E encoding sequence and/or wherein the non-human portions of the MHC I polypeptide is derived from a murine H-2K encoding sequence are also provided. For example, the chimeric MHC II α polypeptide comprises the transmembrane and cytoplasmic domains of a murine H-2E α polypeptide, the chimeric MHC II β polypeptide comprises the transmembrane and cytoplasmic domains of a murine H-2E β polypeptide, and the chimeric MHC I polypeptide comprises the transmembrane and cytoplasmic domains of a murine H-2K polypeptide.

In some embodiments, the unrearranged TCRα variable gene locus is present at an endogenous TCRα variable gene locus and the unrearranged TCRβ variable gene locus is present at an endogenous TCRβ variable gene locus. In some aspects, the unrearranged TCRα variable gene locus comprises a complete repertoire of human unrearranged Vα gene segments and a complete repertoire of human unrearranged Jα gene segments and/or the unrearranged TCRβ variable gene locus comprises a complete repertoire of human unrearranged Vβ gene segments, a complete repertoire of human unrearranged Dβ gene segments and a complete repertoire of human unrearranged Jβ gene segments. In some embodiments, the human unrearranged Vα and Jα gene segments rearrange to form a rearranged human Vα/Jα sequence and/or the human unrearranged Vβ Dβ and Jβ gene segment rearrange to form a rearranged human Vβ/Dβ/Jβ sequence. In some embodiments, a non-human animal as disclosed herein expresses a T cell receptor comprising a human TCRα variable region and/or a human TCRβ variable region on the surface of a T cell. In some embodiments, endogenous non-human Vα and Jα segments are incapable of rearranging to form a rearranged Vα/Jα sequence and/or endogenous non-human Vβ, Dβ, and Jβ segments are incapable of rearranging to form a rearranged Vβ/Dβ/Jβ sequence, e.g., the animal may lack a functional endogenous non-human TCRα variable locus and/or the animal may lack a functional endogenous non-human TCRβ variable locus, e.g., the animal comprises (a) a deletion of all or substantially all functional endogenous Vα gene segments, (b) a deletion of all or substantially all functional endogenous Jα gene segments, (c) a deletion of all or substantially all functional endogenous Vβ gene segments, (d) a deletion of all or substantially all functional endogenous Dβ gene segments, (e) a deletion of all or substantially all functional endogenous Jβ gene segments, and/or (f) a combination thereof. In some embodiments, the endogenous non-human TCRα variable locus lacks all or substantially all functional endogenous Vα gene segments and/or lacks all or substantially all functional endogenous Jα gene segments; and/or the endogenous non-human TCRβ variable locus (a) lacks all or substantially all functional endogenous Vβ gene segments, (b) lacks all or substantially all functional endogenous Dβ gene segments, (c) lacks all or substantially all functional endogenous Jβ gene segments, or (d) any combination of (a), (b), and (c)

In some embodiments, the first, second and/or third nucleotide sequence(s) respectively encoding the chimeric T cell CD4, CD8α and/or CD8 β co-receptor polypeptide(s) is present at endogenous T cell co-receptor loci, e.g., endogenous CD4, CD8α and/or CD8 β co-receptor loci respectively; the unrearranged TCRα variable gene locus is present at an endogenous TCRα variable gene locus; the unrearranged TCRβ variable gene locus is present at an endogenous TCRβ variable gene locus; and/or the first, second and/or third nucleic acid sequence(s) respectively encoding the chimeric MHC II α, MHC II β, and/or MHC I polypeptide(s) is present at endogenous MHC loci; e.g., MHC II α, MHC II β, and/or MHC I loci, respectively. In some embodiments, the nucleotide sequence(s) encoding the chimeric T cell co-receptor(s), the unrearranged TCRα variable gene locus, the unrearranged TCRβ variable gene locus and/or the nucleic acid sequence(s) encoding the chimeric MHC molecule(s) may be operably linked to non-human promoter and regulatory sequences. For example, the first nucleotide sequence may be expressed under regulatory control of endogenous non-human CD4 promoter and regulatory elements, the second nucleotide sequence may be expressed under regulatory control of endogenous non-human CD8α promoter and regulatory elements, and and/or the third nucleotide sequence may expressed under regulatory control of endogenous non-human CD8β promoter and regulatory elements; the unrearranged TCRα variable gene locus may be expressed under regulatory control of endogenous TCRα (variable) regulatory and promoter elements and the unrearranged TCRβ variable gene locus may be expressed under regulatory control of endogenous TCRβ (variable) regulatory and promoter elements; the first nucleic acid sequence may be expressed under regulatory control of endogenous non-human MHC II α promoter and regulatory elements, the second nucleic acid sequence may be expressed under regulatory control of endogenous non-human MHC II β promoter and regulatory elements, and the third nucleic acid sequence may expressed under regulatory control of an endogenous non-human MHC I promoter and regulatory elements.

In some embodiments, a nucleotide sequence encoding the extracellular portion (or parts thereof, e.g., D1, D2, D3 and/or D4) of the human CD4 polypeptide replaces a sequence encoding the extracellular portion (or parts thereof, e.g., D1, D2, D3 and/or D4) of an endogenous non-human (mouse) CD4 co-receptor polypeptide, and may be operably linked to endogenous non-human (mouse) CD4 transmembrane and cytoplasmic domain encoding sequences, at the endogenous non-human (mouse) CD4 co-receptor locus; a nucleotide sequence encoding all or part of the extracellular portion of a human CD8α polypeptide replaces a sequence encoding all or part of an extracellular portion of an endogenous non-human (mouse) T cell CD8α polypeptide, and may be operably linked to endogenous non-human (mouse) CD8α transmembrane and cytoplasmic domain encoding sequences, at the endogenous non-human (mouse) CD8α locus; a nucleotide sequence encoding all or part of the extracellular domain of a human CD8β polypeptide replaces a sequence encoding all or part of an extracellular domain of an endogenous non-human (mouse) T cell CD8β polypeptide and may be operably linked to endogenous non-human CD8β transmembrane and cytoplasmic domain encoding sequences, at the endogenous CD8β locus; an unrearranged TCRα variable gene locus replaces one or more endogenous Vα and/or Jα gene segments at an endogenous non-human (mouse) TCRα variable gene locus; an unrearranged TCRβ variable gene locus replaces one or more endogenous Vβ, Dβ and/or Jα gene segments at an endogenous non-human (mouse) TCRβ variable gene locus; a nucleic acid sequence encoding the extracellular portion (or parts thereof, e.g., α1 and β2 domains) of a human MHC II α polypeptide replaces a sequence encoding the extracellular portion (or parts thereof, e.g., α1 and β2 domains) of an endogenous non-human (mouse) MHC II α polypeptide, and may be operably linked to endogenous non-human (mouse) MHC II α transmembrane and cytoplasmic domain encoding sequences, at an endogenous non-human (mouse) MHC II α locus; a nucleic acid sequence encoding the extracellular portion (or parts thereof, e.g., β1 and β2 domains) of a human MHC II β polypeptide replaces a sequence encoding the extracellular portion (or parts thereof, e.g., β1 and β2 domains) of an endogenous non-human (mouse) MHC II β polypeptide, and may be operably linked to endogenous non-human (mouse) MHC II β transmembrane and cytoplasmic domain encoding sequences, at an endogenous non-human (mouse) MHC II β locus; and/or a nucleic acid sequence encoding the extracellular portion (or parts thereof, e.g., α1, α2 and/or α3 domains) of a human MHC I polypeptide replaces a sequence encoding the extracellular portion (or parts thereof, e.g., α1, α2 and/or α3 domains) of an endogenous non-human (mouse) MHC I polypeptide, and may be operably linked to endogenous non-human (mouse) MHC I transmembrane and cytoplasmic domain encoding sequences, at an endogenous non-human (mouse) MHC I locus.

In some embodiments, a genetically modified non-human animal as disclosed herein does not express a functional endogenous non-human T cell CD4 co-receptor from its endogenous locus, does not express a functional endogenous non-human T cell CD8 co-receptor from its endogenous CD8 locus, does not express a functional TCRα variable domain from an endogenous TCRα variable locus, does not express a function TCRβ variable domain from an endogenous TCRβ variable locus, does not express an extracellular domain of an endogenous MHC II complex from an endogenous MHC II locus (e.g., on a cell surface) and/or does not express an extracellular domain of an endogenous MHC I polypeptide from an endogenous MHC I locus (e.g., on a cell surface).

Any non-human animal disclosed herein may further comprise a β2 microglobulin locus encoding a polypeptide comprising a human or humanized β2 microglobulin amino acid sequence, wherein the non-human animal expresses the human or humanized β2 microglobulin polypeptide. In some embodiments, the non-human animal does not express a functional endogenous non-human animal β2 microglobulin polypeptide from an endogenous non-human β2 microglobulin locus. In some embodiments, the β2 microglobulin locus is operably linked to endogenous non-human β2 microglobulin regulatory elements. In one embodiment, the β2 microglobulin locus comprises a nucleotide sequence set forth in exon 2, exon 3, and exon 4 (e.g., exon 2 to exon 4) of a human β2 microglobulin gene, and optionally, the β2 microglobulin locus further comprises a nucleotide sequence set forth in exon 1 of a non-human, e.g., rodent, β2 microglobulin gene.

Non-human animals as provided herein may be a rodent, e.g., a mouse or a rat.

Also provided herein is a mouse that expresses chimeric human/murine T cell CD4, CD8α, and CD8β co-receptor polypeptides each respectively comprising murine CD4, CD8α, and CD8β transmembrane and cytoplasmic domains; a T cell receptor comprising a human TCRα variable region and a human TCRβ variable region on the surface of a T cell; chimeric human/murine MHD IIα, MHD IIβ, and MHC I polypeptides each respectively comprising extracellular domains of a human MHC II α (e.g., human HLA class II α1 and β2 domains), MHC II β (human HLA class II β1 and β2 domains), and MHC I polypeptide (e.g., human HLA class I α1, α2, and α3 domains); and optionally a human or humanized β2 microglobulin polypeptide. In one embodiment, provided herein are non-human animals, e.g., mice, wherein the first nucleic acid sequence encodes an α chain of a chimeric human/murine HLA-DR/H-2E polypeptide, the second nucleotide sequence encodes a β chain of a chimeric HLA-DR/H-2E polypeptide, and the third nucleic acid sequence encodes a chimeric human/murine HLA-A/H-2K polypeptide, and wherein the mouse expresses HLA-A/H-2K and HLA-DR/H-2E proteins.

Also provided herein is a non-human animal comprising a substantially humanized T cell immune system, e.g., wherein the substantially humanized T cell immune system mounts a substantially humanized T cell immune response against an antigen. In some embodiments, the substantially humanized T cell immune response comprises activated T cells expressing human T cell receptor (TCR) variable domains that recognize antigen presented in the context of human leukocyte antigen (HLA) extracellular domains and/or antigen presenting cells that present antigen in the context of HLA extracellular domains. In some embodiments, the substantially humanized T cell immune system comprises: (a) a non-human T cell that expresses a T cell co-receptor polypeptide comprising a human T cell co receptor domain that binds to a human HLA molecule and/or a T cell receptor (TCR) comprising a TCR variable domain that is encoded by at least one human TCR variable region gene segment; and (b) a non-human antigen presenting cell that presents antigen in the context of human HLA and activates the non-human T cell.

Also provided are methods of making and using the non-human animals disclosed herein. Generally, methods of making a genetically modified non-human animal as disclosed herein comprise (a) introducing into the genome of the non-human animal a first nucleotide sequence encoding a chimeric human/non-human T cell co-receptor polypeptide (e.g., a chimeric CD4 polypeptide), and/or a second nucleotide sequence encoding a second chimeric human/non-human T cell co-receptor polypeptide (e.g., a chimeric CD8α polypeptide) and a third nucleotide sequence encoding a third chimeric human/non-human T cell co-receptor polypeptide (e.g., a CD8β polypeptide), wherein a non-human portion of each chimeric T cell co-receptor polypeptide comprises at least transmembrane and cytoplasmic domains of a non-human T cell co-receptor, and wherein a human portion of each chimeric polypeptide comprises an extracellular portion (or part thereof, e.g., one or more domains) of a human T cell co-receptor; (b) inserting into the genome of the non-human animal an unrearranged T cell receptor (TCR) α variable gene locus comprising at least one human Vα segment and at least one human Jα segment, operably linked to a non-human TCRα constant gene sequence and/or an unrearranged TCRβ variable gene locus comprising at least one human Vβ segment, at least one human Dβ segment, and at least one human Jβ segment, operably linked to a non-human TCR constant gene sequence; and optionally (c) placing into the genome a first nucleic acid sequence encoding a first chimeric human/non-human MHC polypeptide (e.g., a chimeric MHC IIα polypeptide), a second nucleic acid sequence encoding a second chimeric human/non-human MHC polypeptide (e.g., a chimeric MHC IIβ polypeptide) and/or a third nucleic acid sequence encoding a third chimeric human/non-human MHC polypeptide (e.g., a chimeric MHC I polypeptide) and/or (d) adding into the genome of the non-human animal a β2 microglobulin locus encoding a human or humanized β2 microglobulin polypeptide. In some embodiments, the first nucleotide sequence encodes the extracellular portion, or a part thereof, of human CD4 operably linked to at least transmembrane and cytoplasmic domains of a non-human CD4 co-receptor, the second nucleotide sequence encodes the extracellular portion, or a part thereof, of human CD8α and at least the transmembrane and cytoplasmic domains of a non-human CD8α, the third nucleotide sequence encodes the extracellular portion, or a part thereof, of human CD8β and at least the transmembrane and cytoplasmic domains of non-human CD8β, the first nucleic acid sequence encodes the extracellular portion (or part thereof) of a human HLA class II α polypeptide and at least the transmembrane and cytoplasmic domains of a non-human MHC II α polypeptide, the second nucleic acid sequence encodes the extracellular portion (or part thereof) of a human HLA class II β polypeptide and at least the transmembrane and cytoplasmic domains of a non-human MHC II β polypeptide, the third nucleic acid sequence encodes the extracellular portion (or part thereof) of a human HLA class I polypeptide and the transmembrane and cytoplasmic domains of a non-human MHC I polypeptide, and the β2 microglobulin locus comprises a nucleotide sequence set forth in exons 2 to 4 of the human β2 microglobulin gene, e.g., nucleotide sequences set forth in exons 2, 3, and 4 of the human β2 microglobulin gene.

Methods of making non-human animals include embodiments wherein (a) introducing the first, second and/or third nucleotide sequence(s) encoding the chimeric T cell co-receptor polypeptide(s) into the genome of the non-human animal comprises replacing at an endogenous CD4 locus a nucleotide sequence encoding an endogenous non-human CD4 polypeptide with a nucleotide sequence encoding a chimeric human/non-human CD4 polypeptide, and/or replacing at an endogenous CD8α locus a nucleotide sequence encoding an endogenous non-human CD8α polypeptide with a nucleotide sequence encoding a chimeric human/non-human CD8α polypeptide and replacing at an endogenous CD8β locus a nucleotide sequence encoding an endogenous non-human CD8β polypeptide with a nucleotide sequence encoding a chimeric human/non-human CD8β polypeptide; (b) inserting the unrearranged TCRα locus and/or unrearranged TCR locus into the genome of the animal comprises replacing an endogenous non-human TCRα variable gene locus with an unrearranged humanized TCRα variable gene locus comprising at least one human Vα segment and at least one human Jα segment to generate a humanized TCRα variable gene locus, wherein the humanized TCRα variable gene locus is operably linked to endogenous non-human TCRα constant region and/or replacing an endogenous non-human TCRβ variable gene locus with an unrearranged humanized TCRβ variable gene locus comprising at least one human Vβ segment, at least one human Dβ segment, and at least one human Jβ segment to generate a humanized TCRβ variable gene locus, wherein the humanized TCRβ variable gene locus is operably linked to endogenous non-human TCRβ constant region; (c) placing the first, second and/or third nucleic acid sequence(s) encoding chimeric MHC polypeptide(s) into the genome of the non-human animal comprises replacing at an endogenous non-human MHC II locus a nucleotide sequence encoding a non-human MHC II complex with a nucleotide sequence encoding a chimeric human/non-human MHC II complex and replacing at an endogenous non-human MHC I locus a nucleotide sequence encoding a non-human MHC I polypeptide with a nucleotide sequence encoding a chimeric human/non-human MHC I polypeptide and/or (d) adding the β2 microglobulin locus encoding a human or humanized β2 microglobulin polypeptide into the genome of a non-human animal comprises replacing at the endogenous non-human β2 microglobulin locus a nucleotide sequence encoding a non-human β2 microglobulin polypeptide with a nucleotide sequence encoding a human or humanized β2 microglobulin polypeptide.

In some embodiments, (a) introducing the first, second and/or third nucleotide sequence into the genome of the non-human animal respectively comprises (i) replacing at an endogenous CD4 locus a nucleotide sequence encoding the extracellular portion (or a part thereof) of an endogenous non-human CD4 polypeptide with a nucleotide sequence encoding the extracellular portion (or a part thereof) of a human CD4 polypeptide in operable linkage with sequences encoding the endogenous non-human CD4 transmembrane and cytoplasmic domains, (ii) replacing at an endogenous CD8α locus a nucleotide sequence encoding the extracellular portion (or a part thereof) of an endogenous non-human CD8α polypeptide with a nucleotide sequence encoding the extracellular portion (or a part thereof) of a human CD8α polypeptide in operable linkage with sequences encoding the endogenous non-human CD8α transmembrane and cytoplasmic domains and/or (iii) replacing at an endogenous CD8β locus a nucleotide sequence encoding the extracellular portion (or a part thereof) of an endogenous non-human CD8β polypeptide with a nucleotide sequence encoding the extracellular portion (or a part thereof) of a human CD8β polypeptide in operable linkage with sequences encoding the endogenous non-human CD8β transmembrane and cytoplasmic domains; (b) inserting the unrearranged TCRα locus and/or unrearranged TCRβ locus into the genome of the animal respectively comprises (i) replacing an endogenous non-human TCRα variable gene locus with an unrearranged humanized TCRα variable gene locus comprising at least one human Vα segment and at least one human Jα segment to generate a humanized TCRα variable gene locus, wherein the humanized TCRα variable gene locus is operably linked to endogenous non-human TCRα constant region and/or (ii) replacing an endogenous non-human TCRβ variable gene locus with an unrearranged humanized TCRβ variable gene locus comprising at least one human Vβ segment, at least one human Dβ segment, and at least one human Jβ segment to generate a humanized TCRβ variable gene locus, wherein the humanized TCRβ variable gene locus is operably linked to endogenous non-human TCRβ constant region; (c) placing the first, second and/or third nucleic acid sequence into the genome of the non-human animal respectively comprises (i) replacing at an endogenous non-human MHC II α locus a nucleotide sequence encoding the extracellular portion (or a part thereof) of a non-human MHC II α polypeptide with a nucleotide sequence encoding the extracellular portion (or a part thereof) of a human HLA class II α polypeptide in operable linkage with sequences encoding the endogenous non-human MHC II α transmembrane and cytoplasmic domains, (ii) replacing at an endogenous non-human MHC II β locus a nucleotide sequence encoding the extracellular portion (or a part thereof) of a non-human MHC II β polypeptide with a nucleotide sequence encoding the extracellular portion (or a part thereof) of a human HLA class II β polypeptide in operable linkage with sequences encoding the endogenous non-human MHC II β transmembrane and cytoplasmic domains and/or (iii) replacing at an endogenous non-human MHC I locus a nucleotide sequence encoding the extracellular portion (or a part thereof) of a non-human MHC I polypeptide with a nucleotide sequence encoding the extracellular portion (or a part thereof) of a human HLA class I polypeptide in operable linkage with sequences encoding the endogenous non-human MHC I transmembrane and cytoplasmic domains; and/or replacing at an endogenous β2 microglobulin locus a nucleotide sequence set forth in exon 2-exon 4 with a nucleotide sequence comprising exons 2, 3, and 4 of a human β2 microglobulin gene.

In one embodiment, the introducing step comprises replacing in a first non-human animal at an endogenous CD4 locus a nucleotide sequence encoding an endogenous non-human CD4 polypeptide with a nucleotide sequence encoding a chimeric human/non-human CD4 polypeptide, replacing in a second non-human animal at an endogenous CD8α locus a nucleotide sequence encoding an endogenous non-human CD8α polypeptide with a nucleotide sequence encoding a chimeric human/non-human CD8α polypeptide and replacing at an endogenous CD8β locus a nucleotide sequence encoding an endogenous non-human CD8β polypeptide with a nucleotide sequence encoding a chimeric human/non-human CD8β polypeptide. In some embodiments, the introducing step comprises replacing in a first non-human animal at an endogenous CD4 locus a nucleotide sequence encoding the extracellular portion (or a part thereof) of an endogenous non-human CD4 polypeptide with a nucleotide sequence encoding the extracellular portion (or a part thereof) of a human CD4 polypeptide in operable linkage with sequences encoding the endogenous non-human CD4 transmembrane and cytoplasmic domains, replacing in a second non-human animal at an endogenous CD8α locus a nucleotide sequence encoding the extracellular portion (or a part thereof) of an endogenous non-human CD8α polypeptide with a nucleotide sequence encoding the extracellular portion (or a part thereof) of a human CD8α polypeptide in operable linkage with sequences encoding the endogenous non-human CD8α transmembrane and cytoplasmic domains and replacing at an endogenous CD8β locus a nucleotide sequence encoding the extracellular portion (or a part thereof) of an endogenous non-human CD8β polypeptide with a nucleotide sequence encoding the extracellular portion (or a part thereof) of a human CD8β polypeptide in operable linkage with sequences encoding the endogenous non-human CD8β transmembrane and cytoplasmic domains. In some embodiments, the replacing steps are performed simultaneously or in any order.

In some embodiments, the inserting step comprises replacing in a third non-human animal an endogenous non-human TCRα variable gene locus with an unrearranged humanized TCRα variable gene locus comprising at least one human Vα segment and at least one human Jα segment to generate a humanized TCRα variable gene locus, wherein the humanized TCRα variable gene locus is operably linked to endogenous non-human TCRα constant region; replacing in a fourth non-human animal an endogenous non-human TCRβ variable gene locus with an unrearranged humanized TCRβ variable gene locus comprising at least one human Vβ segment, at least one human Dβ segment, and at least one human Jβ segment to generate a humanized TCRβ variable gene locus, wherein the humanized TCRβ variable gene locus is operably linked to endogenous non-human TCRβ constant region. In some embodiments, the replacing steps are performed simultaneously or in any order.

In some embodiments, the placing step comprises, in no particular order, replacing in a fifth non-human animal at an endogenous non-human MHC II locus one or more nucleotide sequence encoding a non-human MHC II complex with one or more nucleotide sequence encoding a chimeric human/non-human MHC II complex; and replacing in the fifth non-human animal at an endogenous non-human MHC I locus a nucleotide sequence encoding a non-human MHC I polypeptide with a nucleotide sequence encoding a chimeric human/non-human MHC I polypeptide. In some embodiments, the placing step comprises replacing in a fifth non-human animal at an endogenous non-human MHC II α locus a nucleotide sequence encoding the extracellular portion (or a part thereof) of a non-human MHC II α polypeptide with a nucleotide sequence encoding the extracellular portion (or a part thereof) of a human MHC II α polypeptide in operable linkage with sequences encoding the endogenous non-human MHC II α transmembrane and cytoplasmic domains and replacing at an endogenous non-human MHC II β locus a nucleotide sequence encoding the extracellular portion (or a part thereof) of a non-human MHC II β polypeptide with a nucleotide sequence encoding the extracellular portion (or a part thereof) of a human MHC II β polypeptide in operable linkage with sequences encoding the endogenous non-human MHC II β transmembrane and cytoplasmic domains; and replacing at an endogenous non-human MHC I locus a nucleotide sequence encoding the extracellular portion (or a part thereof) of a non-human MHC I polypeptide with a nucleotide sequence encoding the extracellular portion (or a part thereof) of a human MHC I polypeptide in operable linkage with sequences encoding the endogenous non-human MHC I transmembrane and cytoplasmic domains in the fifth non-human animal. In some embodiments, the replacing steps are performed simultaneously or in any order.

In some embodiments, the adding step comprises replacing in a sixth non-human animal at the endogenous non-human β2 microglobulin locus a nucleotide sequence encoding a non-human β2 microglobulin polypeptide with a nucleotide sequence encoding a human or humanized β2 microglobulin polypeptide. In some embodiments, the human or humanized β2 microglobulin polypeptide is encoded by the nucleotide sequence set forth in exon 2, exon 3, and exon 4 of the human β2 microglobulin gene.

Methods disclosed herein include embodiments wherein a first, second, and/or third nucleotide sequence(s) encoding chimeric T cell co receptor polypeptide(s) is introduced; the TCRα locus and/or unrearranged TCR locus is inserted; first, second and/or third nucleic acid sequence(s) encoding chimeric MHC polypeptide(s) is placed; and/or the β2 microglobulin locus is added by breeding a non-human animal comprising one or more of the genetic modifications as described herein to another (or more) non-human animal(s) of the same species comprising the remaining genetic modifications. A non-limiting embodiment includes breeding, in any order, the first, second, third, fourth, fifth and sixth non-human animals as described above.

Methods disclosed herein may comprise homologous recombination in non-human embryonic stem (ES) cells. Methods disclosed herein may be used to generate mice as disclosed herein. Non-human animals expressing chimeric human/non-human CD4, CD8α and/or CD8β T cell co-receptor polypeptides, human(ized) TCR α/β proteins, and chimeric MHC II complex and MHC I (with human or humanized β2 microglobulin) may be generated by (a) first introducing each individual human(ized) gene by homologous recombination in individual ES cells respectively and generating each individual non-human animal from such ES cells, and subsequent breeding of each generated non-human animal in any order, (b) introducing all human(ized) genes by sequential homologous recombination in a single ES cell and then generating a non-human animal from such ES cell, or (c) a combination of sequential homologous recombination at some loci in ES cells and breeding. Animals as disclosed herein may also be generated by breeding the progeny of the initial breeding with other animals as appropriate. Breeding and/or homologous recombination may be accomplished in any preferred order.

Also provided are methods of isolating human TCR variable domains specific for an antigen from a non-human animal comprising isolating from a non-human animal provided herein or made according to a method disclosed herein a T cell or TCR protein that binds to the antigen. In some embodiments, the methods may further comprise identifying a first and/or second nucleic acid encoding the TCRα and/or TCRβ variable domains that binds to the antigen and/or culturing a cell comprising one or more vectors in sufficient conditions for expression of the vector(s), wherein the vector(s) comprises a third and/or fourth nucleic acid respectively identical to or substantially identical to the first and/or second nucleic acids, and wherein the third and/or fourth nucleic acid is cloned in-frame with, e.g., a human TCR constant region gene, e.g., a TCRα constant region gene and/or TCR constant region gene, respectively. Tissues and cells comprising the genetic modifications as disclosed herein (which may include rearranged human TCRα and/or TCRβ variable region genes), and nucleic acids encoding such human TCR variable domains expressed by such tissues or cells isolated from a non-human animal modified as described herein are also provided. Also included are (1) recombinant nucleic acids, e.g., expression vectors, comprising the nucleic acid sequences encoding a human TCR variable domain as disclosed herein, e.g., a human rearranged TCRα or human rearranged TCRβ variable region gene, cloned in-frame to an appropriate human TCR constant region gene, e.g., a TCRα constant region gene or TCR constant region gene, respectively, (2) host cells comprising such nucleic acids (e.g., expression vectors) and (3) the TCR expressed by the host cells. In some embodiments, recombinant nucleic acids provided herein comprise a human rearranged TCRδ variable region gene or a TCRγ variable region gene, e.g., derived from a non-human animal genetically modified as disclosed herein or a tissue isolated therefrom, cloned in-frame with a human TCRδ constant region gene or a TCRγ constant region gene, respectively.

A method of generating a humanized T cell response in a non-human animal is also provided, the method generally comprising immunizing a non-human animal a non-human animal genetically modified or having a substantially humanized T cell immune system as described herein with an antigen, e.g., a human antigen, e.g., a human tumor antigen, a human bacterial pathogen, a human viral pathogen, etc. In some embodiments, the non-human animal immunized expresses at least 50% of all functional human TCRVα gene segments and/or at least 50% of all functional human TCRVβ gene segments and/or comprises all or substantially all functional human TCRVα gene segments and/or all or substantially all functional human TCRVβ gene segments.

Also provided are in vitro methods of isolating human TCR specific for an antigen, which generally comprise detecting activation of a first cell of a non-human animal after (a) contact with a second cell of a non-human animal and (b) incubation with the antigen; wherein the first cell expresses a chimeric human/non-human T cell co-receptor and either or both (i) a chimeric human/non-human TCRα chain and (ii) a chimeric human/non-human TCRβ chain, and wherein the second cell expresses a chimeric human/non-human MHC polypeptide. The methods may further comprise isolating a TCR from the first cell, or nucleic acids encoding same.

In the in vitro methods disclosed herein, the antigen may be tumor antigen, a viral antigen, an autoantigen, or a bacterial antigen. In some embodiments, the non-human animal is a rodent, e.g., a rat or a mouse. Also provided herein is tissue, a T cell, a TCR (e.g., a soluble TCR), or a nucleic acid encoding all or part of the TCR that is isolated from a non-human animal genetically modified or having a substantially humanized T cell immune system as described herein, a hybridoma or quadroma derived from such a T cell.

Also provided are compositions, e.g., comprising a first and second cell of a non-human animal; wherein the first cell expresses a chimeric human/non-human T cell co-receptor and optionally, either or both (i) a chimeric human/non-human TCRα chain and (ii) a chimeric human/non-human TCRβ chain, and wherein the second cell expresses a chimeric human/non-human MHC polypeptide that associates with the chimeric human/non-human T cell co-receptor. In some embodiments, the first cell is a non-human T cell. In other embodiments, the second cell is a non-human antigen presenting cell.

BRIEF DESCRIPTION OF THE DRAWINGS

FIG. 1 is a schematic representation (not to scale) of humanized T cell receptor complex comprising humanized TCR alpha and beta proteins, humanized MHC Class I complexed with humanized β2 microglobulin, and humanized CD8 heterodimer (left panel); as well as T cell receptor complex comprising humanized TCR alpha and beta proteins, humanized MHC Class II heterodimer, and humanized CD4 (right panel). Antigen presented by humanized MHC is depicted as a circle. Mouse regions are depicted as filled shapes while human regions are depicted as striped shapes.

FIGS. 2A-C provide a schematic representation (not to scale) of exemplary chimeric MHC I and MHC II loci, e.g., chimeric HLA-A2/H-2K locus (FIG. 2A), chimeric HLA-DR2/H-2E locus (FIG. 2B), and humanized β2M locus (FIG. 2C). Unless otherwise indicated, human sequences are depicted as empty shapes and mouse sequences are depicted as filled shapes. The striped shape represents exon 1 of H-2E derived from a different mouse strain than the endogenous locus (see Example 1.3 and FIG. 3B). Floxed neomycin phosphotransferase cassette(s) are depicted with arrows labeled accordingly.

FIG. 3B is a schematic diagram (not to scale) of an exemplary HLA-DR2/H-2E large targeting vector. Unless otherwise indicated, human sequences are depicted as empty shapes and mouse sequences are depicted as filled shapes. The striped shape represents exon 1 of H-2E derived from a different mouse strain than the endogenous locus (see Example 1.3). A floxed hygromycin cassette is depicted as an arrow labeled accordingly. FIG. 3C is a schematic representation (not to scale) of exemplary genotypes of chimeric human/mouse MHC loci (** represents H-2L gene that is not present in all mouse strains, e.g., is not present in C57BL/6 or 129 mouse strains), where endogenous mouse H-2K and H-2E loci are respectively replaced by chimeric human/mouse HLA-A2/H-2K and HLA-DR2/H-2E loci (striped shapes), H-2A and H-2D loci were deleted (empty shapes outlined with dotted lines), and remaining loci are endogenous mouse genes (solid shapes outlined with solid lines).

(FIGS. 7C, 7D) anti-HLA-A2 or anti-HLA-DR antibodies; (FIGS. 7E, 7F) anti-H-2D and anti-I$^A$I$^E$ antibodies; or (FIG. 7G) anti-mouse CD4 and anti-human CD4 antibodies (top), anti-mouse CD8α and anti-human CD8α antibodies (middle), and anti-mouse CD8β and anti-human CD8β antibodies (bottom).

FIG. 8 provides FACS contour plots of thymic cells isolated from a control mouse or a mouse comprising humanized MHC I, MHC II α and β, TCRα and β, CD4, CD8α and β, and β2M (TM I/II B C4/8), gated on CD3$^+$ CD4$^+$ cells, and stained with anti-mouse FoxP3 and anti-mouse CD25 antibodies

FIG. 14 depicts progression of chronic Clone 13 strain viral infection in either control or TM I/II B C4/8 mice after prior acute Armstrong strain infection; the timeline for the experiment is depicted at the top of the figure, and measurement of viral titers on Day 31 post-infection is depicted in the bottom graph. Mock infected mice were included in the experiment as an additional control.

DETAILED DESCRIPTION

Figure 3A:
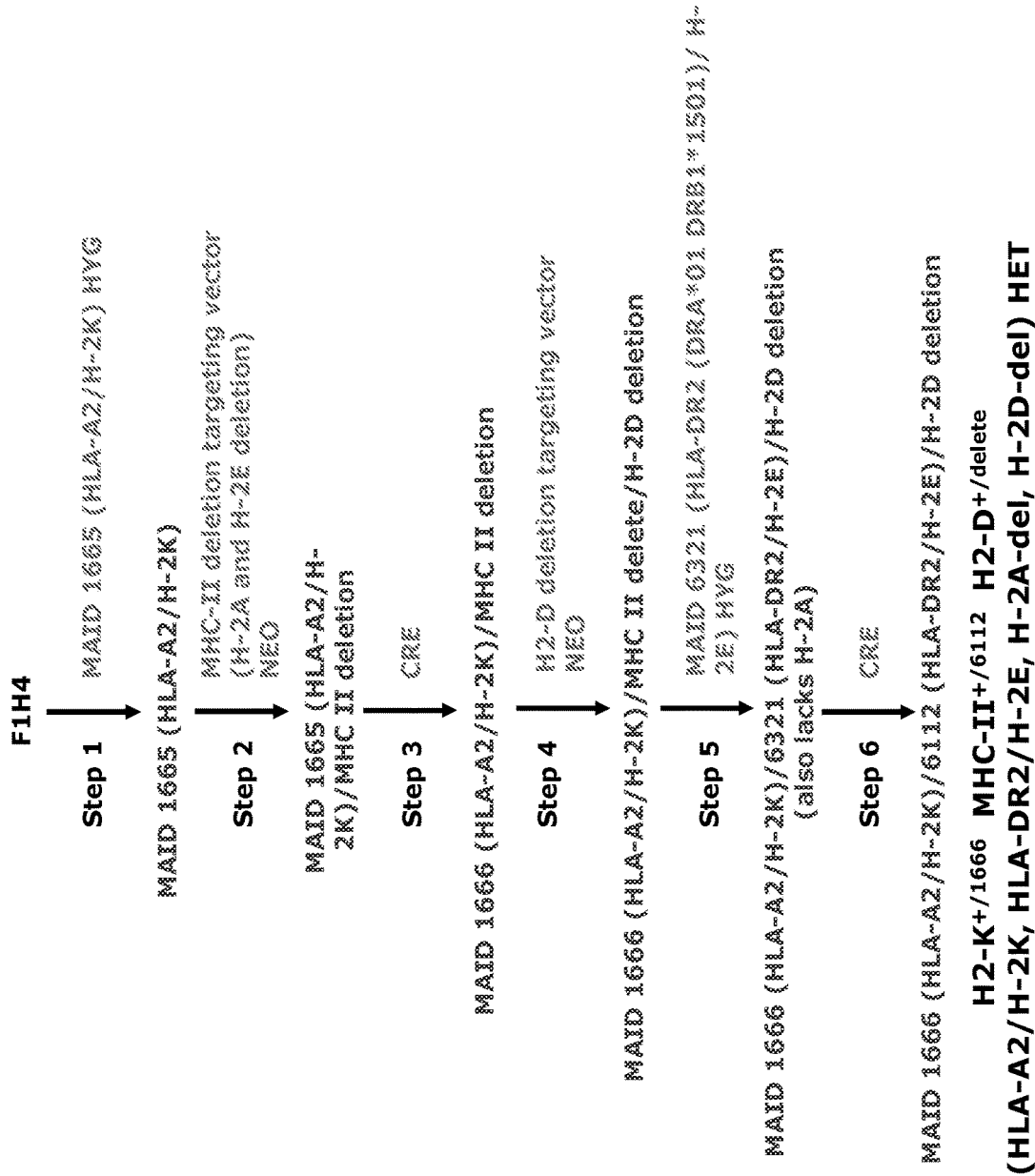
FIGS. 3A-C depicts a strategy for generating a humanized MHC locus comprising humanized MHC I and MHC II genes. In the particular embodiment depicted in FIG. 3A, the MHC locus of the generated mouse comprises chimeric HLA-A2/H-2K and HLA-DR2/H-2E sequences (H2-K$^{+/1666}$ MHC-II$^{+/6112}$) and lacks H2-D sequence (H2-D$^{+/delete}$) and H-2A sequence (the genetic engineering scheme also results in a deletion of H-2A, see Example 1.2). Large Targeting Vectors (LTVECs) or Cre recombinase construct introduced into ES cells at each stage of humanization are depicted to the right of the arrows. MAID or 4 digit numbers refer to modified allele ID number.

Disclosed herein are non-human animals (e.g., rodents, e.g., mice or rats) genetically engineered to express a humanized T cell co-receptor (e.g., humanized CD4 and/or CD8 (e.g., CD8α and/or CD8β)), a human or humanized major histocompatibility complex (MHC) that binds the humanized T cell co-receptor (e.g., human or humanized MHC II (e.g., MHC II α and/or MHC II β chains) and/or MHC I (e.g., MHC Iα), and optionally human or humanized β2 microglobulin) and/or a human or humanized T cell receptor (TCR), as well as embryos, tissues, and cells expressing the same. The development of the cellular arm of the immune system of the non-human animals disclosed herein is comparable to control animals, e.g., the thymus and spleen comprises similar absolute numbers of thymocytes and CD3+ cells. This is in stark contrast to other non-human animals modified to comprise both human TCR (α and β) and a chimeric human/mouse MHC I molecule, see, e.g., Li (2010) Nature Medicine 16:1029-1035 and supplementary materials. Such animals showed a decrease in T cell populations compared not only to wildtype control animals, but also animals modified with only human TCR, and animals modified with only the chimeric human/mouse MHC I molecule, id. Accordingly, provided herein are non-human animals engineered to co-express a humanized CD4 co-receptor and a humanized MHC II and/or a humanized CD8 co-receptor and a humanized MHC I, and optionally a humanized TCR. Methods for making a genetically engineered animal that expresses at least one humanized T cell co-receptor (e.g., humanized CD4 and/or CD8), at least one humanized MHC that associates with the humanized T cell co-receptor (e.g., humanized MHC II and/or MHC I that associate with humanized CD4 and/or CD8, respectively) and/or the humanized TCR are also provided. Methods for using the genetically engineered animals that mount a substantially humanized T cell immune response for developing human therapeutics are also provided.

Substantially Humanized T Cell Immune Responses

Disclosed herein are non-human animals that are genetically modified to mount substantially humanized T cell immune responses. The mice disclosed herein express at least one human or humanized T cell co-receptor, at least one human or humanized major histocompatibility complex (MHC) capable of associating with the at least one human or humanized T cell co-receptor, and/or a human or humanized T cell receptor (TCR), which is preferably capable of recognizing an antigen presented in the context of human or humanized MHC in association with a human or humanized T cell co-receptor and providing activation signals to the non-human cell, e.g., non-human T cell, expressing the human or humanized TCR. The human or humanized T cell co-receptor, human or humanized TCR and/or human or humanized MHC may be encoded by the genome of the non-human animal. In preferred embodiments, upon immunization with an antigen, the non-human animals present HLA restricted epitopes of the antigen to TCR derived from human TCR gene segments, e.g., a human TCRα V segment, a human TCRα J segment, a human TCRβ V segment, human TCRβ D segment and/or a human TCRβ J segment.

Accordingly, encompassed by the invention is a genetically modified non-human animal whose genome comprises (e.g., at an endogenous locus) a nucleotide sequence encoding a humanized T cell co-receptor polypeptide (e.g., CD4 or CD8 polypeptide), wherein the chimeric T cell co-receptor polypeptide comprises conservative amino acid substitutions of the amino acid sequence(s) described herein and/or a nucleic acid sequence encoding a humanized MHC polypeptide that associates with the humanized T cell co-receptor polypeptide, wherein the humanized MHC polypeptide comprises conservative amino acid substitutions of the amino acid sequence(s) described herein.

A conservative amino acid substitution includes substitution of an amino acid residue by another amino acid residue having a side chain R group with similar chemical properties (e.g., charge or hydrophobicity). Conservative amino acid substitutions may be achieved by modifying a nucleotide sequence so as to introduce a nucleotide change that will encode the conservative substitution. In general, a conservative amino acid substitution will not substantially change the functional properties of interest of a protein, for example, the ability of CD4 or CD8 to associate with, e.g., bind to MHC II or MHC I, respectively, and may, e.g., increase sensitivity of TCR to MHC-presented antigen. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/ isoleucine, phenylalanine/tyrosine, lysine/arginine, alanine/ valine, glutamate/aspartate, and asparagine/glutamine. In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet et al. ((1992) Exhaustive Matching of the Entire Protein Sequence Database, Science 256: 1443-45), hereby incorporated by reference. In some embodiments, the substitution is a moderately conservative substitution wherein the substitution has a nonnegative value in the PAM250 log-likelihood matrix.

One skilled in the art would understand that in addition to the nucleic acid residues encoding humanized T cell co-receptor polypeptides, humanized MHC polypeptides, and/ or TCR variable regions described herein, due to the degeneracy of the genetic code, other nucleic acids may encode the polypeptides of the invention. Therefore, in addition to a genetically modified non-human animal that comprises in its genome a nucleotide sequence encoding a humanized T cell co-receptor polypeptide (e.g., CD4 or CD8 polypeptide), an unrearranged T cell receptor variable gene locus (e.g., TCRα and/or TCRβ) comprising human unrearranged gene segments, and/or a nucleic acid sequence encoding a humanized MHC polypeptide capable of associating with the humanized T cell co-receptor polypeptide with conservative amino acid substitutions, also provided is a non-human animal whose genome comprises a nucleotide sequence encoding a humanized T cell co-receptor polypeptide (e.g., CD4 or CD8 polypeptide), an unrearranged T cell receptor variable gene locus (e.g., TCRα and/or TCRβ) comprising human unrearranged gene segments, and/or a nucleic acid sequence encoding a humanized MHC polypeptide capable of associating with the humanized T cell co-receptor polypeptide, which differs from that described herein due to the degeneracy of the genetic code.

The identity of a sequence may be determined by a number of different algorithms known in the art that can be used to measure nucleotide and/or amino acid sequence identity. In some embodiments described herein, identities are determined using a ClustalW v. 1.83 (slow) alignment employing an open gap penalty of 10.0, an extend gap penalty of 0.1, and using a Gonnet similarity matrix (MacVector™ 10.0.2, MacVector Inc., 2008). The length of the sequences compared with respect to identity of sequences will depend upon the particular sequences. In various embodiments, identity is determined by comparing the sequence of a mature protein from its N-terminal to its C-terminal. In various embodiments when comparing a chimeric human/non-human sequence to a human sequence, the human portion of the chimeric human/non-human sequence (but not the non-human portion) is used in making a comparison for the purpose of ascertaining a level of identity between a human sequence and a human portion of a chimeric human/non-human sequence (e.g., comparing a human ectodomain of a chimeric human/mouse protein to a human ectodomain of a human protein).

The terms "homology" or "homologous" in reference to sequences, e.g., nucleotide or amino acid sequences, means two sequences which, upon optimal alignment and comparison, are identical in, e.g., at least about 75% of nucleotides or amino acids, e.g., at least about 80% of nucleotides or amino acids, e.g., at least about 90-95% nucleotides or amino acids, e.g., greater than 97% nucleotides or amino acids. One skilled in the art would understand that, for optimal gene targeting, the targeting construct should contain arms homologous to endogenous DNA sequences (i.e., "homology arms"); thus, homologous recombination can occur between the targeting construct and the targeted endogenous sequence.

The term "operably linked" refers to a juxtaposition wherein the components so described are in a relationship permitting them to function in their intended manner. As such, a nucleic acid sequence encoding a protein may be operably linked to regulatory sequences (e.g., promoter, enhancer, silencer sequence, etc.) so as to retain proper transcriptional regulation. In addition, various portions of the chimeric or humanized protein of the invention may be operably linked to retain proper folding, processing, targeting, expression, and other functional properties of the protein in the cell. Unless stated otherwise, various domains of the chimeric or humanized proteins of the invention are operably linked to each other.

The term "replacement" in reference to gene replacement refers to placing exogenous genetic material at an endogenous genetic locus, thereby replacing all or a portion of the endogenous gene with an orthologous or homologous nucleic acid sequence. As demonstrated in the Examples below, in one embodiment, nucleic acid sequences of endogenous loci encoding portions of mouse CD4 or CD8 (CD8α and/or CD8β) polypeptides were replaced by nucleotide sequences encoding portions of human CD4 or CD8 (CD8α and/or CD8β) polypeptides, respectively.

"Functional" as used herein, e.g., in reference to a functional polypeptide, refers to a polypeptide that retains at least one biological activity normally associated with the native protein. For example, in some embodiments of the invention, a replacement at an endogenous locus (e.g., replacement at an endogenous non-human CD4 or CD8 locus) results in a locus that fails to express a functional endogenous polypeptide.

Humanized T Cell Co-Receptor(s)

Disclosed herein are non-human animals that express at least one human or humanized T cell co-receptor, e.g., CD4, CD8α and/or CD8β). Accordingly, a non-human animal as disclosed herein comprises at least one of a first, second, and/or third nucleotide sequence, each of which encodes a different human or chimeric human/non-human T cell co-receptor polypeptide selected from a human or humanized CD4 polypeptide, a human or humanized CD8α polypeptide, and a human or humanized CD8β polypeptide. Use of the first, second, third designations herein is not to be construed as limiting the non-human animals disclosed herein as requiring all three nucleotide sequences or the presence of any of the co-receptor nucleotide sequences in any order. Accordingly, a non-human animal as disclosed herein may comprise a nucleic acid sequence or nucleic acid sequences encoding a human or humanized CD4 and/or a human or humanized CD8 (e.g., human or humanized CD8α and/or CD8β) polypeptide(s).

In one embodiment, a non-human animal as disclosed herein comprises a first nucleotide sequence encoding a human or humanized CD4 polypeptide. In another embodiment, a non-human animal as disclosed herein comprises a first nucleotide sequence encoding a human or humanized CD8α polypeptide and a second nucleotide sequence encoding a human or humanized CD8β polypeptide. In another embodiment, a non-human animal as disclosed herein comprises first and second nucleotide sequences encoding human or humanized CD8α and CD8β polypeptides and further comprises a third nucleotide sequence encoding a human or humanized CD4 polypeptide.

Human or Humanized CD4

In various embodiments, the invention generally provides genetically modified non-human animals that comprise in their genome, e.g., at an endogenous CD4 locus, a nucleotide sequence encoding a human or humanized CD4 polypeptide; thus, the animals express a human or humanized CD4 polypeptide.

Human CD4 gene is localized to chromosome 12, and is thought to contain 10 exons. CD4 gene encodes a protein with amino-terminal hydrophobic signal sequence, encoded by exons 2 and 3 of the gene. The protein comprises four extracellular immunoglobulin-like domains, Ig1-Ig4, also commonly and respectively referred to as D1-D4 domains. Maddon et al. (1987) Structure and expression of the human and mouse T4 genes, Proc. Natl. Acad. Sci. USA 84:9155-59. D1 domain is believed to be encoded by exon 3 (sequence downstream of signal peptide) and exon 4, while D2, D3, and D4 are encoded by a separate exon each—exons 5, 6, and 7, respectively (see FIG. 5A: D1, D2, D3 and D4 domains are encoded by sequences designated as Ig1, Ig2, Ig3 and Ig4, respectively). Littman (1987) The Structure of the CD4 and CD8 Genes, Ann. Rev. Immunol. 5:561-84; Hanna et al. (1994) Specific Expression of the Human CD4 Gene in Mature CD4+CD8− and Immature CD4+CD8+ T cells and in Macrophages of Transgenic Mice, Mol. Cell. Biol. 14(2):1084-94; Maddon et al., supra. At areas of high protein concentration, such as the area of contact between T cell and antigen-presenting cell, the molecule tends to homodimerize through interactions between opposing D4 domains. Zamoyska (1998) CD4 and CD8: modulators of T cell receptor recognition of antigen and of immune responses? Curr. Opin. Immunol. 10:82-87; Wu et al. (1997) Dimeric association and segmental variability in the structure of human CD4, Nature 387:527; Moldovan et al. (2002) CD4 Dimers Constitute the Functional Component Required for T Cell Activation, J. Immunol. 169:6261-68.

D1 domain of CD4 resembles immunoglobulin variable (V) domain, and, together with a portion of D2 domain, is believed to bind (associate with) MHC II, e.g., at an MHC II co-receptor binding site. Huang et al. (1997) Analysis of the contact sites on the CD4 Molecule with Class II MHC Molecule, J. Immunol. 158:216-25. In turn, MHC II interacts with T cell co-receptor CD4 at the hydrophobic crevice at the junction between MHC II α 2 and β2 domains. Wang and Reinherz (2002) Structural Basis of T Cell Recognition of Peptides Bound to MHC Molecules, Molecular Immunology, 38:1039-49.

Domains D3 and D4 of the CD4 co-receptor are believed to interact with the TCR-CD3 complex as the substitution of these two domains abrogated the ability of CD4 to bind to TCR. Vignali et al. (1996) The Two Membrane Proximal Domains of CD4 Interact with the T Cell Receptor, J. Exp. Med. 183:2097-2107. CD4 molecule exists as a dimer, and residues in the D4 domain of the molecule are believed to be responsible for CD4 dimerization. Moldovan et al. (2002) CD4 Dimers Constitute the Functional Components Required for T Cell Activation, J. Immunol. 169:6261-68.

Exon 8 of the CD4 gene encodes the transmembrane domain, while the remainder of the gene encodes the cytoplasmic domain. CD4 cytoplasmic domain possesses many distinct functions. For example, the cytoplasmic domain of CD4 recruits a tyrosine kinase Lck. Lck is a Src family kinase that is associated with CD4 and CD8 cytoplasmic domains and simultaneous binding of the co-receptors and TCRs to the same MHC leads to increased tyrosine phosphorylation of CD3 and ζ chain of the TCR complex, which in turn leads to recruitment of other factors that play a role in T cell activation. Itano and colleagues have proposed that cytoplasmic tail of CD4 also promotes differentiation of CD4+CD8+ T cells into CD4+ lineage by designing and testing expression of hybrid protein comprising CD8 extracellular domain and CD4 cytoplasmic tail in transgenic mice. Itano et al. (1996) The Cytoplasmic Domain of CD4 Promotes the Development of CD4 Lineage T Cells, J. Exp. Med. 183:731-41. The expression of the hybrid protein led to the development of MHC I-specific, CD4 lineage T cells. Id.

CD4 co-receptor appears to be the primary receptor for HIV virus, with the CD4+ T cell depletion being an indicator of disease progression. The cytoplasmic tail of CD4 appears to be essential for delivering apoptotic signal to CD4+ T cells in HIV-induced apoptosis. Specifically, the interaction of CD4 and Lck was shown to potentiate HIV-induced apoptosis in these cells. Corbeil et al. (1996) HIV-induced Apoptosis Requires the CD4 Receptor Cytoplasmic Tail and Is Accelerated by Interaction of CD4 with p56lck, J. Exp. Med. 183:39-48.

T cells develop in the thymus progressing from immature CD4−/CD8− (double negative or DN) thymocytes to CD4+/CD8+ (double positive or DP) thymocytes, which eventually undergo positive selection to become either CD4+ or CD8+ (single positive or SP) T cells. DP thymocytes that receive signals through MHC I-restricted TCR differentiate into CD8+ T cells, while DP thymocytes that receive signals through MHC II-restricted TCR differentiate into CD4+ T cells. The cues received by the DP cell that lead to its differentiation into either CD4+ of CD8+ T cell have been a subject of much research. Various models for CD4/CD8 lineage choice have been proposed and are reviewed in Singer et al. (2008) Lineage fate and intense debate: myths, models and mechanisms of CD4− versus CD8− lineage choice, Nat. Rev. Immunol. 8:788-801.

Deactivation of a specific T cell co-receptor as a result of positive selection is a product of transcriptional regulation. For CD4, it has been shown that an enhancer located 13 kb upstream of exon 1 of CD4 upregulates CD4 expression in CD4+ and CD8+ T cells. Killeen et al. (1993) Regulated expression of human CD4 rescues helper T cell development in mice lacking expression of endogenous CD4, EMBO J. 12:1547-53. A cis-acting transcriptional silencer located within the first intron of murine CD4 gene functions to silence expression of CD4 in cells other than CD4+ T cells. Siu et al. (1994) A transcriptional silencer control the developmental expression of the CD4 gene, EMBO J. 13:3570-3579.

Because important transcriptional regulators (e.g., promoters, enhancers, silencers, etc.) that control CD4 lineage choice were missing in several strains of previously developed transgenic mice expressing human CD4, these mice were not able to recapitulate normal T cell lineage development, and produced immune cells other than CD4+ T cells that expressed CD4. See, e.g., Law et al. (1994) Human CD4 Restores Normal T Cell Development and Function in Mice Deficient in CD4, J. Exp. Med. 179:1233-42 (CD4 expression in CD8+ T cells and B cells); Fugger et al. (1994) Expression of HLA-DR4 and human CD4 transgenes in mice determines the variable region β-chain T-cell repertoire and mediates an HLA-D-restricted immune response, Proc. Natl. Acad. Sci. USA, 91:6151-55 (CD4 expressed on all CD3+ thymocytes and B cells). Thus, in one embodiment, there may be a benefit in developing a genetically modified animal that retains endogenous mouse promoter and other regulatory elements in order for the animal to produce T cells that are capable of undergoing T cell development and lineage choice.

Thus, in various embodiments, the invention provides a genetically modified non-human animal, comprising, e.g., at its endogenous T cell co-receptor locus (e.g., CD4 locus), a nucleotide sequence encoding a chimeric human/non-human T cell co-receptor polypeptide. In one embodiment, a human portion of the chimeric polypeptide comprises all or substantially all of an extracellular portion (or part thereof, e.g., one or more extracellular domains, e.g., at least two consecutive extracellular domains) of a human T cell co-receptor. In one embodiment, a non-human portion of the chimeric polypeptide comprises transmembrane and cytoplasmic domains of a non-human T cell co-receptor. In one embodiment, the non-human animal expresses a functional chimeric T cell co-receptor polypeptide. Thus, in one aspect, the invention provides a genetically modified non-human animal comprising at its endogenous CD4 locus a nucleotide sequence encoding a chimeric human/non-human CD4 polypeptide, wherein a human portion of the chimeric polypeptide comprises all or substantially all of an extracellular portion of a human CD4, wherein a non-human portion comprises at least transmembrane and cytoplasmic domains of a non-human CD4, and wherein the animal expresses a functional chimeric CD4 polypeptide. In one aspect, the non-human animal only expresses the humanized CD4 polypeptide, i.e., chimeric human/non-human CD4 polypeptide, and does not express a functional endogenous non-human CD4 protein from its endogenous CD4 locus.

In one embodiment, the human portion of the chimeric human/non-human CD4 polypeptide comprises all or substantially all of the extracellular portion of a human CD4 polypeptide. In another embodiment, the human portion of the chimeric human/non-human CD4 polypeptide comprises at least all or substantially all of the MHC II binding domain of the human CD4 polypeptide (e.g., a substantial portion of human D1 and D2 domains); in one embodiment, the human portion of the chimeric human/non-human CD4 polypeptide comprises all or substantially all of D1, D2, and D3 domains of the human CD4 polypeptide; in yet another embodiment, the human portion of the chimeric human/non-human CD4 polypeptide comprises all or substantially all of immunoglobulin-like domains of CD4, e.g., domains termed D1, D2, D3, and D4. In yet another embodiment, the human portion of the chimeric human/non-human CD4 polypeptide comprises in its human portion all or substantially all of the human CD4 sequence that is responsible for interacting with MHC II and/or extracellular portion of a T cell receptor. In yet another embodiment, the human portion of the chimeric human/non-human CD4 polypeptide comprises all or substantially all of the extracellular portion of the human CD4 that is responsible for interacting with MHC II and/or the variable domain of a T cell receptor. Therefore, in one embodiment, the nucleotide sequence encoding the human portion of the chimeric CD4 polypeptide comprises all or substantially all of the coding sequence of domains D1-D2 of the human CD4 (e.g., a portion of exon 3 and exons 4-5 of the human CD4 gene); in another embodiment, it comprises all or substantially all of the coding sequence of D1-D3 of the human CD4 (e.g., portion of exon 3 and exons 4-6 of the human CD4). Thus, in one embodiment, the nucleotide sequence encoding chimeric human/non-human CD4 comprises nucleotide sequences encoding all or substantially all D1-D3 domains of the human CD4. In another embodiment, the nucleotide sequence encoding the human portion of the chimeric CD4 polypeptide comprises the coding sequence of D1-D4 domains of the human CD4 gene. In another embodiment, the nucleotide sequence may comprise the nucleotide sequence encoding mouse CD4 signal peptide, e.g., region encoded by portions of exons 2-3 of the mouse gene. In another embodiment, the nucleotide sequence may comprise the nucleotide sequence encoding a human CD4 signal peptide. In one embodiment, the chimeric human/non-human CD4 polypeptide comprises an amino acid sequence set forth in SEQ ID NO:78, and the human portion of the chimeric polypeptide spans about amino acids 27-319 of SEQ ID NO:78 (set forth separately in SEQ ID NO:79).

In one embodiment, the non-human animal expresses a chimeric human/non-human CD4 polypeptide sequence. In one embodiment, a human portion of the chimeric CD4 sequence comprises one or more conservative or non-conservative modifications.

In one aspect, a non-human animal that expresses a human CD4 sequence is provided, wherein the human CD4 sequence is at least about 85%, 90%, 95%, 96%, 97%, 98%, or 99% identical to a human CD4 sequence. In a specific embodiment, the human CD4 sequence is at least about 90%, 95%, 96%, 97%, 98%, or 99% identical to the human CD4 sequence described in the Examples. In one embodiment, the human CD4 sequence comprises one or more conservative substitutions. In one embodiment, the human CD4 sequence comprises one or more non-conservative substitutions.

In some embodiments, a portion, e.g., a human portion of the chimeric CD4, may comprise substantially all of the sequence indicated herein (e.g., substantially all of a protein domain indicated herein). Substantially all sequence generally includes 85%, 90%, 95%, 96%, 97%, 98%, or 99% of the amino acids believed to represent a particular portion of the protein (e.g., a particular functional domain, etc.). One skilled in the art would understand that the boundaries of a functional domain may vary slightly depending on the alignment and domain prediction methods used.

In one aspect, the non-human portion of the chimeric human/non-human CD4 polypeptide comprises at least transmembrane and cytoplasmic domains of the non-human CD4 polypeptide. Due to the important functions served by CD4 cytoplasmic domain, retention of the endogenous non-human (e.g., mouse) sequence in genetically engineered animals ensures preservation of proper intracellular signaling and other functions of the co-receptor. In one embodiment, the non-human animal is a mouse, and the non-human CD4 polypeptide is a mouse CD4 polypeptide. Although a specific mouse CD4 sequence is described in the Examples, any suitable sequence derived therefrom, e.g., sequence comprising conservative/non-conservative amino acid substitutions, is encompassed herein. In one embodiment, the non-human portion of the chimeric CD4 co-receptor comprises any sequence of the endogenous CD4 that has not been humanized.

The non-human animal described herein may comprise at its endogenous locus a nucleotide sequence encoding a chimeric human/non-human CD4 polypeptide. In one aspect, this results in a replacement of a portion of an endogenous CD4 gene with a nucleotide sequence encoding a portion of a human CD4 polypeptide. In one embodiment, such replacement is a replacement of endogenous nucleotide sequence encoding, e.g., all or substantially all of the extracellular domain of a non-human CD4, e.g., a sequence encoding at least all or substantially all of the first immunoglobulin-like domain (i.e., D1) of a non-human CD4 (e.g., a sequence encoding all or substantially all of domains D1-D2 of a non-human CD4, e.g., a sequence encoding all or substantially all of domains D1-D3 of a non-human CD4, e.g., a sequence encoding all or substantially all of domains D1-D4 of a non-human CD4), with a human nucleotide sequence encoding the same. In one embodiment, the replacement results in a chimeric protein comprising human CD4 sequence that is responsible for interacting with MHC II and/or extracellular portion of a T cell receptor. In yet another embodiment, the replacement results in a chimeric protein comprising human CD4 sequence that is responsible for interacting with MHC II and/or variable domain of a T cell receptor. In one embodiment, the replacement does not comprise a replacement of a CD4 sequence encoding at least transmembrane and cytoplasmic domains of a non-human CD4 polypeptide. Thus, in one aspect, the non-human animal expresses a chimeric human/non-human CD4 polypeptide from the endogenous non-human CD4 locus. In yet another embodiment, the replacement results in a protein comprising a polypeptide sequence set forth in SEQ ID NO:78.

In one embodiment, the nucleotide sequence of the chimeric human/non-human CD4 locus (e.g., chimeric human/rodent CD4 locus, e.g., chimeric human/mouse CD4 locus) described herein is provided. In one aspect, because the chimeric human/non-human (e.g., human/rodent, e.g., human/mouse) CD4 sequence is placed at the endogenous non-human (e.g., rodent, e.g., mouse) CD4 locus, it retains the CD4 enhancer element located upstream of the first CD4 exon. In one embodiment, the replacement at the endogenous non-human (e.g., rodent, e.g., mouse) CD4 locus comprises a replacement of, e.g., a portion of exon 3 encoding D1, and exons 4-6 encoding the rest of D1 and D2-D3 of CD4 polypeptide; thus, in one aspect, the chimeric CD4 locus retains the cis-acting silencer located in intron 1 of the non-human (e.g., mouse) CD4 gene. Thus, in one embodiment, the chimeric locus retains endogenous non-human (e.g., rodent, e.g., mouse) CD4 promoter and regulatory elements. In another embodiment, the chimeric locus may contain human promoter and regulatory elements to the extent those allow proper CD4 expression, CD4+ T cell development, CD4 lineage choice, and co-receptor function. Thus, in some aspects, the animals of the invention comprise a genetic modification that does not alter proper lineage choice and development of T cells. In one aspect, the animals (e.g., rodents, e.g., mice) of the invention do not express chimeric CD4 polypeptide on immune cells other than cells that normally express CD4. In one aspect, animals do not express CD4 on B cells or mature CD8+ T cells. In one embodiment, the replacement results in retention of elements that allow proper spatial and temporal regulation of CD4 expression.

In various embodiments, a non-human animal (e.g., a rodent, e.g., a mouse or rat) that expresses a functional chimeric CD4 protein from a chimeric CD4 locus as described herein displays the chimeric protein on a cell surface, e.g., T cell surface. In one embodiment, the non-human animal expresses the chimeric CD4 protein on a cell surface in a cellular distribution that is the same as observed in a human. In one aspect, the CD4 protein of the invention is capable of interacting with an MHC II protein expressed on the surface of a second cell, e.g., an antigen presenting cell (APC).

Human or Humanized CD8

In various embodiments, the invention generally provides genetically modified non-human animals that comprise in their genome, e.g., at an endogenous CD8 locus, a nucleotide sequence encoding a human or humanized CD8 polypeptide; thus, the animals express a human or humanized CD8 polypeptide. In various embodiments, the invention provides non-human animals that comprise in their genome, e.g., at an endogenous CD8 locus, a nucleotide sequence encoding a human or humanized CD8α polypeptide and/or a nucleotide sequence encoding a human or humanized CD8β polypeptide. Thus, the genetically modified non-human animal of the invention expresses a human or humanized CD8α and/or a human or humanized CD8β polypeptide(s).

Human CD8 protein is typically expressed on cell surface as heterodimer of two polypeptides, CD8α and CD8β, although disulfide-linked homodimers and homomultimers have also been detected (e.g., in NK cells and intestinal γδ T cells, which express CD8αα). The genes encoding human CD8α and CD8β are located in close proximity to each other on chromosome 2. Nakayama et al. (1992) Recent Duplication of the Two Human CD8 β-chain genes, J. Immunol. 148:1919-27. CD8α protein contains a leader peptide, an immunoglobulin V-like region, a hinge region, a transmembrane domain and a cytoplasmic tail. Norment et al. (1989) Alternatively Spliced mRNA Encodes a Secreted Form of Human CD8α. Characterization of the Human CD8α gene, J. Immunol. 142:3312-19. The exons/introns of the CD8α gene are depicted schematically in FIG. 5B.

Human CD8β gene lies upstream of the CD8α gene on chromosome 2. Multiple isoforms generated by alternative splicing of CD8β gene have been reported, with one isoform predicted to lack a transmembrane domain and generate a secreted protein. Norment et al. (1988) A second subunit of CD8 is expressed in human T cells, EMBO J. 7:3433-39. The exons/introns of CD8β gene are also depicted schematically in FIG. 5B.

The membrane-bound CD8β protein contains an N-terminal signal sequence, followed by immunoglobulin V-like domain, a short extracellular hinge region, a transmembrane domain, and a cytoplasmic tail. See, Littman (1987) The structure of the CD4 and CD8 genes, Ann Rev. Immunol. 5:561-84. The hinge region is a site of extensive glycosylation, which is thought to maintain its conformation and protect the protein from cleavage by proteases. Leahy (1995) A structural view of CD4 and CD8, FASEB J. 9:17-25.

CD8 protein is commonly expressed on cytotoxic T cells, and interacts with MHC I molecules. The interaction is mediated through CD8 binding to the $α_3$ domain of MHC I. Although binding of MHC class I to CD8 is about 100-fold weaker than binding of TCR to MHC class I, CD8 binding enhances the affinity of TCR binding. Wooldridge et al. (2010) MHC Class I Molecules with Superenhanced CD8 Binding Properties Bypass the Requirement for Cognate TCR Recognition and Nonspecifically Activate CTLs, J. Immunol. 184:3357-3366.

CD8 binding to MHC class I molecules is species-specific; the mouse homolog of CD8, Lyt-2, was shown to bind H-2D$^d$ molecules at the α3 domain, but it did not bind HLA-A molecules. Connolly et al. (1988) The Lyt-2 Molecule Recognizes Residues in the Class I α3 Domain in Allogeneic Cytotoxic T Cell Responses, J. Exp. Med. 168: 325-341. Differential binding was presumably due to CDR-like determinants (CDR1- and CDR2-like) on CD8 that were not conserved between humans and mice. Sanders et al. (1991) Mutations in CD8 that Affect Interactions with HLA Class I and Monoclonal Anti-CD8 Antibodies, J. Exp. Med. 174:371-379; Vitiello et al. (1991) Analysis of the HLA-restricted Influenza-specific Cytotoxic T Lymphocyte Response in Transgenic Mice Carrying a Chimeric Human- Mouse Class I Major Histocompatibility Complex, J. Exp. Med. 173:1007-1015; and, Gao et al. (1997) Crystal structure of the complex between human CD8αα and HLA-A2, Nature 387:630-634. It has been reported that CD8 binds HLA-A2 in a conserved region of the α3 domain (at position 223-229). A single substitution (V245A) in HLA-A reduced binding of CD8 to HLA-A, with a concomitant large reduction in T cell-mediated lysis. Salter et al. (1989), Polymorphism in the $α_3$ domain of HLA-A molecules affects binding to CD8, Nature 338:345-348. In general, polymorphism in the α3 domain of HLA-A molecules also affected binding to CD8. Id. In mice, amino acid substitution at residue 227 in $H-2D^d$ affected the binding of mouse Lyt-2 to $H-2D^d$, and cells transfected with a mutant $H-2D^d$ were not lysed by CD8+ T cells. Potter et al. (1989) Substitution at residue 227 of H-2 class I molecules abrogates recognition by CD8-dependent, but not CD8-independent, cytotoxic T lymphocytes, Nature 337:73-75. Thus, expression of human or humanized CD8 may be beneficial for studying T cell responses to antigen presented by human or humanized MHC I.

Similarly to CD4, the cytoplasmic domain of CD8 interacts with tyrosine kinase Lck, which in turn leads to T cell activation. Although Lck seems to interact with the cytoplasmic domain of CD8α, it appears that this interaction is regulated by the presence of the cytoplasmic domain of CD8β because mutations or deletion of CD8β cytoplasmic domain resulted in reduced CD8α-associated Lck activity. Irie et al. (1998) The cytoplasmic domain of CD8β Regulates Lck Kinase Activation and CD8 T cell Development, J. Immunol. 161:183-91. The reduction in Lck activity was associated with impairment in T cell development. Id.

Expression of CD8 on appropriate cells, e.g., cytotoxic T cells, is tightly regulated by a variety of enhancer elements located throughout the CD8 locus. For instance, at least 4 regions of DNAse I-hypersensitivity, regions often associated with regulator binding, have been identified at the CD8 locus. Hosert et al. (1997) A CD8 genomic fragment that directs subset-specific expression of CD8 in transgenic mice, J. Immunol. 158:4270-81. Since the discovery of these DNAse I-hypersensitive regions at CD8 locus, at least 5 enhancer elements have been identified, spread throughout the CD8 locus, that regulate expression of CD8α and/or β in T cells of various lineages, including DP, CD8 SP T cells, or cells expressing γδTCR. See, e.g., Kioussis et al. (2002) Chromatin and CD4, CD8A, and CD8B gene expression during thymic differentiation, Nature Rev. 2:909-919 and Online Erratum; Ellmeier et al. (1998) Multiple Development Stage-Specific Enhancers Regulate CD8 Expression in Developing Thymocytes and in Thymus-Independent T cells, Immunity 9:485-96.

Thus, similarly to the benefit derived from retaining endogenous CD4 promoter and regulatory elements for human or humanized CD4 genetically modified animals, in some embodiments, there may be a benefit in developing a genetically modified non-human animal that retains endogenous mouse promoter and regulatory elements that would control expression of human or humanized CD8. There may be a particular benefit in creating genetically modified animals comprising a replacement of endogenous non-human sequences encoding CD8α and/or β proteins with those encoding human or humanized CD8α and/or β proteins, as described herein.

In various embodiments, the invention provides a genetically modified non-human animal comprising in its genome, e.g., at its endogenous CD8 locus, at least one nucleotide sequence encoding a chimeric human/non-human CD8 polypeptide (e.g., CD8α and/or β polypeptide), wherein a human portion of the polypeptide comprises all or substantially all of an extracellular portion (or a part thereof, e.g., an extracellular domain) of a human CD8 polypeptide (e.g., CD8α and/or β), wherein a non-human portion comprises at least transmembrane and cytoplasmic domains of a non-human CD8 (e.g., CD8α and/or β), and wherein the animal expresses the chimeric CD8 polypeptide (e.g., CD8α and/or β polypeptide). Thus, in one embodiment, the invention provides a genetically modified non-human animal comprising at its endogenous non-human CD8 locus a first nucleotide sequence encoding a chimeric human/non-human CD8α polypeptide and a second nucleotide sequence encoding a chimeric human/non-human CD8β polypeptide, wherein the first nucleotide sequence comprises a sequence that encodes all or substantially all of the extracellular portion of a human CD8α polypeptide and at least transmembrane and cytoplasmic domains of a non-human CD8α polypeptide, and wherein the second nucleotide sequence comprises a sequence that encodes all or substantially all of the extracellular portion of a human CD8β polypeptide and at least transmembrane and cytoplasmic domains of a non-human CDβ polypeptide, wherein the animal expresses a functional chimeric human/non-human CD8 protein. In one aspect, the non-human animal only expresses a humanized CD8 polypeptide (e.g., chimeric human/non-human CD8α and/or β polypeptide), and does not express a corresponding functional non-human CD8 polypeptide(s) from the endogenous CD8 locus.

In one embodiment, the chimeric human/non-human CD8α polypeptide comprises in its human portion all or substantially all of the extracellular portion of a human CD8α polypeptide. In one embodiment, the human portion of the chimeric CD8α polypeptide comprises at least the MHC I binding domain of the human CD8α polypeptide. In one embodiment, the human portion of the chimeric CD8α polypeptide comprises the sequence of at least all or substantially all of the immunoglobulin V-like domain of the human CD8α. In one embodiment, the nucleotide sequence encoding the human portion of the chimeric CD8α polypeptide comprises at least the exons that encode an extracellular portion of the human CD8α polypeptide. In one embodiment, the nucleotide sequence comprises at least the exons that encode the Ig V-like domains. In one embodiment, the extracellular portion of a human CD8α polypeptide is a region encompassing the portion of the polypeptide that is not transmembrane or cytoplasmic domain. In one embodiment, the nucleotide sequence encoding the chimeric human/non-human CD8α polypeptide comprises the sequence encoding a non-human (e.g., rodent, e.g., mouse) CD8α signal peptide. Alternatively, the nucleotide sequence may comprise the sequence encoding a human CD8α signal sequence. In one embodiment, the chimeric human/non-human CD8α polypeptide comprises an amino acid sequence set forth in SEQ ID NO:88, and the human portion of the chimeric polypeptide is set forth at amino acids 28-179 of SEQ ID NO:88 (represented separately in SEQ ID NO:89).

Similarly, in one embodiment, the chimeric human/non-human CD8β polypeptide comprises in its human portion all or substantially all of the extracellular portion of a human CD8β polypeptide. In one embodiment, the human portion of the chimeric CD8β polypeptide comprises the sequence of all or substantially all of the immunoglobulin V-like domain of human CD8β. In one embodiment, the nucleotide sequence encoding the human portion of the chimeric CD8β polypeptide comprises at least the exons that encode the extracellular portion of the human CD8β polypeptide. In one embodiment, the nucleotide sequence encoding the human portion of the chimeric human/non-human CD8β polypeptide comprises at least the exons that encode the IgG V-like domain of human CD8β. In one embodiment, the nucleotide sequence encoding the chimeric human/non-human CD8β polypeptide comprises the sequence encoding a non-human (e.g., rodent, e.g., mouse) CD8β signal peptide. Alternatively, the nucleotide sequence may comprise the sequence encoding a human CD8β signal sequence. In one embodiment, the chimeric human/non-human CD8β polypeptide comprises an amino acid sequence set forth in SEQ ID NO:83, and the human portion of the chimeric polypeptide is set forth at amino acids 15-165 of SEQ ID NO:83 (represented separately in SEQ ID NO:84).

In one embodiment, the non-human animal expresses a chimeric human/non-human CD8α and/or CD8β polypeptides. In some embodiments, the human portion of the chimeric human/non-human CD8α and/or β polypeptide comprises one or more conservative or nonconservative modification(s).

In one aspect, a non-human animal that expresses a human CD8α and/or β polypeptide sequence is provided, wherein the human CD8α and/or β polypeptide sequence is at least about 85%, 90%, 95%, 96%, 97%, 98%, or 99% identical to a human CD8α and/or β polypeptide sequence, respectively. In a specific embodiment, the human CD8α and/or β polypeptide sequence is at least about 90%, 95%, 96%, 97%, 98%, or 99% identical to the respective human CD8α and/or β polypeptide sequence described in the Examples. In one embodiment, the human CD8α and/or β polypeptide sequence comprises one or more conservative substitutions. In one embodiment, the human CD8α and/or β polypeptide sequence comprises one or more non-conservative substitutions.

In some embodiments, a portion, e.g., a human portion of the chimeric CD8, may comprise substantially all of the sequence indicated herein (e.g., substantially all of a protein domain indicated herein). Substantially all sequence generally includes 85%, 90%, 95%, 96%, 97%, 98%, or 99% of the amino acids believed to represent a particular portion of the protein (e.g., a particular functional domain, etc.). One skilled in the art would understand that the boundaries of a functional domain may vary slightly depending on the alignment and domain prediction methods used.

In one aspect, the non-human portion of the chimeric human/non-human CD8α and/or β polypeptide comprises at least transmembrane and/or cytoplasmic domain of the non-human CD8α and/or β polypeptide, respectively. Due to the important functions served by CD8 cytoplasmic domain, retention of the endogenous non-human (e.g., mouse) sequence in genetically engineered animals ensures preservation of proper intracellular signaling and other functions of the co-receptor. In one embodiment, the non-human animal is a mouse, and the non-human CD8α and/or β polypeptide is a mouse CD8α and/or β polypeptide, respectively. Although specific mouse CD8α and β sequences are described in the Examples, any suitable sequence derived therefrom, e.g., sequence comprising conservative/non-conservative amino acid substitutions, is encompassed herein. In one embodiment, the non-human animal (e.g., rodent, e.g., mouse) retains any endogenous sequence that has not been humanized.

The non-human animal described herein may comprise at its endogenous locus a nucleotide sequence encoding a chimeric human/non-human CD8α and/or β polypeptide. In one aspect, this results in a replacement of a portion of an endogenous CD8α gene with a nucleotide sequence encoding a portion of a human CD8α polypeptide, and/or a replacement of a portion of an endogenous CD8β gene with a nucleotide sequence encoding a portion of a human CD8β polypeptide. In one embodiment, such replacement is a replacement of endogenous nucleotide sequence encoding all or substantially all of extracellular portion of a non-human CD8α and/or β with a human nucleotide with a human nucleotide sequence encoding the same. In one embodiment, such replacement is a replacement of a sequence encoding at least all or substantially all of the immunoglobulin V-like domain of a non-human CD8α and/or β with a human nucleotide sequence encoding the same. In one embodiment, the replacement does not comprise a replacement of a CD8α and/or β sequence encoding transmembrane and cytoplasmic domain of a non-human CD8α and/or β polypeptide. Thus, the non-human animal expresses a chimeric human/non-human CD8α and/or β polypeptide from the endogenous non-human CD8 locus. In yet another embodiment, the replacement results in a CD8α and/or β protein comprising a polypeptide sequence set forth in SEQ ID NO:88 and/or 84, respectively.

In one embodiment, the nucleotide sequence of the chimeric human/non-human CD8 locus (e.g., chimeric rodent CD8 locus, e.g., chimeric mouse CD8 locus) is provided. In one aspect, because the chimeric human/non-human (e.g., human/rodent, e.g., human/mouse) CD8α and/or β sequence is placed at respective endogenous non-human (e.g., rodent, e.g., mouse) CD8α and/or β locus, it retains endogenous CD8α and/or β promoter and regulatory elements. In another embodiment, the chimeric locus may contain human CD8α and/or β promoter and regulatory elements to the extent those allow proper CD8α and/or β expression (proper spatial and temporal protein expression), CD8+ T cell development, CD8 lineage choice, and co-receptor function. Thus, in one aspect, the animals of the invention comprise a genetic modification that does not alter proper lineage choice and development of T cells. In one aspect, the animals (e.g., rodents, e.g., mice) of the invention do not express chimeric CD8 protein on immune cells other than cells that normally express CD8, e.g., animals do not express CD8 on B cells or mature CD4+ T cells. In one embodiment, the replacement results in retention of elements that allow proper spatial and temporal regulation of CD8α and/or β expression.

In various embodiments, a non-human animal (e.g., a rodent, e.g., a mouse or rat) that expresses a functional chimeric CD8 protein (e.g., CD8α β or CD8αα) from a chimeric CD8 locus as described herein displays the chimeric protein on a cell surface. In one embodiment, the non-human animal expresses the chimeric CD8 protein on a cell surface in a cellular distribution that is the same as observed in a human. In one aspect, the CD8 protein of the invention is capable of interacting with an MHC I protein expressed on the surface of a second cell.

Human or Humanized T Cell Receptor

Disclosed herein are genetically modified non-human animals comprising a substantially humanized T cell immune system. In some embodiment a non-human animal as disclosed herein comprises, e.g., in its genome, (a) a nucleotide sequence encoding a chimeric human/non-human T cell co-receptor, wherein the human portion of the chimeric T cell co-receptor polypeptide is encoded by a sequence encoding an extracellular domain of a human T cell co-receptor, and wherein the sequence encoding the extracellular domain of a human T cell co-receptor is operably linked to a nucleotide comprising a sequence encoding a non-human T cell co-receptor transmembrane and/or cytoplasmic domain; (b) an unrearranged T cell receptor (TCR) variable gene region comprising at least one human V segment, optionally at least on human D segment, and at least one human J segment, wherein the unrearranged V, optionally D, and J segments of the TCR variable region gene can recombine to form a rearranged gene operably linked to a non-human TCR constant gene sequence; and (c) a nucleic acid sequence encoding a chimeric human/non-human MHC polypeptide, wherein a human portion of the chimeric MHC polypeptide comprises an extracellular domain of a human MHC polypeptide that associates with the human portion of the chimeric T cell co-receptor polypeptide. Optionally, the non-human animal also comprises a human or humanized β2 microglobulin polypeptide.

Accordingly, in various embodiments, the invention generally provides genetically modified non-human animals wherein the non-human animals comprise in the genome unrearranged humanized TCR variable gene loci, e.g., an unrearranged human TCR variable gene region comprising human TCR variable segments capable of recombining to form a rearranged TCR variable gene sequence. TCR locus or TCR gene locus (e.g., TCRα locus or TCR locus), as used herein, refer to the genomic DNA comprising the TCR coding region, including the entire TCR coding region, including unrearranged V(D)J sequences, enhancer sequence, constant sequence(s), and any upstream or downstream (UTR, regulatory regions, etc.), or intervening DNA sequence (introns, etc.). TCR variable locus, TCR variable region, or TCR variable gene locus (e.g., TCRα variable gene locus or TCRβ variable gene locus), refers to genomic DNA that includes TCR variable region segments (V(D)J region) but excludes TCR constant sequences and, in various embodiments, enhancer sequences. Other sequences may be included in the TCR variable gene locus for the purposes of genetic manipulation (e.g., selection cassettes, restriction sites, etc.), and these are encompassed herein.

T cells bind epitopes on small antigenic determinants on the surface of antigen-presenting cells that are associated with a major histocompatibility complex (MHC; in mice) or human leukocyte antigen (HLA; in humans) complex. T cells bind these epitopes through a T cell receptor (TCR) complex on the surface of the T cell. T cell receptors are heterodimeric structures composed of two types of chains: an α (alpha) and β (beta) chain, or a γ (gamma) and δ (delta) chain. The a chain is encoded by the nucleic acid sequence located within the α locus (on human or mouse chromosome 14), which also encompasses the entire δ locus, and the β chain is encoded by the nucleic acid sequence located within the β locus (on mouse chromosome 6 or human chromosome 7). The majority of T cells has an αβ TCR; while a minority of T cells bears a γδ TCR. Interactions of TCRs with MHC class I (presenting to CD8+ T cells) and MHC class II (presenting to CD4+ T cells) molecules are shown in FIG. 1 (closed symbols represent non-human sequences; striped symbols represent human sequences, showing one particular embodiment of the TCR protein of the present invention).

T cell receptor α and β polypeptides (and similarly γ and δ polypeptides) are linked to each other via a disulfide bond. Each of the two polypeptides that make up the TCR contains an extracellular domain comprising constant and variable regions, a transmembrane domain, and a cytoplasmic tail (the transmembrane domain and the cytoplasmic tail also being a part of the constant region). The variable region of the TCR determines its antigen specificity, and similar to immunoglobulins, comprises three complementary determining regions (CDRs). Also similar to immunoglobulin genes, T cell receptor variable gene loci (e.g., TCRα and TCRβ loci) contain a number of unrearranged V(D)J segments (variable (V), joining (J), and in TCRβ and δ, diversity (D) segments). During T cell development in the thymus, TCRα variable gene locus undergoes rearrangement, such that the resultant TCR α chain is encoded by a specific combination of VJ segments (Vα/Jα sequence); and TCRβ variable gene locus undergoes rearrangement, such that the resultant TCR β chain is encoded by a specific combination of VDJ segments (vβ/Dβ/Jβ sequence).

Interactions with thymic stroma trigger thymocytes to undergo several developmental stages, characterized by expression of various cell surface markers. A summary of characteristic cell surface markers at various developmental stages in the thymus is presented in Table 1. Rearrangement at the TCRβ variable gene locus begins at the DN2 stage and ends during the DN4 stage, while rearrangement of the TCRα variable gene locus occurs at the DP stage. After the completion of TCRβ locus rearrangement, the cells express TCRβ chain at the cell surface together with the surrogate α chain, pTα. See, Janeway's Immunobiology, Chapter 7, 7$^{th}$ Ed., Murphy et al. eds., Garland Science, 2008.

TABLE 1

Developmental Stages of T cells in the Thymus

| | Developmental Stage | | | | |
|---|---|---|---|---|---|
| | DN1 | DN2 | DN3 | DN4 | DP | SP |
| Marker(s) | CD44+/ CD25− | CD44+/ CD25+ | CD44$^{low}$/ CD25+ | CD44−/ CD25− | CD4+/ CD8+ | CD4+ or CD8+ |

Naive CD4+ and CD8+ T cells exit the thymus and enter the peripheral lymphoid organs (e.g., spleen) where they are exposed to antigens and are activated to clonally expand and differentiate into a number of effector T cells (Teff), e.g., cytotoxic T cells, T$_{REG}$ cells, T$_H$17 cells, T$_H$1 cells, T$_H$2 cells, etc. Subsequent to infection, a number of T cells persist as memory T cells, and are classified as either central memory T cells (Tcm) or effector memory T cells (Tem). Sallusto et al. (1999) Two subsets of memory T lymphocytes with distinct homing potentials and effector functions, Nature 401:708-12 and Commentary by Mackay (1999) Dual personality of memory T cells, Nature 401:659-60. Sallusto and colleagues proposed that, after initial infection, Tem cells represent a readily available pool of antigen-primed memory T cells in the peripheral tissues with effector functions, while Tcm cells represent antigen-primed memory T cells in the peripheral lymphoid organs that upon secondary challenge can become new effector T cells. While all memory T cells express CD45RO isoform of CD45 (naïve T cells express CD45RA isoform), Tcm are characterized by expression of L-selectin (also known as CD62L) and CCR7+, which are important for binding to and signaling in the peripheral lymphoid organs and lymph nodes. Id. Thus, all T cells found in the peripheral lymphoid organs (e.g., naïve T cells, Tcm cells, etc.) express CD62L. In addition to CD45RO, all memory T cells are known to express a number of different cell surface markers, e.g., CD44. For summary of various cell surface markers on T cells, see Janeway's Immunobiology, Chapter 10, supra.

While TCR variable domain functions primarily in antigen recognition, the extracellular portion of the constant domain, as well as transmembrane, and cytoplasmic domains of the TCR also serve important functions. A complete TCR receptor complex requires more than the α and β or γ and δ polypeptides; additional molecules required include CD3γ, CD3δ, and CD3ε, as well as the ζ chain homodimer (ζζ). At the completion of TCRβ rearrangement, when the cells express TCRβ/pTα, this pre-TCR complex exists together with CD3 on the cell surface. TCRα (or pTα) on the cell surface has two basic residues in its transmembrane domain, one of which recruits a CD3δε heterodimer, and another recruits ζζ via their respective acidic residues. TCRβ has an additional basic residue in its transmembrane domain that is believed to recruit CD3δε heterodimer. See, e.g., Kuhns et al. (2006) Deconstructing the Form and Function of the TCR/CD3 Complex, Immunity 24:133-39; Wucherpfennig et al. (2009) Structural Biology of the T-cell Receptor: Insights into Receptor Assembly, Ligand Recognition, and Initiation of Signaling, Cold Spring Harb. Perspect. Biol. 2:α005140. The assembled complex, comprising TCRαβ heterodimer, CD3γε, CD3δε, and ζζ, is expressed on the T cell surface. The polar residues in the transmembrane domain have been suggested to serve as quality control for exiting endoplasmic reticulum; it has been demonstrated that in the absence of CD3 subunits, TCR chains are retained in the ER and targeted for degradation. See, e.g., Call and Wucherpfennig (2005) The T Cell Receptor: Critical Role of the Membrane Environment in Receptor Assembly and Function, Annu. Rev. Immunol. 23:101-25.

CD3 and ζ chains of the assembled complex provide components for TCR signaling as TCRαβ heterodimer (or TCRγδ heterodimer) by itself lacks signal transducing activity. The CD3 chains possess one Immune-Receptor-Tyrosine-based-Activation-Motif (ITAM) each, while the ζ chain contains three tandem ITAMs. ITAMs contain tyrosine residues capable of being phosphorylated by associated kinases. Thus, the assembled TCR-CD3 complex contains 10 ITAM motifs. See, e.g., Love and Hayes (2010) ITAM-Mediated Signaling by the T-Cell Antigen Receptor, Cold Spring Harb. Perspect. Biol. 2:e002485. Following TCR engagement, ITAM motifs are phosphorylated by Src family tyrosine kinases, Lck and Fyn, which initiates a signaling cascade, resulting in Ras activation, calcium mobilization, actin cytoskeleton rearrangements, and activation of transcription factors, all ultimately leading to T cell differentiation, proliferation, and effector actions. Id., see also, Janeway's Immunobiology, supra; both incorporated herein by reference.

Additionally, TCRβ transmembrane and cytoplasmic domains are thought to have a role in mitochondrial targeting and induction of apoptosis; in fact, naturally occurring N-terminally truncated TCRβ molecules exist in thymocytes. Shani et al. (2009) Incomplete T-cell receptor-β peptides target the mitochondrion and induce apoptosis, Blood 113:3530-41. Thus, several important functions are served by the TCR constant region (which, in various embodiments, comprises a portion of extracellular as well as transmembrane and cytoplasmic domains); and in various embodiments the structure of this region should be taken into consideration when designing humanized TCRs or genetically modified non-human animals expressing the same.

Mice transgenic for rearranged T cell receptor sequences are known in the art. The present invention relates to genetically modified non-human animals (e.g., rodents, e.g., rats, mice) that comprise unrearranged human or humanized T cell variable gene loci that are capable of rearranging to form nucleic acid sequences that encode human T cell receptor variable domains, including animals that comprise T cells that comprise rearranged human variable domains and non-human (e.g., mouse or rat) constant regions. The present invention also provides non-human animals (e.g., rodents, e.g., rats, mice) that are capable of generating a diverse repertoire of human T cell receptor variable region sequences; thus, the present invention provides non-human animals that express TCRs with fully human variable domains in response to an antigen of interest and that bind an epitope of the antigen of interest. In some embodiments, provided are non-human animals that generate a diverse T cell receptor repertoire capable of reacting with various antigens, including but not limited to antigens presented by APCs.

In one embodiment, the invention provides genetically modified non-human animals (e.g., rodents, e.g., rats, mice) that comprise in their genome unrearranged human TCR variable region segments (V(D)J segments), wherein the unrearranged human TCR variable region segments replace, at an endogenous non-human (e.g., rodent) TCR variable gene locus (e.g., TCRα, β, δ, and/or γ variable gene locus), endogenous non-human TCR variable region segments. In one embodiment, unrearranged human TCR variable gene locus replaces endogenous non-human TCR variable gene locus.

In another embodiment, the invention provides genetically modified non-human animals (e.g., rodents, e.g., rats, mice) that comprise in their genome unrearranged human TCR variable region segments (V(D)J segments), wherein the unrearranged human TCR variable region segments are operably linked to a non-human TCR constant region gene sequence resulting in a humanized TCR locus, wherein the humanized TCR locus is at a site in the genome other than the endogenous non-human TCR locus. Thus, in one embodiment, a non-human animal (e.g., rodent, e.g., mouse, rat) comprising a transgene that comprises unrearranged human TCR variable region segments operably linked to non-human TCR constant region gene sequence is also provided.

In one aspect, the genetically modified non-human animals of the invention comprise in their genome human TCR variable region segments, while retaining non-human (e.g., rodent, e.g., mouse, rat) TCR constant gene sequence(s) that encode TCR constant domains. In various embodiments, a TCR constant domain includes the transmembrane domain and the cytoplasmic tail of the TCR. Thus, in various embodiments of the present invention, the genetically modified non-human animals retain endogenous non-human TCR transmembrane domain and cytoplasmic tail. In other embodiments, non-human animals comprise non-human non-endogenous TCR constant gene sequences, e.g., encoding non-human non-endogenous TCR transmembrane domain and cytoplasmic tail. As indicated above, the constant domain of the TCR participates in a signaling cascade initiated during antigen-primed T cell activation; thus, endogenous TCR constant domain interacts with a variety of non-human anchor and signaling proteins in the T cell. Thus, in one aspect, the genetically modified non-human animals of the invention express humanized T cell receptors that retain the ability to recruit a variety of endogenous non-human anchor or signaling molecules, e.g., CD3 molecules (e.g., CD3γ, CD3δ, CD3ε), the ζ chain, Lck, Fyn, ZAP-70, etc. A nonlimiting list of molecules that are recruited to the TCR complex is described in Janeway's Immunobiology, supra. It is believed that the ability of T cell development and T cell differentiation processes in the non-human animals to proceed and allow for a robust immune response may be due, at least in part, to the placement of variable regions at the endogenous mouse loci and the maintenance of mouse constant domains.

In some embodiments, a non-human animal is provided that comprises in its genome unrearranged human TCRα variable region segments, wherein the unrearranged human TCRα variable region segments are operably linked to a non-human TCRα constant region gene sequence resulting in a humanized TCRα locus. In one embodiment, the humanized TCRα locus is at a site in the genome other than the endogenous non-human TCRα locus. In another embodiment, the unrearranged human TCRα variable region segments replace endogenous non-human TCRα variable region segments while retaining endogenous non-human TCRα constant region gene sequence(s). In one embodiment, the unrearranged human TCRα variable gene locus replaces endogenous non-human TCRα variable gene locus. In some embodiments, replacement of an endogenous non-human TCRα variable region gene locus with the unrearranged human TCRα variable gene locus comprises a deletion or inactivation of a TCRδ variable gene locus. In other embodiments, replacement of an endogenous non-human TCRα variable region gene with the unrearranged human TCRα gene locus comprises a replacement of an endogenous TCRδ variable gene locus with unrearranged human TCRδ variable region segments. In some embodiments, the animal retains endogenous non-human TCRβ variable region and constant region gene sequence(s). Thus, the animal expresses a TCR that comprises a chimeric human/non-human (i.e., humanized) TCRα chain and a non-human TCR chain.

In some embodiments, a non-human animal is provided that comprises in its genome unrearranged human TCRδ variable region segments, wherein the unrearranged human TCRδ variable region segments are operably linked to a non-human TCRδ constant region gene sequence resulting in a humanized TCRδ locus. In one embodiment, the humanized TCRδ locus is at a site in the genome other than the endogenous non-human TCRδ locus. In another embodiment, the unrearranged human TCRδ variable region segments replace endogenous non-human TCRδ variable region segments while retaining endogenous non-human TCRδ constant region gene sequence(s). In one embodiment, the unrearranged human TCRδ variable gene locus replaces endogenous non-human TCRδ variable gene locus.

In other embodiments, a non-human animal is provided that comprises in its genome unrearranged human TCRβ variable region segments, wherein the unrearranged human TCRβ variable region segments are operably linked to a non-human TCR constant region gene sequence resulting in a humanized TCR locus. In one embodiment, the humanized TCR locus is at a site in the genome other than the endogenous non-human TCRβ locus. In another embodiment, the unrearranged human TCRβ variable region segments replace endogenous non-human TCRβ variable region segments while retaining endogenous non-human TCRβ constant region gene sequence(s). In one embodiment, the unrearranged human TCRβ variable gene locus replaces endogenous non-human TCRβ variable gene locus. In some embodiments, the animal retains endogenous non-human TCRα variable region and constant region gene sequence(s). Thus, the animal expresses a TCR that comprises a chimeric human/non-human (i.e., humanized) TCRβ chain and a non-human TCRα chain.

In some specific embodiments, the invention provides a genetically modified non-human animal (e.g., rodent, e.g., mouse or rat) that comprises in its genome (a) an unrearranged T cell receptor (TCR) α variable gene locus comprising at least one human Vα segment and at least one human Jα segment, operably linked to an endogenous non-human (e.g., rodent, e.g., mouse or rat) TCRα constant gene sequence(s), (b) an unrearranged TCRβ variable gene locus comprising at least one human Vβ segment, at least one human Dβ segment, and at least one human Jβ segment, operably linked to an endogenous non-human (e.g., rodent, e.g., mouse or rat) TCR constant region gene sequence(s) and/or (c) an unrearranged TCRδ variable gene locus comprising at least one human Vδ segment, at least one human Dδ segment, and at least one human Jδ segment, operably linked to an endogenous non-human (e.g., rodent, e.g., mouse or rat) TCRδ constant region gene sequence. Another non-human animal as provided herein comprises in its genome (a) an unrearranged T cell receptor (TCR) α variable gene locus comprising at least one human Vα segment and at least one human Jα segment, operably linked to an endogenous non-human (e.g., rodent, e.g., mouse or rat) TCRα constant gene sequence(s), (b) an unrearranged TCRβ variable gene locus comprising at least one human Vβ segment, at least one human Dβ segment, and at least one human Jβ segment, operably linked to an endogenous non-human (e.g., rodent, e.g., mouse or rat) TCRβ constant gene sequence(s), (c) an unrearranged TCRδ variable gene locus comprising at least one human Vδ segment, at least one human Dδ segment, and at least one human Jδ segment, operably linked to an endogenous non-human (e.g., rodent, e.g., mouse or rat) TCRδ constant region gene sequence(s) and/or (d) an unrearranged TCRγ variable gene locus comprising at least one human Vγ segment, and at least one human Jγ segment, operably linked to an endogenous non-human (e.g., rodent, e.g., mouse or rat) TCRγ constant region gene sequence.

In various embodiments of the invention, the unrearranged human or humanized TCR variable gene locus (e.g., TCRα TCR and/or TCRδ variable gene locus) is comprised in the germline of the non-human animal (e.g., rodent, e.g., mouse or rat). In various embodiments, the replacements of TCR V(D)J segments by unrearranged human TCR V(D)J segments (e.g., Vα and Jα; Vβ and Dβ and Jβ; Vδ and Dδ and Jδ; Vγ and Jγ segments) are at an endogenous non-human TCR variable locus (or loci), wherein the unrearranged human V and J and/or V and D and J segments are operably linked to non-human TCR constant region gene sequences.

In some embodiments of the invention, the non-human animal comprises two copies of the unrearranged human or humanized TCRα variable gene locus, two copies of the unrearranged human or humanized TCRβ variable gene locus and/or two copies of the unrearranged human or humanized TCRδ variable gene locus. Thus, the non-human animal is homozygous for one or more unrearranged human or humanized TCRα, TCRβ and/or TCRδ variable gene loci. In some embodiments of the invention, the non-human animal comprises one copy of the unrearranged human or humanized TCRα variable gene locus one copy of the unrearranged human or humanized TCRβ variable gene locus and/or one copy of the unrearranged human or humanized TCRδ variable gene locus. Thus, the non-human animal is heterozygous for unrearranged human or humanized TCRα, TCRβ and/or TCRδ variable gene locus. In other embodiment, a non-human animal is heterozygous or homozygous for unrearranged human or humanized TCRγ variable gene locus.

In one embodiment, the unrearranged TCRα variable gene locus comprising human variable region segments (e.g., human Vα and Jα segments) is positioned in the non-human genome such that the human variable region segments replace corresponding non-human variable region segments. In one embodiment, the unrearranged TCRα variable gene locus comprising human variable region segments replaces endogenous TCRα variable gene locus. In one aspect, endogenous non-human Vα and Jα segments are incapable of rearranging to form a rearranged Vα/Jα sequence. Thus, in one aspect, the human Vα and Jα segments in the unrearranged TCRα variable gene locus are capable of rearranging to form a rearranged human Vα/Jα sequence.

Similarly, in one embodiment, the unrearranged TCRβ variable gene locus comprising human variable region segments (e.g., human Vβ, Dβ, and Jβ segments) is positioned in the non-human genome such that the human variable region segments replace corresponding non-human variable region segments. In one embodiment, the unrearranged TCRβ variable gene locus comprising human variable region segments replaces endogenous TCRβ variable gene locus. In one aspect, endogenous non-human Vβ, Dβ, and Jβ segments are incapable of rearranging to form a rearranged Vβ/Dβ/Jβ sequence. Thus, in one aspect, the human Vβ, Dβ, and Jβ segments in the unrearranged TCR variable gene locus are capable of rearranging to form a rearranged human Vβ/Dβ/Jβ sequence.

In one embodiment, the unrearranged TCRδ variable gene locus comprising human variable region segments (e.g., human Vδ, Dδ, and Jδ segments) is positioned in the non-human genome such that the human variable region segments replace corresponding non-human variable region segments. In one embodiment, the unrearranged TCRδ variable gene locus comprising human variable region segments replaces endogenous TCRδ variable gene locus. In one aspect, endogenous non-human Vδ, Dδ, and Jδ segments are incapable of rearranging to form a rearranged Vδ/Dδ/Jδ sequence. Thus, in one aspect, the human Vδ, Dδ, and Jδ segments in the unrearranged TCRδ variable gene locus are capable of rearranging to form a rearranged human Vδ/Dδ/Jδ sequence.

In one embodiment, the unrearranged TCRγ variable gene locus comprising human variable region segments (e.g., human Vγ and Jγ segments) is positioned in the non-human genome such that the human variable region segments replace corresponding non-human variable region segments. In one embodiment, the unrearranged TCRγ variable gene locus comprising human variable region segments replaces endogenous TCRγ variable gene locus. In one aspect, endogenous non-human Vα and Jα segments are incapable of rearranging to form a rearranged Vγ/Jγ sequence. Thus, in one aspect, the human Vγ and Jγ segments in the unrearranged TCRγ variable gene locus are capable of rearranging to form a rearranged human Vγ/Jγ sequence.

In yet another embodiment, both the unrearranged TCRα, β, δ and/or γ variable gene loci comprising human variable region segments replace respective endogenous TCRα, β, δ, and γ variable gene loci. In one aspect, endogenous non-human Vα and Jα segments are incapable of rearranging to form a rearranged Vα/Jα sequence, endogenous non-human Vβ, Dβ, and Jβ segments are incapable of rearranging to form a rearranged Vβ/Dβ/Jβ sequence, endogenous Vδ, Dδ, and Jδ segments are incapable of rearranged to form a rearranged Vδ/Dδ/Jδ sequence and/or endogenous non-human Vγ and Jγ segments are incapable of rearranging to form a rearranged Vγ/Jγ sequence. Thus, in one aspect, the human Vα and Jα segments in the unrearranged TCRα variable gene locus are capable of rearranging to form a rearranged human Vα/Jα sequence, the human Vβ, Dβ, and Jβ segments in the unrearranged TCRβ variable gene locus are capable of rearranging to form a rearranged human Vβ/Dβ/Jβ sequence, the human Vδ, Dδ, and Jδ segments in the unrearranged TCRδ variable gene locus are capable of rearranged to form a rearranged human Vδ/Dδ/Jδ sequence and/or the human Vγ and Jγ segments in the unrearranged TCRα variable gene locus are capable of rearranging to form a rearranged human Vγ/Jγ sequence.

In some aspects of the invention, the non-human animal comprising a humanized TCRα, TCR and/or TCR δ gene locus (comprising an unrearranged human TCRα, TCRβ and/or TCR δ variable gene locus) retains an endogenous non-human TCRα TCRβ and/or TCRδ variable gene locus. In one embodiment, the endogenous non-human TCRα, TCRβ and/or TCRδ variable gene locus is a non-functional locus. In one embodiment, the non-functional locus is an inactivated locus, e.g., an inverted locus (e.g., the coding nucleic acid sequence of the variable gene locus is in inverted orientation with respect to the constant region sequence, such that no successful rearrangements are possible utilizing variable region segments from the inverted locus). In one embodiment, the humanized TCRα, TCRβ and/or TCR δ variable gene locus is positioned between the endogenous non-human TCRα, TCRβ and/or TCRδ variable gene locus and the endogenous non-human TCRα, TCRβ and/or TCRδ constant gene locus, respectively. Similar chromosomal arrangements may be made for placing human or humanized TCRγ into the genome of a non-human animal, e.g., at a TCRγ locus.

The number, nomenclature, position, as well as other aspects of V and J and/or V, D, and J segments of the human and mouse TCR loci may be ascertained using the IMGT database, available at the website of the International Immunogenetics Information System (IMGT). The mouse TCRα variable locus is approximately 1.5 megabases and comprises a total of 110Vα and 60 Jα segments. The human TCRα variable locus is approximately 1 megabase and comprises a total of 54Vα and 61Jα segments, with 45Vα and 50Jα believed to be functional. Unless stated otherwise, the numbers of human V(D)J segments referred to throughout the specification refers to the total number of V(D)J segments. In one embodiment of the invention, the genetically modified non-human animal (e.g., rodent, e.g., mouse or rat) comprises at least one human Vα and at least one human Jα segment. In one embodiment, the non-human animal comprises a humanized TCRα locus that comprises 1, 2, 3, 4, 5, 6, 7, 8, 9, 10, 15, 20, 23, 25, 30, 35, 40, 45, 48, 50, or up to 54 human Vα segments. In some embodiments, the humanized TCRα locus comprises 2, 8, 23, 35, 48, or 54 human Vα segments. Thus, in some embodiments, the humanized TCRα locus in the non-human animal may comprise 5%, 10%, 15%, 20%, 25%, 30%, 35%, 40%, 45%, 50%, 55%, 60%, 65%, 70%, 75%, 80%, 85%, 90%, 95%, 96%, 97%, 98% 99%, or 100% of human Vα; in some embodiments, it may comprise about 2%, about 3%, about 15%, about 65%, about 90%, or 100% of human Vα.

In one embodiment, the non-human animal comprises a humanized TCRα locus that comprises a DNA fragment comprising a contiguous human sequence of human Vα40 to Vα41 (Vα segment is also referred to as "TRAV" or "TCRAV") and a DNA fragment comprising a contiguous human sequence of 61 human Jα segments (Jα segment is also referred to as "TRAJ" or "TCRAJ"). In one embodiment, the non-human animal comprises a humanized TCRα locus that comprises a DNA fragment comprising a contiguous human sequence of human TRAV35 to TRAV41 and a DNA fragment comprising a contiguous human sequence of 61 human TRAJs. In one embodiment, the non-human animal comprises a humanized TCRα locus that comprises a DNA fragment comprising a contiguous human sequence of human TRAV22 to TRAV41 and a DNA fragment comprising a contiguous human sequence of 61 human TRAJs. In one embodiment, the non-human animal comprises a humanized TCRα locus that comprises a DNA fragment comprising a contiguous human sequence of human TRAV13-2 to TRAV41 and a DNA fragment comprising a contiguous human sequence of 61 human TRAJs. In one embodiment, the non-human animal comprises a humanized TCRα locus that comprises a DNA fragment comprising a contiguous human sequence of human TRAV6 to TRAV41 and 61 human TRAJs. In one embodiment, the non-human animal comprises a humanized TCRα locus that comprises a DNA fragment comprising a contiguous human sequence of human TRAV1-1 to TRAV 41 and 61 human TRAJs. In various embodiments, the DNA fragments comprising contiguous human sequences of human TCRα variable region segments also comprise restriction enzyme sites, selection cassettes, endonucleases sites, or other sites inserted to facilitate cloning and selection during the locus humanization process. In various embodiments, these additional sites do not interfere with proper functioning (e.g., rearrangement, splicing, etc.) of various genes at the TCRα locus.

In one embodiment, the humanized TCRα locus comprises 61 human Jα segments, or 100% of human Jα segments. In a particular embodiment, humanized TCRα locus comprises 8 human Vα segments and 61 human Jα segments; in another particular embodiment, humanized TCRα locus comprises 23 human Vα segments and 61 human Jα segments. In another particular embodiment, the humanized TCRα locus comprises a complete repertoire of human Vα and Jα segments, i.e., all human variable a region gene segments encoded by the α locus, or 54 human Vα and 61 human Jα segments. In various embodiments, the non-human animal does not comprise any endogenous non-human Vα or Jα segments at the TCRα locus.

The mouse TCRβ variable locus is approximately 0.6 megabases and comprises a total of 33 Vβ, 2 Dβ, and 14 Jβ segments. The human TCRβ variable locus is approximately 0.6 megabases and comprises a total of 67 Vβ, 2 Dβ, and 14 Jβ segments. In one embodiment of the invention, the genetically modified non-human animal (e.g., rodent, e.g., mouse or rat) comprises at least one human Vβ, at least one human Dβ, and at least one human Jα segment. In one embodiment, the non-human animal comprises a humanized TCRβ locus that comprises 1, 2, 3, 4, 5, 6, 7, 8, 9, 10, 15, 20, 23, 25, 30, 35, 40, 45, 48, 50, 55, 60, or up to human 67 Vβ segments. In some embodiments, the humanized TCRβ locus comprises 8, 14, 40, 66, or human 67 Vβ segments. Thus, in some embodiments, the humanized TCRβ locus in the non-human animal may comprise 5%, 10%, 15%, 20%, 25%, 30%, 35%, 40%, 45%, 50%, 55%, 60%, 65%, 70%, 75%, 80%, 85%, 90%, 95%, 96%, 97%, 98% 99%, or 100% of human Vβ; in some embodiments, it may comprise about 20%, about 60%, about 15%, about 98%, or 100% of human V.

In one embodiment, the non-human animal comprises a humanized TCRβ locus that comprises a DNA fragment comprising a contiguous human sequence of human Vβ18 to Vβ29-1 (Vβ segment is also referred to as "TRBV" or "TCRBV"). In one embodiment, the non-human animal comprises a humanized TCRβ locus that comprises a DNA fragment comprising a contiguous human sequence of human TRBV6-5 to TRBV29-1, a separate DNA fragment comprising a contiguous human sequence of human Dβ1-Jβ1 (i.e., human Dβ1-Jβ1-1-Jβ1-6 segments), and a separate DNA fragment comprising a contiguous human sequence of human Dβ2-Jβ2 (i.e., human Dβ2-Jβ2-1-Jβ2-7 segments). In one embodiment, the non-human animal comprises a humanized TCRβ locus that comprises a DNA fragment comprising a contiguous human sequence of human TRBV6-5 to TRBV29-1, a separate DNA fragment comprising a contiguous human sequence of human Dβ1-Jβ1 (i.e., human Dβ1-Jβ1-1-Jβ1-6 segments), and a separate DNA fragment comprising a contiguous human sequence of human Dβ2-Jβ2 (i.e., human Dβ2-Jβ2-1-Jβ2-7 segments). In one embodiment, the non-human animal comprises a humanized TCRβ locus that comprises a DNA fragment comprising a contiguous human sequence of human TRBV1 to TRBV29-1, a separate DNA fragment comprising a contiguous human sequence of human Dβ1-Jβ1, and a separate DNA fragment comprising a contiguous human sequence of human Dβ2-Jβ2. In one embodiment, the non-human animal comprises a humanized TCRβ locus that comprises a DNA fragment comprising a contiguous human sequence of human TRBV1 to TRBV29-1, a separate DNA fragment comprising a contiguous human sequence of human Dβ1-Jβ1, a separate DNA fragment comprising a contiguous human sequence of human Dβ2-Jβ2, and a separate DNA fragment comprising the sequence of human TRBV30. In various embodiments, the DNA fragments comprising contiguous human sequences of human TCRβ variable region segments also comprise restriction enzyme sites, selection cassettes, endonucleases sites, or other sites inserted to facilitate cloning and selection during the locus humanization process. In various embodiments, these additional sites do not interfere with proper functioning (e.g., rearrangement, splicing, etc.) of various genes at the TCR locus.

In one embodiment, the humanized TCR locus comprises 14 human Jβ segments, or 100% of human Jβ segments, and 2 human Dβ segments or 100% of human Jβ segments. In another embodiment, the humanized TCR locus comprises at least one human Vβ segment, e.g., 14 human Vβ segments, and all mouse Dβ and Jβ segments. In a particular embodiment, humanized TCR locus comprises 14 human Vβ segments, 2 human Dβ segments, and 14 human Jβ segments. In another particular embodiment, the humanized TCR locus comprises a complete repertoire of human Vβ, Dβ, and Jβ segments, i.e., all human variable β region gene segments encoded by the β locus or 67 human Vβ, 2 human Dβ, and 14 human Jβ segments. In one embodiment, the non-human animal comprises one (e.g., 5') non-human Vβ segment at the humanized TCR locus. In various embodiments, the non-human animal does not comprise any endogenous non-human Vβ, Dβ, or Jβ segments at the TCR locus.

In various embodiments, wherein the non-human animal (e.g., rodent) comprises a repertoire of human TCRα and TCRβ (and optionally human TCRδ and TCRγ) variable region segments (e.g., a complete repertoire of variable region segments), the repertoire of various segments (e.g., the complete repertoire of various segments) is utilized by the animal to generate a diverse repertoire of TCR molecules to various antigens.

In various aspects, the non-human animals comprise contiguous portions of the human genomic TCR variable loci that comprise V, D, and J, or D and J, or V and J, or V segments arranged as in an unrearranged human genomic variable locus, e.g., comprising promoter sequences, leader sequences, intergenic sequences, regulatory sequences, etc., arranged as in a human genomic TCR variable locus. In other aspects, the various segments are arranged as in an unrearranged non-human genomic TCR variable locus. In various embodiments of the humanized TCR α, β, δ and/or γ locus, the humanized locus can comprise two or more human genomic segments that do not appear in a human genome juxtaposed, e.g., a fragment of V segments of the human variable locus located in a human genome proximal to the constant region, juxtaposed with a fragment of V segments of the human variable locus located in a human genome at the upstream end of the human variable locus.

Figure 4A:
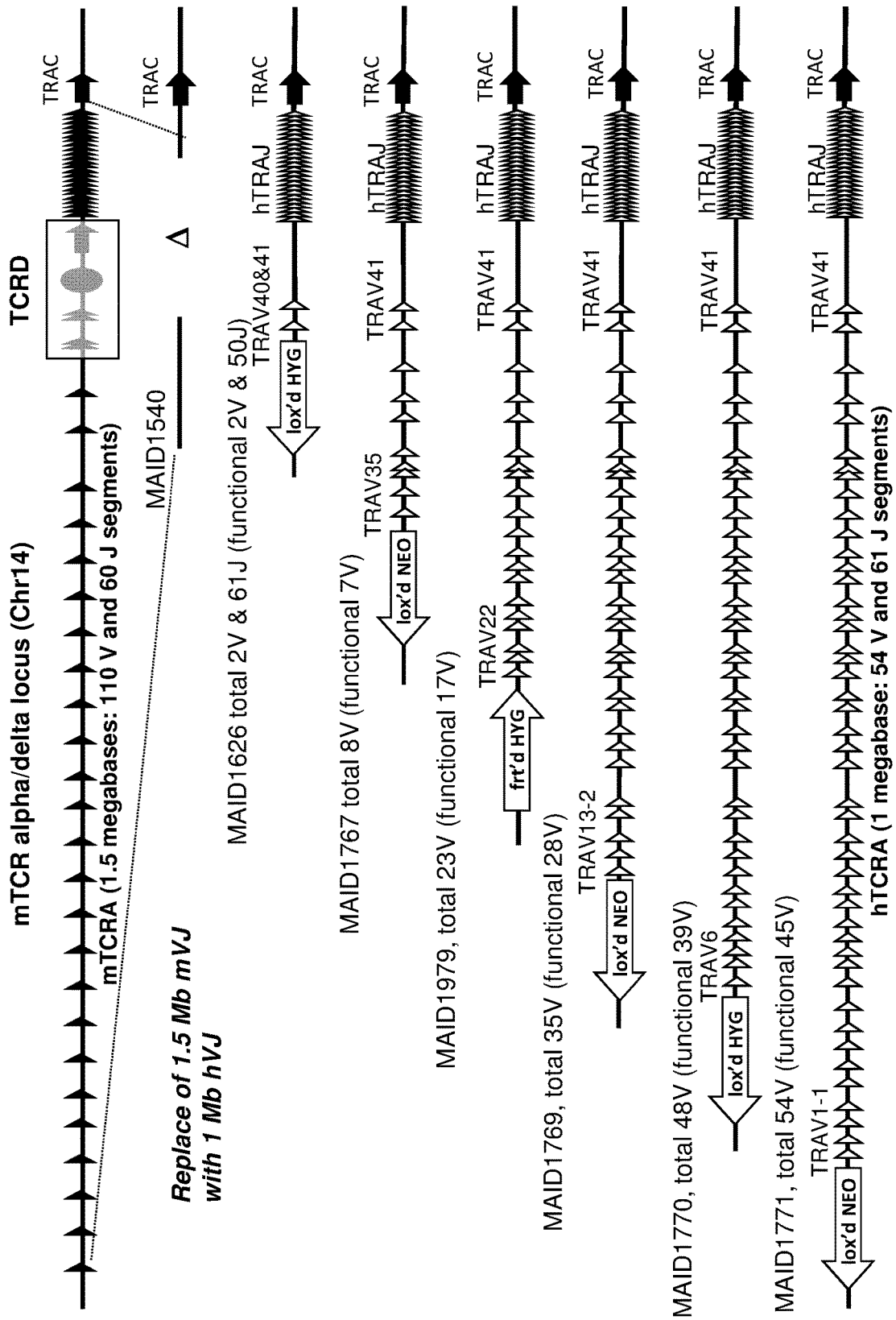
FIG. 4A depicts (not to scale) a progressive strategy for humanization of the mouse TCRα locus, wherein TCRα variable region gene segments are sequentially added upstream of an initial humanization of a deleted mouse locus (MAID1540). Mouse sequence is indicated by filled shapes; human sequence is indicated by empty shapes. MAID refers to modified allele ID number. TRAV=TCR Vα segment, TRAJ=TCR Jα segment (hTRAJ=human TRAJ), TRAC=TCR Cα domain, TCRD=TCRδ.

In both mouse and human, the TCRδ gene segments are located with the TCRα locus (see FIG. 4A, top, TCRD region boxed). TCRδ J and D segments are located between Vα and Jα segments, while TCRδ V segments are interspersed throughout the TCRα locus, with the majority located among various Vα segments. The number and locations of various TCRδ segments can be determined from the IMGT database. Due to the genomic arrangement of TCRδ gene segments within the TCRα locus, successful rearrangement at the TCRα locus may delete or inactivate the TCRδ gene segments.

In some embodiments of the invention, a non-human animal comprising an unrearranged human TCRα variable gene locus also comprises at least one human Vδ segment, e.g., up to complete repertoire of human Vδ segments. Thus, in some embodiments, the replacement of endogenous TCRα variable gene locus results in a replacement of at least one non-human Vδ segment with a human Vδ segment. In other embodiments, the non-human animal of the invention comprises a complete repertoire of human Vδ, Dδ, and Jδ segments at the unrearranged humanized TCRα locus; in yet other embodiments, the non-human animal comprises a complete unrearranged human TCRδ locus at the unrearranged humanized TCRα locus (i.e., a TCRδ locus including human variable region segments, as well as human enhancer and constant region). An exemplary embodiment for constructing an unrearranged humanized TCRα locus comprising complete unrearranged TCRδ locus is depicted in U.S. Pat. No. 9,113,616, incorporated herein by reference.

In yet another embodiment, the non-human animal of the invention further comprises an unrearranged humanized TCRγ locus, e.g., a TCRγ locus comprising at least one human Vγ and at least one human Jγ segments (e.g., a complete repertoire of human Vγ and human Jγ variable region segments). The human TCRγ locus is on chromosome 7, while the mouse TCRγ locus is on mouse chromosome 13. See the IMGT database for more detail on the TCRγ locus.

In one aspect, the non-human animal (e.g., rodent, e.g., mouse or rat) comprising humanized TCRα and β variable gene loci (and, optionally humanized TCRδ/γ variable gene loci) described herein expresses a humanized T cell receptor comprising a human variable region and a non-human (e.g., rodent, e.g., mouse or rat) constant region on a surface of a T cell. In some aspects, the non-human animal is capable or expressing a diverse repertoire of humanized T cell receptors that recognize a variety of presented antigens.

In various embodiments of the invention, the humanized T cell receptor polypeptides described herein comprise human leader sequences. In alternative embodiments, the humanized TCR receptor nucleic acid sequences are engineered such that the humanized TCR polypeptides comprise non-human leader sequences.

The humanized TCR polypeptides described herein may be expressed under control of endogenous non-human regulatory elements (e.g., rodent regulatory elements), e.g., promoter, silencer, enhancer, etc. The humanized TCR polypeptides described herein may alternatively be expressed under control of human regulatory elements. In various embodiments, the non-human animals described herein further comprise all regulatory and other sequences normally found in situ in the human genome.

In various embodiments, the human variable region of the humanized TCR protein is capable of interacting with various proteins on the surface of the same cell or another cell. In one embodiment, the human variable region of the humanized TCR interacts with MHC proteins (e.g., MHC class I or II proteins) presenting antigens on the surface of the second cell, e.g., an antigen presenting cell (APC). In some embodiments, the MHC I or II protein is a non-human (e.g., rodent, e.g., mouse or rat) protein. In other embodiments, the MHC I or II protein is a human(ized) protein. In one aspect, the second cell, e.g., the APC, is an endogenous non-human cell expressing a human or humanized MHC molecule. In a different embodiment, the second cell is a human cell expressing a human MHC molecule.

In one aspect, the non-human animal expresses a humanized T cell receptor with a non-human constant region on the surface of a T cell, wherein the receptor is capable of interacting with non-human molecules, e.g., anchor or signaling molecules expressed in the T cell (e.g., CD3 molecules, the chain, or other proteins anchored to the TCR through the CD3 molecules or the ζ chain). Thus, in one aspect, a cellular complex is provided, comprising (a) a non-human T-cell that expresses (i) a TCR that comprises a humanized TCRα chain as described herein and humanized TCRβ chain as described herein and (ii) a chimeric co-receptor as described herein and (b) a non-human antigen-presenting cell comprising an antigen bound to a chimeric MHC I and/or chimeric MHC II α s described herein. In one embodiment, the non-human constant TCRα and TCRβ chains are complexed with a non-human zeta (ζ) chain homodimer and CD3 heterodimers. In one embodiment, the cellular complex is an in vivo cellular complex. In one embodiment, the cellular complex is an in vitro cellular complex.

In various embodiments, the non-human animals (e.g., rodents, e.g., mice or rats) described herein produce T cells that are capable of undergoing thymic development, progressing from DN1 to DN2 to DN3 to DN4 to DP and to CD4 or CD8 SP T cells. Such T cells of the non-human animal of the invention express cell surface molecules typically produced by a T cell during a particular stage of thymic development (e.g., CD25, CD44, Kit, CD3, pTα, etc.). Thus, in one embodiment, the non-human animals described herein may express pTα complexed with TCRβ at the DN3 stage of thymic development. The non-human animals described herein express T cells capable of undergoing thymic development to produce CD4+ and CD8+ T cells.

In various embodiments, the non-human animals described herein produce T cells that are capable of undergoing T cell differentiation in the periphery. In some embodiments, the non-human animals described herein are capable of producing a repertoire of effector T cells, e.g., CTL (cytotoxic T lymphocytes), $T_H1$, $T_H2$, $T_{REG}$, $T_H17$, etc. Thus, in these embodiments, the non-human animals described herein generate effector T cells that fulfill different functions typical of the particular T cell type, e.g., recognize, bind, and respond to foreign antigens. In various embodiments, the non-human animals described herein produce effector T cells that kill cells displaying peptide fragments of cytosolic pathogens expressed in the context of MHC I molecules; recognize peptides derived from antigens degraded in intracellular vesicles and presented by MHC II molecules on the surface of macrophages and induce macrophages to kill microorganisms; produce cytokines that drive B cell differentiation; activate B cells to produce opsonizing antibodies; induce epithelial cells to produce chemokines that recruit neutrophils to infection sites; etc.

In additional embodiments, the non-human animals described herein comprise CD3+ T cells in the periphery, e.g., in the spleen. In other aspects, the non-human animals described herein are capable of generating a population of memory T cells in response an antigen of interest. For example, the non-human animals generate both central memory T cells (Tcm) and effector memory T cells (Tem) to an antigen, e.g., antigen of interest (e.g., antigen being tested for vaccine development, etc.).

DN1 and DN2 cells that do not receive sufficient signals (e.g., Notch signals) may develop into B cells, myeloid cells (e.g., dendritic cells), mast cells and NK cells. See, e.g., Yashiro-Ohtani et al. (2010) Notch regulation of early thymocyte development, Seminars in Immunology 22:261-69. In some embodiments, the non-human animals described herein develop B cells, myeloid cells (e.g., dendritic cells), mast cells and NK cells. In some embodiments, the non-human animals described herein develop a dendritic cell population in the thymus.

The predominant type of T cell receptors expressed on the surface of T cells is TCRα/β, with the minority of the cells expressing TCRδ/γ. In some embodiments of the invention, the T cells of the non-human animals comprising humanized TCRα and/or β loci exhibit utilization of TCRα/β and TCRδ/γ loci, e.g., utilization of TCRα/β and TCRδ/γ loci that is similar to the wild type animal (e.g., the T cells of the non-human animals described herein express TCRα/β and TCRδ/γ proteins in comparable proportions to that expressed by wild type animals). Thus, in some embodiments, the non-human animals comprising humanized TCRα/p and endogenous non-human TCRδ/γ loci exhibit utilization of all loci.

Human or Humanized MHC Molecules

In various embodiments, provided herein are genetically modified non-human animals that co-express at least one humanized T cell co-receptor, at least one humanized MHC that associates with the humanized T cell co-receptor, and optionally, a humanized TCR, which upon recognizing and binding peptide presented by the humanized MHC, and in conjunction with the humanized co-receptor, provides activation signals to the cell expressing the humanized TCR and chimeric T cell co-receptor polypeptides. Accordingly, a non-human animal as disclosed herein comprises at least one of a first, second, and/or third nucleic acid sequence, each of which encodes a different human or humanized MHC polypeptide selected from the group consisting of a human or humanized MHC II α polypeptide, a human or humanized MHC II β polypeptide, and a human or humanized MHC I α polypeptide; the non-human animal also optionally comprises a human or humanized β2 microglobulin. Use of the first, second, and third designations herein is not to be construed as limiting the non-human animals disclosed herein as requiring all three nucleic acid sequences or the presence of any of the human or humanized MHC polypeptides in any specific order.

Accordingly, in some embodiments, a non-human animal as disclosed herein may comprise, e.g., a first and second nucleotide sequence encoding e.g., a human or chimeric CD8α polypeptide and a human or chimeric CD8β polypeptide, an unrearranged T cell receptor (TCR) α variable gene locus comprising at least one human Vα segment and at least one human Jα segment, operably linked to a non-human TCRα constant gene sequence and/or an unrearranged TCRβ variable gene locus comprising at least one human Vβ segment, at least one human Dβ segment, and at least one human Jβ segment, operably linked to a non-human TCR constant gene sequence, and optionally a first and second nucleic acid sequence encoding, e.g., a human or humanized MHC I α polypeptide and a human or humanized β2-microglobulin polypeptide. In other embodiments, a non-human animal as disclosed herein may comprise, e.g., a first nucleotide sequence encoding, e.g., a chimeric CD4 polypeptide; an unrearranged T cell receptor (TCR) α variable gene locus comprising at least one human Vα segment and at least one human Jα segment, operably linked to a non-human TCRα constant gene sequence and/or an unrearranged TCR variable gene locus comprising at least one human Vβ segment, at least one human Dβ segment, and at least one human Jβ segment, operably linked to a non-human TCR constant gene sequence; and optionally a first and second nucleic acid sequence encoding, e.g., a human or humanized MHC II α polypeptide and a human or humanized MHC II β polypeptide. In some embodiment, a non-human animal as disclosed herein may comprise, e.g., a first, second and third nucleotide sequence encoding e.g., a chimeric CD4 polypeptide, a chimeric CD8α polypeptide, and a chimeric CD8β polypeptide; an unrearranged T cell receptor (TCR) α variable gene locus comprising at least one human Vα segment and at least one human Jα segment, operably linked to a non-human TCRα constant gene sequence and/or an unrearranged TCRβ variable gene locus comprising at least one human Vβ segment, at least one human Dβ segment, and at least one human Jβ segment, operably linked to a non-human TCRβ constant gene sequence; and optionally a first, second, third and fourth nucleic acid sequence encoding, e.g., a human or humanized MHC II α polypeptide, a human or humanized MHC II β polypeptide, a human or humanized MHC I α polypeptide, and a human or humanized a β2-microglobulin polypeptide.

In various embodiments, provided herein is a genetically modified non-human animal, e.g., rodent (e.g., mouse or rat) comprising in its genome a nucleic acid sequence encoding a human or humanized MHC I polypeptide and/or a nucleic acid sequence encoding human or humanized MHC II protein. The MHC I nucleic acid sequence may encode an MHC I polypeptide that is partially human and partially non-human, e.g., chimeric human/non-human MHC I polypeptide, and the MHC II nucleic acid sequence may encode an MHC II protein that is partially human and partially non-human, e.g., chimeric human/non-human MHC II protein (e.g., comprising chimeric human/non-human MHC II α and β polypeptides). In some aspects, the animal does not express endogenous MHC I and/or endogenous MHC II polypeptides, e.g., functional endogenous MHC I and/or MHC II polypeptides on a cell surface. In some embodiments, the only MHC I and/or MHC II molecules expressed on a cell surface of the animal are chimeric MHC I and/or MHC II molecules.

A genetically modified non-human animal comprising in its genome, e.g., at the endogenous locus, a nucleic acid sequence encoding a chimeric human/non-human MHC I polypeptide is disclosed in U.S. Patent Publication Nos. 20130111617 and 20130185819, which publications are incorporated herein by reference in their entireties. A genetically modified non-human animal comprising in its genome, e.g., at the endogenous locus, a nucleic acid sequence encoding humanized, e.g., chimeric human/non-human MHC II polypeptides is disclosed in U.S. Pat. No. 8,847,005 and in U.S. Patent Publication No 20130185820, each of which are incorporated herein by reference in their entireties. A genetically modified non-human animal comprising in its genome, e.g., at the endogenous locus, a nucleic acid sequence encoding a chimeric human/non-human MHC I polypeptide and comprising in its genome, e.g., at the endogenous locus, a nucleic acid sequence encoding humanized, e.g., chimeric human/non-human MHC II polypeptides, is disclosed in U.S. Patent Publication No. 20140245467, which is incorporated herein by reference in its entirety.

In various embodiments provided herein is a genetically modified non-human animal comprising in its genome, e.g., at one or more endogenous MHC loci, a first nucleic acid sequence encoding a chimeric human/non-human MHC I polypeptide, wherein a human portion of the chimeric MHC I polypeptide comprises an extracellular portion (or part thereof, e.g., one or more extracellular domains) of a human MHC I polypeptide; a second nucleic acid sequence encoding a chimeric human/non-human MHC II α polypeptide, wherein a human portion of the chimeric MHC II α polypeptide comprises an extracellular portion (or part thereof, e.g., one or more extracellular domains) of a human MHC II α polypeptide; and/or a third nucleic acid sequence encoding a chimeric human/non-human MHC II β polypeptide, wherein a human portion of the chimeric MHC II β polypeptide comprises an extracellular portion (or part thereof, e.g., one or more extracellular domains) of a human MHC II β polypeptide; wherein the non-human animal expresses functional chimeric human/non-human MHC I and MHC II proteins from its endogenous non-human MHC locus. In one embodiment, the first, second, and/or third nucleic acid sequences are respectively located the endogenous non-human MHC I, MHC II α and MHC II β loci. In one embodiment, wherein the non-human animal is a mouse, the first, second, and/or third nucleic acid sequences are located at the endogenous mouse MHC locus on mouse chromosome 17. In one embodiment, the first nucleic acid sequence is located at the endogenous non-human MHC I locus. In one embodiment, the second nucleic acid sequence is located at the endogenous non-human MHC II α locus. In one embodiment, the third nucleic acid sequence is located at the endogenous non-human MHC II β locus.

In one embodiment, the non-human animal only expresses the chimeric human/non-human MHC I, MHC II α and/or MHC β11 polypeptides and does not express endogenous non-human MHC polypeptides (e.g., functional endogenous MHC I, II α and/or II β polypeptides) from the endogenous non-human MHC locus. In one embodiment, the animal described herein expresses a functional chimeric MHC I and a functional chimeric MHC II on the surface of its cells, e.g., antigen presenting cells, etc. In one embodiment, the only MHC I and MHC II expressed by the animal on a cell surface are chimeric MHC I and chimeric MHC II, and the animal does not express any endogenous MHC I and MHC II on a cell surface.

In one embodiment, the chimeric human/non-human MHC I polypeptide comprises in its human portion a peptide binding cleft, e.g., of a human MHC I polypeptide. In one aspect, the human portion of the chimeric polypeptide comprises an extracellular portion of a human MHC I. In this embodiment, the human portion of the chimeric polypeptide comprises an extracellular domain of an α chain of a human MHC I. In one embodiment, the human portion of the chimeric polypeptide comprises α1 and β2 domains of a human MHC I. In another embodiment, the human portion of the chimeric polypeptide comprises α1, α2, and α3 domains of a human MHC I.

In one aspect, a human portion of the chimeric MHC II α polypeptide and/or a human portion of the chimeric MHC II β polypeptide comprises a peptide-binding domain of a human MHC II α polypeptide and/or human MHC II β polypeptide, respectively. In one aspect, a human portion of the chimeric MHC II α and/or β polypeptide comprises an extracellular portion of a human MHC II α and/or β polypeptide, respectively. In one embodiment, a human portion of the chimeric MHC II α polypeptide comprises α1 domain of a human MHC II α polypeptide; in another embodiment, a human portion of the chimeric MHC II α polypeptide comprises α1 and β2 domains of a human MHC II α polypeptide. In an additional embodiment, a human portion of the chimeric MHC II β polypeptide comprises β1 domain of a human MHC II β polypeptide; in another embodiment, a human portion of the chimeric MHC II β polypeptide comprises β1 and β2 domains of a human MHC II β polypeptide.

In some embodiments, the human or humanized MHC I polypeptide may be derived from a functional human HLA molecule encoded by any of HLA-A, HLA-B, HLA-C, HLA-E, HLA-F, or HLA-G loci. The human or humanized MHC II polypeptide may be derived from a functional human HLA molecule encoded by an of HLA-DP, -DQ, and -DR loci. A list of commonly used HLA antigens and alleles is described in Shankarkumar et al. ((2004) The Human Leukocyte Antigen (HLA) System, Int. J. Hum. Genet. 4(2):91-103), incorporated herein by reference. Shankarkumar et al. also present a brief explanation of HLA nomenclature used in the art. Additional information regarding HLA nomenclature and various HLA alleles can be found in Holdsworth et al. (2009) The HLA dictionary 2008: a summary of HLA-A, -B, -C, -DRB1/3/4/5, and DQB1 alleles and their association with serologically defined HLA-A, -B, -C, -DR, and -DQ antigens, Tissue Antigens 73:95-170, and a recent update by Marsh et al. (2010) Nomenclature for factors of the HLA system, 2010, Tissue Antigens 75:291-455, both incorporated herein by reference. In some embodiments, the MHC I or MHC II polypeptides may be derived from any functional human HLA-A, B, C, DR, or DQ molecules. Thus, the human or humanized MHC I and/or II polypeptides may be derived from any functional human HLA molecules described therein. In some embodiments, all MHC I and MHC II polypeptides expressed on a cell surface comprise a portion derived from human HLA molecules.

Of particular interest are human HLA molecules, specific polymorphic HLA alleles, known to be associated with a number of human diseases, e.g., human autoimmune diseases. In fact, specific polymorphisms in HLA loci have been identified that correlate with development of rheumatoid arthritis, type I diabetes, Hashimoto's thyroiditis, multiple sclerosis, myasthenia gravis, Graves' disease, systemic lupus erythematosus, celiac disease, Crohn's disease, ulcerative colitis, and other autoimmune disorders. See, e.g., Wong and Wen (2004) What can the HLA transgenic mouse tell us about autoimmune diabetes?, Diabetologia 47:1476-87; Taneja and David (1998) HLA Transgenic Mice as Humanized Mouse Models of Disease and Immunity, J. Clin. Invest. 101:921-26; Bakker et al. (2006), A high-resolution HLA and SNP haplotype map for disease association studies in the extended human MHC, Nature Genetics 38:1166-72 and Supplementary Information; and International MHC and Autoimmunity Genetics Network (2009) Mapping of multiple susceptibility variants within the MHC region for 7 immune-mediated diseases, Proc. Natl. Acad. Sci. USA 106:18680-85. Thus, the human or humanized MHC I and/or II polypeptides may be derived from a human HLA molecule known to be associated with a particular disease, e.g., autoimmune disease.

In one specific aspect, the human or humanized MHC I polypeptide is derived from human HLA-A. In a specific embodiment, the HLA-A polypeptide is an HLA-A2 polypeptide (e.g., and HLA-A2.1 polypeptide). In one embodiment, the HLA-A polypeptide is a polypeptide encoded by an HLA-A*0201 allele, e.g., HLA-A*02:01:01:01 allele. The HLA-A*0201 allele is commonly used amongst the North American population. Although the present Examples describe this particular HLA sequence, any suitable HLA-A sequence is encompassed herein, e.g., polymorphic variants of HLA-A2 exhibited in human population, sequences with one or more conservative or non-conservative amino acid modifications, nucleic acid sequences differing from the sequence described herein due to the degeneracy of genetic code, etc.

In another specific aspect, the human portion of the chimeric MHC I polypeptide is derived from human MHC I selected from HLA-B and HLA-C. In one aspect, it is derived from HLA-B, e.g., HLA-B27. In another aspect, it is derived from HLA-A3, -B7, -Cw6, etc.

In one specific aspect, the human portions of the humanized MHC II α and β polypeptides described herein are derived from human HLA-DR, e.g., HLA-DR2. Typically, HLA-DR α chains are monomorphic, e.g., the α chain of HLA-DR complex is encoded by HLA-DRA gene (e.g., HLA-DRα*01 gene). On the other hand, the HLA-DR β chain is polymorphic. Thus, HLA-DR2 comprises an α chain encoded by HLA-DRA gene and a β chain encoded by HLA-DR1β *1501 gene. Although the present Examples describe these particular HLA sequences; any suitable HLA-DR sequences are encompassed herein, e.g., polymorphic variants exhibited in human population, sequences with one or more conservative or non-conservative amino acid modifications, nucleic acid sequences differing from the sequences described herein due to the degeneracy of genetic code, etc.

The human portions of the chimeric MHC II α and/or β polypeptide may be encoded by nucleic acid sequences of HLA alleles known to be associated with common human diseases. Such HLA alleles include, but are not limited to, HLA-DRB1*0401, -DRB1*0301, -DQA1*0501, -DQB1*0201, DRB1*1501, -DRB1*1502, -DQB1*0602, -DQA1*0102, -DQA1*0201, -DQB1*0202, -DQA1*0501, and combinations thereof. For a summary of HLA allele/disease associations, see Bakker et al. (2006), supra, incorporated herein by reference.

In one aspect, the non-human portion of a chimeric human/non-human MHC I, MHC II α and/or MHC II β polypeptide(s) comprises transmembrane and/or cytoplasmic domains of an endogenous non-human (e.g., rodent, e.g., mouse, rat, etc.) MHC I, MHC II α and/or MHC II β polypeptide(s), respectively. Thus, the non-human portion of the chimeric human/non-human MHC I polypeptide may comprise transmembrane and/or cytoplasmic domains of an endogenous non-human MHC I polypeptide. The non-human portion of a chimeric MHC II α polypeptide may comprise transmembrane and/or cytoplasmic domains of an endogenous non-human MHC II α polypeptide. The non-human portion of a chimeric human/non-human MHC II β polypeptide may comprise transmembrane and/or cytoplasmic domains of an endogenous non-human MHC II β polypeptide. In one aspect, the non-human animal is mouse, and a non-human portion of the chimeric MHC I polypeptide is derived from a mouse H-2K protein. In one aspect, the animal is a mouse, and non-human portions of the chimeric MHC II α and β polypeptides are derived from a mouse H-2E protein. Thus, a non-human portion of the chimeric MHC I polypeptide may comprise transmembrane and cytoplasmic domains derived from a mouse H-2K, and non-human portions of the chimeric MHC II α and β polypeptides may comprise transmembrane and cytoplasmic domains derived from a mouse H-2E protein. Although specific H-2K and H-2E sequences are contemplated in the Examples, any suitable sequences, e.g., polymorphic variants, conservative/non-conservative amino acid substitutions, etc., are encompassed herein. In one aspect, the non-human animal is a mouse, and the mouse does not express functional endogenous MHC polypeptides from its H-2D locus. In some embodiments, the mouse is engineered to lack all or a portion of an endogenous H-2D locus. In other aspects, the mouse does not express any functional endogenous mouse MHC I and MHC II on a cell surface.

A chimeric human/non-human polypeptide may be such that it comprises a human or a non-human leader (signal) sequence. In one embodiment, the chimeric MHC I polypeptide comprises a non-human leader sequence of an endogenous MHC I polypeptide. In one embodiment, the chimeric MHC II α polypeptide comprises a non-human leader sequence of an endogenous MHC II α polypeptide. In one embodiment, the chimeric MHC II β polypeptide comprises a non-human leader sequence of an endogenous MHC II β polypeptide. In an alternative embodiment, the chimeric MHC I, MHC II α and/or MHC II β polypeptide(s) comprises a non-human leader sequence of MHC I, MHC II α and/or MHC II β polypeptide(s), respectively, from another non-human animal, e.g., another rodent or another mouse strain. Thus, the nucleic acid sequence encoding the chimeric MHC I, MHC II α and/or MHC II β polypeptide may be operably linked to a nucleic acid sequence encoding a non-human MHC I, MHC II α and/or MHC II β leader sequence, respectively. In yet another embodiment, the chimeric MHC I, MHC II α and/or MHC II β polypeptide(s) comprises a human leader sequence of human MHC I, human MHC II α and/or human MHC II β polypeptide, respectively (e.g., a leader sequence of human HLA-A2, human HLA-DRα and/or human HLA-DRβ1*1501, respectively).

A chimeric human/non-human MHC I, MHC II α and/or MHC II β polypeptide may comprise in its human portion a complete or substantially complete extracellular domain of a human MHC I, human MHC II α and/or human MHC II β polypeptide, respectively. Thus, a human portion may comprise at least 80%, preferably at least 85%, more preferably at least 90%, e.g., 95% or more of the amino acids encoding an extracellular domain of a human MHC I, human MHC II α and/or human MHC II β polypeptide (e.g., human HLA-A2, human HLA-DRα and/or human HLA-DRβ1*1501). In one example, substantially complete extracellular domain of the human MHC I, human MHC II α and/or human MHC II β polypeptide lacks a human leader sequence. In another example, the chimeric human/non-human MHC I, chimeric human/non-human MHC II α and/or the chimeric human/non-human MHC II β polypeptide comprises a human leader sequence.

Moreover, the chimeric MHC I, MHC II α and/or MHC II β polypeptide may be operably linked to (e.g., be expressed under the regulatory control of) endogenous non-human promoter and regulatory elements, e.g., mouse MHC I, MHC II α and/or MHC II β regulatory elements, respectively. Such arrangement will facilitate proper expression of the chimeric MHC I and/or MHC II polypeptides in the non-human animal, e.g., during immune response in the non-human animal.

In a further embodiment, a non-human animal of the invention, e.g., a rodent, e.g., a mouse, comprises (e.g., at an endogenous β2 microglobulin locus) a nucleic acid sequence encoding a human or humanized β2 microglobulin. β2 microglobulin or the light chain of the MHC class I complex (also abbreviated "β2M") is a small (12 kDa) non-glycosylated protein, that functions primarily to stabilize the MHC I α chain. Generation of human or humanized β2 microglobulin animals is described in detail in U.S. Patent Publication No. 20130111617, and is incorporated herein by reference.

The nucleotide sequence encoding the human or humanized β2 microglobulin polypeptide may comprise nucleic acid residues corresponding to the entire human β2 microglobulin gene. Alternatively, the nucleotide sequence may comprise nucleic acid residues encoding amino acid sequence set forth in amino acids 21-119 of a human β2 microglobulin protein (i.e., amino acid residues corresponding to the mature human β2 microglobulin). In an alternative embodiment, the nucleotide sequence may comprise nucleic acid residues encoding amino acid sequence set forth in amino acids 23-115 of a human β2 microglobulin protein, for example, amino acid sequence set forth in amino acids 23-119 of a human β2 microglobulin protein. The nucleic and amino acid sequences of human β2 microglobulin are described in Gussow et al., supra, incorporated herein by reference.

Thus, the human or humanized β2 microglobulin polypeptide may comprise amino acid sequence set forth in amino acids 23-115 of a human β2 microglobulin polypeptide, e.g., amino acid sequence set forth in amino acids 23-119 of a human β2 microglobulin polypeptide, e.g., amino acid sequence set forth in amino acids 21-119 of a human β2 microglobulin polypeptide. Alternatively, the human β2 microglobulin may comprise amino acids 1-119 of a human β2 microglobulin polypeptide.

In some embodiments, the nucleotide sequence encoding a human or humanized β2 microglobulin comprises a nucleotide sequence set forth in exon 2 to exon 4 of a human β2 microglobulin gene. Alternatively, the nucleotide sequence comprises nucleotide sequences set forth in exons 2, 3, and 4 of a human β2 microglobulin gene. In this embodiment, the nucleotide sequences set forth in exons 2, 3, and 4 are operably linked to allow for normal transcription and translation of the gene. Thus, in one embodiment, the human sequence comprises a nucleotide sequence corresponding to exon 2 to exon 4 of a human β2 microglobulin gene. In a specific embodiment, the human sequence comprises a nucleotide sequence corresponding to exon 2 to about 267 bp after exon 4 of a human β2 microglobulin gene. In a specific embodiment, the human sequence comprises about 2.8 kb of a human β2 microglobulin gene.

Thus, the human or humanized β2 microglobulin polypeptide may be encoded by a nucleotide sequence comprising nucleotide sequence set forth in exon 2 to exon 4 of a human β2 microglobulin, e.g., nucleotide sequence corresponding to exon 2 to exon 4 of a human β2 microglobulin gene. Alternatively, the polypeptide may be encoded by a nucleotide sequence comprising nucleotide sequences set forth in exons 2, 3, and 4 of a human β2 microglobulin gene. In a specific embodiment, the human or humanized β2 microglobulin polypeptide is encoded by a nucleotide sequence corresponding to exon 2 to about 267 bp after exon 4 of a human β2 microglobulin gene. In another specific embodiment, the human or humanized polypeptide is encoded by a nucleotide sequence comprising about 2.8 kb of a human β2 microglobulin gene. As exon 4 of the β2 microglobulin gene contains the 5' untranslated region, the human or humanized polypeptide may be encoded by a nucleotide sequence comprising exons 2 and 3 of the β2 microglobulin gene.

It would be understood by those of ordinary skill in the art that although specific nucleic acid and amino acid sequences to generate genetically engineered animals are described herein, sequences of one or more conservative or non-conservative amino acid substitutions, or sequences differing from those described herein due to the degeneracy of the genetic code, are also provided.

Therefore, a non-human animal that expresses a human β2 microglobulin sequence is provided, wherein the β2 microglobulin sequence is at least about 85%, 90%, 95%, 96%, 97%, 98%, or 99% identical to a human β2 microglobulin sequence. In a specific embodiment, the β2 microglobulin sequence is at least about 90%, 95%, 96%, 97%, 98%, or 99% identical to the human β2 microglobulin sequence described herein. In one embodiment, the human β2 microglobulin sequence comprises one or more conservative substitutions. In one embodiment, the human β2 microglobulin sequence comprises one or more non-conservative substitutions.

In addition, provided are non-human animals wherein the nucleotide sequence encoding a human or humanized β2 microglobulin protein also comprises a nucleotide sequence set forth in exon 1 of a non-human β2 microglobulin gene. Thus, in a specific embodiment, the non-human animal comprises in its genome a nucleotide sequence encoding a human or humanized β2 microglobulin wherein the nucleotide sequence comprises exon 1 of a non-human β2 microglobulin and exons 2, 3, and 4 of a human β2 microglobulin gene. Thus, the human or humanized β2 microglobulin polypeptide is encoded by exon 1 of a non-human β2 microglobulin gene and exons 2, 3, and 4 of a human β2 microglobulin gene (e.g., exons 2 and 3 of a human β2 microglobulin gene).

In one embodiment, the non-human animal (e.g., rodent, e.g., mouse) of the invention, in addition to a nucleotide sequence encoding a chimeric CD8 protein, further comprises a nucleic acid sequence encoding a human or humanized MHC I protein, such that the chimeric CD8 protein expressed on the surface of a T cell of the animal is capable of associating, binding and/or interacting with a human or humanized MHC I expressed on a surface of a second cell, e.g., an antigen presenting cell. In one embodiment, the MHC I protein comprises an extracellular domain of a human MHC I polypeptide. In one embodiment, the animal further comprises a human or humanized β2 microglobulin polypeptide. Exemplary genetically modified animals expressing a human or humanized MHC I polypeptide and/or β2 microglobulin polypeptide are described in U.S. Patent Publication Nos. 20130111617 and 20130185819, both incorporated herein by reference in their entireties. Thus, in one embodiment, the animal comprising chimeric CD8 protein described herein may further comprise a humanized MHC I complex, wherein the humanized MHC I complex comprises: (1) a humanized MHC I polypeptide, e.g., wherein the humanized MHC I polypeptide comprises a human MHC I extracellular domain and transmembrane and cytoplasmic domains of an endogenous (e.g., mouse) MHC I, e.g., wherein the humanized MHC I comprises a1, α2, and α3 domains of a human MHC I polypeptide, and (2) a human or humanized β2 microglobulin polypeptide (e.g., the animal comprises in its genome a nucleotide sequence set forth in exons 2, 3, and 4 of a human β2 microglobulin). In one aspect, both humanized MHC I and human or humanized β2 microglobulin polypeptides are encoded by nucleotide sequences located at endogenous MHC I and β2 microglobulin loci, respectively; in one aspect, the animal does not express functional endogenous MHC I and β2 microglobulin polypeptides. Thus, the MHC I expressed by the animals may be a chimeric human/non-human, e.g., human/rodent (e.g., human/mouse) MHC I polypeptide. A human portion of the chimeric MHC I polypeptide may be derived from a human HLA class I protein selected from the group consisting of HLA-A, HLA-B, and HLA-C, e.g., HLA-A2, HLA-B27, HLA-B7, HLA-Cw6, or any other HLA class I molecule present in a human population. In the embodiment, wherein the animal is a mouse, a non-human (i.e., a mouse) portion of the chimeric MHC I polypeptide may be derived from a mouse MHC I protein selected from H-2D, H-2K and H-2L.

In one embodiment, the non-human animal (e.g., rodent, e.g., mouse) of the invention further comprises a nucleotide sequence encoding a human or humanized MHC II protein, such that the chimeric CD4 protein expressed on the surface of a T cell of the animal is capable of interacting with a human or humanized MHC II expressed on a surface of a second cell, e.g., an antigen presenting cell. In one embodiment, the MHC II protein comprises an extracellular domain of a human MHC II α polypeptide and an extracellular domain of a human MHC II β polypeptide. Exemplary genetically modified animals expressing a human or humanized MHC II polypeptide are described in U.S. Pat. No. 8,847,005, issued Sep. 30, 2014, and U.S. Patent Publication No. 20130185820, incorporated herein by reference in their entireties. Thus, in one embodiment, the animal comprising chimeric CD4 protein described herein may further comprise a humanized MHC II protein, wherein the humanized MHC II protein comprises: (1) a humanized MHC II α polypeptide comprising a human MHC II α extracellular domain and transmembrane and cytoplasmic domains of an endogenous, e.g., mouse, MHC II, wherein the human MHC II α extracellular domain comprises α1 and β2 domains of a human MHC II α and (2) a humanized MHC II β polypeptide comprising a human MHC II β extracellular domain and transmembrane and cytoplasmic domains of an endogenous, e.g., mouse, MHC II, wherein the human MHC II β extracellular domain comprises β1 and β2 domains of a human MHC II β. In one aspect, both humanized MHC II α and β polypeptides are encoded by nucleic acid sequences located at endogenous MHC II α and β loci, respectively; in one aspect, the animal does not express functional endogenous MHC II α and β polypeptides. Thus, the MHC II expressed by the animals may be a chimeric human/non-human, e.g., human/rodent (e.g., human/mouse) MHC II protein. A human portion of the chimeric MHC II protein may be derived from a human HLA class II protein selected from the group consisting of HLA-DR, HLA-DQ, and HLA-DP, e.g., HLA-DR4, HLA-DR2, HLA-DQ2.5, HLA-DQ8, or any other HLA class II molecule present in a human population. In the embodiment, wherein the animal is a mouse, a non-human (i.e., a mouse) portion of the chimeric MHC II polypeptide may be derived from a mouse MHC II protein selected from H-2E and H-2A.

Various other embodiments of a genetically modified non-human animal, e.g. rodent, e.g., rat or mouse, would be evident to one skilled in the art from the present disclosure and from the disclosure of U.S. Patent Publication Nos. 20130111617, 20130185819 and 20130185820, and U.S. Pat. No. 8,847,005, incorporated herein by reference.

In various embodiments, the genetically modified non-human animals described herein make cells, e.g., APCs, with human or humanized MHC I and II on the cell surface and, as a result, present peptides as epitopes for T cells in a human-like manner, because substantially all of the components of the complex are human or humanized. The genetically modified non-human animals of the invention can be used to study the function of a human immune system in the humanized animal; for identification of antigens and antigen epitopes that elicit immune response (e.g., T cell epitopes, e.g., unique human cancer epitopes), e.g., for use in vaccine development; for evaluation of vaccine candidates and other vaccine strategies; for studying human autoimmunity; for studying human infectious diseases; and otherwise for devising better therapeutic strategies based on human MHC expression.

Non-Human Animals, Tissues and Cells

The genetically modified non-human animal of the invention may be selected from a group consisting of a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

In one aspect, the non-human animal is a mammal. In one aspect, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, white-tailed rats, Malagasy rats and mice), Platacanthomyidae (e.g., spiny dormice), and Spalacidae (e.g., mole rats, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse.

In a specific embodiment, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In another embodiment, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In an embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In yet another embodiment, the mouse is a mix of a BALB strain and another aforementioned strain. Non-human animals as provided herein may be a mouse derived from any combination of the aforementioned strains.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more strains selected from the group consisting of Wistar, LEA, Sprague Dawley, Fischer, F344, F6, and Dark Agouti.

Thus, in one embodiment of the invention, a genetically modified mouse is provided, wherein the mouse comprises, e.g., in its genome, e.g., in its germline genome, (a) a first nucleotide sequence encoding a first chimeric human/murine T cell co-receptor polypeptide (e.g., CD4), a second nucleotide sequence encoding a second chimeric human/murine T cell co-receptor polypeptide (e.g., CD8α), and/or a third nucleotide sequence encoding a third chimeric human/murine T cell co-receptor polypeptide (e.g., CD8β), wherein a murine portion of each chimeric T cell co-receptor polypeptide comprises at least transmembrane and cytoplasmic domains of a murine T cell co-receptor, wherein a human portion of each chimeric polypeptide comprises an extracellular portion (or part thereof, e.g., one or more extracellular domains) of a human T cell co-receptor, and wherein the mouse expresses the first, second and/or third chimeric T cell co-receptor polypeptide; (b) an unrearranged T cell receptor (TCR) α variable gene locus comprising at least one human Vα segment and at least one human Jα segment, operably linked to a murine TCRα constant gene sequence and/or an unrearranged TCRβ variable gene locus comprising at least one human Vβ segment, at least one human Dβ segment, and at least one human Jβ segment, operably linked to a murine TCRβ constant gene sequence; and optionally, (c) a first nucleic acid sequence encoding a first chimeric human/murine MHC polypeptide (e.g., MHC II α), a second nucleic acid sequence encoding a second chimeric human/murine MHC polypeptide (e.g., MHC II β) and/or a third nucleic acid sequence encoding a third chimeric human/murine MHC polypeptide (e.g., MHC I) and a β2 microglobulin locus encoding a human or humanized β2 microglobulin, wherein a human portion of each chimeric MHC polypeptide comprises an extracellular domain of a human MHC polypeptide that associates with the first, second and/or third chimeric T cell co-receptor polypeptide (e.g., wherein a human portion of a chimeric MHC II complex (e.g., humanized MHC II α and β polypeptides) associates with the chimeric CD4 polypeptide and/or a human portion of the chimeric MHC I polypeptide (or MHC I complex, e.g., humanized MHC Iα and human(ized) β2 microglobulin) associates with the chimeric CD8 co-receptor (e.g., humanized CD8 α and β polypeptides).

Figure 5A:
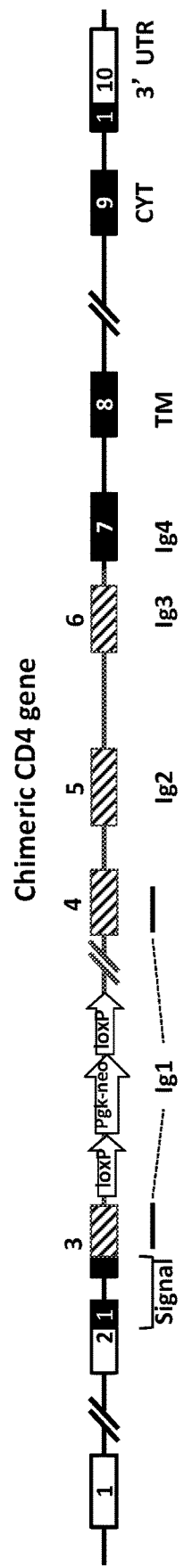
FIG. 5A depicts a schematic representation (not to scale) of the chimeric CD4 locus. Human coding exons are presented by striped shapes, mouse coding exons are presented by filled shapes, and non-coding exons are presented by empty shapes. Immunoglobulin-like domains (Ig), transmembrane (TM), cytoplasmic (CYT) and signal peptide (Signal) coding exons, as well as 3' untranslated regions (UTR), are indicated. A floxed (loxP) neomycin phosphotransferase (Pgk-neo) cassette is depicted with arrows labeled accordingly.

A genetically modified mouse is provided herein comprising in its genome, e.g., at its endogenous CD4 locus, a nucleotide sequence encoding a chimeric human/mouse CD4 polypeptide, wherein a mouse portion of the chimeric polypeptide comprises at least transmembrane and cytoplasmic domains of a mouse CD4 polypeptide, and wherein the mouse expresses a chimeric human/mouse CD4. In one embodiment, a human portion of the chimeric polypeptide comprises at least all or substantially all of the extracellular domain of a human CD4 polypeptide. In one embodiment, a human portion of the chimeric polypeptide comprises at least all or substantially all of the D1 domain of a human CD4 protein. In one embodiment, a human portion of the chimeric polypeptide comprises at least all or substantially all of D1-D2 domains of a human CD4 protein, e.g., at least all or substantially all of D1-D3 domains of a human CD4 protein, e.g., all or substantially all of D1-D4 domains of a human CD4 protein. Thus, in one embodiment, the mouse comprises at the endogenous CD4 locus a nucleotide sequence comprising at least all or substantially all of exons 4, 5, and 6 of the human CD4 gene, e.g., the sequence of exon 3 of the human CD4 gene encoding a portion of the D1 domain of human CD4 and exons 4-6 of the human CD4 gene. In one embodiment, the mouse comprises at the endogenous CD4 locus a chimeric human/mouse CD4 that comprises a human CD4 sequence that is responsible for interacting with MHC II and/or extracellular portion of a T cell receptor. In another embodiment, the mouse comprises at the endogenous CD4 locus a chimeric human/mouse CD4 that comprises a human CD4 sequence that is responsible for interacting with MHC II and/or variable domain of a T cell receptor. In one embodiment, the nucleotide sequence comprises the sequence encoding mouse CD4 signal peptide. In one embodiment, the mouse comprises a replacement of the nucleotide sequence encoding a mouse CD4 extracellular domain with a nucleotide sequence encoding a human CD4 extracellular domain. In another embodiment, the mouse comprises a replacement of the nucleotide sequence encoding at least all or substantially all of mouse CD4 D1 domain, e.g., a nucleotide sequence encoding at least all or substantially all of mouse CD4 D1-D2 domains, e.g., a nucleotide sequence encoding at least all or substantially all of mouse CD4 D1-D3 domains, with human nucleotide sequence encoding the same. In one embodiment, the domains of chimeric CD4 polypeptide are encoded by a nucleotide sequence that is schematically represented in FIG. 5A.

In one embodiment, the mouse does not express a functional endogenous mouse CD4 from it endogenous mouse CD4 locus. In one embodiment, the mouse described herein comprises the chimeric human/mouse CD4 nucleotide sequence in the germline of the mouse.

In one embodiment, the mouse retains any endogenous sequences that have not been humanized, e.g., in the embodiment wherein the mouse comprises a replacement of the nucleotide sequence encoding all or substantially all of D1-D3 domains, the mouse retains endogenous nucleotide sequence encoding mouse CD4 D4 domain as well a nucleotide sequence encoding transmembrane and cytoplasmic domains of mouse CD4.

In one aspect, the mouse expressing chimeric human/mouse CD4 protein retains mouse CD4 promoter and regulatory sequences, e.g., the nucleotide sequence in the mouse encoding chimeric human/mouse CD4 is operably linked to endogenous mouse CD4 promoter and regulatory sequences. In one aspect, these mouse regulatory sequences retained in the genetically engineered animal of the invention include the sequences that regulate expression of the chimeric protein at proper stages during T cell development. Thus, in one aspect, the mouse does not express chimeric CD4 on B cells or mature CD8$^+$ T cells. In one aspect, the mouse also does not express chimeric CD4 on any cell type, e.g., any immune cell type, that normally does not express endogenous CD4.

Figure 5B:
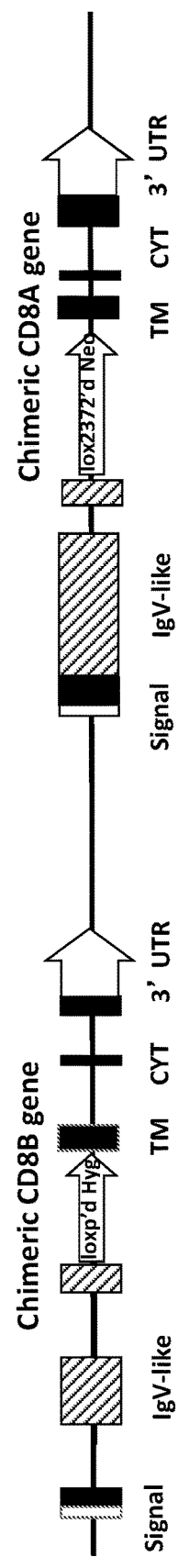
FIG. 5B depicts a schematic representation (not to scale) of the chimeric CD8α and CD8b loci. Human coding exons are presented by striped shapes, mouse coding exons are presented by filled shapes, and non-coding exons are presented by empty shapes. Immunoglobulin-like domains (IgV), transmembrane (TM), cytoplasmic (CYT) and signal peptide (Signal) coding exons, as well as 3' untranslated regions (UTR), are indicated. Floxed (loxP) hygromycin (Hyg) and neomycin phosphotransferase (Pgk-neo) cassettes are depicted with arrows labeled accordingly.

A genetically modified mouse disclosed herein may comprise in its genome, e.g., at its endogenous CD8 locus, a first nucleotide sequence encoding a chimeric human/mouse CD8α polypeptide and a second nucleotide sequence encoding a chimeric human/mouse CD8β polypeptide. In one embodiment, the first nucleotide sequence comprises a sequence that encodes all or substantially all of an extracellular portion of a human CD8α polypeptide and at least transmembrane and cytoplasmic domains of a mouse CD8α polypeptide, and the second nucleotide sequence comprises a sequence that encodes all or substantially all of an extracellular portion of a human CD8β polypeptide and at least transmembrane and cytoplasmic domains of a mouse CD8β polypeptide, and wherein the mouse expresses a functional chimeric human/mouse CD8 protein. In one embodiment, the first nucleotide sequence comprises a sequence that encodes at least the immunoglobulin V-like domain of the human CD8α polypeptide and the remaining sequences of a mouse CD8α polypeptide, and the second nucleotide sequence comprises a sequence that encodes at least the immunoglobulin V-like domain of the human CD8β polypeptide and the remaining sequences of a mouse CD8β polypeptide. In one embodiment, first nucleotide sequence comprises at least the MHC I-binding domain of a human CD8α polypeptide. In one embodiment, the first and the second nucleotide sequences comprise at least the exons that encode the extracellular portion of a human CD8α polypeptide and/or CD8β polypeptide, respectively. In one embodiment, the extracellular portion of a human CD8α polypeptide and/or CD8β polypeptide is a region encompassing the portion of the human CD8α polypeptide and/or CD8β polypeptide that is not transmembrane or cytoplasmic domain. In one embodiment, the domains of a chimeric CD8α polypeptide are encoded by a nucleotide sequence that is schematically represented in FIG. 5B. In one embodiment, the domains of a chimeric CD8β polypeptide are encoded by a nucleotide sequence that is schematically represented in FIG. 5B. In one embodiment, the nucleotide sequence encoding the chimeric human/mouse CD8α polypeptide and/or CD8β polypeptide comprises the sequence encoding a mouse CD8α and/or CD8β signal peptide, respectively. Alternatively, the nucleotide sequence may comprise the sequence encoding a human CD8α and/or CD8β signal sequence. In one embodiment, the mouse comprises a replacement of a nucleotide sequence encoding all or substantially all of the mouse CD8α and/or CD8β extracellular domain with a nucleotide sequence encoding all or substantially all of the human CD8α and/or CD8β extracellular domain, respectively.

In one embodiment, the mouse does not express a functional endogenous mouse CD8α and/or CD8β polypeptide from its endogenous CD8 locus. In one embodiment, the mouse as described herein comprises the chimeric human/mouse CD8 sequence in its germline.

In one aspect, the mouse expressing chimeric human/mouse CD8α and/or CD8β polypeptide retains mouse CD8α and/or CD8β promoter and regulatory sequences, e.g., the nucleotide sequence in the mouse encoding chimeric human/mouse CD8 is operably linked to endogenous mouse CD8 promoter and regulatory sequences. In one aspect, these regulatory sequences retained in the mouse include the sequences regulating CD8 protein expression at proper stages of T cell development. In one aspect, the genetically modified mouse does not express chimeric CD8 on B cells or mature CD4$^+$ T cells, or any cell, e.g., immune cell, that does not normally express endogenous CD8.

The invention also provides a genetically modified mouse comprising in its genome an unrearranged human or humanized TCR variable gene locus, e.g., TCRα, TCRβ, TCRδ, and/or TCRγ variable gene locus. In some embodiments, the unrearranged human or humanized TCR variable gene locus replaces endogenous mouse TCR variable gene locus. In other embodiments, unrearranged human or humanized TCR variable gene locus is at a site in the genome other than the corresponding endogenous mouse TCR locus. In some embodiments, human or humanized unrearranged TCR variable gene locus is operably linked to mouse TCR constant region.

In one embodiment, a genetically modified mouse is provided, wherein the mouse comprises in its genome an unrearranged T cell receptor (TCR) α variable gene locus comprising at least one human Vα segment and least one human Jα segment, operably linked to a mouse TCRα constant gene sequence, and an unrearranged TCRβ variable gene locus comprising at least one human Vβ segment, at least one human Dβ segment, and at least one human Jβ segment, operably linked to a mouse TCR constant gene sequence. In one specific embodiment, the mouse comprises in its genome an unrearranged TCRα variable gene locus comprising a complete repertoire of human Vα segments and a complete repertoire of human Jα segments operably linked to a mouse TCRα constant gene sequence, and an unrearranged TCRβ variable gene locus comprising a complete repertoire of human Vβ segments, a complete repertoire of human Dβ segments, and a complete repertoire of human Jβ segments operably linked to a mouse TCR constant gene sequence.

In some embodiments, the unrearranged TCRα variable gene locus comprising human TCRα variable region segments replaces endogenous mouse TCRα variable gene locus, and the unrearranged TCRβ variable gene locus comprising human TCRβ variable region segments replaces the endogenous mouse TCRβ variable gene locus. In some embodiments, the endogenous mouse Vα and Jα segments are incapable of rearranging to form a rearranged Vα/Jα sequence, and the endogenous mouse Vβ, Dβ, and Jβ segments are incapable of rearranging to form a rearranged Vβ/Dβ/Jβ sequence. In some embodiments, the human Vα and Jα segments rearrange to form a rearranged human Vα/Jα sequence, and the human Vβ, Dβ, and Jβ segments rearrange to form a rearranged human Vβ/Dβ/Jβ sequence.

The invention also relates to a genetically modified mouse that comprises in its genome a nucleic acid sequence encoding a chimeric MHC polypeptide, wherein the human portion of the chimeric MHC polypeptide associates with a human extracellular domain of a chimeric T cell co-receptor as disclosed herein. Genetically modified mice as disclosed herein may comprise a first nucleic acid sequence encoding a chimeric human/mouse MHC I, a second nucleic acid sequence encoding a chimeric human/mouse MHC II α, and/or a third nucleic acid sequence encoding a chimeric human/mouse MHC II β polypeptides. A human portion of the chimeric MHC I, MHC II α, and/or MHC II β may comprise an extracellular domain of a human MHC I, MHC II α, and MHC II β, respectively. In one embodiment, the mouse expresses functional chimeric human/mouse MHC I, MHC II α, and MHC II β polypeptides from its endogenous mouse MHC locus. In one embodiment, the mouse does not express functional mouse MHC polypeptides, e.g., functional mouse MHC I, MHC II α, and MHC II β polypeptides, from its endogenous mouse MHC locus. In other embodiments, the only MHC I and MHC II expressed by the mouse on a cell surface are chimeric MHC I and II.

In one embodiment, a human portion of the chimeric human/mouse MHC I polypeptide comprises a peptide binding domain or an extracellular domain of a human MHC I (e.g., human HLA-A, e.g., human HLA-A2, e.g., human HLA-A2.1). In some embodiments, the mouse does not express a peptide binding or an extracellular domain of an endogenous mouse MHC I polypeptide from its endogenous mouse MHC I locus. The peptide binding domain of the human MHC I may comprise α1 and β2 domains. Alternatively, the peptide binding domain of the human MHC I may comprise al, α2, and α3 domains. In one aspect, the extracellular domain of the human MHC I comprises an extracellular domain of a human MHC I α chain. In one embodiment, the endogenous mouse MHC I locus is an H-2K (e.g., H-2Kb) locus, and the mouse portion of the chimeric MHC I polypeptide comprises transmembrane and cytoplasmic domains of a mouse H-2K (e.g., H-2Kb) polypeptide. Thus, in one embodiment, the mouse of the invention comprises at its endogenous mouse MHC I locus a nucleic acid sequence encoding a chimeric human/mouse MHC I, wherein a human portion of the chimeric polypeptide comprises an extracellular domain of a human HLA-A2 (e.g., HLA-A2.1) polypeptide and a mouse portion comprises transmembrane and cytoplasmic domains of a mouse H-2K (e.g., H-2Kb) polypeptide, and a mouse expresses a chimeric human/mouse HLA-A2/H-2K protein. In other embodiment, the mouse portion of the chimeric MHC I polypeptide may be derived from other mouse MHC I, e.g., H-2D, H-2L, etc.; and the human portion of the chimeric MHC I polypeptide may be derived from other human MHC I, e.g., HLA-B, HLA-C, etc. In one aspect, the mouse does not express a functional endogenous H-2K polypeptide from its endogenous mouse H-2K locus. In one embodiment, the mouse does not express functional endogenous MHC polypeptides from its H-2D locus. In some embodiments, the mouse is engineered to lack all or a portion of an endogenous H-2D locus. In other embodiments, the only MHC I polypeptides expressed by the mouse on a cell surface are chimeric human/mouse MHC I polypeptides.

In one embodiment, a human portion of the chimeric human/mouse MHC II α polypeptide comprises a human MHC II α peptide binding or extracellular domain and a human portion of the chimeric human/mouse MHC II β polypeptide comprises a human MHC II β peptide binding or extracellular domain. In some embodiments, the mouse does not express a peptide binding or an extracellular domain of endogenous mouse a and/or β polypeptide from an endogenous mouse locus (e.g., H-2A and/or H-2E locus). In some embodiments, the mouse comprises a genome that lacks a gene that encodes a functional MHC class II molecule comprising an H-2Ab1, H-2Aa, H-2Eb1, H-2Eb2, H-2Ea, and a combination thereof. In some embodiments, the only MHC II polypeptides expressed by the mouse on a cell surface are chimeric human/mouse MHC II polypeptides. The peptide-binding domain of the human MHC II α polypeptide may comprise α1 domain and the peptide-binding domain of the human MHC II β polypeptide may comprise a β1 domain; thus, the peptide-binding domain of the chimeric MHC II complex may comprise human al and β1 domains. The extracellular domain of the human MHC II α polypeptide may comprise α1 and β2 domains and the extracellular domain of the human MHC II β polypeptide may comprise β1 and β2 domains; thus, the extracellular domain of the chimeric MHC II complex may comprise human α1, α2, β1 and β2 domains. In one embodiment, the mouse portion of the chimeric MHC II complex comprises transmembrane and cytosolic domains of mouse MHC II, e.g. mouse H-2E (e.g., transmembrane and cytosolic domains of mouse H-2E α and β chains). Thus, in one embodiment, the mouse of the invention comprises at its endogenous mouse MHC II locus a nucleic acid sequence encoding a chimeric human/mouse MHC II α, wherein a human portion of the chimeric MHC II α polypeptide comprises an extracellular domain derived from an a chain of a human MHC II (e.g., a chain of HLA-DR2) and a mouse portion comprises transmembrane and cytoplasmic domains derived from an a chain of a mouse MHC II (e.g., H-2E); and a mouse comprises at its endogenous mouse MHC II locus a nucleic acid sequence encoding a chimeric human/mouse MHC II β, wherein a human portion of the chimeric MHC II β polypeptide comprises an extracellular domain derived from a β chain of a human MHC II (e.g., β chain of HLA-DR2) and a mouse portion comprises transmembrane and cytoplasmic domains derived from a β chain of a mouse MHC II (e.g., H-2E); e.g., wherein the mouse expresses a chimeric human/mouse HLA-DR2/H-2E protein. In other embodiment, the mouse portion of the chimeric MHC II protein may be derived from other mouse MHC II, e.g., H-2A, etc.; and the human portion of the chimeric MHC II protein may be derived from other human MHC II, e.g., HLA-DQ, etc. In one aspect, the mouse does not express functional endogenous H-2A and H-2E polypeptides from their endogenous mouse loci (e.g., the mouse does not express H-2Ab1, H-2Aa, H-2Eb1, H-2Eb2, and H-2Ea polypeptides). In some embodiments, the mouse lacks expression of any endogenous MHC I or MHC II molecule on a cell surface.

In various aspects, the human or humanized β2 microglobulin expressed by a genetically modified non-human animal, or cells, embryos, or tissues derived from a non-human animal, preserves all the functional aspects of the endogenous and/or human β2 microglobulin. For example, it is preferred that the human or humanized β2 microglobulin binds the α chain of MHC I polypeptide (e.g., endogenous non-human or human MHC I polypeptide). The human or humanized β2 microglobulin polypeptide may bind, recruit or otherwise associate with any other molecules, e.g., receptor, anchor or signaling molecules that associate with endogenous non-human and/or human β2 microglobulin (e.g., HFE, etc.).

In addition to genetically modified animals (e.g., rodents, e.g., mice or rats), also provided is a tissue or cell, wherein the tissue or cell is derived from a non-human animal as described herein, and comprises a heterologous β2 microglobulin gene or β2 microglobulin sequence, i.e., nucleotide and/or amino acid sequence. In one embodiment, the heterologous β2 microglobulin gene or β2 microglobulin sequence is a human or humanized β2 microglobulin gene or human or humanized β2 microglobulin sequence. Preferably, the cell is a nucleated cell. The cell may be any cell known to express MHC I complex, e.g., an antigen presenting cell. The human or humanized β2 microglobulin polypeptide expressed by said cell may interact with endogenous non-human MHC I (e.g., rodent MHC I), to form a functional MHC I complex. The resultant MHC I complex may be capable of interacting with a T cell, e.g., a cytotoxic T cell. Thus, also provided is an in vitro complex of a cell from a non-human animal as described herein and a T cell.

Also provided are non-human cells that comprise human or humanized β2 microglobulin gene or sequence, and an additional human or humanized sequence, e.g., chimeric MHC I polypeptide presently disclosed. In such an instance, the human or humanized β2 microglobulin polypeptide may interact with, e.g., a chimeric human/non-human MHC I polypeptide, and a functional MHC I complex may be formed. In some aspects, such complex is capable of interacting with a TCR on a T cell, e.g., a human or a non-human T cell. Thus, also provided in an in vitro complex of a cell from a non-human animal as described herein and a human or a non-human T cell.

Another aspect of the disclosure is a rodent embryo (e.g., a mouse or a rat embryo) comprising a heterologous β2 microglobulin gene or β2 microglobulin sequence as described herein. In one embodiment, the embryo comprises an ES donor cell that comprises the heterologous β2 microglobulin gene or β2 microglobulin sequence, and host embryo cells. The heterologous β2 microglobulin gene or β2 microglobulin sequence is a human or humanized β2 microglobulin gene or β2 microglobulin sequence.

This invention also encompasses a non-human cell comprising a chromosome or fragment thereof of a non-human animal as described herein (e.g., wherein the chromosome or fragment thereof comprises a nucleotide sequence encoding a human or humanized β2 microglobulin polypeptide). The non-human cell may comprise a nucleus of a non-human animal as described herein. In one embodiment, the non-human cell comprises the chromosome or fragment thereof as the result of a nuclear transfer.

In one aspect, a non-human induced pluripotent cell comprising a heterologous β2 microglobulin gene or β2 microglobulin sequence is provided. In one embodiment, the induced pluripotent cell is derived from a non-human animal as described herein. In one embodiment, the heterologous β2 microglobulin gene or β2 microglobulin sequence is a human or humanized gene or sequence.

In some embodiments of the invention, the mouse described herein expresses chimeric human/mouse MHC II only on professional antigen presenting cells, e.g., B cell, monocytes/macrophages, and/or dendritic cells of the mouse. In some embodiments, a mouse described herein elicits an immune response, e.g., a cellular immune response, to one or more human antigens. In some embodiments, a mouse described herein elicits a humanized T cell response to one or more human antigens.

In addition to a genetically engineered non-human animal, a non-human embryo (e.g., a rodent, e.g., a mouse or a rat embryo) is also provided, wherein the embryo comprises a donor ES cell that is derived from a non-human animal (e.g., a rodent, e.g., a mouse or a rat) as described herein. In one aspect, the embryo comprises an ES donor cell that comprises the chimeric CD4 gene, the chimeric CD8 (e.g., CD8α and/or CD8β) gene, a humanized MHC I (e.g., MHC I α) nucleic acid sequence, a humanized MHC II (e.g., MHC II α and/or MHC II β) nucleic acid sequence, an unrearranged humanized TCR (e.g., TCRα and/or TCRβ, or TCRδ, and/or TCRγ) locus and/or human or humanized β2 microglobulin gene sequence and host embryo cells.

Also provided is a tissue, wherein the tissue is derived from a non-human animal (e.g., a rodent, e.g., a mouse or a rat) as described herein, and expresses the chimeric CD4 protein, the chimeric CD8 protein (e.g., chimeric CD8α and/or CD8β protein), a humanized TCR polypeptide (e.g., TCRα and/or TCRβ, or TCRδ, and/or TCRγ polypeptide), a humanized MHC I polypeptide (e.g., MHC I α), a humanized MHC II polypeptide (e.g., MHC II α and/or MHC II β polypeptide) and/or a human or humanized β2 microglobulin.

In one aspect, a method for making a chimeric human/non-human CD4 molecule is provided, comprising expressing in a single cell a chimeric CD4 protein from a nucleotide construct as described herein. In one embodiment, the nucleotide construct is a viral vector; in a specific embodiment, the viral vector is a lentiviral vector. In one embodiment, the cell is selected from a CHO, COS, 293, HeLa, and a retinal cell expressing a viral nucleic acid sequence (e.g., a PERC.6™ cell).

In one aspect, a cell that expresses a chimeric CD4 protein is provided. In one embodiment, the cell comprises an expression vector comprising a chimeric CD4 sequence as described herein. In one embodiment, the cell is selected from CHO, COS, 293, HeLa, and a retinal cell expressing a viral nucleic acid sequence (e.g., a PERC.6™ cell).

A chimeric CD4 molecule made by a non-human animal as described herein is also provided, wherein, in one embodiment, the chimeric CD4 molecule comprises an amino acid sequence of all or substantially all of an extracellular domain of a human CD4 protein, and at least transmembrane and cytoplasmic domains from a non-human CD4 protein, e.g., mouse CD4 protein. In another embodiment, a chimeric CD4 molecule made by a non-human animal as described herein is provided, wherein the chimeric CD4 molecule comprises an amino acid sequence of at least all or substantially all D1 domain of a human CD4, e.g., at least all or substantially all D1-D2 domains of a human CD4, e.g., at least all or substantially all D1-D3 domains of a human CD4, e.g., an amino acid sequence of human CD4 that is responsible for binding MHC II and/or extracellular domain of a TCR, e.g., an amino acid sequence of human CD4 that is responsible for binding MHC II and/or a variable domain of a TCR; and wherein the remainder of the protein (e.g., transmembrane domain, cytoplasmic domain, any portion of extracellular domain that has not been humanized) is derived from the endogenous non-human protein sequence. An exemplary chimeric human/non-human CD4 polypeptide comprises an amino acid sequence set forth in SEQ ID NO:78, and the human portion of the chimeric polypeptide spans about amino acids 27-319 of SEQ ID NO:78 (set forth separately in SEQ ID NO:79).

In one aspect, a method for making a chimeric human/non-human CD8 molecule (e.g., CD8α and/or CD8β) is provided, comprising expressing in a single cell a chimeric CD8 polypeptide(s) from a nucleotide construct(s) as described herein. In one embodiment, the nucleotide construct is a viral vector; in a specific embodiment, the viral vector is a lentiviral vector. In one embodiment, the cell is selected from a CHO, COS, 293, HeLa, and a retinal cell expressing a viral nucleic acid sequence (e.g., a PERC.6™ cell).

In one aspect, a cell that expresses a chimeric CD8 protein is provided. In one embodiment, the cell comprises an expression vector comprising a chimeric CD8 sequence(s) as described herein. In one embodiment, the cell is selected from CHO, COS, 293, HeLa, and a retinal cell expressing a viral nucleic acid sequence (e.g., a PERC.6™ cell).

A chimeric CD8 molecule made by a non-human animal as described herein is also provided, wherein the chimeric CD8 molecule comprises all or substantially all of the extracellular domain from a human CD8 protein (e.g., CD8α and/or CD8β), and at least transmembrane and cytoplasmic domains from a non-human CD8 protein, e.g., mouse CD8 protein. Exemplary chimeric CD8α polypeptide is set forth in SEQ ID NO:88, and exemplary chimeric CD8β protein is set forth in SEQ ID NO:83.

A humanized TCR protein made by a non-human animal (e.g., rodent, e.g., mouse or rat) as described herein is also provided, wherein the humanized TCR protein comprises a human variable region and a non-human constant region. Thus, the humanized TCR protein comprises human complementary determining regions (i.e., human CDR1, 2, and 3) in its variable domain and a non-human constant region. Also provided are nucleic acids that encode the human TCR variable domains generated by a non-human animal described herein.

In addition, a non-human cell isolated from a non-human animal as described herein is provided. In one embodiment, the cell is an ES cell. In one embodiment, the cell is a T cell, e.g., a CD4+ T cell. In one embodiment, the cell is a helper T cell ($T_H$ cell). In one embodiment, the $T_H$ cell is an effector $T_H$ cell, e.g., $T_H1$ cell or $T_H2$ cell. In one embodiment, the cell is CD8+ T cell. In one embodiment, the cell is a cytotoxic T cell. Also provided is a non-human cell that expresses a TCR protein comprising a human variable region and a non-human constant region. The TCR protein may comprise TCRα, TCRδ, or a combination thereof. In one embodiment, the cell is a T cell, e.g., a CD4+ or a CD8+ T cell. Additionally, non-human T cells as provided herein may express on its cell surface (a) a chimeric human/non-human T cell co-receptor, e.g., a chimeric CD4 polypeptide or a chimeric CD8 polypeptide, comprising a human T cell co-receptor extracellular domain operably linked to a non-human T cell co-receptor transmembrane and/or intracellular domain; and (b) a TCR protein comprising a human variable region and a non-human constant region.

In another embodiment, the cell is an antigen presenting cell. In one embodiment, the antigen presenting cell presents antigen on humanized MHC I molecules. In another embodiment, the antigen presenting cell is a professional antigen presenting cell, e.g., a B cell, a dendritic cell, and a macrophage. In another embodiment, the antigen presenting cell presents antigen on humanized MHC I and/or humanized MHC II molecules.

In one aspect, a cell that expresses a chimeric human/non-human MHC I and MHC II proteins (e.g., HLA-A2/H-2K and HLA-DR2/H-2E proteins) is provided. In one aspect, the cell is a mouse cell that does not express functional endogenous MHC polypeptides from its H-2D locus. In some embodiments, the cell is a mouse cell engineered to lack all or a portion of an endogenous H-2D locus. In some embodiments, the cell is a mouse cell that does not express any functional endogenous MHC I and MHC II polypeptide on its surface. In one embodiment, the cell comprises an expression vector comprising a chimeric MHC class I sequence and chimeric MHC class II sequence as described herein. In one embodiment, the cell is selected from CHO, COS, 293, HeLa, and a retinal cell expressing a viral nucleic acid sequence (e.g., a PERC.6™ cell).

A chimeric MHC II complex comprising an extracellular domain of HLA-DR2 described herein may be detected by anti-HLA-DR antibodies. Thus, a cell displaying chimeric human/non-human MHC II polypeptide may be detected and/or selected using anti-HLA-DR antibody. The chimeric MHC I complex comprising an extracellular domain of HLA-A2 described herein may be detected using anti-HLA-A, e.g., anti-HLA-A2 antibodies. Thus, a cell displaying a chimeric human/non-human MHC I polypeptide may be detected and/or selected using anti-HLA-A antibody. Antibodies that recognize other HLA alleles are commercially available or can be generated, and may be used for detection/selection.

Although the Examples that follow describe a genetically engineered animal whose genome comprises a replacement of a nucleic acid sequence encoding mouse H-2K, and H-2A and H-2E proteins with a nucleic acid sequence encoding a chimeric human/mouse HLA-A2/H-2K and HLA-DR2/H-2E protein, respectively, one skilled in the art would understand that a similar strategy may be used to introduce chimeras comprising other human MHC I and II genes (other HLA-A, HLA-B, and HLA-C; and other HLA-DR, HLA-DP and HLA-DQ genes). Such animals comprising multiple chimeric human/non-human (e.g., human/rodent, e.g., human/mouse) MHC I and MHC II genes at endogenous MHC loci are also provided. Examples of such chimeric MHC I and MHC II proteins are described in U.S. Publication Nos. 20130111617, 20130185819, 20130185820 and 20140245467 and U.S. Pat. No. 8,847,005, each of which are incorporated herein by reference.

Also provided is a non-human cell comprising a chromosome or fragment thereof of a non-human animal as described herein. In one embodiment, the non-human cell comprises a nucleus of a non-human animal as described herein. In one embodiment, the non-human cell comprises the chromosome or fragment thereof as the result of a nuclear transfer.

In one aspect, a non-human induced pluripotent cell comprising a gene encoding a chimeric CD4 polypeptide, a gene encoding a chimeric CD8 polypeptide (e.g., CD8α and/or CD8β polypeptide), a gene encoding a humanized MHC I polypeptide (e.g., MHC I α and/or β2 microglobulin), a gene encoding a humanized MHC II polypeptide (e.g., MHC II α and/or MHC II β) and/or an unrearranged humanized TCR locus encoding a humanized TCRα and/or TCRβ polypeptide as described herein is provided. In one embodiment, the induced pluripotent cell is derived from a non-human animal as described herein.

In one aspect, a hybridoma or quadroma is provided, derived from a cell of a non-human animal as described herein. In one embodiment, the non-human animal is a mouse or rat.

Making Genetically Modified Non-Human Animals that Mount Substantially Humanized T Cell Immune Responses Also provided is a method for making a genetically engineered non-human animal (e.g., a genetically engineered rodent, e.g., a mouse or rat) described herein. Generally, the methods comprise (a) introducing into the genome of the non-human animal a first nucleotide sequence encoding a chimeric human/non-human T cell co-receptor polypeptide, a second nucleotide sequence encoding a second chimeric human/non-human T cell co-receptor polypeptide, and/or a third nucleotide sequence encoding a third chimeric human/non-human T cell co-receptor polypeptide, wherein a non-human portion of each chimeric T cell co-receptor polypeptide comprises at least transmembrane and cytoplasmic domains of a non-human T cell co-receptor, and wherein a human portion of each chimeric polypeptide comprises an extracellular portion (or part thereof) of a human T cell co-receptor; (b) inserting into the genome of the non-human animal an unrearranged T cell receptor (TCR) α variable gene locus comprising at least one human Vα segment and at least one human Jα segment, operably linked to a non-human TCRα constant gene sequence and/or an unrearranged TCRβ variable gene locus comprising at least one human Vβ segment, at least one human Dβ segment, and at least one human Jβ segment, operably linked to a non-human TCRβ constant gene sequence; and optionally (c) placing into the genome a first nucleic acid sequence encoding a first chimeric human/non-human MHC polypeptide, a second nucleic acid sequence encoding a second chimeric human/non-human MHC polypeptide and/or a third nucleic acid sequence encoding a third chimeric human/non-human MHC polypeptide and/or (d) adding into the genome of the non-human animal a β2 microglobulin locus encoding a human or humanized β2 microglobulin polypeptide. In some embodiments, the steps of introducing, inserting and/or placing comprise targeting sequences encoding the extracellular domain(s) of the T cell co-receptor, the variable domain(s) of the TCR, the extracellular domain(s) of the MHC polypeptide, or a portion of the β2 microglobulin and replacing them with sequences encoding human T cell co-receptor extracellular domain(s), human TCR variable domains, human MHC extracellular domain(s), and/or a human portion of the β2 microglobulin, respectively.

In other embodiments, introducing, inserting, placing and/or adding may comprise breeding, e.g., mating, animals of the same species. In other embodiments, introducing, inserting, placing and/or adding comprises sequential homologous recombination in ES cells. In some embodiments, the ES cells are derived from non-human animals genetically modified to comprise one or more, but not all, of the genetic modifications desired, and homologous recombination in such ES cells completes the genetic modification. In other embodiments, introducing, inserting, placing and/or adding may comprise a combination of breeding and homologous recombination in ES cells, e.g., breeding an animal to another (or more) animal of the same species, wherein some or all of the animals may be generated from ES cells genetically modified via a single homologous recombination or sequential homologous recombination events, and wherein some ES cell may be isolated from a non-human animal comprising one or more of the genetic modifications disclosed herein.

In some embodiments, the method utilizes a targeting construct made using VELOCIGENE® technology, introducing the construct into ES cells, and introducing targeted ES cell clones into a mouse embryo using VELOCI-MOUSE® technology, as described in the Examples. Targeting construct may comprise 5' and/or 3' homology arms that target the endogenous sequence to be replaced, an insert sequence (that replaces the endogenous sequence) and one or more selection cassettes. A selection cassette is a nucleotide sequence inserted into a targeting construct to facilitate selection of cells (e.g., ES cells) that have integrated the construct of interest. A number of suitable selection cassettes are known in the art. Commonly, a selection cassette enables positive selection in the presence of a particular antibiotic (e.g., Neo, Hyg, Pur, CM, SPEC, etc.). In addition, a selection cassette may be flanked by recombination sites, which allow deletion of the selection cassette upon treatment with recombinase enzymes. Commonly used recombination sites are loxP and Frt, recognized by Cre and Flp enzymes, respectively, but others are known in the art. A selection cassette may be located anywhere in the construct outside the coding region. In one embodiment, the selection cassette is located at the 5' end the human DNA fragment. In another embodiment, the selection cassette is located at the 3' end of the human DNA fragment. In another embodiment, the selection cassette is located within the human DNA fragment. In another embodiment, the selection cassette is located within an intron of the human DNA fragment. In another embodiment, the selection cassette is located at the junction of the human and mouse DNA fragment.

In one embodiment, the method for making a genetically engineered non-human animal results in the animal that comprises at an endogenous CD4 locus a nucleotide sequence encoding a chimeric human/non-human CD4 polypeptide. In one embodiment, the invention comprises a method of modifying a CD4 locus of a non-human animal to express a chimeric human/non-human CD4 polypeptide described herein. In one embodiment, the invention provides a method of modifying a CD4 locus of a mouse to express a chimeric human/mouse CD4 polypeptide comprising introducing, e.g., replacing at an endogenous CD4 locus of a non-human animal, e.g., a mouse, a nucleotide sequence encoding an endogenous non-human CD4 polypeptide with a nucleotide sequence encoding a chimeric human/mouse CD4 polypeptide. In one aspect of the method, the chimeric human/mouse CD4 polypeptide comprises all or substantially all of an extracellular domain of a human CD4 polypeptide and at least transmembrane and cytoplasmic domains of an endogenous mouse CD4 polypeptide. In another aspect of the method, the chimeric human/mouse CD4 polypeptide comprises all or substantially all of D1-D2 domains of a human CD4 polypeptide. In yet another embodiment, the chimeric human/mouse CD4 polypeptide comprises all or substantially all of D1-D3 domains of a human CD4 polypeptide. In yet another embodiment, the chimeric human/mouse CD4 polypeptide comprises all or substantially all of amino acid sequence of human CD4 that is responsible for interacting with MHC II and/or an extracellular domain of a T cell receptor. In yet another embodiment, the chimeric human/mouse CD4 polypeptide comprises all or substantially all of amino acid sequence of human CD4 that is responsible for interacting with MHC II and/or a variable domain of a T cell receptor.

Thus, a nucleotide construct for generating genetically modified animals comprising chimeric human/non-human CD4 is provided. In one aspect, the nucleotide sequence comprises 5' and 3' homology arms, a DNA fragment comprising human CD4 gene sequence (e.g., human CD4 extracellular domain gene sequence, e.g., gene sequence of all or substantially all of domains D1-D2 of human CD4, e.g., gene sequence of all or substantially all of domains D1-D3 and/or D2-D3 of human CD4, e.g., gene sequence of all or substantially all of domains D1-D4 of human CD4), and a selection cassette flanked by recombination sites. In one embodiment, human CD4 gene sequence is a genomic sequence that comprises introns and exons of human CD4. In one embodiment, homology arms are homologous to non-human (e.g., mouse) CD4 genomic sequence. An exemplary construct of the invention is depicted in FIG. 5A.

In some embodiments, the method results in an animal that comprises at an endogenous CD8 locus a nucleotide sequence(s) encoding a chimeric human/non-human CD8α and/or CD8β polypeptide. In one embodiment, the invention provides a method of modifying a CD8 locus of a non-human animal to express a chimeric human/non-human CD8 polypeptide described herein. In one aspect, provided is a method of modifying a CD8 locus of a mouse to express a chimeric human/mouse CD8 polypeptide comprising introducing, e.g., replacing, at an endogenous CD8 locus of a non-human animal, e.g., a mouse, a nucleotide sequence encoding an endogenous non-human CD8 polypeptide with a nucleotide sequence encoding a chimeric human/mouse CD8 polypeptide. The CD8 polypeptide may be selected from CD8α, CD8β, and combination thereof. In one aspect, the chimeric polypeptide comprises all or substantially all of an extracellular domain of a human CD8 polypeptide and at least transmembrane and cytoplasmic domains of an endogenous mouse CD8 polypeptide.

Thus, a nucleotide construct for generating genetically modified animals comprising human/non-human CD8 is also provided. In one aspect, the sequence of the nucleotide construct comprises 5' and 3' homology arms, a DNA fragment comprising human CD8α or CD8β sequence, and a selection cassette flanked by recombination sites. In some embodiments, the human sequence comprises introns and exons of human CD8α or CD8β, e.g., exons encoding the extracellular domain of the human CD8α or CD8β, respectively. In one embodiment, homology arms are homologous to non-human CD8α or CD8β sequence. Exemplary constructs for CD8α and CD8β are depicted in FIG. 5B.

Because of close chromosomal localization of the genes encoding CD8α and CD8β, sequential targeting of the two genes improves the chances of successful humanization. In one embodiment, the targeting strategy comprises introducing chimeric CD8β construct described herein into ES cells, generating a mouse from the targeted ES cells, deriving genetically modified ES cells from said mouse, and introducing chimeric CD8α construct described herein into said genetically modified ES cells. In another embodiment, the targeting strategy comprises introducing a chimeric CD8β construct described herein into ES cells, selecting the cells that have incorporated the chimeric CD8β construct, introducing a chimeric CD8α construct described herein into ES cells that have incorporated and are harboring the chimeric CD8β construct, and selecting the cells that have incorporated both chimeric CD8β and CD8α. In one aspect of this embodiment, the steps of selecting are performed utilizing different selection markers. In alternative embodiments, CD8α humanization can be accomplished first. Upon completion of gene targeting, ES cells of genetically modified non-human animals can be screened to confirm successful incorporation of exogenous nucleotide sequence of interest or expression of exogenous polypeptide by a variety of methods known in the art (e.g., modification of allele assay described in Valenzuela et al. (2003) High-throughput engineering of the mouse genome coupled with high-resolution expression analysis, Nature Biotech. 21(6):652-659).

In some embodiments, the method for making a genetically modified non-human animal results in the animal whose genome comprises a humanized unrearranged TCR locus (e.g., a humanized unrearranged TCRα, TCRβ, TCRδ, and/or TCRγ locus). In one embodiment, a method for making a genetically modified non-human animal (e.g., rodent, e.g., mouse or rat) that expresses a T cell receptor comprising a human variable region and a non-human (e.g., rodent, e.g., mouse or rat) constant region on a surface of a T cell is provided, wherein the method comprises inserting, e.g., replacing, in a first non-human animal an endogenous non-human TCRα variable gene locus with an unrearranged humanized TCRα variable gene locus comprising at least one human Vα segment and at least one human Jα segment, wherein the humanized TCRα variable gene locus is operably linked to endogenous TCRα constant region; inserting, e.g., replacing in a second non-human animal an endogenous non-human TCRβ variable gene locus with an unrearranged humanized TCRβ variable gene locus comprising at least one human Vβ segment, one human Dβ segment, and one human Jβ segment, wherein the humanized TCRβ variable gene locus is operably linked to endogenous TCR constant region; and breeding the first and the second non-human animal to obtain a non-human animal that expresses a T cell receptor comprising a human variable region and a non-human constant region. In other embodiments, the invention provides methods of making a genetically modified non-human animal whose genome comprises a humanized unrearranged TCRα locus, or a non-human animal whose genome comprises a humanized unrearranged TCR locus. In various embodiments, the replacements are made at the endogenous loci. In various embodiments, the method comprises progressive humanization strategy, wherein a construct comprising additional variable region segments is introduced into ES cells at each subsequent step of humanization, ultimately resulting in a mouse comprising a complete repertoire of human variable region segments (see, e.g., FIGS. 4A and 4B).

The disclosure also provides a method of modifying a TCR variable gene locus (e.g., TCRα, TCRβ, TCRδ, and/or TCRγ gene locus) of a non-human animal to express a humanized TCR protein described herein. In one embodiment, the invention provides a method of modifying a TCR variable gene locus to express a humanized TCR protein on a surface of a T cell wherein the method comprises inserting, e.g., replacing, in a non-human animal an endogenous non-human TCR variable gene locus with an unrearranged humanized TCR variable gene locus. In one embodiment wherein the TCR variable gene locus is a TCRα variable gene locus, the unrearranged humanized TCR variable gene locus comprises at least one human Vα segment and at least one human Jα segment. In one embodiment wherein the TCR variable gene locus is a TCRβ variable gene locus, the unrearranged humanized TCR variable gene locus comprises at least one human Vβ segment, at least one human Dβ segment, and at least one human Jβ segment. In various aspects, the unrearranged humanized TCR variable gene locus is operably linked to the corresponding endogenous non-human TCR constant region.

Thus, nucleotide constructs for generating genetically modified animals comprising humanized TCR variable region genes are also provided. In one aspect, the nucleotide construct comprises: 5' and 3' homology arms, a human DNA fragment comprising human TCR variable region gene segment(s), and a selection cassette flanked by recombination sites. In one embodiment, the human DNA fragment is a TCRα gene fragment and it comprises at least one human TCRα variable region segment. In another embodiment, the human DNA fragment is a TCRβ fragment and it comprises at least one human TCRβ variable region gene segment. In one aspect, at least one homology arm is a non-human homology arm and it is homologous to non-human TCR locus (e.g., non-human TCRα or TCRβ locus).

In various aspects of the invention, the sequence(s) encoding a chimeric human/non-human MHC I and MHC II polypeptides are located at an endogenous non-human MHC locus (e.g., mouse H-2K and/or H-2E locus). In one embodiment, this results in placement, e.g., replacement, of an endogenous MHC gene(s) or a portion thereof with a nucleic acid sequence(s) encoding a human or humanized MHC I polypeptides. Since the nucleic acid sequences encoding MHC I, MHC II α and MHC II β polypeptides are located in proximity to one another on the chromosome, in order to achieve the greatest success in humanization of both MHC I and MHC II in one animal, the MHC I and MHC II loci should be targeted sequentially. Thus, also provided herein are methods of generating a genetically modified non-human animal comprising nucleic acid sequences encoding chimeric human/non-human MHC I, MHC II α and MHC II β polypeptides as described herein.

Thus, a nucleotide construct for generating genetically modified animals comprising chimeric human/non-human MHC is provided. In one aspect, the nucleic acid construct comprises: 5' and 3' non-human homology arms, a human DNA fragment comprising human MHC gene sequences (e.g., human HLA-A2 or human HLA-DRs gene sequences), and a selection cassette flanked by recombination sites. In one embodiment, the human DNA fragment is a genomic fragment that comprises both introns and exons of a human MHC gene (e.g., human HLA-A2 or HLA-DR2 gene). In one embodiment, the non-human homology arms are homologous to a non-human MHC locus (e.g., MHC I or MHC II locus).

In one embodiment, the 5' and 3' non-human homology arms comprise genomic sequence at 5' and 3' locations, respectively, of an endogenous non-human (e.g., murine) MHC class I or class II gene locus (e.g., 5' of the first leader sequence and 3' of the α3 exon of the mouse MHC I gene, or upstream of mouse H-2Ab1 gene and downstream of mouse H-2Ea gene). In one embodiment, the endogenous MHC class I locus is selected from mouse H-2K, H-2D and H-2L. In a specific embodiment, the endogenous MHC class I locus is mouse H-2K. In one embodiment, the endogenous MHC II locus is selected from mouse H-2E and H-2A. In one embodiment, the engineered MHC II construct allows replacement of both mouse H-2E and H-2A genes. In one embodiment, the mouse does not express functional endogenous MHC polypeptides from its H-2D locus. In some embodiments, the mouse is engineered to lack all or a portion of an endogenous H-2D locus. In another embodiment, the mouse does not express any functional endogenous MHC I and MHC II polypeptides on a cell surface. In one embodiment, the only MHC I and MHC II expressed by the mouse on a cell surface are chimeric human/mouse MHC I and MHC II.

The disclosure also provides methods for making a genetically engineered non-human animal (e.g., a genetically engineered rodent, e.g., a mouse or a rat) whose genome comprises a β2 microglobulin locus encoding a human or humanized β2 microglobulin polypeptide. In one aspect, the methods result in a genetically engineered rodent, e.g., mouse, whose genome comprises at an endogenous β2 microglobulin locus a nucleotide sequence encoding a human or humanized β2 microglobulin polypeptide. In some instances, the mouse does not express a functional mouse β2 microglobulin from an endogenous mouse β2 microglobulin locus. In some aspects, the methods utilize a targeting construct, e.g., made using VELOCIGENE® technology, introducing the construct into ES cells, and introducing targeted ES cell clones into a mouse embryo, e.g., using VELOCIMOUSE® technology, as described in herein.

Also provided is a nucleotide construct used for generating genetically engineered non-human animals. The nucleotide construct may comprise: 5' and 3' non-human homology arms, a human DNA fragment comprising human β2 microglobulin sequences, and a selection cassette flanked by recombination sites. In one embodiment, the human DNA fragment is a genomic fragment that comprises both introns and exons of a human β2 microglobulin gene. In one embodiment, the non-human homology arms are homologous to a non-human β2 microglobulin locus. The genomic fragment may comprise exons 2, 3, and 4 of the human β2 microglobulin gene. In one instance, the genomic fragment comprises, from 5' to 3': exon 2, intron, exon 3, intron, and exon 4, all of human β2 microglobulin sequence. The selection cassette may be located anywhere in the construct outside the β2 microglobulin coding region, e.g., it may be located 3' of exon 4 of the human β2 microglobulin. The 5' and 3' non-human homology arms may comprise genomic sequence 5' and 3' of endogenous non-human β2 microglobulin gene, respectively. In another embodiment, the 5' and 3' non-human homology arms comprise genomic sequence 5' of exon 2 and 3' of exon 4 of endogenous non-human gene, respectively.

Another aspect of the invention relates to a method of modifying a β2 microglobulin locus of a non-human animal (e.g., a rodent, e.g., a mouse or a rat) to express a human or humanized β2 microglobulin polypeptide described herein. One method of modifying a β2 microglobulin locus of a non-human animal, e.g., mouse, to express a human or humanized β2 microglobulin polypeptide, comprises replacing at an endogenous β2 microglobulin locus a nucleotide sequence encoding a mouse β2 microglobulin with a nucleotide sequence encoding the human or humanized β2 microglobulin polypeptide. In one embodiment of such method, the non-human animal, e.g., mouse does not express a functional β2 microglobulin polypeptide from an endogenous non-human, e.g., mouse β2 microglobulin locus. In some specific embodiments, the nucleotide sequence encoding the human or humanized β2 microglobulin polypeptide comprises nucleotide sequence set forth in exons 2 to 4 of the human β2 microglobulin gene. In other embodiments, the nucleotide sequence encoding the human or humanized β2 microglobulin polypeptide comprises nucleotide sequences set forth in exons 2, 3, and 4 of the human β2 microglobulin gene.

Various exemplary embodiments of the humanized loci described herein are presented in FIGS. 2-5.

Upon completion of gene targeting, ES cells or genetically modified non-human animals are screened to confirm successful incorporation of exogenous nucleotide sequence of interest or expression of exogenous polypeptide. Numerous techniques are known to those skilled in the art, and include (but are not limited to) Southern blotting, long PCR, quantitative PCR (e.g., real-time PCR using TAQMAN®), fluorescence in situ hybridization, Northern blotting, flow cytometry, Western analysis, immunocytochemistry, immunohistochemistry, etc. In one example, non-human animals (e.g., mice) bearing the genetic modification of interest can be identified by screening for loss of mouse allele and/or gain of human allele using a modification of allele assay described in Valenzuela et al. (2003) High-throughput engineering of the mouse genome coupled with high-resolution expression analysis, Nature Biotech. 21(6):652-659. Other assays that identify a specific nucleotide or amino acid sequence in the genetically modified animals are known to those skilled in the art.

In some embodiments, animals are generated herein by breeding.

In one non-limiting aspect, for example, a non-human animal comprising the chimeric human/non-human CD8 described herein and the humanized MHC I and/or β2 microglobulin may be generated by breeding an animal comprising a chimeric CD8 locus (e.g., chimeric CD8 α and/or β locus) as described herein with an animal comprising a humanized MHC I and/or β2 microglobulin locus. The animal may also be generated by introducing into ES cells of an animal comprising humanized MHC I and/or β2 microglobulin locus a nucleotide sequence encoding chimeric CD8 (e.g., chimeric CD8 α and/or β), e.g., for replacement at the endogenous CD8 locus (e.g., chimeric CD8 α and/or β locus); or introducing into ES cells of an animal comprising a chimeric CD8 locus (e.g., chimeric CD8 α and/or β locus) a nucleotide sequence(s) encoding humanized MHC I and/or β2 microglobulin.

In some embodiments, the animal comprising a chimeric CD8 locus may first be bred with an animal comprising a humanized TCR variable gene locus to create an animal comprising humanized CD8 and TCR variable region loci, which may then be bred with an animal comprising humanized MHC I and/or β2 microglobulin loci to generate an animal comprising humanized MHC I, TCR variable gene and/or β2 microglobulin loci.

Alternatively, the animal comprising a humanized MHC I and/or β2 microglobulin loci may first be bred with an animal comprising a humanized TCR variable gene locus to create an animal comprising humanized MHC I and TCR variable region loci, which may then be bred with an animal comprising a chimeric CD8 locus generate an animal comprising humanized MHC I, TCR variable gene and/or β2 microglobulin loci, respectively.

In one aspect, the non-human animal comprising a chimeric human/non-human CD4 and the humanized MHC II may be generated by breeding an animal comprising a chimeric CD4 locus as described herein with an animal comprising a humanized MHC II locus. The animal may also be generated by introducing into ES cells of an animal comprising humanized MHC II locus a nucleotide sequence encoding chimeric CD4, e.g., for replacement at the endogenous CD4 locus; or introducing into ES cells of an animal comprising a chimeric CD4 locus a nucleotide sequence encoding humanized MHC II.

In some embodiments, the animal comprising a chimeric CD4 locus may first be bred with an animal comprising a humanized TCR variable gene locus to create an animal comprising humanized CD4 and TCR variable region loci, which may then be bred with an animal comprising a humanized MHC II locus to generate an animal comprising humanized CD4, MHC II and TCR variable gene loci. Alternatively, the animal comprising a comprising humanized MHC II locus may first be bred with an animal comprising a humanized TCR variable gene locus to create an animal comprising humanized MHC II and TCR variable region loci, which may then be bred with an animal comprising a chimeric CD4 locus generate an animal comprising humanized MHC II, TCR variable gene and/or β2 microglobulin loci, respectively.

In some embodiments, a non-human animal comprising the chimeric human/non-human CD8 described herein and the humanized MHC I and/or β2 microglobulin is bred with an animal comprising a chimeric CD4 locus as described herein and an animal comprising a humanized MHC II locus to generate a non-human animal comprising chimeric CD4 and CD8 polypeptides and humanized MHC I (and/or β2 microglobulin) and MHC II molecules. In some embodiments, the animal comprising chimeric human/non-human CD4 and CD8 polypeptides and humanized MHC I and MHC II molecules is bred with an animal comprising a humanized TCR variable domain to generate an animal comprising a substantially humanized T cell immune system, e.g., chimeric human/non-human CD4 and CD8 polypeptides, humanized MHC I (and/or β2 microglobulin) and MHC II molecules and humanized TCR variable domains.

Any of the genetically modified no-human animal (e.g., mouse) described herein may comprise one or two copies of the genes encoding chimeric human/non-human CD8 (e.g., CD8α and/or CD8β); chimeric human/non-human CD4; human or humanized MHC I; human or humanized β2 microglobulin; human or humanized MHC II (e.g., MHC IIα and/or MHC IIβ); and human or humanized TCR (e.g., TCR α and/or TCRβ). Accordingly, the animal may be heterozygous or homozygous for any or all of these genes.

Using Genetically Modified Non-Human Animals that Mount Substantially Humanized T Cell Immune Responses The genetically modified non-human animals, e.g., rodents, e.g., mice or rats, comprising either humanized CD4 and MHC II or humanized CD8 and MHC I (and β2 microglobulin), or both, present peptides to T cells (CD4+ or CD8+ T cells, respectively) in a human-like manner, because substantially all of the components of the complex are human or humanized. The genetically modified non-human animals of the invention can be used to study the function of a human immune system in the humanized animal; for identification of antigens and antigen epitopes that elicit immune response (e.g., T cell epitopes, e.g., unique human cancer epitopes), e.g., for use in vaccine development; for identification of high affinity T cells to human pathogens or cancer antigens (i.e., T cells that bind to antigen in the context of human MHC I complex with high avidity), e.g., for use in adaptive T cell therapy; for evaluation of vaccine candidates and other vaccine strategies; for studying human autoimmunity; for studying human infectious diseases; and otherwise for devising better therapeutic strategies based on human MHC and CD4/CD8 expression.

Thus, in various embodiments, the genetically engineered animals of the present invention are useful, among other things, for evaluating the capacity of an antigen to initiate an immune response in a human, and for generating a diversity of antigens and identifying a specific antigen that may be used in human vaccine development.

In one aspect, a method for determining whether a peptide will provoke a cellular immune response in a human is provided, comprising exposing a genetically modified non-human animal as described herein to the peptide, allowing the non-human animal to mount an immune response, and detecting in the non-human animal a cell (e.g., a CD8+ or CD4+ T cell, comprising a human CD8 or CD4, respectively) that binds a sequence of the peptide presented by a chimeric human/non-human MHC I or II molecule as described herein. In one embodiment, the non-human animal following exposure comprises an MHC class I-restricted CD8+ cytotoxic T lymphocyte (CTL) that binds the peptide. In another embodiment, the non-human animal following exposure comprises an MHC II-restricted CD4+ T cell that binds the peptide.

In one aspect, a method for identifying a human T cell epitope is provided, comprising exposing a non-human animal as described herein to an antigen comprising a putative T cell epitope, allowing the non-human animal to mount an immune response, isolating from the non-human animal an MHC class I- or MHC class II-restricted T cell that binds the epitope, and identifying the epitope bound by said T cell.

In one aspect, a method is provided for identifying an antigen that generates a T cell response in a human, comprising exposing a putative antigen to a mouse as described herein, allowing the mouse to generate an immune response, and identifying the antigen bound by the HLA class I- or class II-restricted molecule.

In one aspect, a method is provided for determining whether a putative antigen contains an epitope that upon exposure to a human immune system will generate an HLA class I- or class II-restricted immune response, comprising exposing a mouse as described herein to the putative antigen and measuring an antigen-specific HLA class I- or HLA class II-restricted immune response in the mouse.

In addition, the genetically engineered non-human animals described herein may be useful for identification of T cell receptors, e.g., high-avidity T cell receptors, that recognize an antigen of interest, e.g., a tumor or another disease antigen. The method may comprise: exposing the non-human animal described herein to an antigen, allowing the non-human animal to mount an immune response to the antigen, isolating from the non-human animal a T cell comprising a T cell receptor that binds the antigen presented by a human or humanized MHC I or MHC II, and determining the sequence of said T cell receptor.

Non-human animals expressing a diverse repertoire of functional human TCR V(D)J gene segments may be useful for the study of human diseases. Accordingly, in one embodiment, the genetically engineered non-human animals described herein may express a TCR repertoire substantially similar to a TCR repertoire expressed in a human, e.g., the TCR repertoire of a non-human animal disclosed herein may be derived from at least about 50%, at least about 60%, at least about 70%, at least about 75%, at least about 80%, at least about 85%, at least about 90%, at least about 95%, at least about 97%, or at least about 99% of all functional human TCR α, TCR β, TCRγ and/or TCRδ gene segments. In some embodiments, a non-human animal as disclosed expresses a TCR repertoire derived from (i) at least about 50%, at least about 60%, at least about 70%, at least about 75%, at least about 80%, at least about 85%, at least about 90%, at least about 95%, at least about 97%, or at least about 99% of all functional human TCR Vα gene segments;

(ii) at least about 50%, at least about 60%, at least about 70%, at least about 75%, at least about 80%, at least about 85%, at least about 90%, at least about 95%, at least about 97%, or at least about 99% of all functional human TCR Jα gene segments;

(iii) at least about 50%, at least about 60%, at least about 70%, at least about 75%, at least about 80%, at least about 85%, at least about 90%, at least about 95%, at least about 97%, or at least about 99% of all functional human TCR Vβ gene segments;

(iv) at least about 50%, at least about 60%, at least about 70%, at least about 75%, at least about 80%, at least about 85%, at least about 90%, at least about 95%, at least about 97%, or at least about 99% of all functional human TCR Dβ gene segments; and/or (v) at least about 50%, at least about 60%, at least about 70%, at least about 75%, at least about 80%, at least about 85%, at least about 90%, at least about 95%, at least about 97%, or at least about 99% of all functional human TCR Jβ gene segments.

In one embodiment, the mouse produces a T cell repertoire comprising all or substantially all functional human TCR Vα gene segments, and comprising all or substantially all functional human TCR Vβ gene segments. In one embodiment, the mouse provided herein utilizes human TCR Vα and/or Vβ genes with a frequency similar to the frequency of human TCR Vα and/or Vβ genes, respectively, utilized by human T cells in a human. Methods of detecting the gene segments expressed in the TCR repertoire of the non-human animal include, e.g., flow cytometric and/or sequencing methods (e.g., real time PCR, Next Generation Sequencing, etc.).

In one embodiment, a method is provided for determining T cell activation by a putative human therapeutic, comprising exposing a genetically modified animal as described herein to a putative human therapeutic (or e.g., exposing a human or humanized MHC II- or MHC I-expressing cell of such an animal to a peptide sequence of the putative therapeutic), exposing a cell of the genetically modified animal that displays a human or humanized MHC/peptide complex to a T cell comprising a chimeric human/non-human (e.g., human/mouse) CD4 or CD8 capable of binding the cell of the genetically modified animal, and measuring activation of the T cell that is induced by the peptide-displaying cell of the genetically modified animal.

In addition to the ability to identify antigens and antigen epitopes from human pathogens or neoplasms, the genetically modified animals of the invention can be used to identify autoantigens of relevance to human autoimmune diseases, e.g., type I diabetes, multiple sclerosis, etc. Also, the genetically modified animals of the invention can be used to study various aspects of human autoimmune disease, and may be utilized as autoimmune disease models.

In various embodiments, the genetically modified non-human animals of the invention make T cells with humanized TCR molecules on their surface, and as a result, would recognize peptides presented to them by MHC complexes in a human-like manner. The genetically modified non-human animals described herein may be used to study the development and function of human T cells and the processes of immunological tolerance; to test human vaccine candidates; to generate TCRs with certain specificities for TCR gene therapy; to generate TCR libraries to disease associated antigens (e.g., tumor associated antigens (TAAs); etc.

There is a growing interest in T cell therapy in the art, as T cells (e.g., cytotoxic T cells) can be directed to attack and lead to destruction of antigen of interest, e.g., viral antigen, bacterial antigen, tumor antigen, etc., or cells that present it. Initial studies in cancer T cell therapy aimed at isolation of tumor infiltrating lymphocytes (TILs; lymphocyte populations in the tumor mass that presumably comprise T cells reactive against tumor antigens) from tumor cell mass, expanding them in vitro using T cell growth factors, and transferring them back to the patient in a process called adoptive T cell transfer. See, e.g., Restifo et al. (2012) Adoptive immunotherapy for cancer: harnessing the T cell response, Nature Reviews 12:269-81; Linnermann et al. (2011) T-Cell Receptor Gene Therapy: Critical Parameters for Clinical Success, J. Invest. Dermatol. 131:1806-16. However, success of these therapies have thus far been limited to melanoma and renal cell carcinoma; and the TIL adoptive transfer is not specifically directed to defined tumor associated antigens (TAAs). Linnermann et al., supra.

Attempts have been made to initiate TCR gene therapy where T cells are either selected or programmed to target an antigen of interest, e.g., a TAA. Current TCR gene therapy relies on identification of sequences of TCRs that are directed to specific antigens, e.g., tumor associated antigens. For example, Rosenberg and colleagues have published several studies in which they transduced peripheral blood lymphocytes derived from a melanoma patient with genes encoding TCRα and β chains specific for melanoma-associated antigen MART-1 epitopes, and used resulting expanded lymphocytes for adoptive T cell therapy. Johnson et al. (2009) Gene therapy with human and mouse T-cell receptors mediates cancer regression and targets normal tissues expressing cognate antigen, Blood 114:535-46; Morgan et al. (2006) Cancer Regression in Patients After Transfer of Genetically Engineered Lymphocytes, Science 314:126-29. The MART-1 specific TCRs were isolated from patients that experienced tumor regression following TIL therapy. However, identification of such TCRs, particularly high-avidity TCRs (which are most likely to be therapeutically useful), is complicated by the fact that most tumor antigens are self antigens, and TCRs targeting these antigens are often either deleted or possess suboptimal affinity, due primarily to immunological tolerance.

In various embodiments, the present invention solves this problem by providing genetically engineered non-human animals comprising in their genome an unrearranged human TCR variable gene locus. The non-human animal described herein is capable of generating T cells with a diverse repertoire of humanized T cell receptors. Thus, the non-human animals described herein may be a source of a diverse repertoire of humanized T cell receptors, e.g., high-avidity humanized T cell receptors for use in adoptive T cell transfer.

Thus, in one embodiment, the present invention provides a method of generating a T cell receptor to a human antigen comprising immunizing a non-human animal (e.g., a rodent, e.g., a mouse or a rat) described herein with an antigen of interest, allowing the animal to mount an immune response, isolating from the animal an activated T cell with specificity for the antigen of interest, and determining the nucleic acid sequence of the T cell receptor expressed by the antigen-specific T cell.

In one embodiment, the invention provides a method of producing a human T cell receptor specific for an antigen of interest (e.g., a disease-associated antigen) comprising immunizing a non-human animal described herein with the antigen of interest; allowing the animal to mount an immune response; isolating from the animal a T cell reactive to the antigen of interest; determining a nucleic acid sequence of a human TCR variable region expressed by the T cell; cloning the human TCR variable region into a nucleotide construct comprising a nucleic acid sequence of a human TCR constant region such that the human TCR variable region is operably linked to the human TCR constant region; and expressing from the construct a human T cell receptor specific for the antigen of interest. In one embodiment, the steps of isolating a T cell, determining a nucleic acid sequence of a human TCR variable region expressed by the T cell, cloning the human TCR variable region into a nucleotide construct comprising a nucleic acid sequence of a human TCR constant region, and expressing a human T cell receptor are performed using standard techniques known to those of skill the art.

In one embodiment, the nucleotide sequence encoding a T cell receptor specific for an antigen of interest is expressed in a cell. In one embodiment, the cell expressing the TCR is selected from a CHO, COS, 293, HeLa, PERC.6™ cell, etc.

The antigen of interest may be any antigen that is known to cause or be associated with a disease or condition, e.g., a tumor associated antigen; an antigen of viral, bacterial or other pathogenic origin; etc. Many tumor associated antigens are known in the art. A selection of tumor associated antigens is presented in Cancer Immunity (A Journal of the Cancer Research Institute) Peptide Database (archive.cancerimmunity.org/peptidedatabase/Tcellepitopes.htm). In some embodiments of the invention, the antigen of interest is a human antigen, e.g., a human tumor associated antigen. In some embodiments, the antigen is a cell type-specific intracellular antigen, and a T cell receptor is used to kill a cell expressing the antigen.

In one embodiment, provided herein is a method of identifying a T cell with specificity against an antigen of interest, e.g., a tumor associated antigen, comprising immunizing a non-human animal described herein with the antigen of interest, allowing the animal to mount an immune response, and isolating from the non-human animal a T cell with specificity for the antigen.

The present invention provides new methods for adoptive T cell therapy. Thus, provided herein is a method of treating or ameliorating a disease or condition (e.g., a cancer) in a subject (e.g., a mammalian subject, e.g., a human subject) comprising immunizing a non-human animal described herein with an antigen associated with the disease or condition, allowing the animal to mount an immune response, isolating from the animal a population of antigen-specific T cells, and infusing isolated antigen-specific T cells into the subject. In one embodiment, the invention provides a method of treating or ameliorating a disease or condition in a human subject, comprising immunizing the non-human animal described herein with an antigen of interest (e.g., a disease- or condition-associated antigen, e.g., a tumor associated antigen), allowing the animal to mount an immune response, isolating from the animal a population of antigen-specific T cells, determining the nucleic acid sequence of a T cell receptor, (e.g., a first and/or second nucleic acid sequence encoding the human rearranged TCRα and/or human rearranged TCRβ variable region gene); a third and/or fourth nucleic acid sequence encoding the human rearranged TCRδ variable region gene or a TCRγ variable region gene, expressed by the antigen-specific T cells, cloning the nucleic acid sequence of the T cell receptor, e.g., the first, second, third and/or fourth nucleic acid sequence respectively encoding the human rearranged TCRα variable region gene, human rearranged TCRβ variable region gene, TCRδ variable region gene or a TCRγ variable region gene, into an expression vector (e.g., a retroviral vector), e.g., optionally wherein the first, second, third and/or fourth nucleic acid sequence respectively encoding the human rearranged TCRα variable region gene, human rearranged TCRβ variable region gene, TCRδ variable region gene or a TCRγ variable region gene is respectively cloned in-frame with a human TCRα constant gene, human TCRβ constant gene, TCRδ constant gene or a TCRγ constant gene, introducing the vector into T cells derived from the subject such that the T cells express the antigen-specific T cell receptor, and infusing the T cells into the subject. In one embodiment, the T cell receptor nucleic acid sequence is further humanized prior to introduction into T cells derived from the subject, e.g., the sequence encoding the non-human constant region is modified to further resemble a human TCR constant region (e.g., the non-human constant region is replaced with a human constant region). In some embodiments, the disease or condition is cancer. In some embodiments, an antigen-specific T cell population is expanded prior to infusing into the subject. In some embodiments, the subject's immune cell population is immunodepleted prior to the infusion of antigen-specific T cells. In some embodiments, the antigen-specific TCR is a high avidity TCR, e.g., a high avidity TCR to a tumor associated antigen. In some embodiments, the T cell is a cytotoxic T cell. In other embodiments, the disease or condition is caused by a virus or a bacterium.

In another embodiment, a disease or condition is an autoimmune disease. TREG cells are a subpopulation of T cells that maintain tolerance to self-antigens and prevent pathological self-reactivity. Thus, also provided herein are methods of treating autoimmune disease that rely on generation of antigen-specific TREG cells in the non-human animal of the invention described herein.

Also provided herein is a method of treating or ameliorating a disease or condition (e.g., a cancer) in a subject comprising introducing the cells affected by the disease or condition (e.g., cancer cells) from the subject into a non-human animal, allowing the animal to mount an immune response to the cells, isolating from the animal a population of T cells reactive to the cells, determining the nucleic acid sequence of a T cell receptor variable domain expressed by the T cells, cloning the T cell receptor variable domain encoding sequence into a vector (e.g., in-frame and operably linked to a human TCR constant gene), introducing the vector into T cells derived from the subject, and infusing the subject's T cells harboring the T cell receptor into the subject.

Also provided herein is the use of a non-human animal as described herein to make nucleic acid sequences encoding human TCR variable domains (e.g., TCR α and/or β variable domains). In one embodiment, a method is provided for making a nucleic acid sequence encoding a human TCR variable domain, comprising immunizing a non-human animal as described herein with an antigen of interest, allowing the non-human animal to mount an immune response to the antigen of interest, and obtaining therefrom a nucleic acid sequence encoding a human TCR variable domain that binds the antigen of interest. In one embodiment, the method further comprises making a nucleic acid sequence encoding a human TCR variable domain that is operably linked to a non-human TCR constant region, comprising isolating a T cell from a non-human animal described herein and obtaining therefrom the nucleic acid sequence encoding the TCR variable domain linked to the non-human constant region TCR constant region, and cloning the nucleic acid sequence(s) encoding the TCR variable domain (e.g., a first, second, third or fourth nucleic acid sequence respectively encoding a human rearranged TCRα variable region gene, human rearranged TCRβ variable region gene, TCRδ variable region gene or a TCRγ variable region gene) in-frame with an appropriate human constant region (e.g., a human TCRα constant region gene, human TCRβ constant region gene, TCRδ constant region gene or a TCRγ variable region gene, respectively).

Thus, provided herein are TCR variable region nucleic acid sequences, such as rearranged TCR variable nucleic acid sequences, e.g., rearranged TCRα and/or TCRβ variable region nucleic acid sequences, generated in the non-human animals described herein, and encoded respectively by, e.g., a human rearranged Vα/Jα gene sequence and a rearranged human VβDβJβ gene sequence. Also, provided are TCR variable region amino acid sequences encoded by such rearranged TCR variable region nucleic acid sequences. Such rearranged TCR variable region nucleic acid sequences (TCRα and/or TCRβ variable region nucleic acid sequences) obtained in the non-human animals described herein may be cloned in operable linkage with human TCR constant region (TCRα and/or TCRβ constant region), and utilized for various uses described herein, e.g., as a human therapeutic, in a human.

Also provided herein is the use of a non-human animal as described herein to make a human therapeutic, comprising immunizing the non-human animal with an antigen of interest (e.g., a tumor associated antigen), allowing the non-human animal to mount an immune response, obtaining from the animal T cells reactive to the antigen of interest, obtaining from the T cells a nucleic acid sequence(s) encoding a humanized TCR protein or human TCR variable domain that binds the antigen of interest, and employing the nucleic acid sequence(s) encoding a humanized TCR protein or a human TCR variable domain in a human therapeutic.

Thus, also provided is a method for making a human therapeutic, comprising immunizing a non-human animal as described herein with an antigen of interest, allowing the non-human animal to mount an immune response, obtaining from the animal T cells reactive to the antigen of interest, obtaining from the T cells a nucleic acid sequence(s) encoding a humanized T cell receptor that binds the antigen of interest, and employing the humanized (or fully human) T cell receptor in a human therapeutic.

In one embodiment, the human therapeutic is a T cell (e.g., a human T cell, e.g., a T cell derived from a human subject) harboring a nucleic acid sequence of interest (e.g., transfected or transduced or otherwise introduced with the nucleic acid of interest) such that the T cell expresses the humanized TCR protein with affinity for an antigen of interest. In one aspect, a subject in whom the therapeutic is employed is in need of therapy for a particular disease or condition, and the antigen is associated with the disease or condition. In one aspect, the T cell is a cytotoxic T cell, the antigen is a tumor associated antigen, and the disease or condition is cancer. In one aspect, the T cell is derived from the subject.

In another embodiment, the human therapeutic is a T cell receptor. In one embodiment, the therapeutic receptor is a soluble T cell receptor. Much effort has been expanded to generate soluble T cell receptors or TCR variable regions for use therapeutic agents. Generation of soluble T cell receptors depends on obtaining rearranged TCR variable regions. One approach is to design single chain TCRs comprising TCRα and TCRβ, and, similarly to scFv immunoglobulin format, fuse them together via a linker (see, e.g., International Application No. WO 2011/044186). The resulting scTv, if analogous to scFv, would provide a thermally stable and soluble form of TCRα/β binding protein. Alternative approaches included designing a soluble TCR having TCRβ constant domains (see, e.g., Chung et al., (1994) Functional three-domain single-chain T-cell receptors, Proc. Natl. Acad. Sci. USA. 91:12654-58); as well as engineering a non-native disulfide bond into the interface between TCR constant domains (reviewed in Boulter and Jakobsen (2005) Stable, soluble, high-affinity, engineered T cell receptors: novel antibody-like proteins for specific targeting of peptide antigens, Clinical and Experimental Immunology 142:454-60; see also, U.S. Pat. No. 7,569,664). Other formats of soluble T cell receptors have been described. The non-human animals described herein may be used to determine a sequence of a T cell receptor that binds with high affinity to an antigen of interest, and subsequently design a soluble T cell receptor based on the sequence.

A soluble T cell receptor derived from the TCR receptor sequence expressed by the non-human animal can be used to block the function of a protein of interest, e.g., a viral, bacterial, or tumor associated protein. Alternatively, a soluble T cell receptor may be fused to a moiety that can kill an infected or cancer cell, e.g., a cytotoxic molecules (e.g., a chemotherapeutic), toxin, radionuclide, prodrug, antibody, etc. A soluble T cell receptor may also be fused to an immunomodulatory molecule, e.g., a cytokine, chemokine, etc. A soluble T cell receptor may also be fused to an immune inhibitory molecule, e.g., a molecule that inhibits a T cell from killing other cells harboring an antigen recognized by the T cell. Such soluble T cell receptors fused to immune inhibitory molecules can be used, e.g., in blocking autoimmunity. Various exemplary immune inhibitory molecules that may be fused to a soluble T cell receptor are reviewed in Ravetch and Lanier (2000) Immune Inhibitory Receptors, Science 290:84-89, incorporated herein by reference.

The present invention also provides methods for studying immunological response in the context of human TCR, including human TCR rearrangement, T cell development, T cell activation, immunological tolerance, etc.

Also provided are methods of testing vaccine candidates. In one embodiment, provided herein is a method of determining whether a vaccine will activate an immunological response (e.g., T cell proliferation, cytokine release, etc.), and lead to generation of effector, as well as memory T cells (e.g., central and effector memory T cells).

In one aspect, an in vitro preparation is provided that comprises a T cell that bears a chimeric CD8 protein on its surface and a second cell that binds the chimeric CD8. In one embodiment, the second cell is a cell expressing an MHC I polypeptide, e.g., a chimeric human/non-human MHC I protein. In one embodiment, the chimeric CD8 on the surface of the first cell interacts with chimeric MHC I on the surface of the second cell. In one embodiment, the chimeric CD8 protein retains interaction with endogenous cytosolic molecules, e.g., endogenous cytosolic signaling molecules (e.g., endogenous Lck, etc.).

In one aspect, an in vitro preparation is provided that comprises a T cell that bears a chimeric CD4 protein on its surface and a second cell that binds the chimeric CD4. In one embodiment, the second cell is a cell, e.g., an APC, expressing an MHC II polypeptide, e.g., a chimeric human/non-human MHC II protein. In one embodiment, the chimeric CD4 on the surface of the first cell interacts with chimeric MHC II on the surface of the second cell. In one embodiment, the chimeric CD4 protein retains interaction with endogenous cytosolic molecules, e.g., endogenous cytosolic signaling molecules (e.g., endogenous Lck, etc.).

Other uses of the genetically modified animals described herein, i.e., animals comprising a human or humanized T cell co-receptor (e.g., chimeric human/non-human CD4 or CD8), optionally further comprising a human or humanized MHC II or I protein, will be apparent from the present disclosure.

EXAMPLES

The following examples are provided so as to describe to those of ordinary skill in the art how to make and use methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. The Examples do not include detailed descriptions of conventional methods that would be well known to those of ordinary skill in the art (molecular cloning techniques, etc.). Unless indicated otherwise, parts are parts by weight, molecular weight is average molecular weight, temperature is indicated in Celsius, and pressure is at or near atmospheric.

Example 1

Generation of Humanized MHC Mice

The various steps involved in engineering a mouse comprising humanized MHC I and MHC II loci, with corresponding and additional endogenous MHC I and MHC II loci deletions (HLA-A2/H-2K, HLA-DR2/H-2E, H-2A-del, H-2D-del) are depicted in FIG. 3A. Detailed description of the steps appears below.

Example 1.1

Generation and Characterization of Humanized MHC I Mice

Generation of humanized MHC I mice has previously been described in U.S. Patent Publication No. 20130111617, incorporated herein by reference. Briefly, the mouse H-2K gene was humanized in a single step by construction of a unique targeting vector from human and mouse bacterial artificial chromosome (BAC) DNA using VELOCIGENE® technology (see, e.g., U.S. Pat. No. 6,586,251 and Valenzuela et al. (2003) High-throughput engineering of the mouse genome coupled with high-resolution expression analysis. Nat. Biotech. 21(6): 652-659). DNA from mouse BAC clone RP23-173k21 (Invitrogen) was modified by homologous recombination to replace the genomic DNA encoding the α1, α2 and α3 domains of the mouse H-2K gene with human genomic DNA encoding the α1, α2 and α3 subunits of the human HLA-A gene (FIG. 2A).

Specifically, the genomic sequence encoding the mouse the α1, α2 and α3 subunits of the H-2K gene is replaced with the human genomic DNA encoding the α1, α2 and α3 domains of the human HLA-A*0201 gene in a single targeting event using a targeting vector comprising a hygromycin cassette flanked by loxP sites with a 5' mouse homology arm containing sequence 5' of the mouse H-2K locus including the 5' untranslated region (UTR) and a 3' mouse homology arm containing genomic sequence 3' of the mouse H-2K α3 coding sequence.

The final construct for targeting the endogenous H-2K gene locus from 5' to 3' included (1) a 5' homology arm containing ~200 bp of mouse genomic sequence 5' of the endogenous H-2K gene including the 5'UTR, (2) ~1339 bp of human genomic sequence including the HLA-A*0201 leader sequence, the HLA-A*0201 leader/α1 intron, the HLA-A*0201 α1 exon, the HLA-A*0201 α1-α2 intron, the HLA-A*0201 α2 exon, ~316 bp of the 5' end of the α2-α3 intron, (3) a 5' loxP site, (4) a hygromycin cassette, (5) a 3' loxP site, (6) ~580 bp of human genomic sequence including ~304 bp of the 3' end of the α2-α3 intron, the HLA-A*0201 α3 exon, and (7) a 3' homology arm containing ~200 bp of mouse genomic sequence including the intron between the mouse H-2K α3 and transmembrane coding sequences. The sequence of 149 nucleotides at the junction of the mouse/human sequences at the 5' of the targeting vector is set forth in SEQ ID NO: 90, and the sequence of 159 nucleotides at the junction of the human/mouse sequences at the 3' of the targeting vector is set forth in SEQ ID NO:91. Homologous recombination with this targeting vector created a modified mouse H-2K locus containing human genomic DNA encoding the α1, α2 and α3 domains of the HLA-A*0201 gene operably linked to the endogenous mouse H-2K transmembrane and cytoplasmic domain coding sequences which, upon translation, leads to the formation of a chimeric human/mouse MHC class I protein. The selection cassette present in the targeting construct may be later removed using various methods known in the art.

The targeted BAC DNA was used to electroporate mouse F1H4 ES cells to create modified ES cells for generating mice that express a chimeric MHC class I protein on the surface of nucleated cells (e.g., T and B lymphocytes, macrophages, neutrophils) (see, e.g., step 1 in the scheme depicted in FIG. 3A). ES cells containing an insertion of human HLA sequences were identified by a quantitative TAQMAN™ assay (Valenzuela et al. (2003), supra).

To generate mice expressing chimeric MHC I, targeted ES cells described herein are used as donor ES cells and introduced into an 8-cell stage mouse embryo by the VELOCIMOUSE® method (see, e.g., U.S. Pat. No. 7,294, 754 and Poueymirou et al. (2007) F0 generation mice that are essentially fully derived from the donor gene-targeted ES cells allowing immediate phenotypic analyses Nature Biotech. 25(1):91-99). VELOCIMICE® (F0 mice fully derived from the donor ES cell) independently bearing a chimeric MHC class I gene are identified by genotyping using a modification of allele assay (Valenzuela et al., supra) that detects the presence of the unique human HLA-A*0201 gene sequences. Heterozygous mice generated by this method are bred to homozygosity. Expression of chimeric HLA-A2/H-2K is confirmed by flow cytometry using antibodies specific for HLA-A and H-2K.

Targeted ES cells described above comprising the chimeric HLA-A2/H-2K were used in further genetic engineering steps described in Examples 1.2-1.3 to generate mice comprising both humanized MHC I and MHC II loci and lacking endogenous MHC I and MHC II loci (See FIG. 3A).

Example 1.2

Generation of Mouse ES Cells Comprising MHC I and MHC II Loci Deletions

Deletion of endogenous MHC II loci is described in U.S. Patent Application Number No. 20130111616, incorporated herein by reference. Briefly, the targeting vector for introducing a deletion of the endogenous MHC class II H-2Ab1, H-2Aa, H-2Eb1, H-2Eb2, and H-2Ea genes was made using VELOCIGENE® genetic engineering technology (see, e.g., U.S. Pat. No. 6,586,251 and Valenzuela et al., supra). Bacterial Artificial Chromosome (BAC) RP23-458i22 (Invitrogen) DNA was modified to delete the endogenous MHC class II genes H-2Ab1, H-2Aa, H-2Eb1, H-2Eb2, and H-2Ea.

Specifically, upstream and downstream homology arms were derived by PCR of mouse BAC DNA from locations 5' of the H-2Ab1 gene and 3' of the H-2Ea gene, respectively. These homology arms were used to make a cassette that deleted ~79 kb of RP23-458i22 comprising genes H-2Ab1, H-2Aa, H-2Eb1, H-2Eb2, and H-2Ea of the MHC class II locus by bacterial homologous recombination (BHR). This region was replaced with a neomycin cassette flanked by lox2372 sites. The final targeting vector from 5' to 3' included a 26 kb homology arm comprising mouse genomic sequence 5' to the H-2Ab1 gene of the endogenous MHC class II locus, a 5' lox2372 site, a neomycin cassette, a 3' lox2372 site and a 63 kb homology arm comprising mouse genomic sequence 3' to the H-2Ea gene of the endogenous MHC class II locus.

The BAC DNA targeting vector (described above) was used to electroporate mouse ES cells comprising humanized MHC I locus (from Example 1.1 above; see, e.g., step 2 in FIG. 3A) to create modified ES cells comprising a deletion of the endogenous MHC class II locus (both H-2A and H-2E were deleted). Positive ES cells containing a deleted endogenous MHC class II locus were identified by the quantitative PCR assay using TAQMAN™ probes (Lie and Petropoulos (1998) Curr. Opin. Biotechnology 9:43-48). The upstream region of the deleted locus was confirmed by PCR using primers 5111U F (CAGAACGCCAGGCTGTAAC; SEQ ID NO:1) and 5111U R (GGAGAGCAGGGTCAGTCAAC; SEQ ID NO:2) and probe 5111U P (CACCGCCACTCACAGCTCCTTACA; SEQ ID NO:3), whereas the downstream region of the deleted locus was confirmed using primers 5111 D F (GTGGGCACCATCTTCATCATTC; SEQ ID NO:4) and 5111 D R (CTTCCTTTCCAGGGTGTGACTC; SEQ ID NO:5) and probe 5111 D P (AGGCCTGCGATCAGGTGGCACCT; SEQ ID NO:6). The presence of the neomycin cassette from the targeting vector was confirmed using primers NEOF (GGTGGAGAGGCTATTCGGC; SEQ ID NO:7) and NEOR (GAACACGGCGGCATCAG;SEQ ID NO:8) and probe NEOP (TGGGCACAACAGACAATCGGCTG; SEQ ID NO:9). The nucleotide sequence across the upstream deletion point (SEQ ID NO:10) included the following, which indicates endogenous mouse sequence upstream of the deletion point (contained within the parentheses below) linked contiguously to cassette sequence present at the deletion point: (TTTGTAAACA AAGTCTACCC AGAGACAGAT GACAGACTTC AGCTCCAATG CTGATTGGTT CCTCACTTGG GACCAACCCT) ACCGGTATAA CTTCGTATAA GGTATCCTAT ACGAAGTTAT ATGCATGGCC TCCGCGCCGG. The nucleotide sequence across the downstream deletion point (SEQ ID NO:11) included the following, which indicates cassette sequence contiguous with endogenous mouse sequence downstream of the deletion point (contained within the parentheses below): CGACCTGCAG CCGGCGCGCC ATAACTTCGT ATAAGGTATC CTATACGAAG TTATCTCGAG (CACAGGCATT TGGGTGGGCA GGGATGGACG GTGACTGGGA CAATCGGGAT GGAAGAGCAT AGAATGGGAG TTAGGGAAGA).

Subsequently to generation of the ES cells comprising both the MHC I humanization and endogenous MHC II deletion described above, the loxed neomycin cassette was removed using CRE (see, e.g., step 3 in FIG. 3A). Specifically, a plasmid encoding Cre recombinase was electroporated into ES cells to remove the neomycin cassette. Neo cassette may also be removed using other methods known in the art.

To delete mouse H-2D locus, BHR was used to modify mouse BAC clone bMQ-218H21 (Sanger Institute), replacing 3756 bp of the H2-D gene (from the ATG start codon to 3 bp downstream of the TGA stop codon, exons 1-8 of mouse H-2D) with a 6,085 bp cassette containing from 5' to 3': a LacZ gene in frame with a 5' loxp site, UbC promoter, Neomycin gene, and 3' loxp site.

The BAC DNA targeting vector (described above) was used to electroporate mouse ES cells comprising humanized MHC I locus and a deletion of mouse MHC II, described above (see, e.g., step 4 in FIG. 3A). Positive ES cells containing a deleted endogenous H-2D locus were identified by the quantitative PCR assay, as described above. Table 2 contains primers and probes used for the quantitative PCR assay.

TABLE 2

TAQMAN ™ Loss of Allele Assay Primers and Probes for Detection of Deleted H-2D Locus

| Name (location) | Forward Primer | Reverse Primer | Probe |
|---|---|---|---|
| 5152 mTU (upstream) | CGAGGAGCCCCG GTACA (SEQ ID NO: 12) | AAGCGCACGAACTC CTTGTT (SEQ ID NO: 13) | CTCTGTCGGCTAT GTGG (SEQ ID NO: 14) |

TABLE 2-continued

TAQMAN™ Loss of Allele Assay Primers and Probes for Detection of Deleted H-2D Locus

| Name (location) | Forward Primer | Reverse Primer | Probe |
|---|---|---|---|
| 5152 mTD (downstream) | GGACTCCCAGAAT CTCCTGAGA (SEQ ID NO: 15) | GAGTCATGAACCATC ACTGTGAAGA (SEQ ID NO: 16) | TGGTGGGTTGCTG GAA (SEQ ID NO: 17) |

Example 1.3

Introduction of Chimeric Human/Mouse MHC II Locus

To generate a vector comprising humanized HLA-DR2/H-2E, first, mouse H-2Ea gene was modified in accordance with the description in U.S. Pat. No. 8,847,005, issued Sep. 30, 2014, incorporated herein by reference, to generate a vector comprising sequence encoding a chimeric H-2Ea/HLA-DRA1*01 protein.

For mouse H-2Eb gene, synthesized human HLA-DR2 β chain (DRB1*1501) was used to generate a vector comprising DRβ1*02(1501) exons and introns, and swapped using bacterial homologous recombination into the vector comprising chimeric H-2Ea/HLA-DRA1*01 protein. H-2Eb1 gene was modified essentially as described in U.S. Patent Publication No. 20130185820, and U.S. Pat. No. 8,847,005, each incorporated herein by reference. A hygromycin selection cassette was used.

Figure 3B:
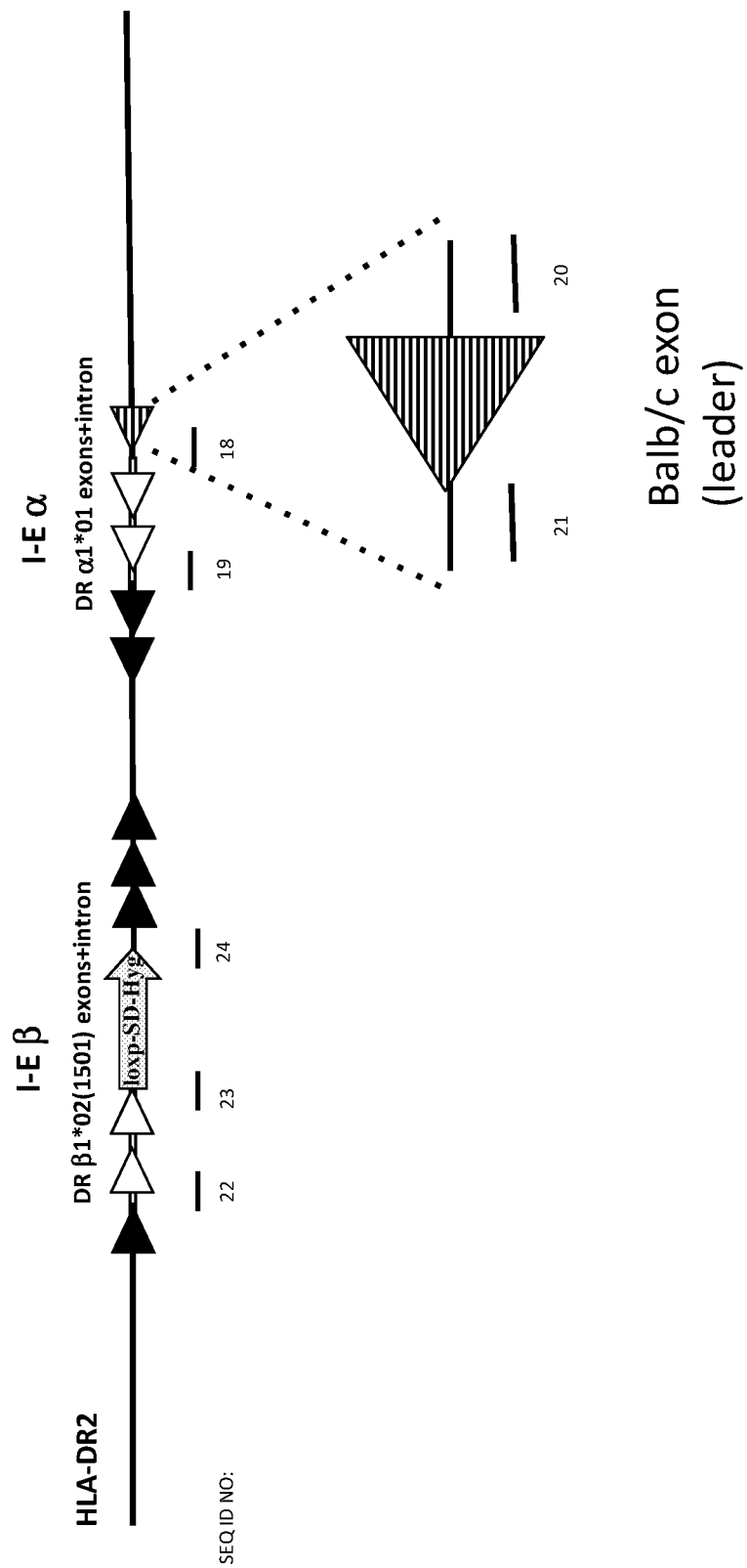

The resulting HLA-DR2/H-2E large targeting vector (LTVEC) is depicted in FIGS. 2B and 3B. The various nucleotide sequence junctions of the resulting LTVECs (e.g., mouse/human sequence junctions, human/mouse sequence junctions, or junctions of mouse or human sequence with selection cassettes) are summarized below in Table 3 and listed in the Sequence Listing; their locations are indicated in the schematic diagram of FIG. 3B. In Table 3 below, with the exception of sequences marked with asterisks (*, see Table legend) the mouse sequences are in regular font; the human sequences are in parentheses; the Lox sequences are italicized; and the restriction sites introduced during cloning steps and other vector-based sequences (e.g., multiple cloning sites, etc.) are bolded.

TABLE 3

Nucleotide Sequence Junctions of Chimeric HLA-DR2/H-2E Locus

| SEQ ID NO: | Nucleotide Sequence |
|---|---|
| 18 | CTGTTTCTTC CCTAACTCCC ATTCTATGCT CTTCCATCCC GA CCGCGG(CCCA ATCTCTCTCC ACTACTTCCT GCCTACATGT ATGTAGGT) |
| 19 | (CAAGGTTTCC TCCTATGATG CTTGTGTGAA ACTCGG) GGCC GGCC AGCATTTAAC AGTACAGGGA TGGGAGCACA GCTCAC |
| 20* | (GAAAGCAGTC TTCCCAGCCT TCACACTCAG AGGTACAAAT) CCCCATTTTC ATATTAGCGA TTTTAATTTA TTCTAGCCTC |
| 21* | TCTTCCCTAA CTCCCATTCT ATGCTCTTCC ATCCCGA CCG CGG (CCCAATC TCTCTCCACT ACTTCCTGCC TACATGTATG) |
| 22 | GAGTTCCTCCATCACTTCACTGGGTAGCACAGCTGTAACTGTCCAGCCTG (TCCTGGGCTGCAGGTGGTGGGCGTTGCGGGTGGGGCCGGTTAAGGTTCCA) |
| 23 | (TCCCACATCCTATTTTAATTTGCTCCATGTTCTCATCTCCATCAGCACAG) CTCGAG *ATAACTTCGTATAATGTATGCTATACGAAGTTAT* ATGCATGCC |
| 24 | *ATACGAAGTTAT* GCTAGTAACTATAACGGTCCTAAGGTAGCGAGTGGCTT ACAGGTAGGTGCGTGAAGCTTCTACAAGCACAGTTGCCCCCTGGGAAGCA |

Sequences marked with asterisk are C57BL/6-BALB/c junction sequences where C57BL/6 sequences are in parentheses. During cloning of the chimeric H-2Ea gene, exon 1 and the remainder of intron 1 of the C57BL/6 allele of H-2Ea was replaced with the equivalent 2616 bp region from the BALB/c allele of H-2Ea. This was done because exon 1 of the C57BL/6 allele of H-2Ea contains a deletion which renders the gene nonfunctional, while exon 1 of BALB/c allele of H-2Ea is functional. For a more detailed description, see U.S. Pat. No. 8,847,005, incorporated herein by reference.

The targeted BAC DNA described above was used to electroporate mouse ES cells comprising humanized MHC I (HLA-A2), as well as MHC II and H-2D deletion to create modified ES cells for generating mice that express chimeric MHC I and MHC II genes and lack functional endogenous mouse H-2E, H-2A, H-2K, and H-2D loci (see, e.g., step 5 in FIG. 3A). ES cells containing an insertion of human HLA sequences were identified by a quantitative PCR (TAQMAN™) assay, using primers and probes in Table 4.

TABLE 4

TAQMAN ™ Primer and Probe Sequences for Detection of MHC I and MHC II Loci Humanization

| Name (location) | Forward Primer | Reverse Primer | Probe |
|---|---|---|---|
| Hyg cassette | TGCGGCCGATCTT AGCC (SEQ ID NO: 25) | TTGACCGATTCCTTG CGG (SEQ ID NO: 26) | ACGAGCGGGTTC GGCCCATTC (SEQ ID NO: 27) |
| 7092 hTUP1 (Exon 2 of DRB1*1501) | CCCCACAGCACGT TTCCT (SEQ ID NO: 28) | CGTCCCATTGAAGAA ATGACACT (SEQ ID NO: 29) | TGGCAGCCTAAGA GG (SEQ ID NO: 30) |
| 7092 hTUP2 (Exon 2 of DRB1*1501) | CCCCACAGCACGT TTCCT (SEQ ID NO: 31) | ACCCGCTCCGTCCC ATT (SEQ ID NO: 32) | AGCCTAAGAGGG AGTGTC (SEQ ID NO: 33) |
| 7092 hTDP1 (Exon 3 of DRB1*1501) | AGACCCTGGTGAT GCTGGAA (SEQ ID NO: 34) | CGCTTGGGTGCTCC ACTT (SEQ ID NO: 35) | TCGAAGTGGAGA GGTTTA (SEQ ID NO: 36) |
| 7092 hTDP2 (exon 3 of DRB1*1501) | TGGAATGGAGTGA GCAGCTTT (SEQ ID NO: 37) | GCACGGTCCCCTTC TTAGTG (SEQ ID NO: 38) | TGACTTCCTAAAT TTCTC (SEQ ID NO: 39) |
| hDRAIU (exon 2 of DRA) | CTGGCGGCTTGAA GAATTTGG (SEQ ID NO: 40) | CATGATTTCCAGGTT GGCTTTGTC (SEQ ID NO: 41) | CGATTTGCCAGCT TTGAGGCTCAAGG (SEQ ID NO: 42) |
| 1751jxn2[1] (loss-of-allele assay, sequence present in H-2A and H-2E delete only) | CCTCACTTGGGAC CAACCCTA (SEQ ID NO: 43) | TTGTCCCAGTCACCG TCCAT (SEQ ID NO: 44) | TGCATCTCGAGCA CAGGCATTGG (SEQ ID NO: 45) |

[1]All sequences except this one are used in the gain-of-allele assay.

The selection cassette may be removed by methods known by the skilled artisan. For example, ES cells bearing the chimeric human/mouse MHC class I locus may be transfected with a construct that expresses Cre in order to remove the "loxed" selection cassette introduced by the insertion of the targeting construct (see, e.g., step 6 in FIG. 3A). The selection cassette may optionally be removed by breeding to mice that express Cre recombinase. Optionally, the selection cassette is retained in the mice.

Targeted ES cells containing all of the modifications described herein (HLA-A2/H-2K, HLA-DR2/H-2E, H-2A-del, H-2D-del of FIG. 3A) were verified using a quantitative TAQMAN® assay described above using the primer/probe sets described herein for individual modifications. An additional primer/probe set was used to determine that during cassette-deletion step, no inverted clone was created due to lox sites present in opposing orientation.

Figure 3C:
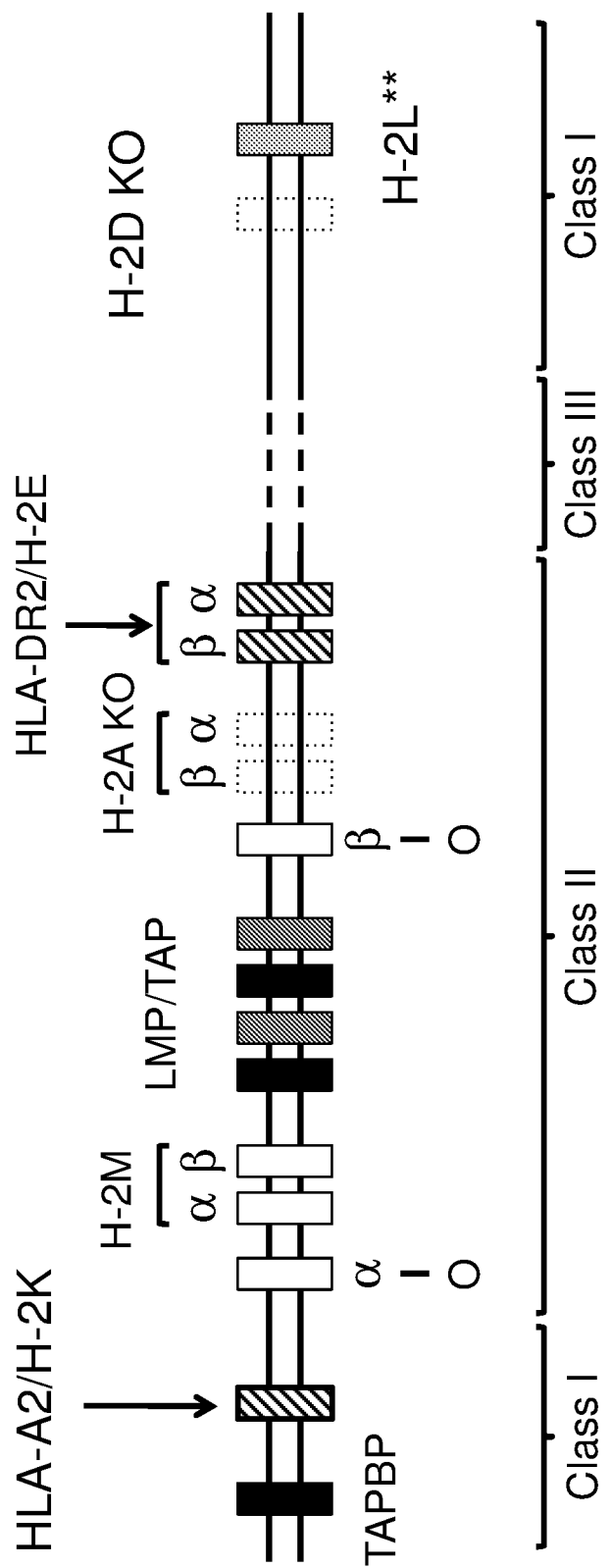

Targeted ES cells described above were used as donor ES cells and introduced into an 8-cell stage mouse embryo by the VELOCIMOUSE® method (see, e.g., U.S. Pat. No. 7,294,754 and Poueymirou et al. (2007), supra). VELOCIMICE® (F0 mice fully derived from the donor ES cell) independently bearing a chimeric MHC class I and MHC II genes were identified by genotyping using a modification of allele assay (Valenzuela et al., supra) that detects the presence of the unique human gene sequences. A schematic representation of the genotype of MHC loci in the resulting mice is depicted in FIG. 3C (** represents H-2L gene which is not present in all mouse strains). Expression of both chimeric human/mouse MHC I and MHC II proteins is confirmed using antibodies specific for human HLA-DR2 and HLA-A2. Heterozygous mice are bred to homozygosity.

Example 1.4

Generation of Humanized β2 Microglobulin Mice

Generation of β2 microglobulin mice was described in U.S. Patent Application Publication No. 20130111617, incorporated herein by reference. Briefly, mouse β2 microglobulin (β2m) gene was humanized in a single step by construction of a unique targeting vector from human and mouse bacterial artificial chromosome (BAC) DNA using VELOCIGENE® technology (see, e.g., U.S. Pat. No. 6,586,251 and Valenzuela et al., supra).

Specifically, a targeting vector was generated by bacterial homologous recombination containing mouse β2m upstream and downstream homology arms from BAC clone 89C24 from the RPCI-23 library (Invitrogen). The mouse homology arms were engineered to flank a 2.8 kb human β2m DNA fragment extending from exon 2 to about 267 nucleotides downstream of non-coding exon 4 (FIG. 2C). A drug selection cassette (neomycin) flanked by recombinase recognition sites (e.g., loxP sites) was engineered into the targeting vector to allow for subsequent selection. The final targeting vector was linearized and electroporated into a F1H4 mouse ES cell line (Valenzuela et al., supra).

Targeted ES cell clones with drug cassette removed (by introduction of Cre recombinase) were introduced into an 8-cell stage mouse embryo by the VELOCIMOUSE® method (see, e.g., U.S. Pat. No. 7,294,754 and Poueymirou et al., supra). VELOCIMICE® (F0 mice fully derived from the donor ES cell) bearing the humanized β2m gene were identified by screening for loss of mouse allele and gain of human allele using a modification of allele assay (Valenzuela et al., supra). Heterozygous mice are bred to homozygosity. Expression of human β2 microglobulin was confirmed by flow cytometry using antibodies specific for human β2 microglobulin.

Example 2

Generation of Humanized T Cell Receptor Mice

Mice comprising a deletion of endogenous TCR (α or β) variable loci and replacement of endogenous V and J or V, D, and J segments are made using VELOCIGENE® genetic engineering technology (see, e.g., U.S. Pat. No. 6,586,251 and Valenzuela, D. M., et al. (2003), supra), wherein human sequences derived from BAC libraries using bacterial homologous recombination are used to make large targeting vectors (LTVECs) comprising genomic fragments of human TCR variable loci flanked by targeting arms to target the LTVECs to endogenous mouse TCR variable loci in mouse ES cells. Detailed description of the humanization of the TCR alpha and beta loci is described in U.S. Pat. No. 9,113,616, incorporated herein by reference. LTVECs re linearized and electroporated into a mouse ES cell line according to Valenzuela et al. ES cells are selected for hygromycin or neomycin resistance, and screened for loss of mouse allele or gain of human allele.

Targeted ES cell clones are introduced into 8-cell stage (or earlier) mouse embryos by the VELOCIMOUSE® method (Poueymirou, W. T. et al. (2007, supra). VELOCIMICE® (F0 mice fully derived from the donor ES cell) bearing humanized TCR loci are identified by screening for loss of endogenous TCR variable allele and gain of human allele using a modification of allele assay (Valenzuela et al., supra). F0 pups are genotyped and bred to homozygosity. Mice homozygous for humanized TCRα and/or TCRβ variable loci are made as described herein.

Example 2.1

Humanization of TCR Alpha Locus 1.5 megabases of DNA at mouse TCRα locus corresponding to 110 V and 60 J mouse segments was replaced with 1 megabase of DNA corresponding to 54V and 61J segments of human TCRα using a progressive humanization strategy summarized in FIG. 4A and described in U.S. Pat. No. 9,113,616. Junctional nucleic acid sequences of various targeting vectors used for progressive humanization strategy of TCRα locus are summarized in Table 5, and included in the Sequence Listing.

TABLE 5

Junctional Nucleic Acid Sequences for Various TCRα Locus Targeting Vectors

| MAID NO. | SEQ ID NO | Description |
|---|---|---|
| 1626 | 46 | Junctional nucleic acid sequence between the 3' end of mouse sequence upstream of the TCRα variable locus and the 5' end of loxP-Ub-Hyg-loxP cassette. |
|  | 47 | Junctional nucleic acid sequence between the 3' end of loxP-Ub-Hyg-loxP cassette and the 5' end of human TCRVα40-TCRVα41-TCRJα1 insertion, including AsiSI site. |
|  | 48 | Junctional nucleic acid sequence between the 3' end of human TCRVα40-TCRVα41-TCRJα1 insertion and the 5' end of the mouse sequence downstream of the human TCRα variable locus, including NotI site. |
| 1767 | 49 | Junctional nucleic acid sequence between the 3' end of mouse sequence upstream of the TCRα variable locus and the 5' end of loxP-Ub-Neo-loxP cassette. |
|  | 50 | Junctional nucleic acid sequence between the 3' end of loxP-Ub-Neo-loxP cassette and the 5' end of human TCRVα35-TCRVα39 insertion, including AsiSI site. |
| 1979 | 51 | Junctional nucleic acid sequence between the 3' end of mouse sequence upstream of the TCRα variable locus and the 5' end of frt-Pgk-Hyg-frt cassette. |
|  | 52 | Junctional nucleic acid sequence between the 3' end of frt-Pgk-Hyg-frt cassette and the 5' end of human TCRVα22-TCRVα34 insertion, including AsiSI site. |
| 1769 | 53 | Junctional nucleic acid sequence between the 3' end of mouse sequence upstream of the TCRα variable locus and the 5' end of loxP-Ub-Neo-loxP cassette. |
|  | 54 | Junctional nucleic acid sequence between the 3' end of loxP-Ub-Neo-loxP cassette and the 5' end of human TCRVα13-2-TCRVα21 insertion, including AsiSI site. |
| 1770 | 55 | Junctional nucleic acid sequence between the 3' end of mouse sequence upstream of the TCRα variable locus and the 5' end of loxP-Ub-Hyg-loxP cassette. |
|  | 56 | Junctional nucleic acid sequence between the 3' end of loxP-Ub-Hyg-loxP cassette and the 5' end of human TCRVα6-TCRVα8-5 insertion, including AsiSI site. |
| 1771 | 57 | Junctional nucleic acid sequence between the 3' end of mouse sequence upstream and the TCRα variable locus to the 5' end of loxP-Ub-Neo-loxP cassette. |

TABLE 5-continued

Junctional Nucleic Acid Sequences for Various TCRα Locus Targeting Vectors

| MAID NO. | SEQ ID NO | Description |
|---|---|---|
| | 58 | Junctional nucleic acid sequence between the 3' end of loxP-Ub-Neo-loxP cassette and the 5' end of human TCRVα1-1-TCRVα5 insertion, including AsiSI site. |

Human TCRα variable region segments are numbered as in IMGT database. At least 100 bp at each junction (about 50 bp from each end) are included in the Sequence Listing.

First, DNA from mouse BAC clone RP23-6A14 (Invitrogen) was modified by homologous recombination and used as a targeting vector to replace TCRAJ1-TCRAJ28 region of the endogenous mouse TCRα locus with a Ub-hygromycin cassette followed by a loxP site. DNA from mouse BAC clone RP23-117i19 (Invitrogen) was modified by homologous recombination and used as a targeting vector to replace ~15 kb region surrounding (and including) TCRAV1 of the endogenous mouse TCRα and δ locus with a PGK-neomycin cassette followed by a loxP site. ES cells bearing a double-targeted chromosome (i.e., a single endogenous mouse TCRα locus targeted with both of these targeting vectors) were confirmed by karyotyping and screening methods (e.g., TAQMAN™) known in the art. Modified ES cells were treated with CRE recombinase, thereby mediating the deletion of the region between the two loxP sites (i.e., the region consisting of the endogenous mouse TCRα locus from TCRAV1 to TCRAJ1) and leaving behind only a single loxP site, neomycin cassette and the mouse constant and enhancer regions. This strategy resulted in generation of a deleted mouse TCR a/δ locus (MAID 1540, FIG. 4A, second diagram).

The first human targeting vector for TCRα had 191,660 bp of human DNA from the CTD2216p1 and CTD2285m07 BAC clones (Invitrogen) that contained the first two consecutive human TCRα V gene segments (TRAV40 & 41) and 61 TCRα J (50 functional) gene segments. This BAC was modified by homologous recombination to contain a Not1 site 403 bp downstream (3') of the TCRα J1 gene segment for ligation of a 3' mouse homology arm and a 5' AsiSI site for ligation of a 5' mouse homology arm. Two different homology arms were used for ligation to this human fragment: the 3' homology arm contained endogenous mouse TCRα sequences from the RP23-6A14 BAC clone and the 5' homology arm contained endogenous TCRα sequence 5' of mouse TCRα V from mouse BAC clone RP23-117i19. This mouse-human chimeric BAC was used as a targeting vector (MAID 1626) for making an initial insertion of human TCRα gene segments plus an upstream loxp-ub-hygromycin-loxp cassette at the mouse TCRα loci. The junctional nucleic acid sequences (SEQ ID NOs: 46-48) for the MAID 1626 targeting vector are described in Table 5.

Subsequently, a series of human targeting vectors were made that utilized the same mouse 5' arm that contained endogenous TCRα sequence 5' of mouse TCRα V from mouse BAC clone RP23-117i19 with alternating loxP-neomycin-loxP and loxP-hygromycin-loxP (or frt-hygromycin-frt for MAID 1979) selection cassettes. The specific constructs are described in U.S. Pat. No. 9,113,616, as well as depicted in FIG. 4A, with junctional sequences for each insertion included in Table 5 and the Sequence Listing. The final TCRα locus contained a 5' loxp-ub-neomycin-loxP cassette plus a total of 54 human TCRα V (45 functional) and 61 human TCRα J gene segment operably linked to mouse TCRα constant genes and enhancers. The junctional nucleic acid sequences (SEQ ID NOs: 57 and 58) for the MAID 1771 targeting vector are described in Table 5.

In any of progressive humanization steps, the selection cassettes are removed by deletion with Cre or Flp recombinase. In addition, human TCRδ locus may be reintroduced into the TCR alpha sequence.

Example 2.2

Figure 4B:
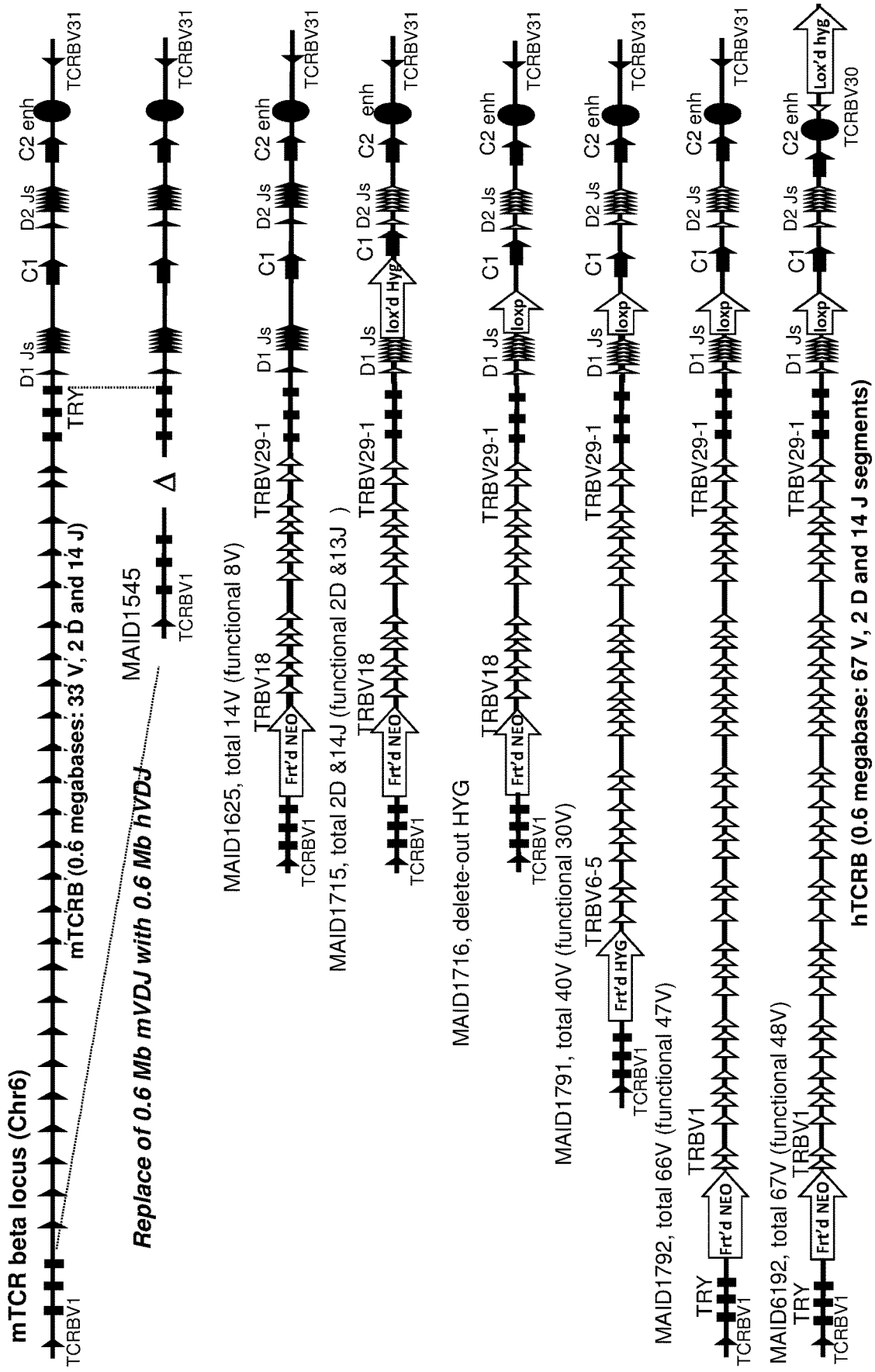
FIG. 4B depicts (not to scale) a progressive strategy for humanization of the mouse TCRβ locus, wherein TCRβ variable region gene segments are sequentially added to a deleted mouse TCRβ variable locus. Mouse sequence is indicated by filled shapes; human sequence is indicated by empty shapes. MAID refers to modified allele ID number. TRBV or TCRBV=TCRβ V segment.

Humanization of TCRβ Variable Locus 0.6 megabases of DNA at mouse TCRβ locus corresponding to 33 V, 2 D, and 14 J mouse segments were replaced with 0.6 megabases of DNA corresponding to 67 V, 2D, and 14 J segments of human TCRβ using a progressive humanization strategy summarized in FIG. 4B and described in detail in U.S. Pat. No. 9,113,616. Junctional nucleic acid sequences of various targeting vectors used for progressive humanization strategy of TCRβ locus are summarized in Table 6, and included in the Sequence Listing.

TABLE 6

Junctional Nucleic Acid Sequences for Various TCRβ Locus Targeting Vectors

| MAID NO. | SEQ ID NO | Description |
|---|---|---|
| 1625 | 59 | Junctional nucleic acid sequence between the 3' end of mouse sequence upstream of the TCRβ variable locus (nearby the upstream mouse trypsinogen genes) and the 5' end of frt-Ub-Neo-frt cassette. |
| | 60 | Junctional nucleic acid sequence between the 3' end of frt-Ub-Neo-frt cassette and the 5' end of human TCRVβ18-TCRVβ29-1 insertion. |
| | 61 | Junctional nucleic acid sequence between the 3' end of human TCRVβ18-TCRVβ29-1 insertion and the 5' end of the mouse sequence downstream of the mouse TCRVβ segments (nearby downstream mouse trypsinogen genes). |

TABLE 6-continued

Junctional Nucleic Acid Sequences for Various TCRβ Locus Targeting Vectors

| MAID NO. | SEQ ID NO | Description |
|---|---|---|
| 1715 | 62 | Junctional nucleic acid sequence between 3' of the downstream mouse trypsinogen genes and the 5' end of human TCRDβ1-TCRJβ1-1-TCRJβ1-6 insertion, including IceuI site. |
|  | 63 | Junctional nucleic acid sequence between the 3' end of human TCRDβ1-TCRJβ1-1-TCRJβ1-6 insertion and the 5' end of loxP-Ub-Hyg-loxP cassette. |
|  | 64 | Junctional nucleic acid sequence between the 3' end of loxP-Ub-Hyg-loxP cassette and the 5' end of mouse sequence nearby the mouse Cβ1 gene. |
|  | 65 | Junctional nucleic acid sequence between the 3' end of the mouse sequence nearby the mouse Cβ1 gene and the 5' end of human TCRDβ2-TCRJβ2-1-TCRJβ2-7 insertion, including NotI site. |
|  | 66 | Junctional nucleic acid sequence between the 3' end of human TCRDβ2-TCRJβ2-1-TCRJβ2-7 insertion and the 5' end of the mouse sequence downstream of the TCRβ variable locus (nearby the Cβ2 mouse sequence). |
| 1791 | 67 | Junctional nucleic acid sequence between the 3' end of mouse sequence upstream of the TCRβ variable locus (nearby the upstream mouse trypsinogen genes) and the 5' end of frt-Ub-Hyg-frt cassette. |
|  | 68 | Junctional nucleic acid sequence between the 3' end of frt-Ub-Hyg-frt cassette and the 5' end of human TCRVβ6-5-TCRVβ17 insertion. |
| 1792 | 69 | Junctional nucleic acid sequence between the 3' end of mouse sequence upstream of the TCRβ variable locus (nearby the upstream mouse trypsinogen genes) and the 5' end of frt-Ub-Neo-frt cassette. |
|  | 70 | Junctional nucleic acid sequence between the 3' end of frt-Ub-Hyg-frt cassette and the 5' end of human TCRVβ1-TCRVβ12-2 insertion. |
| 6192 | 71 | Junctional nucleic acid sequence between the 3' end of mouse sequence nearby the mouse Cβ2 gene and the 5' end of the human TCRBV30 exon 2 sequence. |
|  | 72 | Junctional nucleic acid sequence between the 3' end human TCRBV30 exon 1 sequence and the 5' end of mouse sequence downstream of TCRβ locus. |

Human TCRβ variable region segments are numbered as in IMGT database. At least 100 bp at each junction (about 50 bp from each end) are included in the Sequence Listing.

Specifically, DNA from mouse BAC clone RP23-153p19 (Invitrogen) was modified by homologous recombination and used as a targeting vector to replace 17 kb region (including TCRBV30) just upstream of the 3' trypsinogen (TRY) gene cluster in the endogenous mouse TCRβ locus with a PGK-neo cassette followed by a loxP site. DNA from mouse BAC clone RP23-461h15 (Invitrogen) was modified by homologous recombination and used as a targeting vector to replace 8355 bp region (including TCRBV2 and TCRBV3) downstream of 5' trypsinogen (TRY) gene cluster in the endogenous mouse TCRβ locus with a Ub-hygromycin cassette followed by a loxP site. ES cells bearing a double-targeted chromosome (i.e., a single endogenous mouse TCRβ locus targeted with both targeting vectors) were confirmed by karyotyping and screening methods (e.g., TAQMAN™) known in the art. Modified ES cells were treated with CRE recombinase, mediating the deletion of the region between the 5' and 3' loxP sites (consisting of the endogenous mouse TCRβ locus from TCRBV2 to TCRBV30) and leaving behind only a single loxP site, hygromycin cassette and the mouse TCRBDs, TCRBJs, constant, and enhancer sequences. One mouse TCRVβ was left upstream of the 5' cluster of trypsinogen genes, and one mouse TCRVβ was left downstream of the mouse Eβ, as noted in FIG. 4B.

The first human targeting vector for TCRβ had 125,781 bp of human DNA from the CTD2559j2 BAC clone (Invitrogen) that contained the first 14 consecutive human TCRβV gene segments (TRBV18-TRBV29-1); the junctional nucleic acid sequences (SEQ ID NOs: 59-61) for the MAID 1625 targeting vector are described in Table 6.

In order to replace mouse TCRβ D and J segments with human TCRβ D and J segments, DNA from mouse BAC clone RP23-302p18 (Invitrogen) and from human BAC clone RP11-701D14 (Invitrogen) was modified by homologous recombination and used as a targeting vector (MAID 1715) into the ES cells that contained the TCRβV mini-locus described above (i.e., MAID 1625). This modification replaced ~18540 bp region (from 100 bp downstream of the polyA of the 3' trypsinogen genes to 100 bp downstream from the J segments in the D2 cluster which included mouse TCRBD1-J1, mouse constant 1, and mouse TCRBD2-J2) in the endogenous mouse TCRβ locus with ~25425 bp of sequence containing human TCRBD1-J1, loxP Ub-hygromycin-loxP cassette, mouse constant 1, human TCRBD2-J2. ES cells bearing a double-targeted chromosome (i.e., a single endogenous mouse TCRβ locus targeted with both targeting vectors) were confirmed by karyotyping and screening methods (e.g., TAQMAN™) known in the art. Modified ES cells were treated with CRE recombinase thereby mediating the deletion the hygromycin cassette leaving behind only a single loxP site downstream from human J segments in D1J cluster. The junctional nucleic acid sequences (SEQ ID NOs: 62-66) for the MAID 1715 targeting vector are described in Table 6.

Subsequently, a series of human targeting vectors were made that utilized the same mouse 5' arm that contained endogenous TCRβ sequence surrounding the upstream mouse trypsinogen genes from mouse BAC clone RP23-461h15 with alternating selection cassette. The specific constructs are described in U.S. Pat. No. 9,113,616, as well as depicted in FIG. 4B, with junctional sequences for each insertion included in Table 6 and the Sequence Listing.

Finally, a human TCRβ mini-locus containing a total 66 human TCRβV (47 functional) and the human TCRβ D and J segments (MAID 1792) operably linked to mouse TCRβ constant genes and enhancers was generated. The junctional nucleic acid sequences (SEQ ID NOs: 69 and 70) for the MAID 1792 targeting vector are described in Table 6.

Mouse TCRBV31 is located ~9.4 kb 3' of TCRBC2 (second TCRB constant region sequence) and is in the opposite orientation to the other TCRBV segments. The equivalent human V segment is TCRBV30, which is located in a similar position in the human TCRB locus. To humanize TCRBV31, the mouse BAC clone containing mouse TCRBV31, was modified by bacterial homologous recombination to make LTVEC MAID 6192. The entire coding region, beginning at the start codon in exon 1, the intron, the 3' UTR, and the recombination signal sequences (RSS) of TCRBV31 were replaced with the homologous human TCRBV30 sequences. FIG. 4B depicts the selection cassette located in the intron between exon 1 and exon 2 of the hTCRBV30 gene.

The junctional nucleic acid sequences (SEQ ID NOs: 71 and 72) for the MAID 6192 targeting vector are described in Table 6. MAID 6192 DNA is electroporated into MAID1792 ES cells, and cells are screened for loss of mouse TCRB31 allele and gain of human TCRB30 allele.

Similar engineering strategy is used to optionally delete the remaining 5' mouse TCRβ V segment.

In any of the above steps, the selection cassettes are removed by deletion with Cre or Flp recombinase.

Mice homozygous for humanized TCRα variable locus are bred with mice homozygous for humanized TCRβ variable locus to form progeny comprising humanized TCRα and TCRβ variable loci. Progeny are bred to homozygosity with respect to humanized TCRα and humanized TCRβ loci.

Mice comprising humanized TCRα and TCRβ variable loci are confirmed to undergo normal T cell development and comprise T cell receptors that express variable domains derived from a variety of variable gene segments.

Example 3

Humanization of T Cell Co-Receptor Loci

Humanization of CD4 and CD8 loci (both CD8alpha and CD8 beta loci) is described in detail in U.S. Patent Application Publication No. 20140245466, incorporated herein in its entirety by reference.

Example 3.1

Humanization of CD4 Locus

Specifically, mouse CD4 locus was humanized in a single step by construction of a unique targeting vector from human and mouse bacterial artificial chromosome (BAC) DNA using VELOCIGENE® technology (see, e.g., U.S. Pat. No. 6,586,251 and Valenzuela et al. (2003), supra). To generate the targeting vector, a series of bacterial homologous recombinations (BHRs) using Bacterial Artificial Chromosome (BAC) DNA, as well as other engineering steps, were carried out as described in detail in U.S. Patent Application Publication No. 20140245466.

The human CD4 Targeting Vector was linearized with NotI and electroporated into F1H4 mouse ES cells. Targeted ES cells bearing a humanized CD4 locus were identified by genotyping using a modification of allele assay (Valenzuela et al.) that detected the presence of the neomycin cassette and the human CD4 gene, as well as one copy of the mouse CD4 gene.

The final humanized CD4 locus derived from successful incorporation of humanized CD4 targeting vector into ES cells is depicted in FIG. 5A. The sequence across the human intron 3—lox-neo cassette junction (5' end of the cassette) is set forth in SEQ ID NO:75, and the sequence across lox-neo cassette—human intron 3 junction (3' end of the cassette) is set forth in SEQ ID NO:76; both sequences are also listed in Table 7. The complete nucleic acid sequence of the humanized CD4 piece, including the pgk-neo cassette depicted in FIG. 5A is set forth in SEQ ID NO:77. The pgk-neo cassette is spans residues 307-2176 of SEQ ID NO:77, the two lox sites are located at residues 267-300 and 2182-2215, while the human sequence spans residues 1-234 and 2222-18263. The amino acid sequence of complete humanized CD4 protein is set forth in SEQ ID NO:78, with human sequence spanning amino acids 27-319 (set forth in SEQ ID NO:79).

TABLE 7

Junction Sequences of the Chimeric CD4 Targeting Vector

| Junction | Sequence | SEQ ID NO |
|---|---|---|
| 5' mouse/<br>human<br>junction | AGGGGAAACCCGCAAAGGATGGGACATAGGGAGACAGCTGT<br>TAACATCTGAAACATGACCTTCTTTTCTGTGCAGCACAACTCC<br>TAGCTGTCACTCAAGGG(AAGAAAGTGGTGCTGGGCAAAAAA<br>GGGGATACAGTGGAACTGACCTGTACAGCTTCCCAGAAGAA<br>GAGCATACAATTCCACTGGAAAAACTCCAACCAGAT) | 73 |
| 3' human/<br>mouse<br>junction | (CTGGTCACCTGGATGAAGTGAGGGAGGGCCCTCTGGGTTTG<br>GGGCTGGTTTTGAACTGAGACATCCATGAGCCAGCCTGGGG<br>CTGGCTTCACTGAAGATC)ATCTATGTCGGGTGCGGAGAAAG<br>AGGTAATGAAATGGCACATGCTATGTACAAACTCTATTGCTG<br>AGCAGCACCCAGTCCTGAGCTGGCTCTGAATTGAGGGTGAA<br>ATTCACACATTCTCCCCCAACATCTATAATCTGG | 74 |

TABLE 7-continued

Junction Sequences of the Chimeric CD4 Targeting Vector

| Junction | Sequence | SEQ ID NO |
|---|---|---|
| Human/5' lox site | (TATGGAGTGAAAGCCTTTGGTGTCTGAGATCTGGTCTTAGT TAAACTCTGGGATC)  *GGCGCGCCGAATTCCTGCAGCCCGGG CTCGAGATAACTTCGTATAATGTATGCTATACGAAGTTATATG CATCCGGGTAGGGGAGGCGCTTTTCCC* | 75 |
| 3' lox site/ human | *AGTATTGTTTTGCCAAGTTCTAATTCCATCAGACCTCGACCTG CAGCCCTAGATAACTTCGTATAATGTATGCTATACGAAGTTAT CCTAGG*(CCAGAGGGCTTGGGTTGACAGAAACTCAGTGGCAT TCTTATCCAGAGTTTCTCTACACC) | 76 |

Human sequences are in parenthesis and sequence containing restriction enzyme site (PI-Sce I) is bolded. Selection cassette sequences are italicized.

Floxed neomycin resistance cassette is removed by electroporation of plasmid expressing Cre recombinase into ES cells containing humanized CD4 locus.

Targeted ES cells bearing a humanized CD4 locus without resistance marker are identified by genotyping that detected absence of the neomycin cassette, the presence of one copy of the human CD4 gene and one copy of the mouse CD4 gene.

Targeted ES cells described above were used as donor ES cells and introduced into an 8-cell stage mouse embryo by the VELOCIMOUSE® method (see, e.g., U.S. Pat. No. 7,294,754 and Poueymirou et al. (2007, supra). VELOCIMICE® (F0 mice fully derived from the donor ES cell) independently bearing a chimeric CD4 gene were identified by genotyping using a modification of allele assay (Valenzuela et al., supra) that detects the presence of the unique human CD4 gene sequences. Expression of humanized CD4 proteins on the surface of T cells was detected using anti-human CD4 antibodies. Mice heterozygous for humanized CD4 protein described herein were bred to homozygosity.

Example 3.2

Humanization of CD8 Loci

CD8α and CD8β genes are colocalized in the genome, e.g., on mouse chromosome 6, they are located about 37 kb away from each other. Due to close linkage, sequential targeting, by first introducing one gene, e.g., CD8β, followed by introduction of the second gene, e.g., CD8α, is performed. Specific detailed steps of humanization are described in U.S. Patent Application Publication No. 20140245466, incorporated herein by reference.

Briefly, mouse CD8β locus was humanized in a single step by construction of a unique targeting vector from mouse bacterial artificial chromosome (BAC) DNA using VELOCIGENE® technology. DNA from BAC RP23-431M6 was modified by BHR to generate a large targeting vector (LTVEC), MAID 1737, to contain a replacement of mouse exons 2-3 encoding the CD8 ecto domain (from the 5' junction in intron 1 to the 3' junction in intron 3), with homologous human sequences (FIG. 5B). A loxp-Ub-Hyg cassette was inserted at the 3' junction in intron 3. The nucleotide sequence at various junctions of the resulting vector are listed in Table 8 and set forth in Sequence Listing. The complete amino acid sequence of humanized CD8β protein is set forth in SEQ ID NO:83; with human sequences spanning amino acids 15-165 (set forth in SEQ ID NO:84).

TABLE 8

Junction Sequences of the Chimeric CD8l3 Targeting Vector

| Junction | Sequence | SEQ ID NO |
|---|---|---|
| Mouse/human in intron 1 | TGTTTGCCTGTGACATGAACTCATTGTGACACAAA CCACTGTGCTAGGGGGGATCCACTAGTAACGGC CGCCAGTGTGCTGGAATTCGCCC(TCGCAAGGG CCAGGCATATAAGTACACAATAAACAAATGGCAG CTCTCTCC) | 80 |
| Human/5' of lox site in intron 3 | (CCCCTCCTTCCTTCCCCAGGCACTTTCCAAGTGTC AACTCTAGAGCCTAT)*CGCGGCCGCACCGGT*ATA *ACTTCGTATAATGTATGCTATACGAAGTTAT* | 81 |
| 3' of lox site/ mouse in intron 3 | *ATAACTTCGTATAATGTATGCTATACGAAGTTAT*GTCG ACGTAGCCTATTTCTCTAGATCCAAAATGATGACA ACAAAAGGTACCTTGTG | 82 |

Human sequences are in parenthesis, lox sites are italicized, and restriction enzyme sites, multiple cloning sites, and vector-derived sequences are bolded.

Targeting vector was electroporated into F1H4 mouse ES cells. Targeted ES cells bearing a humanized CD8β locus were identified by genotyping using a modification of allele assay (Valenzuela et al.) that detected the presence of the human CD8β gene.

Mouse CD8α locus was also humanized in a single step by construction of a unique targeting vector from mouse bacterial artificial chromosome (BAC) DNA using VELOCIGENE® technology. DNA from BAC RP23-431M6 was modified by BHR to generate a large targeting vector (LTVEC), MAID 1738, to contain a replacement of mouse exons 1-2 encoding the CD8α ecto domain (from the 5' junction at Ala codon 27 in mouse exon 1 to the 3' junction in mouse intron 2), with the homologous human sequences (from the 5' junction in human exon 2 to the 3' junction in intron 3 (FIG. 5A)). This retains the mouse leader sequence at the beginning of exon 1. A lox2372-Ub-Neo cassette was inserted at the 3' junction of human/mouse sequences. The nucleotide sequences at various junctions of the resulting vector are listed in Table 9 and set forth in Sequence Listing. The complete amino acids sequence of humanized CD8α polypeptide is set forth in SEQ ID NO:88, with human sequence spanning amino acids 28-179 (set forth in SEQ ID NO:89).

TABLE 9

Junction Sequences of the Chimeric CD8a Targeting Vector

| Junction | Sequence | SEQ ID NO |
|---|---|---|
| Mouse/human at exon 1 (mouse) and exon 2 (human) | TGAACCTGCTGCTGCTGGGTGAGTCGATTATCCTGGGGAGT GGAGAAGCT(AGGCCGAGCCAGTTCCGGGTGTCGCCGCTGG ATCGGACCTGGAACCTGGG) | 85 |
| Human/5' of lox 2372 site | (ATGCCAGGGACAGCCCTGATACTGTAGGTAGAGTCAAGG GCTGTCCAAGT)ACCGGTATAACTTCGTATAAGGTATCCTAT ACGAAGTTAT | 86 |
| 3' of lox 2372 site/mouse | ATAACTTCGTATAAGGTATCCTATACGAAGTTATCTCGACCTG ATCTTGGAGGGAGACCTGGACCGGGAGACGTGCTGGGGGC AGGGTT | 87 |

Human sequences are in parenthesis, lox sites are italicized, and restriction enzyme sites, multiple cloning sites, and vector-derived sequences are bolded.

Humanized CD8α targeting vector described above was electroporated into mouse ES cells that contained a humanized CD8b locus to create modified ES cells that comprise humanized CD8b and CD8α loci (FIG. 5B). Targeted ES cells bearing a humanized CD8α and CD8b loci were identified by genotyping using a modification of allele assay (Valenzuela et al.).

Targeted ES cells described above were used as donor ES cells and introduced into an 8-cell stage mouse embryo by the VELOCIMOUSE® method (see, e.g., U.S. Pat. No. 7,294,754 and Poueymirou et al, supra). VELOCIMICE® (F0 mice fully derived from the donor ES cell) bearing a chimeric CD8b gene and a chimeric CD8α gene were identified by genotyping using a modification of allele assay (Valenzuela et al., supra) that detects the presence of the unique human CD8b and CD8α gene sequences.

The selection cassettes in CD8α and CD8β loci may be removed by methods known by the skilled artisan. Mice heterozygous for humanized CD8α and CD8β loci as described herein are bred to homozygosity. Expression of humanized CD8α and CD8β on the surface of T cells is detected using anti-human CD8 antibodies.

Example 4

Generation of Mice Comprising Humanized Cellular Immune System Components

In order to generate mice comprising humanized cellular immune system components, mice homozygous for humanization of various components, e.g., MHC I, MHC II α and β, TCRα and β, CD4, CD8α and β, and β2M may be bred together in any combination to create mice that have different components of the T cell immune response humanized. For example, a mouse comprising a humanized MHC I may be bred with a mouse comprising a humanized β2M to generate a mouse expressing humanized MHC I/β2M. Mice homozygous for humanization of various components, e.g., MHC I, MHC II α and β, TCRα and β, CD4, CD8α and β, and β2M are bred together using methods known in the art to obtain a mouse comprising all nine humanizations ("TM I/II B C4/8" mice). Mice are bred to homozygosity using methods known in the art. Alternatively, targeting vectors comprising each humanized gene can be introduced via sequential targeting into the same ES cell to obtain an ES cell comprising all nine humanizations, and the resultant ES cell is introduced into 8-cell stage mouse embryo by the VELOCIMOUSE® method, described in Examples 1-3 above.

Example 5

Characterization of Mice Comprising Humanized Cellular Immune System Components

Mice homozygous for humanized MHC I, MHC II α and β, TCRα and β, CD4, CD8α and β and for humanized β2M were characterized. Specifically, spleen and thymic, from mice were harvested and single cell suspensions were obtained. Suspensions were centrifuged at 1200 rpm for 5 min at 4° C. to pellet cells, and cells from each tissue were lysed with 4 mL of ACK lysing buffer (GIBCO) to lyse red blood cells. Cells were filtered through cell strainer, centrifuged to pellet, resuspended in media and counted.

Cell surface expression of CD19, CD3, CD4 and CD8α depicted in FIGS. 6A-C and FIGS. 9A-C was analyzed by FACS using fluorochrome-conjugated antibodies: anti-mouse CD3 (17A2, BD), anti-mouse CD19 (1D3, BD), anti-mouse F4/80 (BM8, Biolegend), anti-mouse CD8α (53-6.7, BD), anti-mouse CD4 (RM4-5, eBioscience), anti-human CD8α (SK1, BD), and anti-human CD4 (RPA-T4, BD). Cell surface expression of mouse H2Db, human HLA molecules (HLA-A2, B2m, and HLA-DR) and mouse MHC $I^AI^E$ molecules in FIGS. 7A-F and 10A-F was analyzed by FACS using fluorochrome-conjugated antibodies: anti-mouse CD19 (6D5, Biolegend), anti-mouse F4/80 (BM8, Biolegend), anti-mouse H2Db (KH95, Biolegend), anti-human HLA-A2 (BB7.2, BD), anti-human HLA-DR (G46-6, BD), anti-human B2-mibroglobulin (2M2, Biolegend) and anti-mouse $I^AI^E$ (M5/114.15.2, eBioscience). Cell surface expression of mouse and human CD4 and CD8 in FIG. 7G and FIG. 10G was analyzed by FACS using fluorochrome-conjugated antibodies: anti-mouse CD3 (17A2, Biolegend), anti-mouse CD4 (GK1.5, eBiosciences), anti-mouse CD8α (53-6.7, BD 2), anti-mouse CD8β (H35-17.2, eBioscience), anti-human CD4 (OKT4, eBioscience), anti-human CD8α (RPA-T8, BD 6), anti-human CD8β (2ST8.5H7, BD). Cell surface expression of FoxP3 and CD25 shown in FIG. 8 or FIG. 11 was analyzed by FACS anti-FoxP3 (FJK-16s, eBioscience) and anti-CD25 (PC61, Biolegend) Cell surface expression of CD44 and CD62L shown in FIGS. 9D-9E was analysed using anti-CD44 (IM7, BD) and anti-CD62L (MEL-14, Biolegend).

All flow cytometry was performed using BD Fortessa. Data was analyzed using FlowJo.

Figure 6C:
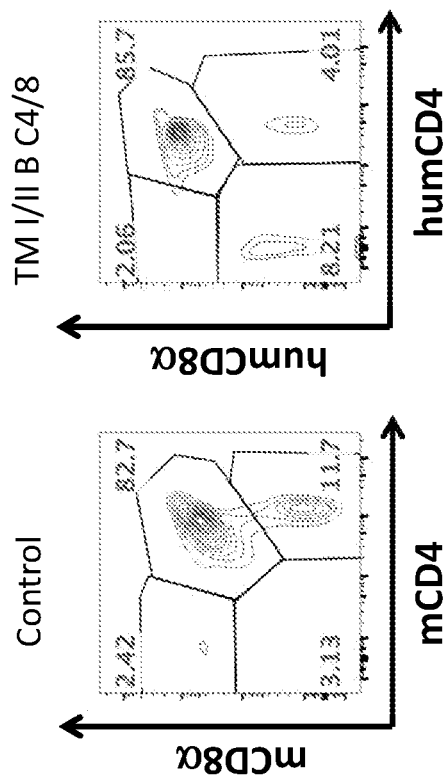
FIGS. 6A-C are FACS contour plots of thymic cells isolated from a control mouse or a mouse comprising humanized MHC I, MHC II α and β, TCRα and β, CD4, CD8α and β, and β2M (TM I/II B C4/8) loci, gated on singlets, and stained with (FIG. 6A) anti-mouse CD19 and anti-mouse CD3 antibodies, (FIG. 6B) anti-mouse CD19 and anti-mouse F4/80 antibodies, or (FIG. 6C) anti-mouse CD8α and anti-mouse CD4 antibodies (left panel) or anti-human CD8α and anti-human CD4 antibodies (right panel).
Figure 6A:
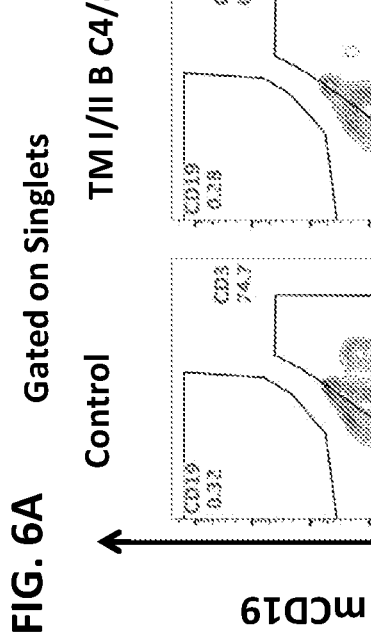
Figure 6B:
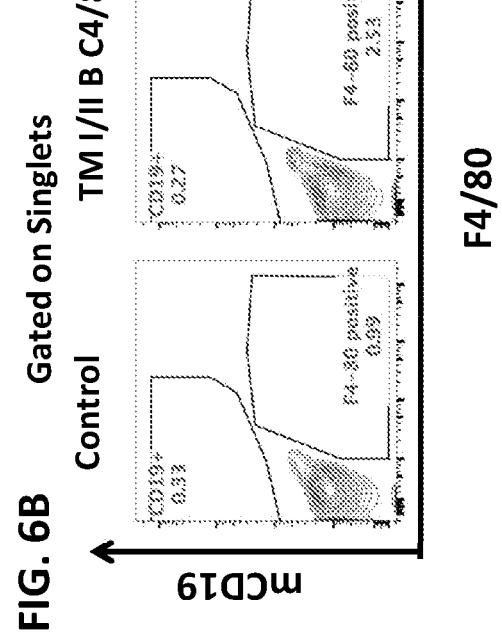
Figure 7A:
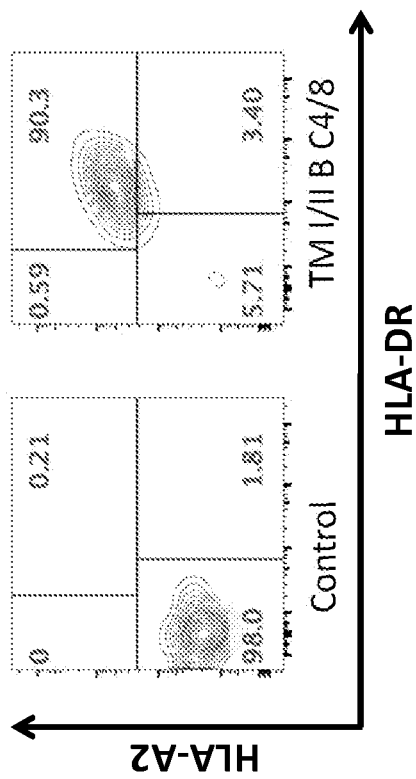
FIGS. 7A-G are FACS contour plots of thymic cells isolated from a control mouse or a mouse comprising humanized MHC I, MHC II α and β, TCRα and β, CD4, CD8α and β, and β2M (TM I/II B C4/8) loci, gated on CD19+ cells, F4/80+ cells or CD3+ cells, and stained with (FIGS. 7A, 7B) anti-human B2M or anti-mouse H-2D antibodies.
Figure 7B:
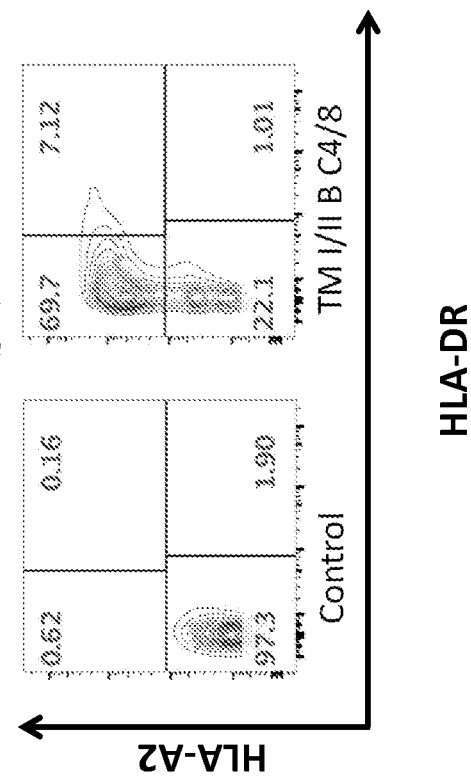
Figure 7C:
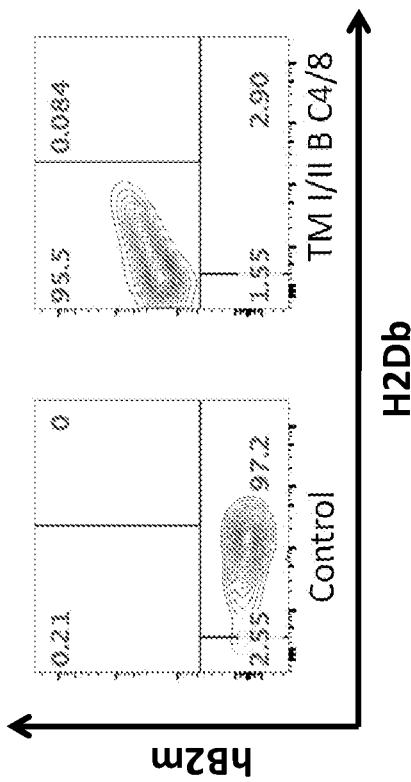
Figure 7D:
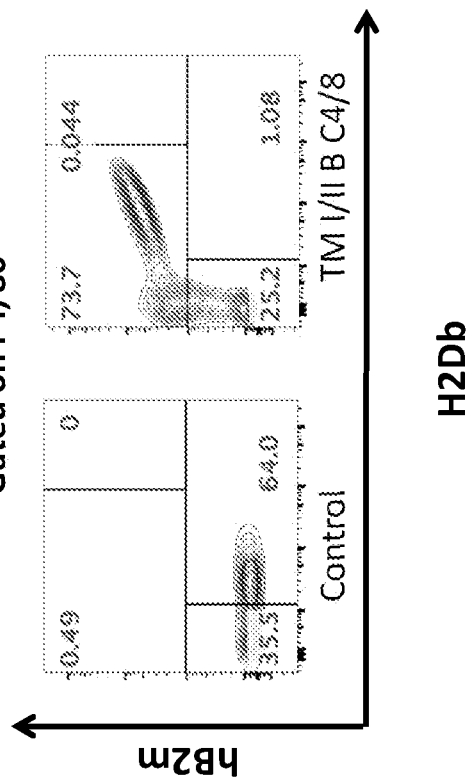
Figure 7E:
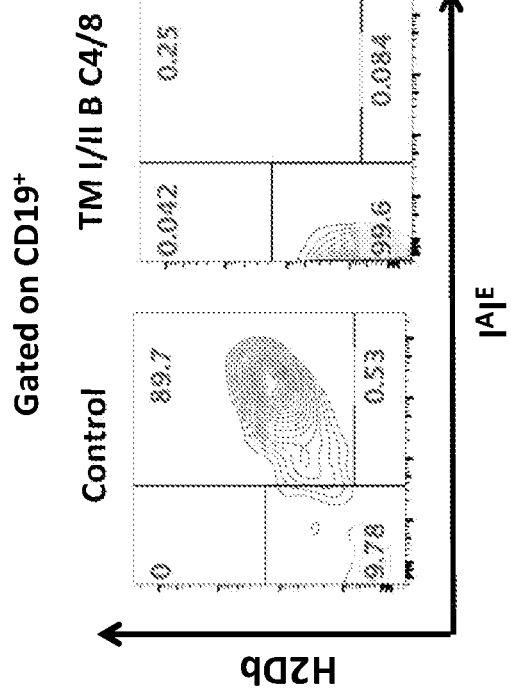
Figure 7F:
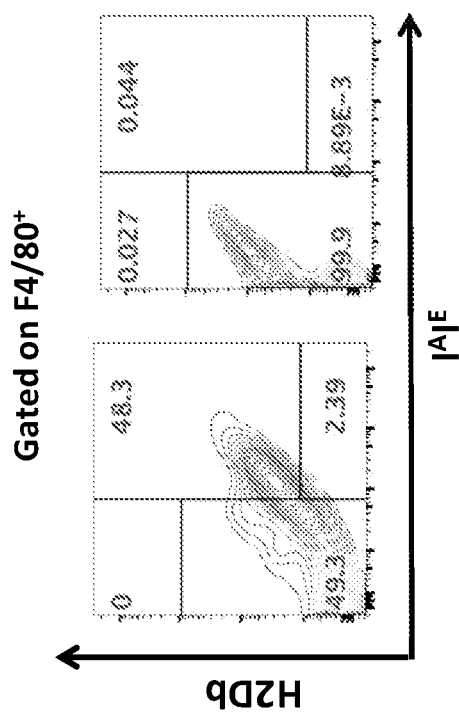
Figure 7G:
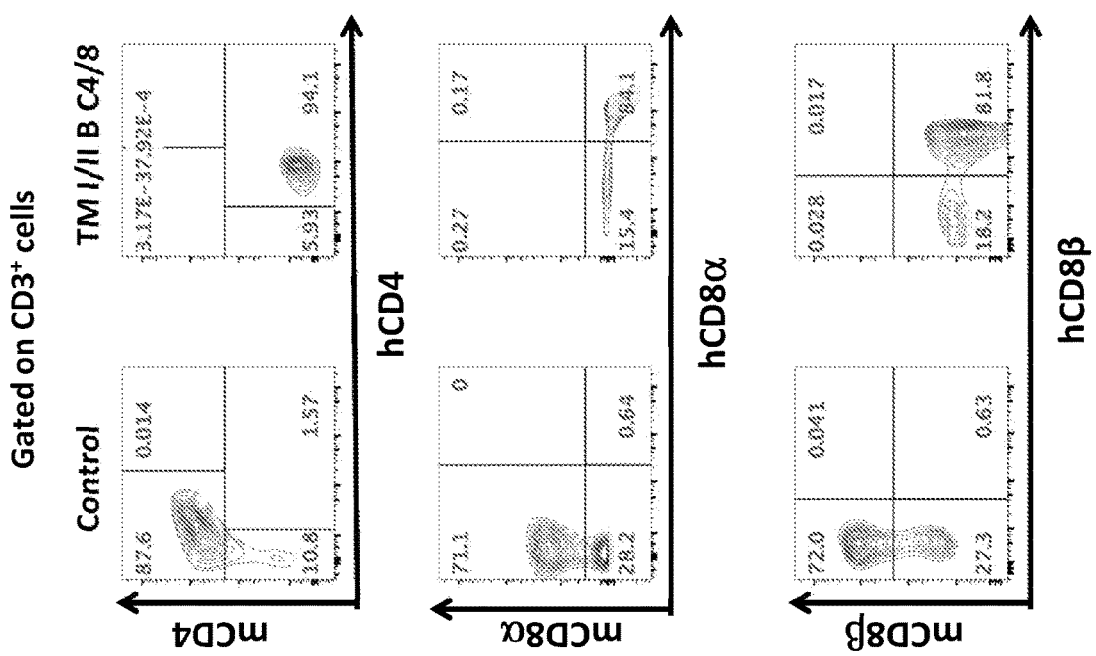

Expression in thymus is depicted in FIGS. 6A-C, 7A-G and 8. The absolute numbers of thymocytes and CD3+ cells, and the overall development of thymic T cells, were comparable in control mice and humanized TM I/II B CD4/8 mice (data not shown). FIG. 6A shows that the proportion of B cells and T cells in the thymi of mice having a humanized cellular immune system (TM I/II B C4/8) is similar to the proportion found in control mice. The frequency and number of F4/80 cells in the thymi of TM I/II B C4/8 mice was compared to control mice (FIG. 6B and data not shown). Also, humanized CD4 and CD8 are expressed on thymic cells of a mouse humanized for all nine cellular immunity genes (TM I/II B C4/8), similar to the expression of mouse CD4 and CD8 in non-humanized control mice (FIG. 6C). Humanized β2M is expressed on the surface of B cells and macrophages in humanized TM I/II B C4/8 mice, while its expression is absent from the B cells and macrophages of control mice (FIGS. 7A and 7B). Similarly, humanized MHC I and II are present on the surface of both B cells and macrophages of humanized TM I/II B C4/8 mice (FIGS. 7C and 7D) whereas mouse MHC class I and II molecules were undetectable (FIGS. 7E and 7F). Humanized CD4, CD8 α and CD8β are expressed on the surface of CD3+ thymic cells obtained from humanized TM I/II B C4/8 mice while absent from CD3+ thymic cells in the control mice (FIG. 7G). Humanized TM I/II B CD4/8 express regulatory T cells (Treg) (FIG. 8), NK cells (CD335$^+$CD3$^-$) and monocytes (CD11b$^+$) (data not shown).

Figure 9C:
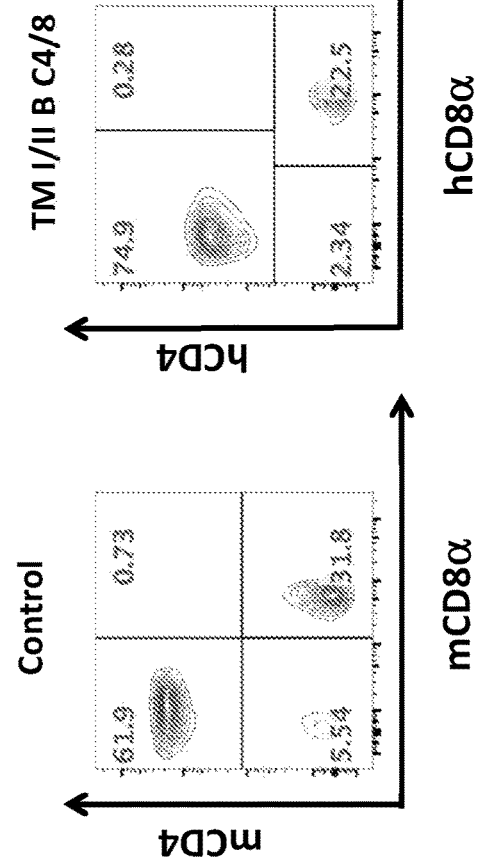
FIGS. 9A-E are FACS contour plots of splenic cells isolated from a control mouse or a mouse comprising humanized MHC I, MHC II α and β, TCRα and β, CD4, CD8α and β, and β2M (TM I/II B C4/8) loci, gated on singlets, CD3+ cells, CD4+ T cells, or CD8+ T cells, and stained with (FIG. 9A) anti-mouse CD19 and anti-mouse CD3, (FIG. 9B) anti-mouse CD19 and anti-mouse F4/80 antibodies, (FIG. 9C) anti-mouse CD4 and anti-mouse CD8α antibodies (left) or anti-human CD4 and anti-human CD8α antibodies (right), or (FIGS. 9D, 9E) anti-mouse CD44 and anti-mouse CD62L antibodies.
Figure 9A:
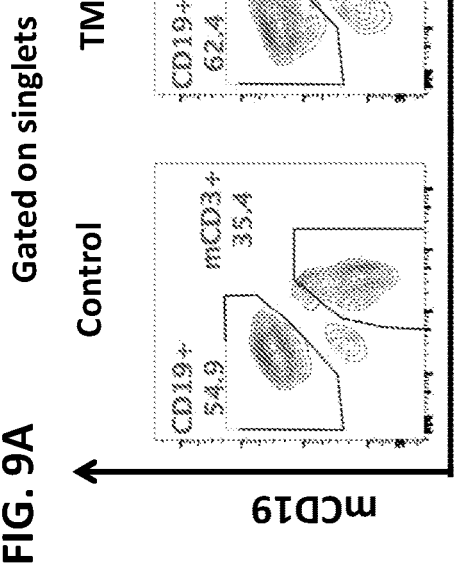
Figure 9B:
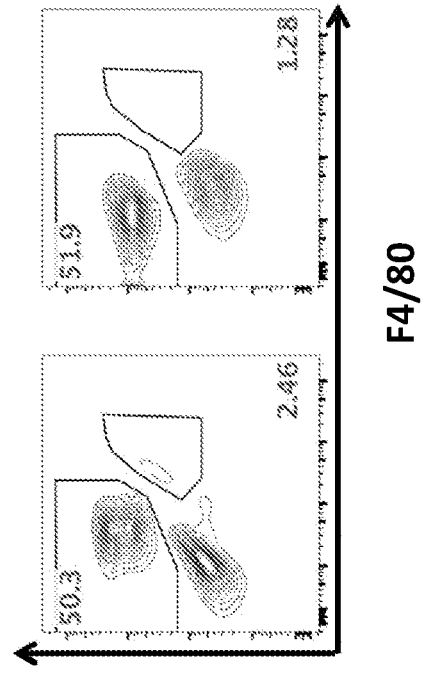
Figure 9D:
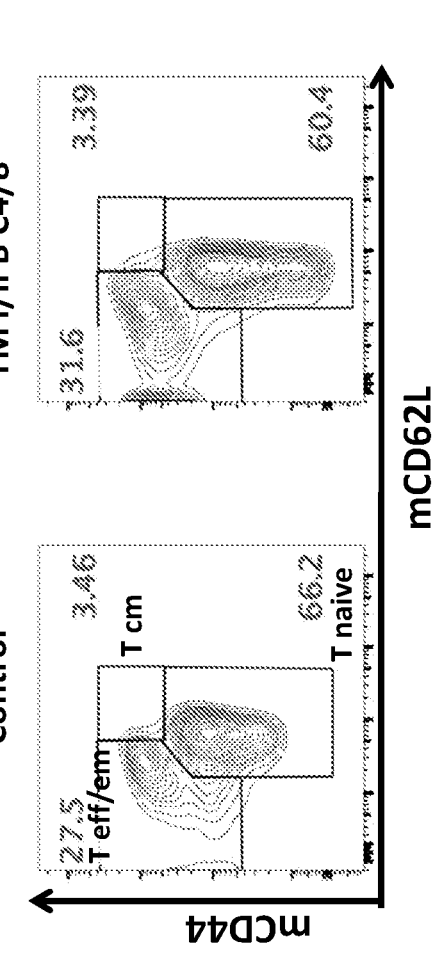
Figure 9E:
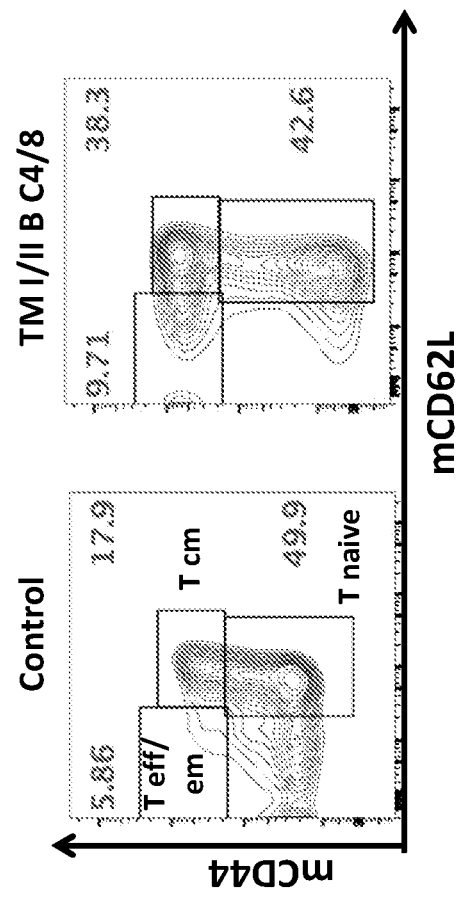

Expression in the spleen is depicted in FIGS. 9A-D, and 10A-10G. Spleens of mice humanized for cellular immune system components (TM I/II B CD4/8) comprised comparable absolute numbers of CD3+ cells, and nearly normal proportion of B and T cells (FIG. 9A and data not shown). The frequency and number of F4/80 cells in the spleens of TM I/II B C4/8 mice were compared to control mice (FIG. 9B and data not shown). Mice humanized for cellular immune system components (TM I/II B CD4/8) expressed humanized CD4 and CD8α on CD3+ splenic cells (FIG. 9C). Humanized TM I/II B CD4/8 mice comprised memory effector (CD44$^+$CD62L$^-$) CD4$^+$ and CD8$^+$ T cells and central memory (CD44$^+$ CD62L$^+$) CD8+ T cells (FIGS. 9D and 9E).

Figure 10A:
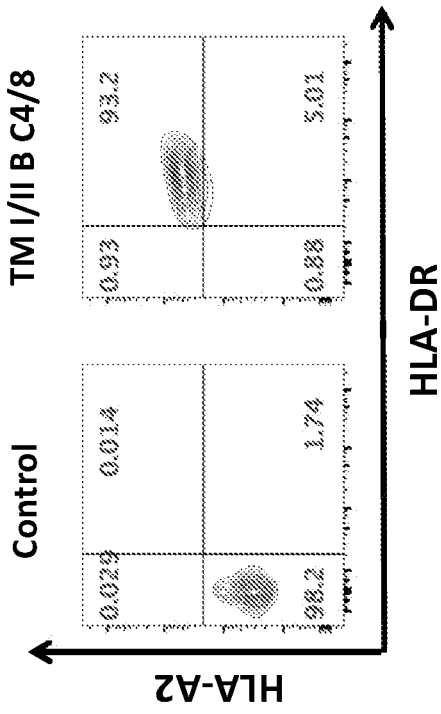
FIGS. 10A-G are FACS contour plots of splenic cells isolated from a control mouse or a mouse comprising humanized MHC I, MHC II α and β, TCRα and β, CD4, CD8α and β, and β2M (TM I/II B C4/8) loci, gated on CD19+ cells, F4/80+ cells, or CD3$^+$ cells, and stained with (FIGS. 10A, 10B) anti-human B2M or anti-mouse H-2D antibodies, (FIGS. 10C, 10D) anti-HLA-A2 or anti-HLA-DR antibodies, (FIGS. 10E, 10F) anti-H-2D and anti-I$^A$I$^E$ antibodies, or (FIG. 10G) anti-mouse CD4 and anti-human CD4 antibodies (top), anti-mouse CD8α and anti-human CD8α antibodies (middle), and anti-mouse CD8β and anti-human CD8β antibodies (bottom).
Figure 10C:
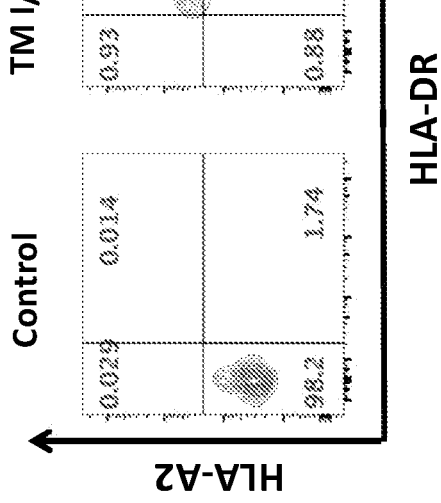
Figure 10B:
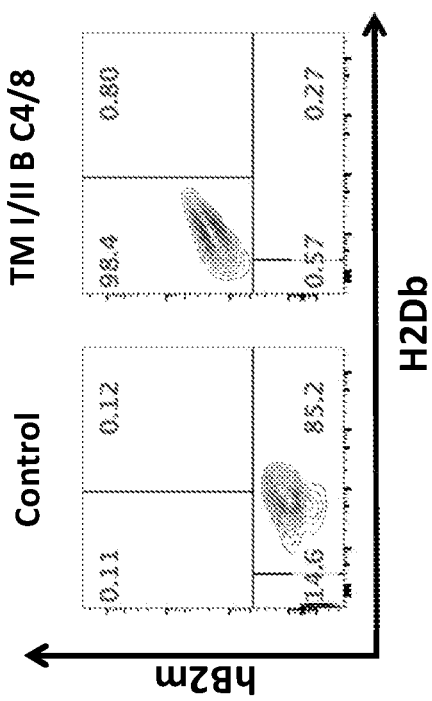
Figure 10D:
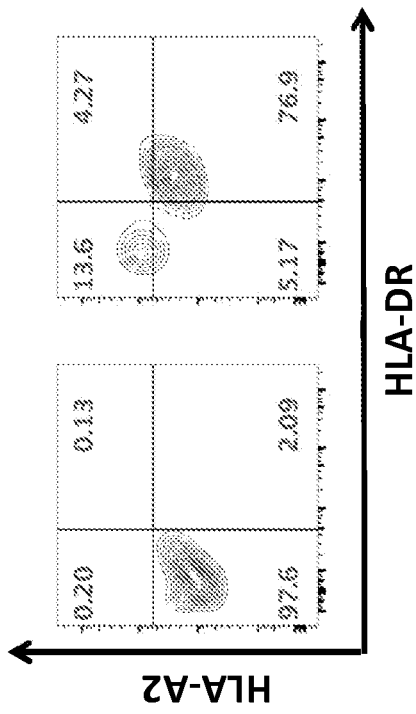
Figure 10E:
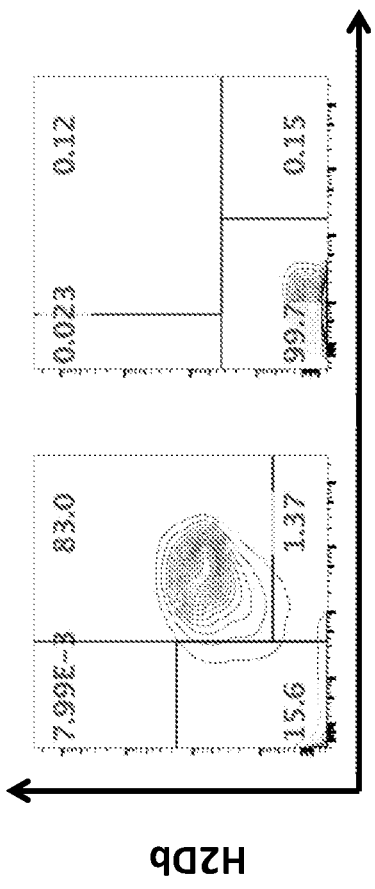
Figure 10F:
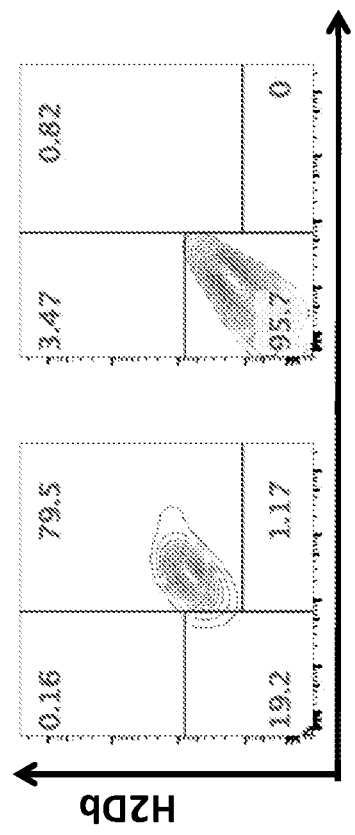
Figure 10G:
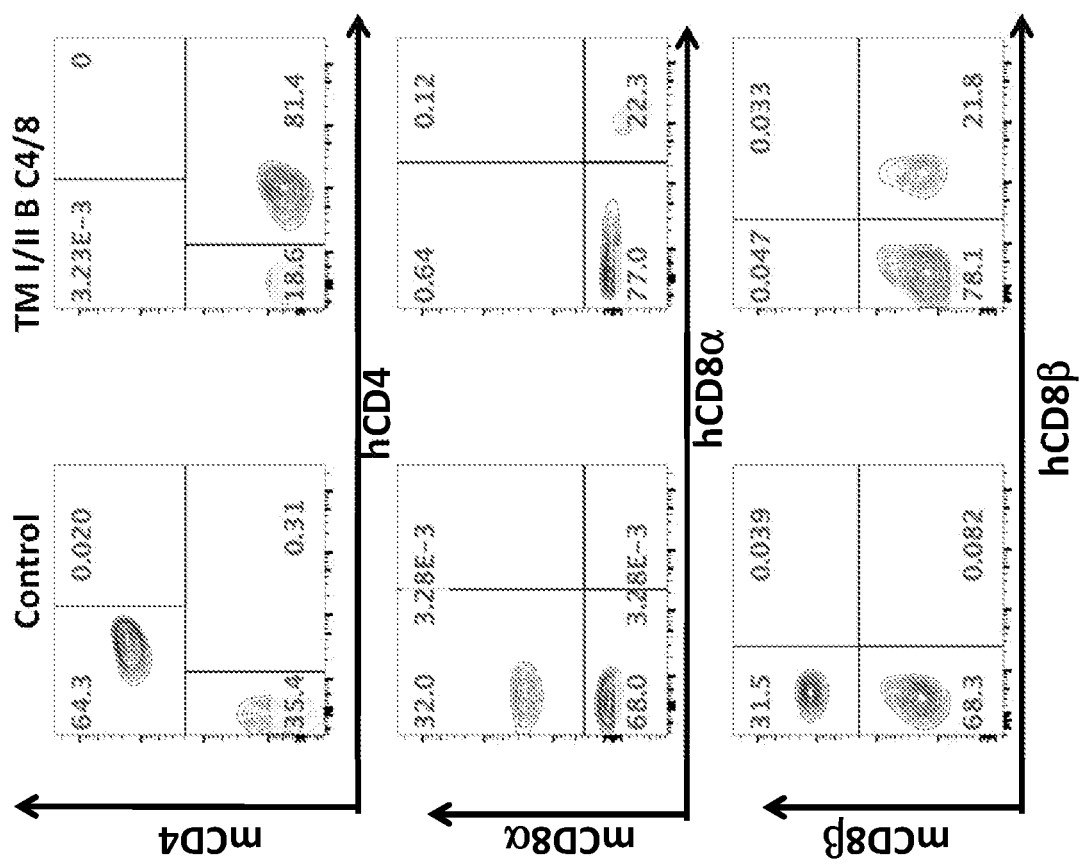
Figure 11:
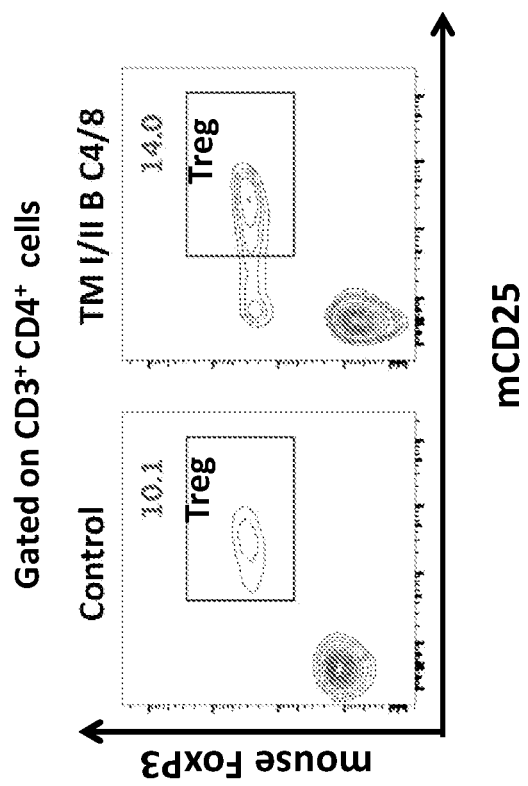
FIG. 11 provides FACS contour plots of splenic cells isolated from a control mouse or a mouse comprising humanized MHC I, MHC II α and β, TCRα and β, CD4, CD8α and β, and β2M (TM I/II B C4/8), gated on CD3$^+$ CD4$^+$ cells, and stained with anti-mouse FoxP3 and anti-mouse CD25 antibodies.

As depicted in FIGS. 10A and 10B, humanized β2M is expressed on the surface of B cells and macrophages in the spleen of humanized TM I/II B C4/B mice, while its expression, and the expression of mouse MHC molecules, are absent from the B cells and macrophages in the spleen of control mice. Similarly, humanized MHC I and II are present on the surface of both B cells and macrophages in the spleen of humanized TM I/II B C4/B mice (FIGS. 10C and 10D) whereas mouse MHC class I and II molecules were undetectable (FIGS. 10E and 10F). Humanized CD4, CD8 α and CD8β are expressed on the surface of CD3+ splenic cells obtained from humanized TM I/II B C4/8 mice while absent from CD3+ splenic cells in the control mice (FIG. 10G). TM I/II B C4/8 mice have near normal expression of splenic regulatory T cells compared to control mice (FIG. 11), and express splenic NK cells (CD335$^+$CD3$^+$) and monocytes (CD11b$^+$).

Example 6

Evaluation of Presentation to and Activation of T Cells with Human Peptide

To determine whether the mice comprising humanized cellular immune system components exhibited humanized T cell immune responses, the ability of splenocytes from mice humanized for cellular immune system components (TM I/II B CD4/8) to present and respond to MAGE-A3, a peptide presented specifically by human HLA-A2, was tested.

MAGE-A3, a peptide presented specifically by human HLA-A2, is synthesized (Celtek Biosciences), diluted in PBS, and mixed in equal volume with Complete Freund's Adjuvant (CFA; Chondrex, Inc.) such that 200 μg of the MAGE-A3 is contained in the 200 μl emulsion. 50 μl of emulsion is injected into 4 spots on each animal. Two spots are each in a hind flank and 2 spots each are near each shoulder of mice homozygous for humanized MHC I, MHC II α and β, TCRα and β, CD4, CD8α and β, and β2M (TM I/II B CD4/8) or control mice which express endogenous MHC I, MHC II α and β, TCRα and β, CD4, CD8α and β, and β2M.

Spleen suspensions from immunized mice are obtained and dissociated. Red blood cells are lysed in ACK lysis buffer (Life Technologies), and splenocytes are suspended in RPMI complete media. $2 \times 10^5$ of isolated splenocytes in the absence or in the presence of 10 μg/mL or 1 μg/mL of diluted MAGE-A3 peptide are tested per well of PVDF plates (Millipore) coated with 5 μg/mL of the mouse IFN-γ capture antibody (BD Biosciences) in an ELISPOT assay. After a 16-20 hour incubation with peptide, the plates are washed and incubated with biotinylated detection antibody (BD Biosciences), washed, treated with Streptavidin-HRP (MabTech), washed and developed with TMB substrate (Mabtech), and counted by AID Elispot reader.

Figure 12:
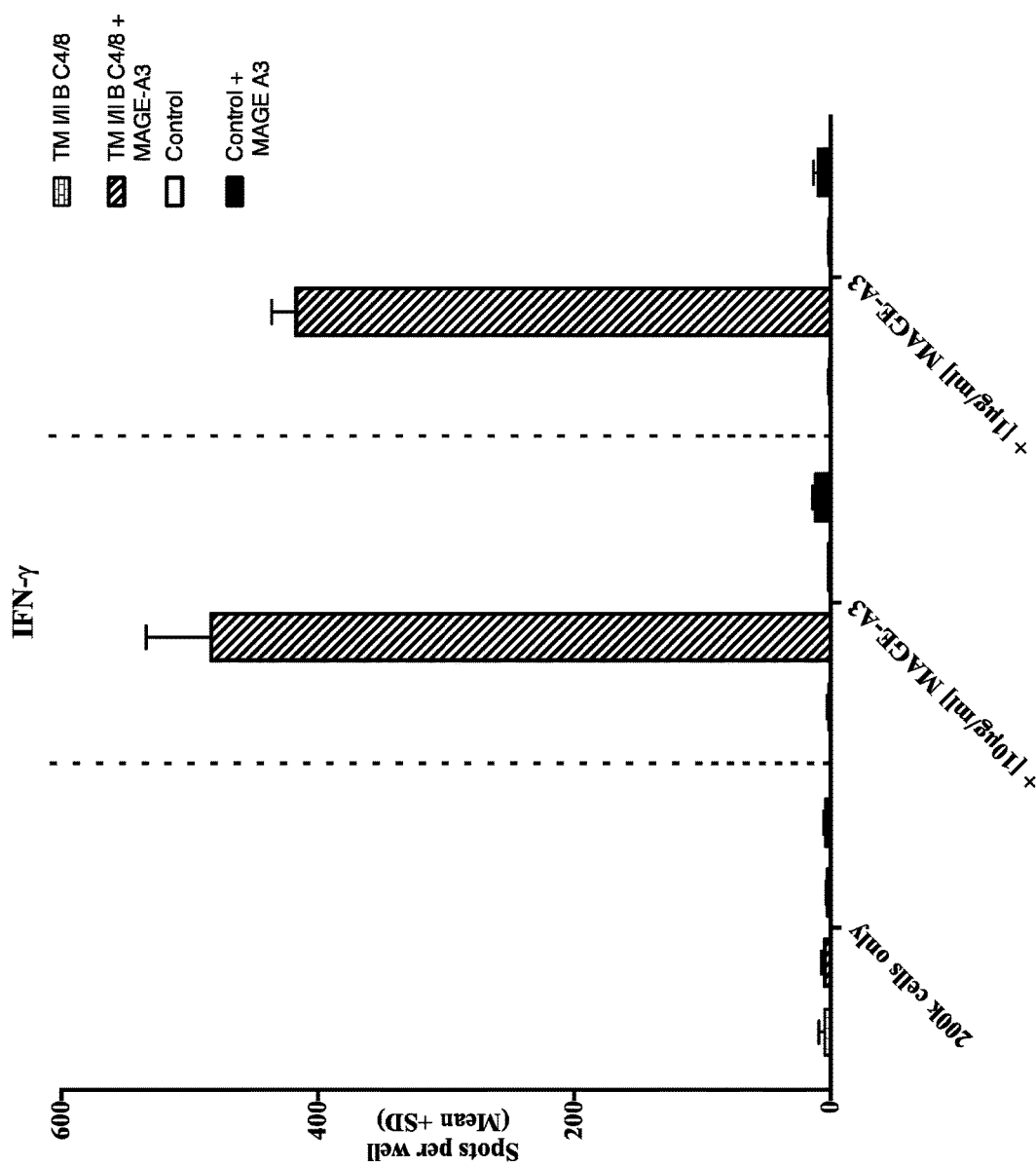
FIG. 12 provides the number of splenic cells (spots per well (Mean+SD); y-axis) that produce IFN-γ in an enzyme-linked immunosorbent spot assay after isolation from a control mouse or a mouse comprising humanized MHC I, MHC II α and β, TCRα and β, CD4, CD8α and β, and β2M (TM I/II B C4/8) loci and incubation in the absence of peptide (200 k cells only; x-axis) or presence of 10 μg/ml or 1 μg/ml MAGE-A3 peptide (x-axis).

While only one mouse per genotype is shown, several mice of each genotype were tested, and all samples were run in triplicate with standard deviation shown by error bars. As shown in FIG. 12, only samples from mice homozygous for each of humanized MHC I, MHC II α and β, TCRα and β, CD4, CD8α and β, and β2M (TM I/II B CD4/8) responded by secreting IFN-γ after treatment with HLA-A2-specific peptide MAGE-A3, indicating that T cells from these mice were activated after presentation of MAGE-A3 by humanized HLA-A2.

Example 7

Evaluation of T Cell Function Using LCMV Infection Model

To determine whether the mice comprising humanized cellular immune system components exhibited normal response to infection, the ability of humanized mice to clear lymphocytic choriomeningitis virus (LCMV) was tested.

LCMV is a mouse tropic virus, where the fate of infection depends on the viral strain. Exposure to Armstrong strain results in an acute infection, where mice can quickly mount a T cell response against the virus and clear the infection in about a week. On the other hand, Clone 13 virus cannot be cleared, and T cells become "exhausted" (expressing markers associated with T cell exhaustion, e.g., PD1, Lag3, Tim3) and chronic infection is established. It has been shown that infection of CD8 depleted or MHC class I deficient mice with Armstrong strain results in maintenance of high viral titers (J. Virol. 68:8056-63 (1994)). Thus, since viral infection depends on T cell activity, LCMV is an ideal model to test for T cell function.

To determine if mice comprising humanized cellular immune system components, e.g., MHC I, MHC II α and β, TCRα and β, CD4, CD8α and β, and β2M, exhibit normal T cell function, both control and humanized (TM I/II B C4/8) mice were infected with $2 \times 10^5$ ffu of Armstrong virus strain i.p. on Day 0. On Days 3, 6, 9, and 12, organs were harvested and viral titers were measured. As shown in FIG. 13A, both control and humanized mice were able to clear Armstrong infection.

Figure 13C:
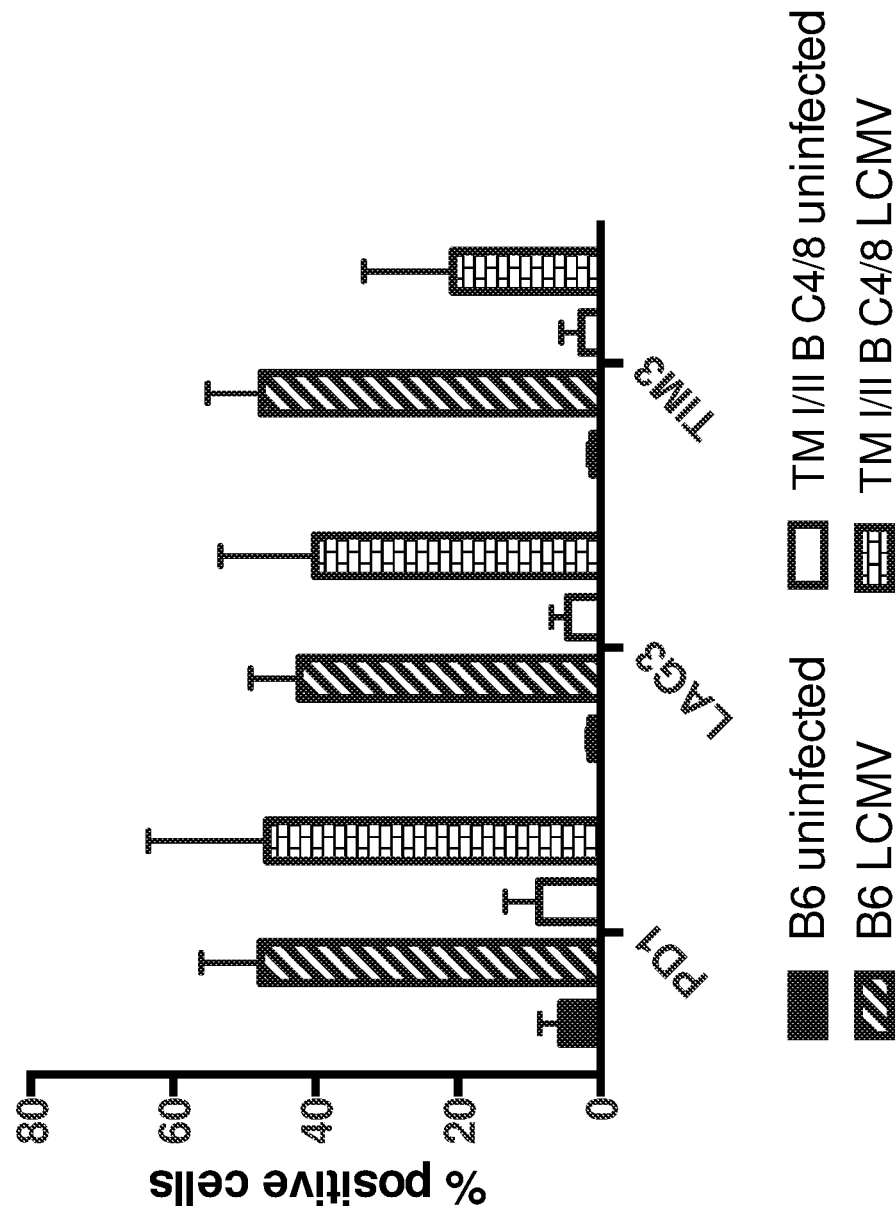
FIG. 13A depicts progression of acute Armstrong strain viral infection in either control or mice comprising humanized MHC I, MHC II α and β, TCRα and β, CD4, CD8α and β, and β2M (TM I/II B C4/8) loci; the timeline for the experiment is depicted at the top of the figure, and measurement of viral titers on various days post-infection for both mouse strains is depicted in the bottom graph.
FIG. 13B depicts progression of chronic Clone 13 strain viral infection in either control or mice comprising humanized MHC I, MHC II α and β, TCRα and β, CD4, CD8α and β, and β2M (TM I/II B C4/8) loci; the timeline for the experiment is depicted at the top of the figure, and the measurement of viral titers on Day 21 post-infection for both mouse strains is depicted in the bottom graph. T cells from uninfected or chronically infected TM I/II B C4/8 or control B6 mice were stained with anti-PD1, anti-Lag3, and anti-Tim3 antibodies (FIG. 13C; x-axis); the figure provides a quantification of cells staining positive (% positive cells; y-axis).

Both control and humanized mice were also infected with $4.5 \times 10^5$ ffu of Clone 13 virus i.v. on Day 0, and on Day 21 organs were harvested and viral titers measured. As depicted in FIG. 13B, both mouse strains were able to establish chronic LCMV infection. The ability of humanized mice to express PD1, Lag3, and Tim3, markers of T cell exhaustion, was also measured. Blood was taken from uninfected mice and infected humanized mice 3 weeks post-infection and stained using flow cytometry with PE-Cy7 conjugated anti-PD1 antibody (BIOLEGEND), PerCpCy5.5 conjugated Lag3 antibody (BIOLEGEND), and PE conjugated Tim3 antibody (R&D Systems). Data in FIG. 13C is a quantification of cells staining positive for the indicated receptors. Both humanized (TM I/II B C4/8) mice and control B6 mice expressed all three markers of T cell exhaustion 3 weeks after infection with chronic LCMV Clone 13 strain.

To evaluate memory T cell responses in mice humanized for cellular immune system components, 5 control and 4 humanized mice were infected with $2 \times 10^5$ ffu of Armstrong strain, and on Day 17 super-infected with $4.5 \times 10^5$ ffu Clone 13 strain (2 of each humanized and control mice were mock-infected as an additional control). On Day 31 post initial infection, organs were harvested and viral titers were analyzed. As depicted in FIG. 14, 5/5 control mice and 3/4 humanized mice that have encountered an acute LCMV infection were subsequently protected from chronic LCMV infection, demonstrating intact memory T cell responses in these animals.

To analyze the nature of the cellular responses, control and humanized mice were infected on Day 0 with $2 \times 10^5$ ffu of Armstrong virus strain. On Day 10 (FIGS. 15A-B) or at the indicated time points post infection (FIGS. 15C-D) the specificity of the cellular response was analyzed using three HLA-A2 restricted peptides known to activate human CD8+ T cells (GPC10-18, N69-77 or Z49-58), see Botten et al. (2007) *J. ViroL* 81:2307-17, or gp33, an immunodominant LCMV peptide recognized by mice on a H-2D$^b$ background. Specifically, CD8+ T cells were isolated from harvested spleens and pulsed with the peptides. CD8+ cells producing interferon-γ (IFNγ) were measured by ELISpot (FIGS. 15A-B) or by staining for intracellular IFNγ (FIGS. 15C-D).

Figure 15B:
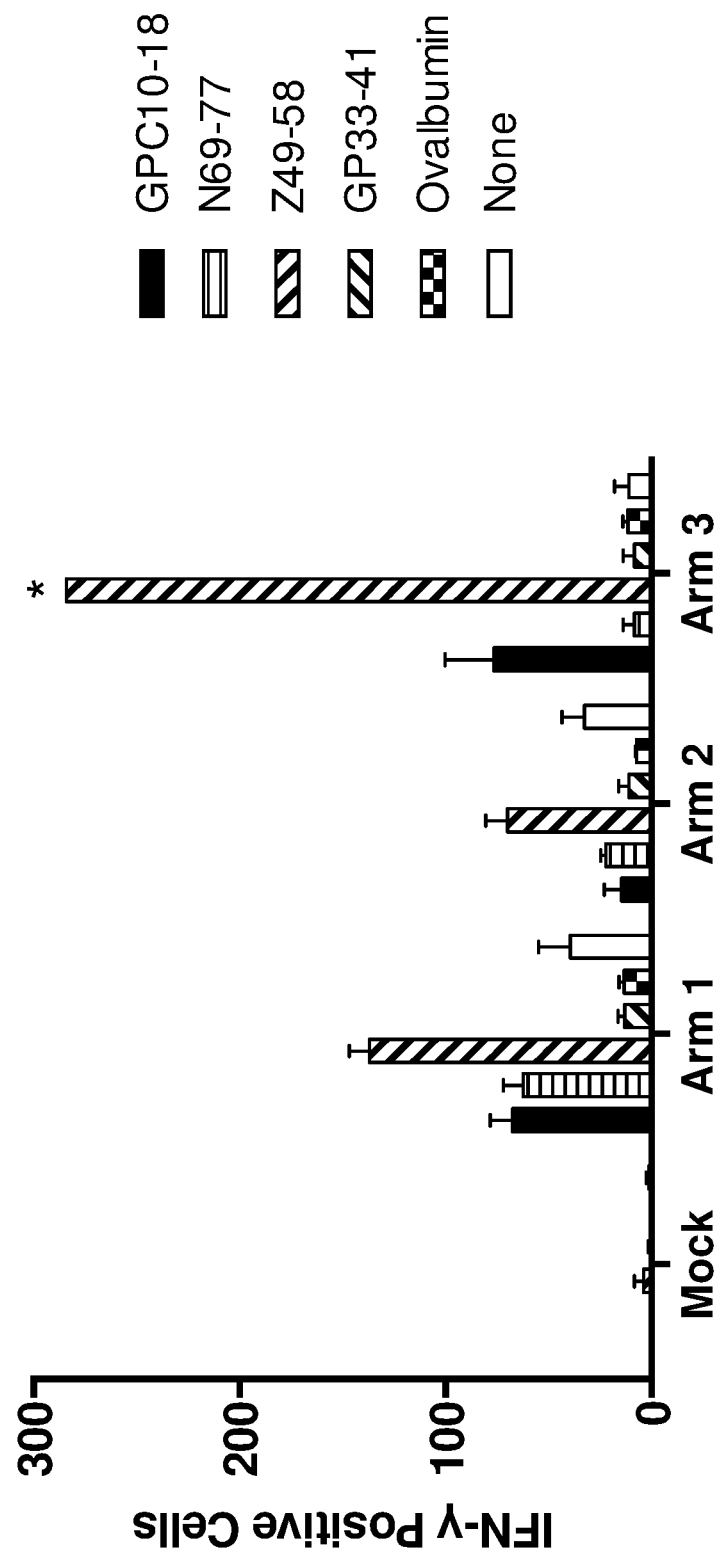
FIGS. 15A-B depicts the number of CD8$^+$ cells (y-axis; IFN-γ Positive Cells) that produced IFN-γ in response to LCMV peptides that are HLA-A2 restricted (GPC10-18; N69-77; Z49-58), H2D$^b$ restricted (GP33-41), ovalbumin, or incubation alone and were isolated from either control animals (FIG. 15A) or mice comprising humanized MHC I, MHC II α and β, TCRα and β, CD4, CD8α and β, and β2M (TM I/II B C4/8) loci (FIG. 15B), each of which received a mock infection (mock; n=1 each group) or an acute Armstrong strain infection (Arm; n=3 each group). The % of IFNγ+CD8+ lymphocytes (y-axis) after stimulation with the indicated peptides (OVA, GP33, NP69, GPC10, GPC447 or Z49) during a time course of infection (days post infection; x-axis) in mice comprising humanized MHC I, MHC II α and β, TCRα and β, CD4, CD8α and β, and β2M (TM I/II B C4/8) loci or control B6 animals are shown in FIGS. 15C and 15D, respectively.
Figure 15C:
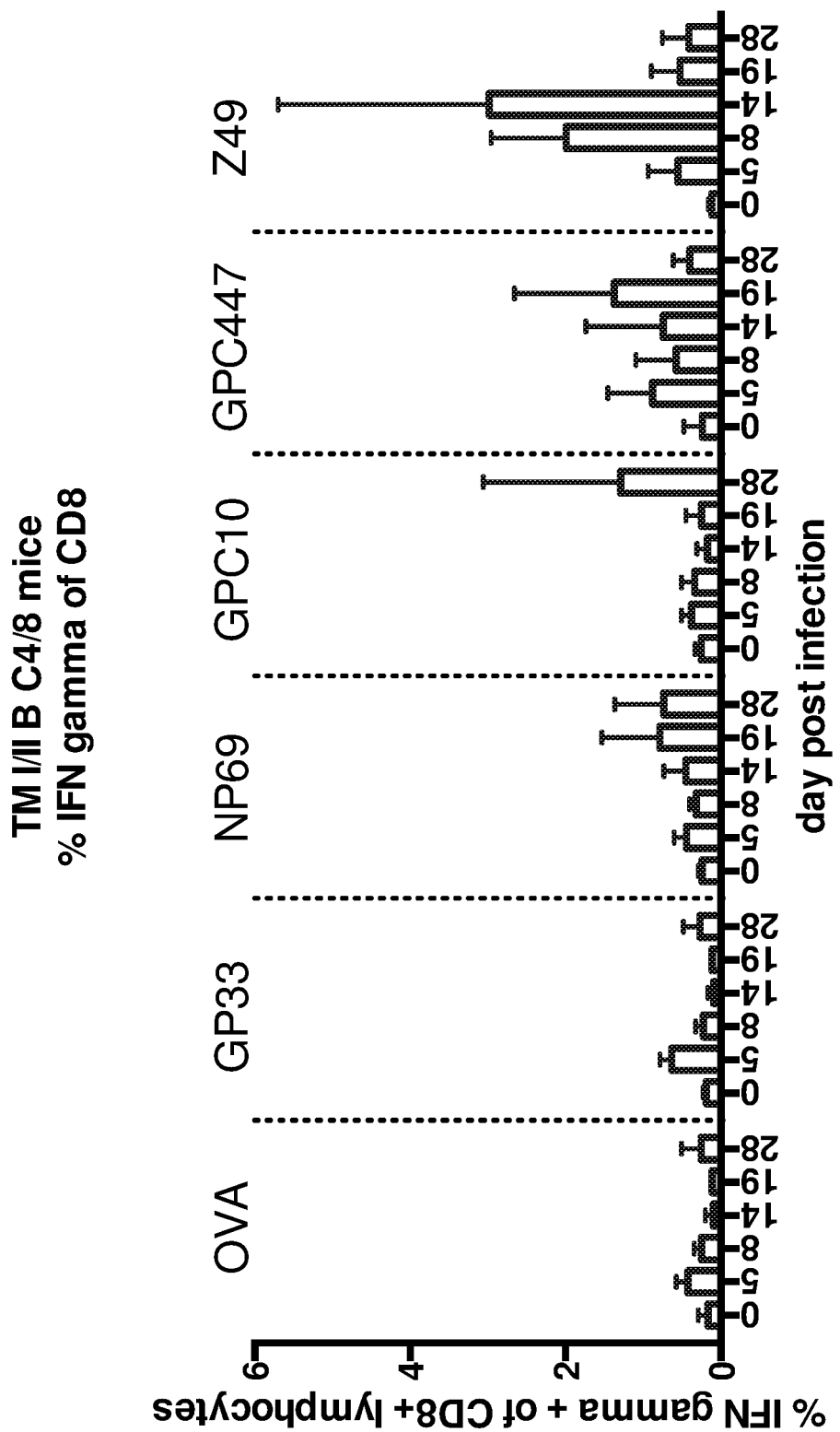
Figure 15D:
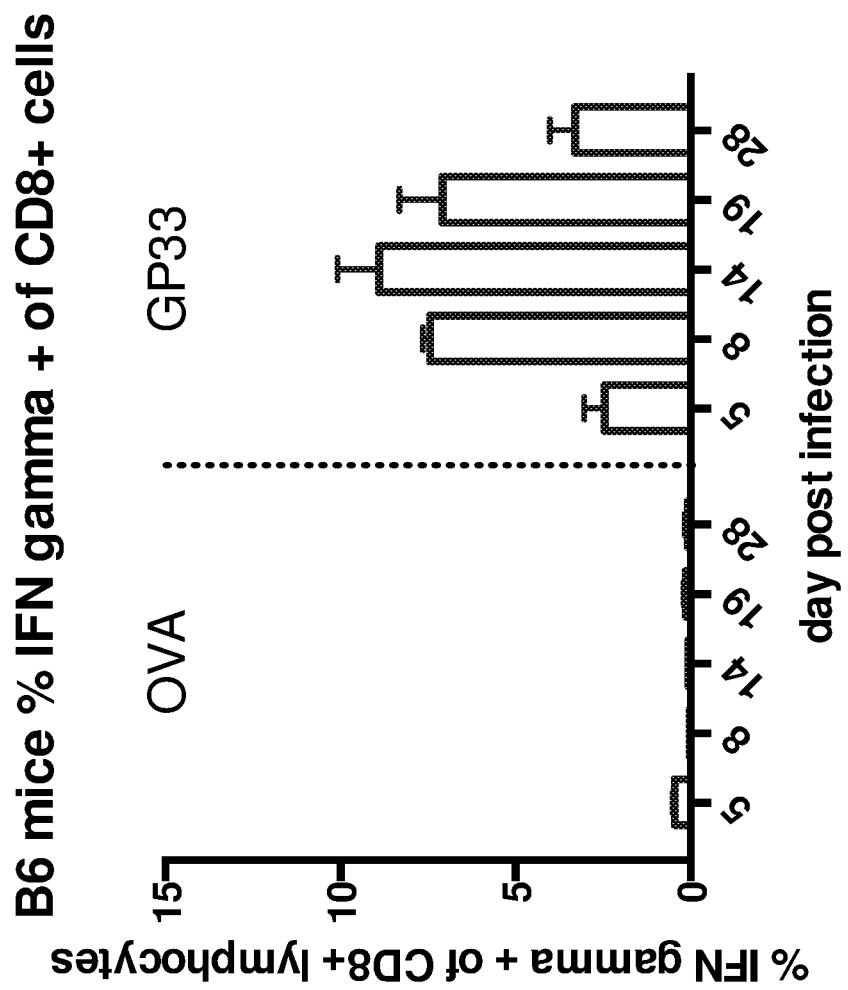

CD8+ T cells isolated from control animals are specifically activated by the gp33 peptide (FIG. 15A), while CD8+ T cells isolated from humanized animals are activated by the HLA-A2 restricted peptides (FIG. 15B). The time course of CD8+ T cell activation, as monitored by their ability to express IFNγ when stimulated with the peptides, shows in both control and humanized mice CD8+ T cells expand during the first two weeks post infection and are undetectable after the virus is cleared (FIGS. 15C-D). Although the response to gp33 peptide appeared stronger in control animals, it should be noted that gp33 is a known immunodominant LCMV epitope while the immunodominant HLA-A2 restricted LCMV epitope has not been identified. In conclusion, animals comprising a humanized, or substantially humanized T cell immune system are capable of processing LCMV expressed protein, presenting them on humanized MHC molecules and activating T cells via a humanized T cell receptor.

Equivalents

Those skilled in the art will recognize, or be able to ascertain using no more than routine experimentation, many equivalents of the specific embodiments of the invention described herein. Such equivalents are intended to be encompassed by the following claims.

Entire contents of all non-patent documents, patent applications and patents cited throughout this application are incorporated by reference herein in their entirety.

What is claimed is:

1. A genetically modified mouse comprising in its genome
   (a) a first nucleotide sequence encoding a chimeric human/mouse CD4 co-receptor that comprises D1, D2 and D3 domains of a human CD4 polypeptide and transmembrane and cytoplasmic domains of a mouse CD4 polypeptide;
   (b) a second nucleotide sequence encoding a chimeric human/mouse CD8α polypeptide and a third nucleotide sequence encoding a chimeric human/mouse CD8β polypeptide,
   wherein the chimeric human/mouse CD8α polypeptide comprises an IgV-like domain of a human CD8α polypeptide and transmembrane and cytoplasmic domains of a mouse CD8α polypeptide,
   wherein the chimeric human/mouse CD8β polypeptide comprises an IgV-like domain of a human CD8β polypeptide and transmembrane and cytoplasmic domains of a mouse CD8β polypeptide;
   (c) a first nucleic acid sequence encoding a chimeric human/mouse MHC II α polypeptide and a second nucleic acid sequence encoding a chimeric human/mouse MHC II β polypeptide,
   wherein the chimeric human/mouse MHC II α polypeptide comprises α1 and α2 domains of a human HLA class II α polypeptide and transmembrane and cytoplasmic domains of a mouse MHC II α polypeptide,
   wherein the chimeric human/mouse MHC II β polypeptide comprises β1 and β2 domains of a human HLA class II β polypeptide and transmembrane and cytoplasmic domains of a mouse MHC II β polypeptide;
   (d) a third nucleic acid sequence encoding a chimeric human/mouse MHC I polypeptide,
   wherein the chimeric human/mouse MHC I polypeptide comprises α1, α2, and α3 domains of a human HLA class I polypeptide and transmembrane and cytoplasmic domains of a mouse MHC I polypeptide; and
   (e) an unrearranged T cell receptor (TCR) α variable region sequence comprising at least one human Vα segment and at least one human Jα segment, wherein the unrearranged T cell receptor (TCR) α variable region sequence is operably linked to a mouse TCRα constant region sequence; and an unrearranged TCRβ variable region sequence comprising at least one human Vβ segment, at least one human Dβ segment, and at least one human Jβ segment, wherein the unrearranged TCRβ variable region sequence is operably linked to a mouse TCRβ constant region sequence,
   wherein the mouse expresses:
   (A) the chimeric human/mouse CD4 co-receptor,
   (B) a chimeric human/mouse CD8 co-receptor comprising the chimeric human/mouse CD8α polypeptide and the chimeric human/mouse CD8β polypeptide,
   (C) a chimeric human/mouse MHC II complex comprising the chimeric human/mouse MHC II_α polypeptide and the chimeric human/mouse MHC II β polypeptide, wherein the chimeric human/mouse MHC II complex is capable of binding the chimeric human/mouse CD4 co-receptor,
   (D) the chimeric human/mouse MHC I polypeptide, wherein the chimeric human/mouse MHC I polypeptide is capable of binding the chimeric human/mouse CD8 co-receptor, and (E) a T cell receptor comprising a humanized TCRα chain and a humanized TCRβ chain, wherein the humanized TCRα chain is encoded by a rearranged human Vα/Jα sequence operably linked to the mouse TCRα constant region sequence, wherein the rearranged human Vα/Jα sequence is formed by rearrangement of the at least one human Vα segment and the at least one human Jα segment, wherein the humanized TCRβ chain is encoded by a rearranged human Vβ/Dβ/Jβ sequence operably linked to the mouse TCRβ constant region sequence, wherein the rearranged human Vβ/Dβ/Jβ sequence is formed by rearrangement of the at least one human Vβ segment, the at least one Dβ segment, and the at least one human Jβ segment.

2. The genetically modified mouse of claim 1, comprising in its germline genome
(a) the first nucleotide sequence encoding the chimeric human/mouse CD4 co-receptor;
(b) the second nucleotide sequence encoding the chimeric human/mouse CD8α polypeptide and the third nucleotide sequence encoding the chimeric human/mouse CD8β polypeptide;
(c) the first nucleic acid sequence encoding the chimeric human/mouse MHC II α polypeptide and the second nucleic acid sequence encoding the chimeric human/mouse MHC II β polypeptide;
(d) the third nucleic acid sequence encoding the chimeric human/mouse MHC I polypeptide; and
(e) the unrearranged TCR α variable region sequence operably linked to the mouse TCRα constant region sequence and the unrearranged TCRβ variable region sequence operably linked to the mouse TCRβ constant region sequence.

3. The genetically modified mouse of claim 1, wherein
(a) the first nucleotide sequence is present at an endogenous CD4 locus;
(b) the second nucleotide sequence is present at an endogenous CD8α locus and the third nucleotide sequence is present at an endogenous CD8β locus;
(c) the first nucleic acid sequence is present at an endogenous MHC II α locus and the second nucleic acid sequence is present at an endogenous MHC II β locus;
(d) the third nucleic acid sequence is present at an endogenous MHC I locus;
(e) the unrearranged TCRα variable region sequence is present at an endogenous TCRα variable region locus and the unrearranged TCRβ variable region sequence is present at an endogenous TCRβ variable region locus, or
(f) any combination of (a)-(e).

4. The genetically modified mouse of claim 3, wherein
(a) the first nucleotide sequence is present at the endogenous CD4 locus and expressed under regulatory control of mouse CD4 promoter and regulatory elements;
(b) the second nucleotide sequence is present at the endogenous CD8α locus and expressed under regulatory control of mouse CD8α promoter and regulatory elements, and the third nucleotide sequence is present at an endogenous CD8β locus and expressed under regulatory control of mouse CD8β promoter and regulatory elements;
(c) the first nucleic acid sequence is present at the endogenous MHC II α locus and expressed under regulatory control of mouse MHC II α promoter and regulatory elements, and the second nucleic acid sequence is present at an endogenous MHC II β locus and expressed under regulatory control of mouse MHC II β promoter and regulatory elements;
(d) the third nucleic acid sequence is present at the endogenous MHC I locus and expressed under regulatory control of mouse MHC I promoter and regulatory elements; or
(e) any combination of (a)-(d).

5. The genetically modified mouse of claim 4, wherein the chimeric human/mouse CD4 co-receptor comprises D1, D2 and D3 domains of the human CD4 polypeptide operably linked to D4, transmembrane, and cytoplasmic domains of the mouse CD4 polypeptide.

6. The genetically modified mouse of claim 1, wherein
(a) the human HLA class II α polypeptide is selected from the group consisting of any α chain of HLA-DR, HLA-DQ, and HLA-DP;
(b) the human HLA class II β polypeptide is selected from the group consisting of any β chain of HLA-DR, HLA-DQ, and HLA-DP;
(c) the human HLA class I polypeptide is selected from the group consisting of HLA-A, HLA B, and HLA-C gene; or
(d) any combination of (a)-(c).

7. The genetically modified mouse of claim 6, wherein the human HLA class II α polypeptide is the α chain of HLA-DR and the human HLA class II β polypeptide is the β chain of HLA-DR, and
wherein the human HLA class I polypeptide is HLA-A.

8. The genetically modified mouse of claim 7, wherein the chimeric human/mouse MHC II complex comprises α1, α2, β1, and β2 domains of a human HLA-DR2 protein.

9. The genetically modified mouse of claim 7, wherein the chimeric human/mouse MHC I polypeptide comprises α1, α2, and α3 domains of a human HLA-A2 protein.

10. The genetically modified mouse of claim 1, wherein
(a) the unrearranged TCRα variable region sequence comprises a complete repertoire of human Vα gene segments and a complete repertoire of human Jα gene segments,
(b) the unrearranged TCRβ variable region sequence comprises a complete repertoire of human Vβ gene segments, a complete repertoire of human Dβ gene segments, and a complete repertoire of human Jβ gene segments, or
(c) the unrearranged TCRα variable region sequence comprises a complete repertoire of human Vα gene segments and a complete repertoire of human Jα gene segments and the unrearranged TCRβ variable region sequence comprises a complete repertoire of human Vβ gene segments, a complete repertoire of human Dβ gene segments, and a complete repertoire of human Jβ gene segments.

11. The genetically modified mouse of claim 1, wherein:
(i) an endogenous TCRα variable region locus (a) lacks all or substantially all functional endogenous Vα gene segments, (b) lacks all or substantially all functional endogenous Jα gene segments, or (c) lacks all or substantially all functional endogenous Vα gene segments and lacks all or substantially all functional endogenous Jα gene segment;
(ii) an endogenous TCRβ variable region locus (a) lacks all or substantially all functional endogenous Vβ gene segments, (b) lacks all or substantially all functional endogenous Dβ gene segments, (c) lacks all or substantially all functional endogenous Jβ gene segments, or (d) lacks all or substantially all functional endogenous Vβ gene segments, lacks all or substantially all functional Dβ gene segments, and lacks all or substantially all functional Jβ gene segments; or (iii) the endogenous TCRα variable region locus lacks all or substantially all functional endogenous Vα gene segments and lacks all or substantially all functional endogenous Jα gene segment, and the endogenous TCRβ variable region locus lacks all or substantially all functional endogenous Vβ gene segments, lacks all or substantially all functional Dβ gene segments, and lacks all or substantially all functional Jβ gene segments.

12. The genetically modified mouse of claim 1, wherein
(a) the first nucleotide sequence comprises a sequence encoding D1, D2 and D3 domains of the human CD4 polypeptide that, at an endogenous CD4 locus, (i) replaces a sequence encoding D1, D2 and D3 domains of a mouse CD4 polypeptide and (ii) is operably linked to mouse CD4 D4, transmembrane and cytoplasmic domains encoding sequences;
(b) the second nucleotide sequence comprises a sequence encoding the IgV-like domain of the human CD8α polypeptide that, at an endogenous CD8α locus, (i) replaces a sequence encoding the IgV-like domain of a mouse CD8α polypeptide and (ii) is operably linked to mouse CD8α transmembrane and cytoplasmic domain encoding sequences, and
the third nucleotide sequence comprises a sequence encoding the IgV-like domain of the human CD8β polypeptide that, at an endogenous CD8β locus, (i) replaces a sequence encoding the IgV-like domain of a mouse CD8β polypeptide and (ii) is operably linked to mouse CD8β transmembrane and cytoplasmic domain encoding sequences;
(c) the first nucleic acid sequence comprises a sequence encoding α1 and α2 domains of the human HLA class II α polypeptide that, at an endogenous MHC II α locus, (i) replaces a sequence encoding α1 and α2 domains of a mouse MHC II α polypeptide and (ii) is operably linked to mouse MHC II α polypeptide transmembrane and cytoplasmic domain encoding sequences, and
the second nucleic acid comprises a sequence encoding β1 and β2 domains of the human HLA class II β polypeptide that, at an endogenous MHC II β locus, (i) replaces a sequence encoding β1 and β2 domains of a mouse MHC II β polypeptide and (ii) is operably linked to mouse MHC II β polypeptide transmembrane and cytoplasmic domain encoding sequences;
(d) the third nucleic acid sequence comprises a sequence encoding α1, α2, and α3 domains of the human HLA class I polypeptide that, at an endogenous MHC I locus, (i) replaces a sequence encoding α1, α2, and α3 domains of a mouse MHC I polypeptide and (ii) is operably linked to mouse MHC I polypeptide transmembrane and cytoplasmic domain encoding sequences;
(e) the unrearranged TCRα variable region sequence replaces one or more endogenous Vα and/or Jα gene segments at an endogenous TCRα variable region locus and the unrearranged TCRβ variable region sequence replaces one or more endogenous Vβ, Dβ and/or Jβ gene segments at an endogenous TCRβ variable region locus; or
(f) any combination of (a)-(e).

13. The genetically modified mouse of claim 1, wherein the mouse does not express:

(a) a functional mouse CD4 co-receptor from an endogenous CD4 locus;
(b) a functional mouse CD8 co-receptor from an endogenous CD8 locus;
(c) a mouse TCRα variable domain from an endogenous TCRα locus;
(d) a mouse TCRβ variable domain from an endogenous TCRβ locus;
(e) on a cell surface, an extracellular domain of a classical MHC class I polypeptide from an endogenous MHC I locus;
(f) on a cell surface, an extracellular domain of a classical MHC class II polypeptide from an endogenous MHC II locus; or
(e) any combination of (a)-(f).

14. The genetically modified mouse of claim 1, further comprising a β2 microglobulin locus comprising a sequence encoding a polypeptide comprising a human β2 microglobulin amino acid sequence, wherein the mouse expresses a human or humanized β2 microglobulin polypeptide.

15. The genetically modified mouse of claim 14, wherein the mouse does not express a functional endogenous mouse β2 microglobulin polypeptide from an endogenous mouse β2 microglobulin locus.

16. The genetically modified mouse of claim 14, wherein the sequence encoding the polypeptide comprising the human β2 microglobulin amino acid sequence is operably linked to mouse β2 microglobulin regulatory elements.

17. The genetically modified mouse of claim 14, wherein the β2 microglobulin locus comprises a nucleotide sequence set forth in exon 2, exon 3, and exon 4 of a human β2 microglobulin gene.

18. The genetically modified mouse of claim 17, wherein the β2 microglobulin locus further comprises a nucleotide sequence set forth in exon 1 of a mouse β2 microglobulin gene.

19. The genetically modified mouse of claim 1, wherein the mouse expresses:
(a) at least 50% of all functional human TCRVα gene segments;
(b) at least 50% of all functional human TCRVβ gene segments; or
(c) at least 50% of all functional human TCRVα gene segments and at least 50% of all functional human TCRVβ gene segments.

20. A method of making the genetically modified mouse of claim 1 comprising modifying the genome of the mouse to comprise:
(a) the first nucleotide sequence encoding the chimeric human/mouse CD4 co-receptor;
(b) the second nucleotide sequence encoding the chimeric human/mouse CD8α polypeptide and the third nucleotide sequence encoding the chimeric human/mouse CD8β polypeptide;
(c) the first nucleic acid sequence encoding the chimeric human/mouse MHC II α polypeptide and the second nucleic acid sequence encoding the chimeric human/mouse MHC II β polypeptide;
(d) the third nucleic acid sequence encoding the chimeric human/mouse MHC I polypeptide; and
(e) the unrearranged TCR α variable region sequence operably linked to the mouse TCRα constant region sequence and the unrearranged TCRβ variable region sequence operably linked to the mouse TCRβ constant region sequence; and (f) optionally, a β2 microglobulin locus comprising a sequence encoding a human or humanized β2 microglobulin polypeptide.

21. The method of claim 20, wherein modifying the genome comprises homologous recombination in one or more mouse ES cell(s) such that the first, second, and third nucleotide sequences; the unrearranged TCRα variable region sequence and unrearranged TCRβ variable region sequence; the first, second, and third nucleic acid sequences; and optionally the β2 microglobulin locus; are added, in any order, into the genome of the one or more mouse ES cell(s).

22. The method of claim 21, further comprising generating a mouse from the one or more mouse ES cell(s).

23. A method of obtaining any one of: (1) a TCR protein that is specific for an antigen and comprises a human TCR variable domain, (2) the human TCR variable domain and (3) a nucleic acid sequence encoding the human TCR variable domain,
the method comprising
isolating from a mouse according to claim 1 any one of:
(1) a T cell expressing a TCR protein that is specific for an antigen and comprises both a human TCR α variable domain and a human TCR β variable domain,
(2) either or both (i) the human TCR α variable domain and (ii) the human TCR β variable domain, and
(3) either or both (i) a nucleic acid sequence encoding the human TCR α variable domain and (ii) a nucleic acid sequence encoding the human TCR β variable domain.

24. The method of claim 23, wherein the method comprises isolating from the mouse a nucleic acid sequence encoding the human TCR α variable domain and a nucleic acid sequence encoding the human TCR β variable domain, the method further comprising
culturing a host cell in sufficient conditions for expressing (i) the nucleic acid sequence encoding the human TCR α variable domain in operable linkage with a human TCR α constant region and (ii) the nucleic acid sequence encoding the human TCR β variable domain in operable linkage with a human TCR β constant region,
wherein the nucleic acid sequences encoding the human TCR α variable domain and the human TCR β variable domain are on the same or different expression vectors.

25. The method of claim 23, wherein the antigen is a tumor antigen, a viral antigen, or a bacterial antigen.

26. A genetically modified mouse embryonic stem cell comprising in its genome
(a) a first nucleotide sequence encoding a chimeric human/mouse CD4 co-receptor that comprises D1, D2 and D3 domains of a human CD4 polypeptide and transmembrane and cytoplasmic domains of a mouse CD4 polypeptide,
(b) a second nucleotide sequence and a third nucleotide sequence respectively encoding a chimeric human/mouse CD8α polypeptide and a chimeric human/mouse CD8β polypeptide,
wherein the chimeric human/mouse CD8α polypeptide comprises an IgV-like domain of a human CD8α polypeptide and transmembrane and cytoplasmic domains of a mouse CD8α polypeptide,
wherein the chimeric human/mouse CD8β polypeptide comprises an IgV-like domain of a human CD8β polypeptide and transmembrane and cytoplasmic domains of a mouse CD8β polypeptide, and (c) a first nucleic acid sequence and a second nucleic acid sequence respectively encoding a chimeric human/mouse MHC II α polypeptide and a chimeric human/mouse MHC II β polypeptide,
wherein the chimeric human/mouse MHC II α polypeptide comprises α1 and α2 domains of a human HLA class II α polypeptide and transmembrane and cytoplasmic domains of a mouse MHC II α polypeptide,
wherein the chimeric human/mouse MHC II β polypeptide comprises β1 and β2 domains of a human HLA class II β polypeptide and transmembrane and cytoplasmic domains of a mouse MHC II β polypeptide,
(d) a third nucleic acid sequence encoding a chimeric human/mouse MHC I polypeptide,
wherein the chimeric human/mouse MHC I polypeptide comprises α1, α2, and α3 domains of a human HLA class I polypeptide and transmembrane and cytoplasmic domains of a mouse MHC I polypeptide, and
(e) an unrearranged T cell receptor (TCR) α variable region sequence comprising at least one human Vα segment and at least one human Jα segment, wherein the unrearranged TCR α variable region sequence is operably linked to a mouse TCRα constant region sequence; and an unrearranged TCRβ variable region sequence comprising at least one human Vβ segment, at least one human Dβ segment, and at least one human Jβ segment, wherein the unrearranged TCRβ variable region sequence is operably linked to a mouse TCRβ constant region sequence.

27. The genetically modified mouse embryonic stem cell of claim 26, wherein
(a) the first nucleotide sequence is present at an endogenous CD4 locus;
(b) the second nucleotide sequence is present at an endogenous CD8α locus, and the third nucleotide sequence is present at an endogenous CD8β locus;
(c) the first nucleic acid sequence is present at an endogenous MHC II α locus and the second nucleic acid sequence is present at an endogenous MHC II β locus;
(d) the third nucleic acid sequence is present at an endogenous MHC I locus; and/or
(e) the unrearranged TCRα variable region sequence is present at an endogenous TCRα variable region locus and the unrearranged TCRβ variable region sequence is present at an endogenous TCRβ variable region locus.

28. The genetically modified mouse embryonic stem cell of claim 27, wherein
(a) the first nucleotide sequence is present at the endogenous CD4 locus and operably linked to mouse CD4 promoter and regulatory elements;
(b) the second nucleotide sequence is present at the endogenous CD8α locus and operably linked to mouse CD8α promoter and regulatory elements, and the third nucleotide sequence is present at the endogenous CD8β locus and operably linked to mouse CD8β promoter and regulatory elements;
(c) the first nucleic acid sequence is present at the endogenous MHC II α locus and operably linked to mouse MHC II α promoter and regulatory elements and the second nucleic acid sequence is present at the endogenous MHC II β locus and operably linked to mouse MHC II β promoter and regulatory elements; and/or
(d) the third nucleic acid sequence is present at the endogenous MHC I locus and operably linked to mouse MHC I promoter and regulatory elements.

29. The genetically modified mouse embryonic stem cell of claim 26, wherein (a) the chimeric human/mouse CD4 co-receptor comprises D1, D2 and D3 domains of the human CD4 polypeptide operably linked to transmembrane and cytoplasmic domains of the mouse CD4 polypeptide, and/or (b) the chimeric human/mouse CD8α polypeptide comprises an extracellular portion of the human CD8α polypeptide operably linked to transmembrane and cytoplasmic domains of the mouse CD8α polypeptide and the chimeric human/mouse CD8β polypeptide comprises an extracellular portion of the human CD8β polypeptide operably linked to transmembrane and cytoplasmic domains of the mouse CD8β polypeptide.

30. A mouse embryonic stem (ES) cell made by a method comprising the steps of adding into the genome of the ES cell by homologous recombination in any order (a) a first nucleotide sequence encoding a chimeric human/mouse CD4 co-receptor that comprises D1, D2 and D3 domains of a human CD4 polypeptide and transmembrane and cytoplasmic domains of a mouse CD4 polypeptide, (b) a second nucleotide sequence encoding a chimeric human/mouse CD8α polypeptide and a third nucleotide sequence encoding a chimeric human/mouse CD8β polypeptide, wherein the chimeric human/mouse CD8α polypeptide comprises an IgV-like domain of a human CD8α polypeptide and transmembrane and cytoplasmic domains of a mouse CD8α polypeptide, wherein the chimeric human/mouse CD8β polypeptide comprises an IgV-like domain of a human CD8β polypeptide and transmembrane and cytoplasmic domains of a mouse CD8β polypeptide, (c) a first nucleic acid sequence encoding a chimeric human/mouse MHC II α polypeptide and a second nucleic acid sequence encoding a chimeric human/mouse MHC II β polypeptide, wherein the chimeric human/mouse MHC II α polypeptide comprises α1 and α2 domains of a human HLA class II α polypeptide and transmembrane and cytoplasmic domains of a mouse MHC II α polypeptide, wherein the chimeric human/mouse MHC II β polypeptide comprises β1 and β2 domains of a human HLA class II β polypeptide and transmembrane and cytoplasmic domains of a mouse MHC II β polypeptide, (d) a third nucleic acid sequence encoding a chimeric human/mouse MHC I polypeptide, wherein the chimeric human/mouse MHC I polypeptide comprises α1, α2, and α3 domains of a human HLA class I polypeptide and transmembrane and cytoplasmic domains of a mouse MHC I polypeptide, and (e) an unrearranged T cell receptor (TCR) α variable region sequence comprising at least one human Vα segment and at least one human Jα segment, wherein the unrearranged TCR α variable region sequence is operably linked to a mouse TCRα constant region sequence; and an unrearranged TCRβ variable region sequence comprising at least one human Vβ segment, at least one human Dβ segment, and at least one human Jβ segment, wherein the unrearranged TCR β variable region sequence is operably linked to a mouse TCRβ constant region sequence.

31. The genetically modified mouse of claim 4, wherein the chimeric human/mouse CD8α polypeptide comprises an extracellular portion of the human CD8α polypeptide operably linked to transmembrane and cytoplasmic domains of the mouse CD8α polypeptide and the chimeric human/mouse CD8β polypeptide comprises an extracellular portion of the human CD8β polypeptide operably linked to transmembrane and cytoplasmic domains of the mouse CD8β polypeptide.

\* \* \* \* \*

UNITED STATES PATENT AND TRADEMARK OFFICE
CERTIFICATE OF CORRECTION

| | | |
|---|---|---|
| PATENT NO. | : 11,259,510 B2 | Page 1 of 1 |
| APPLICATION NO. | : 15/564723 | |
| DATED | : March 1, 2022 | |
| INVENTOR(S) | : Macdonald et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 170 days.

Signed and Sealed this
Twentieth Day of May, 2025

Coke Morgan Stewart
*Acting Director of the United States Patent and Trademark Office*